US012480117B2

(12) United States Patent
Kahvejian et al.

(10) Patent No.: US 12,480,117 B2
(45) Date of Patent: Nov. 25, 2025

(54) COMPOSITIONS COMPRISING MODIFIED CIRCULAR POLYRIBONUCLEOTIDES AND USES THEREOF

(71) Applicant: Flagship Pioneering Innovations VI, LLC, Cambridge, MA (US)

(72) Inventors: Avak Kahvejian, Lexington, MA (US); Nicholas McCartney Plugis, Cohasset, MA (US); Alexandra Sophie De Boer, Somerville, MA (US); Ki Young Paek, Brighton, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 1001 days.

(21) Appl. No.: 17/442,212

(22) PCT Filed: Mar. 25, 2020

(86) PCT No.: PCT/US2020/024789

§ 371 (c)(1),
(2) Date: Sep. 23, 2021

(87) PCT Pub. No.: WO2020/198403

PCT Pub. Date: Oct. 1, 2020

(65) Prior Publication Data

US 2023/0072532 A1 Mar. 9, 2023

Related U.S. Application Data

(60) Provisional application No. 62/823,573, filed on Mar. 25, 2019.

(51) Int. Cl.
*C12N 15/113* (2010.01)
*C12N 15/85* (2006.01)

(52) U.S. Cl.
CPC ............ *C12N 15/113* (2013.01); *C12N 15/85* (2013.01); *C12N 2310/113* (2013.01); *C12N 2310/532* (2013.01); *C12N 2840/203* (2013.01)

(58) Field of Classification Search
None
See application file for complete search history.

(56) References Cited

U.S. PATENT DOCUMENTS 5,223,409 A 6/1993 Ladner et al.
5,426,180 A 6/1995 Kool
5,438,119 A 8/1995 Rutter et al.
5,440,016 A 8/1995 Blondelle et al.
5,463,564 A 10/1995 Agrafiotis et al.
5,523,735 A 6/1996 Goseberg et al.
5,525,735 A 6/1996 Gallop et al.
5,541,061 A 7/1996 Fodor et al.
5,545,568 A 8/1996 Ellman
5,549,974 A 8/1996 Holmes
5,565,324 A 10/1996 Still et al.
5,571,698 A 11/1996 Ladner et al.
5,574,656 A 11/1996 Agrafiotis et al.
5,593,853 A 1/1997 Chen et al.
5,639,603 A 6/1997 Dower et al.
5,641,862 A 6/1997 Rutter et al.
5,684,711 A 11/1997 Agrafiotis et al.
5,688,696 A 11/1997 Lebl
5,688,997 A 11/1997 Baldwin et al.
5,697,673 A 12/1997 Favaretto
5,698,673 A 12/1997 Blondelle et al.
5,708,153 A 1/1998 Dower et al.
5,712,128 A 1/1998 Been et al.
5,721,099 A 2/1998 Still et al.
5,731,423 A 3/1998 Kakarla et al.
5,734,018 A 3/1998 Rutter et al.
5,741,713 A 4/1998 Brown et al.
5,766,903 A 6/1998 Sarnow et al.
5,773,244 A 6/1998 Ares, Jr. et al.
5,877,160 A 3/1999 Harper et al.
6,210,931 B1 4/2001 Feldstein et al.
8,084,599 B2 12/2011 Rossi et al.
8,349,809 B2 1/2013 Brown
8,513,207 B2 8/2013 Brown
9,822,378 B2 11/2017 Kruse
10,407,683 B2 9/2019 Nelson et al.
10,953,033 B2 3/2021 Stewart et al.
11,000,547 B2 5/2021 Goldberg et al.
2003/0082768 A1 5/2003 Baskerville et al.
2005/0015829 A1 1/2005 Koop et al.
2005/0059005 A1 3/2005 Tuschl et al.
2005/0112639 A1 5/2005 Wang et al.
2005/0176940 A1 8/2005 King
2005/0261218 A1 11/2005 Esau et al.
2006/0292611 A1 12/2006 Berka et al.
2010/0129877 A1 5/2010 Sahin et al.
(Continued)

FOREIGN PATENT DOCUMENTS

CN 104169420 A 11/2014
CN 105664239 A 6/2016
(Continued)

OTHER PUBLICATIONS

Abe et al., "Rolling circle translation of circular RNA in living human cells," Sci Rep. 5:16435 (2015) (9 pages).
Abouhaidar et al., "Novel coding, translation, and gene expression of a replicating covalently closed circular RNA of 220 nt," Proc Natl Acad Sci U S A. 111(40):14542-7 (2014) (8 pages).
Agresti et al., "Selection of Ribozymes that Catalyse Multiple-Turnover Diels-Alder Cycloadditions by Using in Vitro Compartmentalization," Proc Natl Acad Sci U S A. 102(45):16170-5 (2005).
(Continued)

*Primary Examiner* — Christopher M Babic
*Assistant Examiner* — Kimberly A Aron
(74) *Attorney, Agent, or Firm* — Clark & Elbing LLP

(57) ABSTRACT

This invention relates generally to pharmaceutical compositions and preparations of modified circular polyribonucleotides and uses thereof.

12 Claims, 55 Drawing Sheets

Specification includes a Sequence Listing.

(56) References Cited

U.S. PATENT DOCUMENTS

| | | | |
|---|---|---|---|
| 2010/0137407 | A1 | 6/2010 | Abe et al. |
| 2014/0068797 | A1 | 3/2014 | Doudna et al. |
| 2014/0134636 | A1 | 5/2014 | Kim et al. |
| 2015/0064236 | A1 | 3/2015 | Bancel et al. |
| 2015/0079630 | A1 | 3/2015 | Abe et al. |
| 2015/0299702 | A1 | 10/2015 | Kjems et al. |
| 2016/0194368 | A1 | 7/2016 | Hoge et al. |
| 2017/0042782 | A1 | 2/2017 | Wendel et al. |
| 2018/0023079 | A1 | 1/2018 | Dimmeler et al. |
| 2018/0037894 | A1 | 2/2018 | Bovell et al. |
| 2020/0306286 | A1 | 10/2020 | Stewart et al. |
| 2021/0292761 | A1 | 9/2021 | Kahvejian et al. |
| 2022/0088049 | A1 | 3/2022 | Kahvejian et al. |
| 2022/0142896 | A1 | 5/2022 | Kahvejian et al. |

FOREIGN PATENT DOCUMENTS

| | | | |
|---|---|---|---|
| CN | 106222174 | A | 12/2016 |
| DE | 102005001784 | A1 | 10/2006 |
| EP | 1598421 | A2 | 11/2005 |
| EP | 1723958 | A2 | 11/2006 |
| EP | 2996697 | B1 | 6/2019 |
| WO | WO-92/01813 | A1 | 2/1992 |
| WO | WO-2007/016507 | A2 | 2/2007 |
| WO | WO-2010/084371 | A1 | 7/2010 |
| WO | WO-2013/053481 | A1 | 4/2013 |
| WO | WO-2013/151663 | A1 | 10/2013 |
| WO | WO-2013/151664 | A1 | 10/2013 |
| WO | WO-2013/151665 | A2 | 10/2013 |
| WO | WO-2013/151666 | A2 | 10/2013 |
| WO | WO-2013/151668 | A2 | 10/2013 |
| WO | WO-2013/151669 | A1 | 10/2013 |
| WO | WO-2013/151670 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2014/164253 | A1 | 10/2014 |
| WO | WO-2014/186334 | A1 | 11/2014 |
| WO | WO-2015/023975 | A1 | 2/2015 |
| WO | WO-2015/034925 | A1 | 3/2015 |
| WO | WO-2015/164674 | A1 | 10/2015 |
| WO | WO-2016/011222 | A2 | 1/2016 |
| WO | WO-2016/197121 | A1 | 12/2016 |
| WO | WO-2017/001570 | A2 | 1/2017 |
| WO | WO-2017/222911 | A1 | 12/2017 |
| WO | WO-2018/191722 | A1 | 10/2018 |
| WO | WO-2018/237372 | A1 | 12/2018 |
| WO | WO-2019/118919 | A1 | 6/2019 |
| WO | WO-2019/236673 | A1 | 12/2019 |
| WO | WO-2020/023655 | A1 | 1/2020 |
| WO | WO-2020/173171 | A1 | 9/2020 |
| WO | WO-2020/180751 | A1 | 9/2020 |
| WO | WO-2020/180752 | A1 | 9/2020 |
| WO | WO-2020/181013 | A1 | 9/2020 |
| WO | WO-2020/198403 | A2 | 10/2020 |
| WO | WO-2020/252436 | A1 | 12/2020 |
| WO | WO-2020/257727 | A1 | 12/2020 |
| WO | WO-2020/257730 | A1 | 12/2020 |
| WO | WO-2021/155171 | A1 | 8/2021 |
| WO | WO-2021/155175 | A1 | 8/2021 |
| WO | WO-2021/155177 | A1 | 8/2021 |
| WO | WO-2021/236930 | A1 | 11/2021 |
| WO | WO-2021/236952 | A1 | 11/2021 |
| WO | WO-2021/236980 | A1 | 11/2021 |

OTHER PUBLICATIONS

Alhasan et al., "Circular RNA enrichment in platelets is a signature of transcriptome degradation," Blood. 127(9):e1-e11 (2016) (12 pages).

Anand et al., "MicroRNA-Mediated Regulation of the Angiogenic Switch," available in PMC May 1, 2012, published in final edited form as: Curr Opin Hematol. 18(3):171-6 (2011) (11 pages).

Angenendt et al., "Cell-Free Protein Expression and Functional Assay in Nanowell Chip Format," Anal Chem. 76(7):1844-9 (2004).

Angenendt et al., "Generation of High Density Protein Microarrays by Cell-free in Situ Expression of Unpurified PCR Products," Mol Cell Proteomics. 5(9):1658-66 (2006).

Ausländer et al., "A ligand-dependent hammerhead ribozyme switch for controlling mammalian gene expression," Mol Biosyst. 6(5):807-14 (2010).

Bartel, "MicroRNA target recognition and regulatory functions," available in PMC Oct. 10, 2013, published in final edited form as: Cell. 136(2):215-33 (2009) (33 pages).

Bartel, "MicroRNAs: Genomics, Biogenesis, Mechanism, and Function," Cell. 116(2):281-97 (2004).

Beaudry et al., "An efficient strategy for the synthesis of circular RNA molecules," Nucleic Acids Res. 23(15):3064-6 (1995).

Beeharry et al., "Conserved Features of an RNA Promoter for RNA Polymerase II Determined from Sequence Heterogeneity of a Hepatitis Delta Virus Population," Virology. 450-451:165-73 (2014).

Bird et al., "Single-chain antigen-binding proteins," Science. 242(4877):423-6 (1988) (5 pages).

Birmingham et al., "3' UTR Seed Matches, but Not Overall Identity, are Associated with RNAi Off-Targets," Nat Methods. 3(3):199-204 (2006).

Bonauer et al., "Vascular MicroRNAs," Curr Drug Targets. 11(8):943-9 (2010).

Carmona, Ellese, Dissertation: "Circular RNA: Design Criteria for Optimal Therapeutical Utility," PhD, Division of Medical Sciences, Harvard University, 2019. Retrieved from <http://nrs.harvard.edu/urn-3:HUL.InstRepos:41121328>, (135 pages).

Chatterjee et al., "Protein technologies," Curr Opin Biotechnology. 17:334-6 (2006).

Chen et al., "Fusion protein linkers: Property, design and functionality," Adv Drug Deliv Rev. 65(10):1357-69 (2013).

Chen et al., "Sensing Self and Foreign Circular RNAs by Intron Identity," Mol Cell. 67(2):228-38.e5 (2017) (17 pages).

Chesnoy et al., "Structure and function of lipid-DNA complexes for gene delivery," Annu Rev Biophys Biomol Struct. 29:27-47 (2000) (23 pages).

Cong et al., "Multiplex genome engineering using CRISPR/Cas systems," available in PMC Oct. 11, 2013, published in final edited form as: Science 339(6121):819-23 (2013) (9 pages).

Contreras et al., "MicroRNAs in Inflammation and Immune Responses," Leukemia. 26(3):404-13 (2012).

Costello et al., "Reinventing the Wheel: Synthetic Circular RNAs for Mammalian Cell Engineering," Trends Biotechnol. 38(2):217-30 (2020) (15 pages).

Defenbaugh et al., "Hepatitis Delta Antigen Requires a Minimum Length of the Hepatitis Delta Virus Unbranched Rod RNA Structure for Binding," J Virol. 83(9):4548-56 (2009).

Ding et al., "Three-Dimensional RNA Structure Refinement by Hydroxyl Radical Probing," available in PMC Dec. 1, 2012, published in final edited form as: Nat Methods. 9(6):603-8 (2012) (20 pages).

Doench et al., "siRNAs can function as miRNAs," Genes Dev. 17(4):438-42 (2003).

Dudekula et al., "CircInteractome: A web tool for exploring circular RNAs and their interacting proteins and microRNAs," RNA Biol. 13(1):34-42 (2016) (10 pages).

Elabd et al., "DNA Methyltransferase-3-Dependent Nonrandom Template Segregation in Differentiating Embryonic Stem Cells," J Cell Biol. 203(1):73-85 (2013).

Final Office Action for U.S. Appl. No. 16/438,073, mailed Apr. 27, 2020 (24 pages).

Gentner et al., "Exploiting MicroRNA Regulation for Genetic Engineering," Tissue Antigens. 80(5):393-403 (2012).

Goldstein, "Effect of Alcohol on Cellular Membranes," Ann Emerg Med. 15(9):1013-8 (1986).

Gori et al., "Delivery and Specificity of CRISPR/Cas9 Genome Editing Technologies for Human Gene Therapy," Hum Gene Ther. 26(7):443-51 (2015).

Griffin et al., "Hepatitis Delta Antigen Requires a Flexible Quasi-Double-Stranded RNA Structure to Bind and Condense Hepatitis Delta Virus RNA in a Ribonucleoprotein Complex," J Virol. 88(13):7402-11 (2014).

(56) References Cited

OTHER PUBLICATIONS

Grimson et al., "MicroRNA Targeting Specificity in Mammals: Determinants Beyond Seed Pairing," Mol Cell. 27(1):91-105 (2007).
Guedj et al., "Understanding early serum hepatitis D virus and HBsAg kinetics during pegylated interferon-alfa therapy via mathematical modeling," available in PMC Dec. 1, 2015, published in final edited form as: Hepatology. 60(6):1902-10 (2014) (14 pages).
He et al., "Arraying proteins by cell-free synthesis," Biomol Eng. 24(4):375-80 (2007).
He et al., "DiscernArray™ technology: a cell-free method for the generation of protein arrays from PCR DNA," J Immunol Methods. 274(1-2):265-70 (2003).
He et al., "In situ synthesis of protein arrays," Curr Opin Biotechnol. 19(1):4-9 (2008).
He et al., "Printing protein arrays from DNA arrays," Nat Methods. 5(2):175-7 (2008).
He et al., "Single step generation of protein arrays from DNA by cell-free expression and in situ immobilisation (PISA method)," Nucleic Acids Res. 29(15):E73-3 (2001) (6 pages).
Hendel et al., "Chemically modified guide RNAs enhance CRISPR-Cas genome editing in human primary cells," Nat Biotechnol. 33(9):985-9 (2015) (7 pages).
Huston et al., "Protein engineering of antibody binding sites: recovery of specific activity in an anti-digoxin single-chain Fv analogue produced in *Escherichia coli*," Proc Natl Acad Sci U S A. 85(16):5879-83 (1988).
Ingolfsson et al., "Alcohol's Effects on Lipid Bilayer Properties," Biophys J. 101(4):847-55 (2011).
International Preliminary Report on Patentability for International Application No. PCT/US2020/020560, mailed Apr. 26, 2021 (16 pages).
International Report on Patentability for International Patent Application No. PCT/US2020/024789, issued Sep. 28, 2021 (11 pages).
International Search Report and Written Opinion for International Application No. PCT/US2018/065836, mailed Mar. 28, 2019 (13 pages).
International Search Report and Written Opinion for International Application No. PCT/US2019/043272, mailed Dec. 6, 2019 (18 pages).
International Search Report and Written Opinion for International Application No. PCT/US2020/038835, mailed Oct. 9, 2020 (19 pages).
International Search Report and Written Opinion for International Patent Application No. PCT/US2020/020561, mailed Jun. 9, 2020 (11 pages).
Iwasaki et al., "Rocaglates Convert DEAD-Box Protein eIF4A into a Sequence-Selective Translational Repressor," available in PMC Dec. 15, 2016, published in final edited form as: Nature 534(7608):558-61 (2016) (33 pages).
Izuogu et al., "Analysis of human ES cell differentiation establishes that the dominant isoforms of the IncRNAs RMST and FIRRE are circular," BMC Genomics. 19(1):276 (2018) (18 pages).
Kash et al., "Selective Translation of Eukaryotic mRNAs: Functional Molecular Analysis of GRSF-1, a Positive Regulator of Influenza Virus Protein Synthesis," J Virol. 76(20):10417-26 (2002).
Katzen et al., "The past, present and future of cell-free protein synthesis," Trends Biotechnol. 23(3):150-6 (2005).
Kilb et al., "Protein microarray generation by in situ protein expression from template DNA," Eng Life Sci. 14:352-64 (2014).
Kimoto et al., "Genetic Alphabet Expansion Transcription Generating Functional RNA Molecules Containing a Five-Letter Alphabet Including Modified Unnatural and Natural Base Nucleotides by Thermostable T7 RNA Polymerase Variants," Accepted Manuscript, published in final edited form as: Chem Commun (Camb). 53(91):12309-12312 (2017) (5 pages).
Kinpara et al., "A Picoliter Chamber Array for Cell-Free Protein Synthesis," J Biochem 136(2):149-54 (2004).
Kolonko et al., "Transcription of Potato Spindle Tuber Viroid by RNA Polymerase II Starts in the Left Terminal Loop," Virology. 347:392-404 (2006).
Kramer et al., "Combinatorial control of Drosophila circular RNA expression by intronic repeats, hnRNPs, and SR proteins," Genes Dev. 29(20):2168-82 (2015) (16 pages).
Kuznetsova et al., "Efficient Synthesis of DNA Dumbbells Using Template-Induced Chemical Ligation in Double-Stranded Polynucleotides Closed by Minihairpin Fragments," Antisense Nucleic Acid Drug Dev. 9(1):95-100 (1999).
Laganà et al., "Computational Design of Artificial RNA Molecules for Gene Regulation," available in PMC May 8, 2015, published in final edited form as: Methods Mol Biol. 1269:393-412 (2015) (21 pages).
Landgraf et al., "A Mammalian MicroRNA Expression Atlas Based on Small RNA Library Sequencing," available in PMC May 13, 2009, published in final edited form as: Cell. 129(7):1401-14 (2007) (22 pages).
Legnini et al., "Circ-ZNF609 Is a Circular RNA that Can Be Translated and Functions in Myogenesis," Mol Cell. 66(1):22-37.e9 (2017) (42 pages).
Leontieva et al., "Contact Inhibition and High Cell Density Deactivate the Mammalian target of Rapamycin Pathway, thus Suppressing the Senescence Program," Proc Natl Acad Sci U S A. 111(24):8832-7 (2014).
Lewis et al., "RNA Modifications and Structures Cooperate to Guide RNA-Protein Interactions," available in PMC Aug. 3, 2017, published in final edited form as: Nat Rev Mol Cell Biol. 18(3):202-10 (2017) (21 pages).
Li et al., "Discovering the interactions between circular RNAs and RNA-binding proteins from CLIP-seq Data using circScan," bioRxiv preprint, <https://www.biorxiv.org/content/10.1101/115980v1>, retrieved on Mar. 11, 2017 (19 pages).
Lim et al., "Microarray analysis shows that some microRNAs downregulate large numbers of target mRNAs," Nature. 433(7027):769-73 (2005).
Lingor et al., "Transfection of 'Naked' siRNA Results in Endosomal Uptake and Metabolic Impairment in Cultured Neurons," Biochem Biophys Res Commun. 315(4):1126-33 (2004).
Liu et al., "VSV-G Viral Envelope Glycoprotein Prepared from Pichia Pastoris Enhances Transfection of DNA into Animal Cells," J Microbiol Biotechnol. 27(6):1098-105 (2017).
Mair et al., "Size-Uniform 200 nm Particles: Fabrication and Application to Magnetofection," available in PMC Feb. 9, 2010, published in final edited form as: J Biomed Nanotechnol. 5(2):182-91 (2009) (19 pages).
Marchanka et al., "RNA structure determination by solid-state NMR spectroscopy," Nat Commun. 6:7024 (2015) (7 pages).
Matsuda et al., "Determinants of Initiation Codon Selection during Translation in Mammalian Cells," PLoS One. 5(11):e15057 (2010) (13 pages).
Mignone et al., "Untranslated regions of mRNAs," Genome Biol. 3(3):REVIEWS0004 (2002) (10 pages).
Miller et al., "Non-Viral CRISPR/Cas Gene Editing In Vitro and In Vivo Enabled by Synthetic Nanoparticle Co-Delivery of Cas9 mRNA and sgRNA," Angew Chem Int Ed Engl. 56(4):1059-1063 (2017).
Muller et al., "An Efficient Method for Electroporation of Small Interfering RNAs into ENCODE Project Tier 1 GM12878 and K562 Cell Lines," J Biomol Tech. 26(4):142-9 (2015).
Müller et al., "In vitro circularization of RNA," RNA Biol. 14(8):1018-1027 (2017).
Neuhaus et al., "Nanoparticles as transfection agents: a comprehensive study with ten different cell lines," RSC Adv. 6:18102-18112 (2016).
Office Action for U.S. Appl. No. 16/438,073, mailed Aug. 24, 2020 (13 pages).
Office Action for U.S. Appl. No. 16/438,073, mailed Jan. 13, 2020 (16 pages).
Ogawa, "Rational design of artificial riboswitches based on ligand-dependent modulation of internal ribosome entry in wheat germ extract and their applications as label-free biosensors," RNA. 17(3):478-88 (2011).
Olton et al., "Nanostructured calcium phosphates (NanoCaPs) for non-viral gene delivery: Influence of the synthesis parameters on transfection efficiency," Biomaterials. 28(6):1267-79 (2007).

(56) References Cited

OTHER PUBLICATIONS

Petkovic et al., "RNA circularization strategies in vivo and in vitro," Nucleic Acids Res. 43(4):2454-65 (2015).
Qin et al., "Structure, Regulation, and Function of Linear and Circular Long Non-Coding RNAs," Front Genet. 11:150 (2020) (15 pages).
Rajewsky, "MicroRNA target predictions in animals," Nat Genet. 38 Suppl:S8-13 (2006).
Ramachandran et al., "Self-Assembling Protein Microarrays," Science. 305(5680):86-90 (2004) (6 pages).
Ran et al., "Genome engineering using the CRISPR-Cas9 system," available in PMC Mar. 30, 2014, published in final edited form as: Nat Protoc. 8(11):2281-2308 (2013) (49 pages).
Roulston, Claire, Thesis: "Occurrence & Function of Cellular 2A Sequences," PhD, University of St Andrews, 2015. Retrieved from <http://hdl.handle.net/10023/7062>, (279 pages).
Rozenski et al., "The RNA Modification Database: 1999 update," Nucleic Acids Res. 27(1):196-7 (1999).
Schlake et al., "Developing mRNA-vaccine technologies," RNA Biol. 9(11):1319-30 (2012).
Sooter et al., "Toward Automated Nucleic Acid Enzyme Selection," Biol Chem. 382(9):1327-34 (2001) (9 pages).
Stadel et al., "Orphan G protein-coupled receptors: a neglected opportunity for pioneer drug discovery," Trends Pharmacol Sci. 18(11):430-7 (1997).
Steeland et al., "Nanobodies as therapeutics: big opportunities for small antibodies," Drug Discov Today. 21(7):1076-113 (2016).
Stevens, "Design of high-throughput methods of protein production for structural biology," Structure. 8(9):R177-85 (2000).
Takulapalli et al., "High Density Diffusion-Free Nanowell Arrays," J Proteome Res. 11(8):4382-91 (2012).
Tannous, "Gaussia luciferase reporter assay for monitoring of biological processes in culture and in vivo," available in PMC Jul. 1, 2009, published in final edited form as: Nat Protoc. 4(4):582-91 (2009) (19 pages).
Tao et al., "Protein chip fabrication by capture of nascent polypeptides," Nat Biotechnol. 24(10):1253-4 (2006) (3 pages).
Tijerina et al., "DMS Footprinting of Structured RNAs and RNA-Protein Complexes," available in PMC Jun. 25, 2009, published in final edited form as: Nat Protoc. 2(10):2608-23 (2007) (36 pages).
Touriol et al., "Generation of protein isoform diversity by alternative initiation of translation at non-AUG codons," Biol Cell. 95(3-4):169-78 (2003).
Tucker et al., "Riboswitches as versatile gene control elements," Curr Opin Struct Biol. 15(3):342-8 (2005).
Tonges et al., "Stearylated octaarginine and artificial virus-like particles for transfection of siRNA into primary rat neurons," RNA. 12(7):1431-8 (2006) (9 pages).
Wang et al., "Efficient backsplicing produces translatable circular mRNAs," RNA. 21(2):172-9 (2015) (9 pages).
Ward et al., "Binding activities of a repertoire of single immunoglobulin variable domains secreted from *Escherichia coli*," Nature. 341(6242):544-6 (1989).
Wesselhoeft et al., "Engineering circular RNA for potent and stable translation in eukaryotic cells," Nat Commun. 9(1):2629 (2018) (10 pages).
Wesselhoeft et al., "RNA circularization diminishes immunogenicity and can extend translation duration in vivo," available in PMC May 2, 2020, published in final edited form as: Mol Cell. 74(3):508-520.e4 (2019) (30 pages).
Winkler et al., "Control of gene expression by a natural metabolite-responsive ribozyme," Nature. 428(6980):281-6 (2004).
Wu et al., "MicroRNAs direct rapid deadenylation of mRNA," Proc Natl Acad Sci U S A. 103(11):4034-9 (2006).
Yu et al., "RNA editing by ADAR1 marks dsRNA as "self"," Cell Res. 25(12):1283-4 (2015).
Zeng et al., "Both Natural and Designed Micro RNAs Can Inhibit the Expression of Cognate mRNAs When Expressed in Human Cells," Mol Cell. 9(6):1327-33 (2002).
Zhang et al., "Cell-penetrating peptides as noninvasive transmembrane vectors for the development of novel multifunctional drug-delivery systems," J Control Release. 229:130-139 (2016).
Ziehler et al., "Probing RNA Structure with Chemical Reagents and Enzymes," available in PMC Aug. 19, 2013, published in final edited form as: Curr Protoc Nucleic Acid Chem. Chapter 6:Unit 6.1. (2001) (24 pages).
Zuris et al., "Cationic lipid-mediated delivery of proteins enables efficient protein-based genome editing in vitro and in vivo," Advance Online Publication published online Oct. 30, 2014, published in final edited form as: Nat Biotechnol. 33(1):73-80 (2015) (10 pages).

Example of helical part of construct

Conventions

C Circularization mix

C+R Circularization mix + Rnase R

1 Circular product

2 Parental Linear

3 Linear byproduct

4 Linear Splicing intermediates

COMPOSITIONS COMPRISING MODIFIED CIRCULAR POLYRIBONUCLEOTIDES AND USES THEREOF

CROSS REFERENCE

This application claims the benefit of U.S. Provisional Application No. 62/823,573, filed Mar. 25, 2019, the entire contents of which are incorporated by reference.

SEQUENCE LISTING

The instant application contains a Sequence Listing which has been submitted electronically in ASCII format and is hereby incorporated by reference in its entirety. Said ASCII copy, created on Jun. 30, 2021 is named 51509-044004_Sequence_Listing_6_30_21_ST25 and is 76,319 bytes in size.

BACKGROUND

Certain circular polyribonucleotides are ubiquitously present in human tissues and cells, including tissues and cells of healthy individuals.

SUMMARY

The present disclosure provides pharmaceutical compositions comprising a pharmaceutically acceptable carrier or excipient and a circular polyribonucleotide comprising a first portion of contiguous unmodified nucleotides. In some embodiments, the circular polyribonucleotide comprises at least one modified polyribonucleotide and a first portion of contiguous unmodified nucleotides. In some embodiments, the modified circular polyribonucleotide is delivered to a subject.

The present disclosure provides a method of decreasing or reducing immunogenicity of a circular polyribonucleotide in a subject comprising: providing a hybrid modified circular polyribonucleotide, wherein the hybrid modified circular polyribonucleotide comprises at least one modified nucleotide and a first portion comprising at least about 5 to 1000 contiguous nucleotides having no more than 5% modified nucleotides; administering the hybrid modified circular polyribonucleotide to the subject; and obtaining decreased immunogenicity for the hybrid modified circular polyribonucleotide compared to a corresponding unmodified circular polyribonucleotide in a cell or tissue of the subject. In some embodiments, a method of reducing or decreasing immunogenicity of a circular polyribonucleotide in a subject comprises providing a hybrid modified circular polyribonucleotide, wherein the hybrid modified circular polyribonucleotide comprises at least one modified polyribonucleotide and a first portion of contiguous unmodified nucleotides, administering the hybrid modified circular polyribonucleotide to the subject, and obtaining reduced or decreased immunogenicity for the hybrid modified circular polyribonucleotide compared to a corresponding unmodified circular polyribonucleotide in a cell or tissue of the subject. In some embodiments, the first portion comprises an IRES. In some embodiments, the first portion comprises at least about 5 to 1000 contiguous unmodified nucleotides. In some embodiments, the first portion lacks 5'-methylcytidine pseudouridine, or N1-methyl-pseudouridine. In some embodiments, no more than 5% of nucleotides in the first portion are modified nucleotides. In some embodiments, no more than 5% of nucleotides in the IRES of the first portion are modified nucleotides.

The present disclosure provides a method of expressing one or more expression sequences in a subject comprising: providing a hybrid modified circular polyribonucleotide, wherein the hybrid modified circular polyribonucleotide comprises at least one modified nucleotide and a first portion comprising at least about 5 to 1000 contiguous nucleotides having no more than 5% modified nucleotides; administering the hybrid modified circular polyribonucleotide to the subject, and obtaining increased expression of the one or more expression sequences compared to expression of a one or more expression sequences in a fully modified circular polyribonucleotide counterpart in a cell or tissue of the subject. In some embodiments, a method of expressing one or more expression sequences in a subject comprises providing a hybrid modified circular polyribonucleotide comprising at least one modified polyribonucleotide, a first portion of contiguous unmodified nucleotides, and the one or more expression sequences, administering the hybrid modified circular polyribonucleotide to the subject, and obtaining increased expression of the one or more expression sequences compared to expression of a one or more expression sequences in a fully modified circular polyribonucleotide counterpart in a cell or tissue of the subject. In some embodiments, the first portion comprises an IRES. In some embodiments, the first portion comprises at least about 5 to 1000 contiguous unmodified nucleotides. In some embodiments, the first portion lacks 5'-methylcytidine, pseudouridine, or N1-methyl-pseudouridine. In some embodiments, no more than 5% of nucleotides in the first portion are modified nucleotides. In some embodiments, no more than 5% of nucleotides in the IRES of the first portion are modified nucleotides.

The present disclosure provides a method of increasing stability of a circular polyribonucleotide in a subject comprising: providing a hybrid modified circular polyribonucleotide, wherein the hybrid modified circular polyribonucleotide comprises at least one modified nucleotide and a first portion comprising at least about 5 to 1000 contiguous nucleotides having no more than 5% modified nucleotides; administering the hybrid modified circular polyribonucleotide to the subject, and obtaining increased stability for the hybrid modified circular polyribonucleotide compared to a corresponding unmodified circular polyribonucleotide. in a cell or tissue of the subject. In some embodiments, a method of increasing stability of a circular polyribonucleotide in a subject comprises providing a hybrid modified circular polyribonucleotide, wherein the hybrid modified circular polyribonucleotide comprises at least one modified polyribonucleotide and a first portion of contiguous unmodified nucleotides, administering the hybrid modified circular polyribonucleotide to the subject, and obtaining increased stability for the hybrid modified circular polyribonucleotide compared to a corresponding unmodified circular polyribonucleotide. in a cell or tissue of the subject. In some embodiments, the first portion comprises an IRES. In some embodiments, the first portion comprises at least about 5 to 1000 contiguous unmodified nucleotides. In some embodiments, the first portion lacks 5'-methylcytidine, pseudouridine, or or N1-methyl-pseudouridine. In some embodiments, no more than 5% of nucleotides in the first portion are modified nucleotides. In some embodiments, no more than 5% of nucleotides in the IRES of the first portion are modified nucleotides.

In some aspects, a method of decreasing immunogenicity of a circular polyribonucleotide in a subject comprises: providing a hybrid modified circular polyribonucleotide, wherein the hybrid modified circular polyribonucleotide comprises at least one modified nucleotide and a first portion comprising at least about 5 to 1000 contiguous unmodified nucleotides; administering the hybrid modified circular polyribonucleotide to the subject; and obtaining decreased immunogenicity for the hybrid modified circular polyribonucleotide compared to a corresponding unmodified circular polyribonucleotide in a cell or tissue of the subject.

In some aspects, a method of reducing immunogenicity of a circular polyribonucleotide in a subject comprises: providing a hybrid modified circular polyribonucleotide, wherein the hybrid modified circular polyribonucleotide comprises at least one modified nucleotide and a first portion comprising at least about 5 to 1000 contiguous unmodified nucleotides; administering the hybrid modified circular polyribonucleotide to the subject; and obtaining decreased immunogenicity for the hybrid modified circular polyribonucleotide compared to a corresponding unmodified circular polyribonucleotide in a cell or tissue of the subject.

In some embodiments, the first portion comprises at least about 5, 10, 20, 50, 100, 200, 300, 400, 500, 600, 700, 800, 900, or 1000 contiguous unmodified nucleotides. In some embodiments, the first portion lacks 5'-methylcytidine or pseudouridine. In some embodiments, no more than 5% of nucleotides in the first portion are modified nucleotides. In some embodiments, the circular polyribonucleotide is translationally competent. In some embodiments, the hybrid modified circular polyribonucleotide: a) has at least about 0.7, 0.8, 0.9, 1.0, 1.1, 1.2, 1.3, 1.5, 1.6, 1.8, 2, 2.2, 2.5, 2.8, or 3 fold higher expression than a corresponding unmodified circular polyribonucleotide; b) has a half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide; c) has a higher half-life than a corresponding unmodified circular polyribonucleotide; or d) has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide, as assessed by expression or signaling or activation of at least one of RIG-I, TLR-3, TLR-7, TLR-8, MDA-5, LGP-2, OAS, OASL, PKR, and IFN-beta. In some embodiments, the at least one modified nucleotide is selected from the group consisting of: a) N(6)methyladenosine (m6A), 5'-methylcytidine, and pseudouridine; b) 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite; or c) any modified nucleotide from TABLE 2. In some embodiments, at least about 10%, 20%, 30%, 40%, 50%, 60%, 70%, 80%, 90%, 95%, or 99% nucleotides of the hybrid modified circular polyribonucleotide are modified nucleotides. In some embodiments, the hybrid modified circular polyribonucleotide comprises a binding site configured to bind to a protein, peptide, biomolecule, DNA, RNA, or a cell target, consisting of unmodified nucleotides. In some embodiments, the hybrid modified circular polyribonucleotide comprises one or more expression sequences. In some embodiments, the first portion comprises an IRES consisting of unmodified nucleotides. In some embodiments, one or more expression sequences of the hybrid modified circular polyribonucleotide have: a) a higher translation efficiency than a fully modified circular polyribonucleotide counterpart; b) a translation efficiency that is at least about 0.7, 0.8, 0.9, 1.0, 1.1, 1.2, 1.3, 1.5, 1.6, 1.8, 2, 2.2, 2.5, 2.8, or 3 fold higher than a fully modified circular polyribonucleotide counterpart; c) has a higher translation efficiency than a corresponding unmodified circular polyribonucleotide; or d) a translation efficiency that is at least about 0.7, 0.8, 0.9, 1.0, 1.1, 1.2, 1.3, 1.5, 1.6, 1.8, 2, 2.2, 2.5, 2.8, or 3 fold higher than a corresponding unmodified circular polyribonucleotide.

In some aspects, a method of expressing one or more expression sequences in a subject comprises: providing a hybrid modified circular polyribonucleotide comprising one or more expression sequences, wherein the hybrid modified circular polyribonucleotide comprises at least one modified nucleotide and a first portion comprising at least about 5, 10, 20, 50, 100, 200, 300, 400, 500, 600, 700, 800, 900, or 1000 contiguous unmodified nucleotides; administering the hybrid modified circular polyribonucleotide to the subject; and obtaining increased expression of the one or more expression sequences compared to expression of a corresponding one or more expression sequences in a fully modified circular polyribonucleotide counterpart in a cell or tissue of the subject.

In some aspects, a method of increasing stability of a circular polyribonucleotide in a subject comprising: providing a hybrid modified circular polyribonucleotide, wherein the hybrid modified circular polyribonucleotide comprises a modified circular polyribonucleotide and a first portion comprising at least about 5, 10, 20, 50, 100, 200, 300, 400, 500, 600, 700, 800, 900, or 1000 contiguous unmodified nucleotides; administering the hybrid modified circular polyribonucleotide to the subject; and obtaining increased stability for the hybrid modified circular polyribonucleotide compared to a corresponding unmodified circular polyribonucleotide in a cell or tissue of the subject.

In some embodiments, the first portion comprises an IRES.

In one aspect, the present disclosure provides a pharmaceutical composition comprising a pharmaceutically acceptable carrier or excipient and a hybrid modified circular polyribonucleotide, wherein the hybrid modified circular polyribonucleotide comprises at least one modified nucleotide and a first portion, and wherein the first portion comprises at least about 5, 10, 20, 50, 100, 200, 300, 400, 500, 600, 700, 800, 900, or 1000 contiguous unmodified nucleotides. In certain embodiments of this aspect, the first portion comprises no more than 5% modified nucleotides.

In another aspect, the present disclosure provides a pharmaceutical composition comprising a pharmaceutically acceptable carrier or excipient and a hybrid modified circular polyribonucleotide, wherein the hybrid modified circular polyribonucleotide comprises at least one modified nucleotide and a first portion, and wherein the first portion comprises at least about 5, 10, 20, 50, 100, 200, 300, 400, 500, 600, 700, 800, 900, or 1000 contiguous nucleotides and wherein the first portion lacks 5'-methylcytidine or pseudouridine. In certain embodiments of this aspect, the first portion comprises no more than 5% modified nucleotides.

In some aspects, a pharmaceutical composition comprises a hybrid modified circular polyribonucleotide, wherein the hybrid modified circular polyribonucleotide comprises: at least one modified nucleotide; a first portion comprising a first binding site configured to bind a first binding moiety of a first target, e.g., a RNA, DNA, protein, or a cell target, wherein the first binding moiety is a first circular polyribonucleotide (circRNA)-binding motif consisting of unmodified nucleotides; wherein the first target and the hybrid modified circular polyribonucleotide form a complex.

In some aspects, a pharmaceutical composition comprises a hybrid modified circular polyribonucleotide, wherein the hybrid modified circular polyribonucleotide comprises: at least one modified nucleotide; a first portion comprising a first binding site configured to bind a first binding moiety of a first target, e.g., a RNA, DNA, protein, or a cell target, wherein the first binding moiety is a first circular polyribonucleotide (circRNA)-binding motif consisting of unmodified nucleotides; and a second binding site configured to bind a second binding moiety of a second target, wherein the second binding moiety is a second circRNA-binding motif, wherein the first binding moiety is different than the second binding moiety, wherein the first target, the second target, and the hybrid modified circular polyribonucleotide form a complex, and wherein the first target or the second target is a not a microRNA.

In some aspects, a pharmaceutical composition comprising a hybrid modified circular polyribonucleotide, wherein the hybrid modified circular polyribonucleotide comprises: at least one modified nucleotide; a first portion comprising a first binding site configured to bind a first binding moiety of a first target, wherein the first binding moiety is a first circular polyribonucleotide (circRNA)-binding motif; and a second binding site configured to bind a second binding moiety of a second target, wherein the second binding moiety is a second circRNA-binding motif, wherein the first binding moiety is different than the second binding moiety, and wherein the first target and the second target are both a microRNA. In some embodiments, the hybrid modified circular polyribonucleotide has a lower immunogenicity than a corresponding unmodified circular polyribonucleotide. In some embodiments, the hybrid modified circular polyribonucleotide has a half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide. In some embodiments, the hybrid modified circular polyribonucleotide has a higher half-life than a corresponding unmodified circular polyribonucleotide. In some embodiments, the hybrid modified circular polyribonucleotide has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide, as assessed by expression or signaling or activation of at least one of RIG-I, TLR-3, TLR-7, TLR-8, MDA-5, LGP-2, OAS, OASL, PKR, and IFN-beta. In some embodiments, the hybrid modified circular polyribonucleotide has a higher half-life than a corresponding unmodified circular polyribonucleotide. In some embodiments, the at least one modified nucleotide is selected from the group consisting of: N(6)methyladenosine (m6A), 5'-methylcytidine, and pseudouridine. In some embodiments, the at least one modified nucleic acid is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, at least about 10%, 20%, 30%, 40%, 50%, 60%, 70%, 80%, 90%, 95%, or 99% nucleotides of the hybrid modified circular polyribonucleotide are modified nucleotides. In some embodiments, the modified circular polyribonucleotide comprises a binding site configured to bind a peptide, protein, biomolecule, DNA, RNA, or a cell target, consisting of unmodified nucleotides. In some embodiments, the first portion comprises the binding site. In some embodiments, the modified circular polyribonucleotide comprises an internal ribosome entry site (IRES) consisting of unmodified nucleotides. In some embodiments, the the first portion comprises an IRES. In certain embodiments, the IRES comprises no more than 5% modified nucleotides.

In some embodiments, the hybrid modified circular polyribonucleotide comprises one or more expression sequences. In some embodiments, the hybrid modified circular polyribonucleotide comprises the one or more expression sequences and the IRES, and wherein the hybrid modified circular polyribonucleotide comprises a 5'-methylcytidine, a pseudouridine, or a combination thereof outside the IRES. In some embodiments, the one or more expression sequences of the hybrid modified circular polyribonucleotide have a higher translation efficiency than a corresponding fully modified circular polyribonucleotide. In some embodiments, the one or more expression sequences of the hybrid modified circular polyribonucleotide have a translation efficiency of that is at least about 0.7, 0.8, 0.9, 1.0, 1.1, 1.2, 1.3, 1.5, 1.6, 1.8, 2, 2.2, 2.5, 2.8, or 3 fold higher than a fully modified circular polyribonucleotide counterpart. In some embodiments, the fully modified circular polyribonucleotide counterpart comprises at least one modified nucleotide outside a first portion and more than 5% modified nucleotides in the first portion. In some embodiments, the one or more expression sequences of the hybrid modified circular polyribonucleotide have a higher translation efficiency than a corresponding unmodified circular polyribonucleotide. In some embodiments, the one or more expression sequences of the hybrid modified circular polyribonucleotide have a translation efficiency of that is at least about 0.7, 0.8, 0.9, 1.0, 1.1, 1.2, 1.3, 1.5, 1.6, 1.8, 2, 2.2, 2.5, 2.8, or 3 fold higher than a corresponding unmodified circular polyribonucleotide. In some embodiments, the one or more expression sequences of the hybrid modified circular polyribonucleotide have a higher translation efficiency than a fully modified circular polyribonucleotide counterpart. In some embodiments, the one or more expression sequences of the hybrid modified circular polyribonucleotide have a higher translation efficiency than a fully modified circular polyribonucleotide having a first portion comprising more than 10% modified nucleotides. In some embodiments, the one or more expression sequences of the hybrid modified circular polyribonucleotide have a higher translation efficiency than a fully modified circular polyribonucleotide having a first portion comprising 100% modified psuedouridine or 5'methylcytosine. In some embodiments, the one or more expression sequences of the hybrid modified circular polyribonucleotide have a translation efficiency that is at least about 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a fully modified circular polyribonucleotide counterpart having a first portion comprising a modified nucleotide. In some embodiments, the translation efficiency is measured either in a cell comprising the hybrid modified circular polyribonucleotide or the fully modified circular polyribonucleotide counterpart, or in an in vitro translation system (e.g., rabbit reticulocyte lysate). In some embodiments, the hybrid modified circular polyribonucleotide is competent for rolling circle translation.

In some embodiments, each of the one or more expression sequences is separated from a succeeding expression sequence by a stagger element on the hybrid modified circular polyribonucleotide, wherein the rolling circle translation of the one or more expression sequences generates at least two polypeptide molecules. In some embodiments, the pharmaceutically acceptable carrier or excipient is ethanol. In some embodiments, the stagger element prevents generation of a single polypeptide (a) from two rounds of translation of a single expression sequence or (b) from one or more rounds of translation of two or more expression sequences. In some embodiments, the stagger element is a sequence separate from the one or more expression sequences. In some embodiments, the stagger element comprises a portion of an expression sequence of the one or more expression sequences. In some embodiments, the hybrid modified circular polyribonucleotide is competent for rolling circle translation, wherein the hybrid modified circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the hybrid modified circular polyribonucleotide are discrete polypeptides, and wherein each of the discrete polypeptides is generated from a single round of translation or less than a single round of translation of the one or more expression sequences. In some embodiments, the hybrid modified circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the hybrid modified circular polyribonucleotide are the discrete polypeptides, and wherein amount ratio of the discrete products over the total polypeptides is tested in an in vitro translation system. In some embodiments, the in vitro translation system comprises rabbit reticulocyte lysate. In some embodiments, the stagger element is at a 3' end of at least one of the one or more expression sequences, and wherein the stagger element is configured to stall a ribosome during rolling circle translation of the hybrid modified circular polyribonucleotide. In some embodiments, the stagger element encodes a peptide sequence selected from the group consisting of a 2A sequence and a 2A-like sequence. In some embodiments, the stagger element encodes a sequence with a C-terminal sequence that is GP. In some embodiments, the stagger element encodes a sequence with a C-terminal consensus sequence that is D(V/I)ExNPGP, where x=any amino acid (SEQ ID NO: 66). In some embodiments, the stagger element encodes a sequence selected from the group consisting of GDVESNPGP (SEQ ID NO: 67), GDIEENPGP (SEQ ID NO: 68), VEPNPGP (SEQ ID NO: 69), IETNPGP (SEQ ID NO: 70), GDIESNPGP (SEQ ID NO: 71), GDVELNPGP (SEQ ID NO: 72), GDIETNPGP (SEQ ID NO: 73), GDVENPGP (SEQ ID NO: 74), GDVEENPGP (SEQ ID NO: 75), GDVEQNPGP (SEQ ID NO: 76), IESNPGP (SEQ ID NO: 77), GDIELNPGP (SEQ ID NO: 78), HDIETNPGP (SEQ ID NO: 79), HDVETNPGP (SEQ ID NO: 80), HDVEMNPGP (SEQ ID NO: 81), GDMESNPGP (SEQ ID NO: 82), GDVETNPGP (SEQ ID NO: 83), GDIEQNPGP (SEQ ID NO: 84), and DSEFNPGP (SEQ ID NO: 85). In some embodiments, the stagger element is at 3' end of each of the one or more expression sequences. In some embodiments, the stagger element of a first expression sequence in the hybrid modified circular polyribonucleotide is upstream of (5' to) a first translation initiation sequence of an expression sequence succeeding the first expression sequence in the hybrid modified circular polyribonucleotide, and wherein a distance between the stagger element and the first translation initiation sequence enables continuous translation of the first expression sequence and the succeeding expression sequence. In some embodiments, the stagger element of a first expression sequence in the hybrid modified circular polyribonucleotide is upstream of (5' to) a first translation initiation sequence of an expression sequence succeeding the first expression in the hybrid modified circular polyribonucleotide, wherein the hybrid modified circular polyribonucleotide is continuously translated, wherein a corresponding hybrid modified circular polyribonucleotide comprising a second stagger element upstream of a second translation initiation sequence of a second expression sequence in the hybrid modified corresponding circular polyribonucleotide is not continuously translated, and wherein the second stagger element in the corresponding hybrid modified circular polyribonucleotide is at a greater distance from the second translation initiation sequence, e.g., at least 2×, 3×, 4×, 5×, 6×, 7×, 8×, 9×, 10×, or greater than a distance between the stagger element and the first translation initiation in the hybrid modified circular polyribonucleotide. In some embodiments, the distance between the stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater. In some embodiments, the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the tagger element and the first translation initiation. In some embodiments, the expression sequence succeeding the first expression sequence on the hybrid modified circular polyribonucleotide is an expression sequence other than the first expression sequence. In some embodiments, the succeeding expression sequence of the first expression sequence on the hybrid modified circular polyribonucleotide is the first expression sequence.

In some embodiments, the hybrid modified circular polyribonucleotide comprises at least one structural element selected from: a) an encryptogen; b) a stagger element; c) a regulatory element; d) a replication element; and f) quasi-double-stranded secondary structure. In some embodiments, the hybrid modified circular polyribonucleotide comprises at least one functional characteristic selected from: a) greater translation efficiency than a linear counterpart; b) a stoichiometric translation efficiency of multiple translation products; c) less immunogenicity than a counterpart lacking an encryptogen; d) increased half-life over a linear counterpart; and e) persistence during cell division. In some embodiments, the hybrid modified circular polyribonucleotide has a translation efficiency at least 5%, at least 10%, at least 15%, at least 20%, at least 30%, at least 40%, at least 50%, at least 60%, at least 70%, at least 80%, at least 90%, at least 100%, at least 150%, at least 2 fold, at least 3 fold, at least 4 fold, at least 5 fold, at least 6 fold, at least 7 fold, at least 8 fold, at least 9 fold, at least 10 fold, at least 20 fold, at least 50 fold, or at least 100 fold greater than a linear counterpart. In some embodiments, the hybrid modified circular polyribonucleotide has a translation efficiency at least 5 fold greater than a linear counterpart. In some embodiments, the hybrid modified circular polyribonucleotide lacks at least one of: a) a 5'-UTR; b) a 3'-UTR; c) a poly-A sequence; d) a 5'-cap; e) a termination element; f) degradation susceptibility by exonucleases; and g) binding to a cap-binding protein. In some embodiments, the one or more expression sequences comprise a Kozak initiation sequence. In some embodiments, the quasi-helical structure comprises at least one double-stranded RNA segment with at least one non-double-stranded segment. In some embodiments, the quasi-helical structure comprises a first sequence and a second sequence linked with a repetitive sequence, e.g., an A-rich sequence. In some embodiments, the encryptogen comprises a splicing element. In some embodiments, the encryptogen comprises a protein binding site, e.g., ribonucleotide binding protein. In some embodiments, the encryptogen comprises an immunoprotein binding site, e.g., to evade immune responses, e.g., CTL responses. In some embodiments, the hybrid modified circular polyribonucleotide has at least 2× less immunogenicity than a counterpart lacking the encryptogen, e.g., as assessed by expression or signaling or activation of at least one of RIG-I, TLR-3, TLR-7, TLR-8, MDA-5, LGP-2, OAS, OASL, PKR, and IFN-beta. In some embodiments, the hybrid modified circular polyribonucleotide further comprises a riboswitch. In some embodiments, the hybrid modified circular polyribonucleotide further comprises an aptazyme. In some embodiments, the hybrid modified circular polyribonucleotide comprises a non-canonical translation initiation sequence, e.g., GUG, CUG start codon, e.g., a translation initiation sequence that initiates expression under stress conditions. In some embodiments, the one or more expression sequences encodes a peptide. In some embodiments, the hybrid modified circular polyribonucleotide comprises a regulatory nucleic acid, e.g., a non-coding RNA. In some embodiments, the hybrid modified circular polyribonucleotide has a size in the range of about 20 bases to about 20 kb. In some embodiments, the hybrid modified circular polyribonucleotide is synthesized through circularization of a linear polyribonucleotide. In some embodiments, the hybrid modified circular polyribonucleotide comprises a plurality of expression sequences having either a same nucleotide sequence or different nucleotide sequences. In some embodiments, the hybrid modified circular polyribonucleotide is substantially resistant to degradation, e.g., exonuclease.

In some embodiments, the hybrid modified circular polyribonucleotide comprises: a modified circular polyribonucleotide comprising: a first binding site configured to bind a first binding moeity of a first target, e.g., a RNA, DNA, protein, membrane of cell etc., wherein the first binding moeity is a first circular polyribonucleotide (circRNA)-binding motif; and a second binding site configured to bind a second binding moeity of a second target, wherein the second binding moeity is a second circRNA-binding motif, wherein the first binding moeity is different than the second binding moeity, wherein the first target, the second target, and the hybrid modified circular polyribonucleotide form a complex, and wherein the first target or the second target is a not a microRNA.

In some embodiments, the hybrid modified circular polyribonucleotide comprises: a hybrid modified circular polyribonucleotide comprising: a first binding site configured to bind a first binding moeity of a first target, wherein the first binding moeity is a first circular polyribonucleotide (circRNA)-binding motif; and a second binding site configured to bind a second binding moiety of a second target, wherein the second binding moiety is a second circRNA-binding motif, wherein the first binding moiety is different than the second binding moiety, and wherein the first target and the second target are both a microRNA.

In some embodiments, the first and second targets interact with each other. In some embodiments, the complex modulates a cellular process. In some embodiments, the first and second targets are the same, and the first and second binding sites bind different moieties. In some embodiments, the first and second targets are different. In some embodiments, the hybrid modified circular polyribonucleotide further comprises one or more additional binding sites configured to bind a third or more binding moieties. In some embodiments, one or more targets are the same and one or more binding sites are configured to bind different moieties. In some embodiments, formation of the complex modulates a cellular process. In some embodiments, the hybrid modified circular polyribonucleotide modulates a cellular process associated with the first or second target when contacted to the first and second targets. In some embodiments, the first and second targets interact with each other in the complex. In some embodiments, the cellular process is associated with pathogenesis of a disease or condition. In some embodiments, the cellular process is different than translation of the hybrid modified circular polyribonucleic acid. In some embodiments, the cellular process is associated with pathogenesis of a disease or condition. In some embodiments, the first target comprises a deoxyribonucleic acid (DNA) molecule, and the second target comprises a protein. In some embodiments, the complex modulates directed transcription of the DNA molecule, epigenetic remodeling of the DNA molecule, or degradation of the DNA molecule. In some embodiments, the first target comprises a first protein, and the second target comprises a second protein. In some embodiments, the complex modulates degradation of the first protein, translocation of the first protein, or signal transduction, or modulates a native protein function, or inhibits formation of a complex formed by direct interaction between the first and second proteins. In some embodiments, the first target comprises a first ribonucleic acid (RNA) molecule, and the second target comprises a second RNA molecule. In some embodiments, the complex modulates degradation of the first RNA molecule. In some embodiments, the first target comprises a protein, and the second target comprises a RNA molecule. In some embodiments, the complex modulates translocation of the protein or inhibits formation of a complex formed by direct interaction between the protein and the RNA molecule. In some embodiments, the first binding moiety comprises a receptor, and the second binding moiety comprises a substrate of the receptor. In some embodiments, the complex inhibits activation of the receptor. In some embodiments, the modified circular polyribonucleotide comprises a binding site configured to bind a binding moiety of a target, wherein the binding moiety is a ribonucleic acid (RNA)-binding motif, wherein the hybrid modified circular polyribonucleotide is translation incompetent or translation defective, and wherein the target is not a microRNA. In some embodiments, the hybrid modified circular polyribonucleotide comprises a binding site configured to bind a binding moiety of a target, wherein the binding moiety is a ribonucleic acid (RNA)-binding motif, wherein the hybrid modified circular polyribonucleotide is translation incompetent or translation defective, and wherein the target is a microRNA. In some embodiments, the target comprises a DNA molecule. In some embodiments, binding of the binding moeity to the hybrid modified circular polyribonucleotide modulates interference of transcription of a DNA molecule. In some embodiments, the target comprises a protein. In some embodiments, binding of the binding moeity to the hybrid modified circular polyribonucleotide inhibits interaction of the protein with other molecules. In some embodiments, the protein is a receptor, and wherein binding of the first binding moiety to the modified circular polyribonucleotide activates the receptor. In some embodiments, the protein is a first enzyme, wherein the hybrid modified circular polyribonucleotide further comprises a second binding site configured to bind to a second enzyme, and wherein binding of the first and second enzymes to the hybrid modified circular polyribonucleotide modulates enzymatic activity of the first and second enzymes. In some embodiments, the target comprises a messenger RNA (mRNA) molecule. In some embodiments, binding of the binding moiety to the hybrid modified circular polyribonucleotide modulates interference of translation of the mRNA molecule. In some embodiments, the target comprises a ribosome. In some embodiments, binding of the binding moiety to the hybrid modified circular polyribonucleotide modulates interference of a translation process. In some embodiments, the target comprises a circular RNA molecule. In some embodiments, binding of the binding moiety to the hybrid modified circular polyribonucleotide sequesters the circular RNA molecule. In some embodiments, binding of the binding moiety to the hybrid modified circular polyribonucleotide sequesters the microRNA molecule. In some embodiments, the hybrid modified circular polyribonucleotide comprises a binding site configured to bind a binding moiety on a membrane of a cell target; and wherein the binding moiety is a ribonucleic acid (RNA)-binding motif. In some embodiments, the hybrid modified circular polyribonucleotide further comprises a second binding site configured to bind a second binding moiety on a second cell target, wherein the second binding moiety is a second RNA-binding motif. In some embodiments, the hybrid modified circular polyribonucleotide is configured to bind to both targets. In some embodiments, the hybrid modified circular polyribonucleotide further comprises a second binding site configured to bind a second binding moiety, and wherein binding of both targets to the hybrid modified circular polyribonucleotide induces a conformational change in the first target, thereby inducing signal transduction downstream of the target.

In some embodiments, the present disclosure provides the composition as described herein formulated in a carrier, e.g., membrane or lipid bilayer.

In one aspect, the present disclosure provides a method of treatment, comprising administering the pharmaceutical composition as described herein to a subject with a disease or condition.

In one aspect, the present disclosure provides a method of producing a pharmaceutical composition, comprising generating the hybrid modified circular polyribonucleotide as described herein.

In one aspect, the present disclosure provides a method of making the hybrid modified circular polyribonucleotide as described herein, comprising circularizing a linear polyribonucleotide having a nucleic acid sequence as the hybrid modified circular polyribonucleotide.

In one aspect, the present disclosure provides an engineered cell comprising the composition as described herein.

Definitions

The present invention will be described with respect to particular embodiments and with reference to certain figures but the invention is not limited thereto but only by the claims. Terms as set forth hereinafter are generally to be understood in their common sense unless indicated otherwise.

The term "pharmaceutical composition" is intended to also disclose that the circular polyribonucleotide comprised within a pharmaceutical composition can be used for the treatment of the human or animal body by therapy. It is thus meant to be equivalent to "a circular polyribonucleotide for use in therapy".

The circular polyribonucleotides, compositions comprising such circular polyribonucleotides, methods using such circular polyribonucleotides, etc. as described herein are based in part on the examples which illustrate how circular polyribonucleotides effectors comprising different elements, for example a replication element, an expression sequence, a stagger element and an encryptogen (see e.g., example 10) or for example an expression sequences, a stagger element and a regulatory element (see e.g., examples 32 and 40) can be used to achieve different technical effects (e.g., increased translation efficiency than a linear counterpart in examples 10 and 40 and increased half-life over a linear counterpart in example 40). It is on the basis of inter alia these examples that the description hereinafter contemplates various variations of the specific findings and combinations considered in the examples.

As used herein, the terms "circRNA" or "circular polyribonucleotide" or "circular RNA" are used interchangeably and mean a polyribonucleotide molecule that has a structure having no free ends (i.e., no free 3' and/or 5' ends), for example a polyribonucleotide that forms a circular or endless structure through covalent or non-covalent bonds.

As used herein, the terms "modified circular polyribonucleotide" or "modified circular RNA" or "modified circRNA" are used interchangeably and mean a circular polyribonucleotide comprising at least one modified nucleotide. A modified circular RNA may or may not be uniformly modified along the entire length of the molecule.

As used herein, the terms "hybrid modified circular polyribonucleotide counterpart" or "hybrid modified circular polyribonucleotide" or "hybrid modified circRNA" or "hybrid modified circular RNA" are used interchangeably and mean a modified circular polyribonucleotide having the same nucleotide sequence as a reference modified circular polyribonucleotide and having a first portion of contiguous nucleotides comprising no more than 5% modified nucleotides as described herein. In some embodiments, the first portion of contiguous nucleotides comprises unmodified nucleotides (i.e., no modified nucleotides or only unmodified nucleotides). For example, a first portion of contiguous unmodified nucleotides comprises an IRES. A hybrid modified circular RNA may or may not be modified along its entire length. For example, in a particular embodiment, a hybrid modified circular RNA is [(all cytosines=methylcytosine)+(all uridine=pseudouridine)+(unmodified IRES)]. In another example, a hybrid modified is [(all adenosine=m6a)+unmodified IRES].

As used herein, the terms "fully modified circular polyribonucleotide counterpart" or "completely modified circular polyribonucleotide counterpart" or "full-length modified circular polyribonucleotide" or "fully modified circular RNA" are used interchangeably and mean a modified circular polyribonucleotide having the same nucleotide sequence as a reference hybrid modified circular polyribonucleotide and having a first portion comprising more than 5% modified nucleotide that corresponds to the first portion of the reference hybrid circular polyribonucleotide. For example, the first portion comprises an IRES with more than 5% modified nucleotides (i.e., a modified IRES). A fully modified circular RNA may or may not be uniformly modified along the entire length of the molecule. For example, a fully modified circular polyribonucleotide comprises a first portion comprising an IRES having more than 5% modified nucleotides and 50% of the nucleotides outside the first portion are modified nucleotides (e.g., 50% of uridines outside the first portion are pseudouridines). In a particular embodiment, a fully modified circular polyribonucleotide is [(all cytosines=methylcytosine)+(all uridine=pseudouridine)+ modified IRES]. In another example, a fully modified circular polyribonucleotide is [(all adenosine=m6a)+modified IRES].

As used herein, the term "modified ribonucleotide" means any ribonucleotide analog or derivative that has one or more chemical modifications to the chemical composition of an unmodified natural ribonucleotide, such as a natural unmodified nucleotide adenosine (A), uridine (U), guanine (G), cytidine (C) as shown by the chemical formulae in TABLE 1, infra, and monophosphate. In some embodiments, the chemical modifications of the modified ribonucleotide are modifications to any one or more functional groups of the ribonucleotide, such as, the sugar the nucleobase, or the internucleoside linkage (e.g. to a linking phosphate/to a phosphodiester linkage/to the phosphodiester backbone).

As used herein, the term "linear counterpart" is a polyribonucleotide molecule (and its fragments) having the same or similar nucleotide sequence (e.g., 100%, 95%, 90%, 85%, 80%, 75%, or any percentage therebetween of sequence similarity) as a circular polyribonucleotide and having two free ends (i.e., the uncircularized version (and its fragments) of the circularized polyribonucleotide). In some embodiments, the linear counterpart (e.g., a pre-circularized version) is a polyribonucleotide molecule (and its fragments) having the same or similar nucleotide sequence (e.g., 100%, 95%, 90%, 85%, 80%, 75%, or any percentage therebetween sequence similarity) and same or similar nucleic acid modifications as a circular polyribonucleotide and having two free ends (i.e., the uncircularized version (and its fragments) of the circularized polyribonucleotide). In some embodiments, the linear counterpart is a polyribonucleotide molecule (and its fragments) having the same or similar nucleotide sequence (e.g., 100%, 95%, 90%, 85%, 80%, 75%, or any percentage therebetween of sequence similarity) and different or no nucleic acid modifications as a circular polyribonucleotide and having two free ends (i.e., the uncircularized version (and its fragments) of the circularized polyribonucleotide). In some embodiments, a fragment of the polyribonucleotide molecule that is the linear counterpart is any portion of linear counterpart polyribonucleotide molecule that is shorter than the linear counterpart polyribonucleotide molecule. In some embodiments, the linear counterpart further comprises a 5' cap. In some embodiments, the linear counterpart further comprises a poly adenosine tail. In some embodiments, the linear counterpart further comprises a 3' UTR. In some embodiments, the linear counterpart further comprises a 5' UTR.

As used herein, the term "fragment" means any portion of a nucleotide molecule that is at least one nucleotide shorter than the nucleotide molecule. For example, a nucleotide molecule can be a circular polyribonucleotide molecule and a fragment thereof can be a polyribonucleotide or any number of contiguous polyribonucleotides that are a portion of the circular polyribonucleotide molecule. As another example, a nucleotide molecule can be a linear polyribonucleotide molecule and a fragment thereof can be a monoribonucleotide or any number of contiguous polyribonucleotides that are a portion of the linear polyribonucleotide molecule.

As used herein, the term "encryptogen" is a nucleic acid sequence or structure of the circular polyribonucleotide that aids in reducing, evading, and/or avoiding detection by an immune cell and/or reduces induction of an immune response against the circular polyribonucleotide.

As used herein, the term "expression sequence" is a nucleic acid sequence that encodes a product, e.g., a peptide or polypeptide, or a regulatory nucleic acid. An exemplary expression sequence that codes for a peptide or polypeptide can comprise a plurality of nucleotide triads, each of which can code for an amino acid and is termed as a "codon".

As used herein, the term "immunoprotein binding site" is a nucleotide sequence that binds to an immunoprotein. In some embodiments, the immunoprotein binding site aids in masking the circular polyribonucleotide as exogenous, for example, the immunoprotein binding site can be bound by a protein (e.g., a competitive inhibitor) that prevents the circular polyribonucleotide from being recognized and bound by an immunoprotein, thereby reducing or avoiding an immune response against the circular polyribonucleotide. As used herein, the term "immunoprotein" is any protein or peptide that is associated with an immune response, e.g., such as against an immunogen, e.g., the circular polyribonucleotide. Non-limiting examples of immunoprotein include T cell receptors (TCRs), antibodies (immunoglobulins), major histocompatibility complex (MHC) proteins, complement proteins, and RNA binding proteins.

As used herein, the phrase "quasi-helical structure" is a higher order structure of the circular polyribonucleotide, wherein at least a portion of the circular polyribonucleotide folds into a helical structure.

As used herein, the phrase "quasi-double-stranded secondary structure" is a higher order structure of the circular polyribonucleotide, wherein at least a portion of the circular polyribonucleotide creates an internal double strand.

As used herein, the term "regulatory element" is a moiety, such as a nucleic acid sequence, that modifies expression of an expression sequence within the circular polyribonucleotide.

As used herein, the term "repetitive nucleotide sequence" is a repetitive nucleic acid sequence within a stretch of DNA or RNA or throughout a genome. In some embodiments, the repetitive nucleotide sequence includes poly CA or poly TG (UG) sequences. In some embodiments, the repetitive nucleotide sequence includes repeated sequences in the Alu family of introns.

As used herein, the term "replication element" is a sequence and/or motifs useful for replication or that initiate transcription of the circular polyribonucleotide.

As used herein, the term "stagger element" is a moiety, such as a nucleotide sequence, that induces ribosomal pausing during translation. In some embodiments, the stagger element is a non-conserved sequence of amino-acids with a strong alpha-helical propensity followed by the consensus sequence -D(V/I)ExNPGP, where x=any amino acid (SEQ ID NO: 66). In some embodiments, the stagger element may include a chemical moiety, such as glycerol, a non nucleic acid linking moiety, a chemical modification, a modified nucleic acid, or any combination thereof.

As used herein, the term "substantially resistant" means one that has at least 50%, 55%, 60%, 65%, 70%, 75%, 80%, 85%, 90%, 95%, 96%, 97%, 98%, or 99% resistance as compared to a reference.

As used herein, the term "stoichiometric translation" is a substantially equivalent production of expression products translated from the circular polyribonucleotide. For example, for a circular polyribonucleotide having two expression sequences, stoichiometric translation of the circular polyribonucleotide can mean that the expression products of the two expression sequences can have substantially equivalent amounts, e.g., amount difference between the two expression sequences (e.g., molar difference) can be about 0, or less than 1%, 2%, 3%, 4%, 5%, 6%, 7%, 8%, 9%, 10%, 15%, or 20%, or any percentage therebetween.

As used herein, the term "translation initiation sequence" is a nucleic acid sequence that initiates translation of an expression sequence in the circular polyribonucleotide.

As used herein, the term "termination element" is a moiety, such as a nucleic acid sequence, that terminates translation of the expression sequence in the circular polyribonucleotide.

As used herein, the term "translation efficiency" means a rate or amount of protein or peptide production from a ribonucleotide transcript. In some embodiments, translation efficiency can be expressed as amount of protein or peptide produced per given amount of transcript that codes for the protein or peptide, e.g., in a given period of time, e.g., in a given translation system, e.g., an in vitro translation system like rabbit reticulocyte lysate, or an in vivo translation system like a eukaryotic cell or a prokaryotic cell.

As used herein, the term "circularization efficiency" means a measurement of resultant circular polyribonucleotide versus its starting material.

As used herein, the term "immunogenic" is a potential to induce an immune response to a substance. In some embodiments, an immune response may be induced when an immune system of an organism or a certain type of immune cells is exposed to an immunogenic substance. The term "non-immunogenic" is a lack of or absence of an immune response above a detectable threshold to a substance. In some embodiments, no immune response is detected when an immune system of an organism or a certain type of immune cells is exposed to a non-immunogenic substance. In some embodiments, a non-immunogenic circular polyribonucleotide as provided herein, does not induce an immune response above a pre-determined threshold when measured by an immunogenicity assay. For example, when an immunogenicity assay is used to measure an innate immune response against a circular polyribonucleotide (such as measuring inflammatory markers), a non-immunogenic polyribonucleotide as provided herein can lead to production of an innate immune response at a level lower than a predetermined threshold. The predetermined threshold can be, for instance, at most 1.5 times, 2 times, 3 times, 4 times, 5 times, 6 times, 7 times, 8 times, 9 times, or 10 times the level of a marker(s) produced by an innate immune response for a control reference.

As used herein, the term "pharmaceutically acceptable" refers to a component that is not biologically or otherwise undesirable, e.g., the component may be incorporated into a pharmaceutical formulation of the invention and administered to a subject as described herein without causing any significant undesirable biological effects or interacting in a deleterious manner with any of the other components of the formulation in which it is contained. In certain embodiments, when the term "pharmaceutically acceptable" is used to refer to an excipient, it implies that the component has met the required standards of toxicological and manufacturing testing or that it is included on the Inactive Ingredient Guide prepared by the U.S. Food and Drug Administration.

As used herein, the term "carrier" means a compound, composition, reagent, or molecule that facilitates the transport or delivery of a composition (e.g., a circular polyribonucleotide) into a cell by a covalent modification of the circular polyribonucleotide, via a partially or completely encapsulating agent, or a combination thereof. Non-limiting examples of carriers include carbohydrate carriers (e.g., an anhydride-modified phytoglycogen or glycogen-type material), nanoparticles (e.g., a nanoparticle that encapsulates or is covalently linked binds to the circular polyribonucleotide), liposomes, fusosomes, ex vivo differentiated reticulocytes, exosomes, protein carriers (e.g., a protein covalently linked to the circular polyribonucleotide), or cationic carriers (e.g., a cationic lipopolymer or transfection reagent).

As used herein, the term "naked delivery" means a formulation for delivery to a cell without the aid of a carrier and without covalent modification to a moiety that aids in delivery to a cell. A naked delivery formulation is free from any transfection reagents, cationic carriers, carbohydrate carriers, nanoparticle carriers, or protein carriers. For example, naked delivery formulation of a circular polyribonucleotide is a formulation that comprises a circular polyribonucleotide without covalent modification and is free from a carrier.

The term "diluent" means vehicle comprising an inactive solvent in which a composition described herein (e.g., a composition comprising a circular polyribonucleotide) may be diluted or dissolved. A diluent can be an RNA solubilizing agent, a buffer, an isotonic agent, or a mixture thereof. A diluent can be a liquid diluent or a solid diluent. Non-limiting examples of liquid diluents include water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and 1,3-butanediol. Non-limiting examples of solid diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, or powdered sugar.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The following detailed description of the embodiments of the invention will be better understood when read in conjunction with the appended drawings. For the purpose of illustrating the invention, there are shown in the drawings embodiments, which are presently exemplified. It should be understood, however, that the invention is not limited to the precise arrangement and instrumentalities of the embodiments shown in the drawings.

DETAILED DESCRIPTION

Figure 1A:
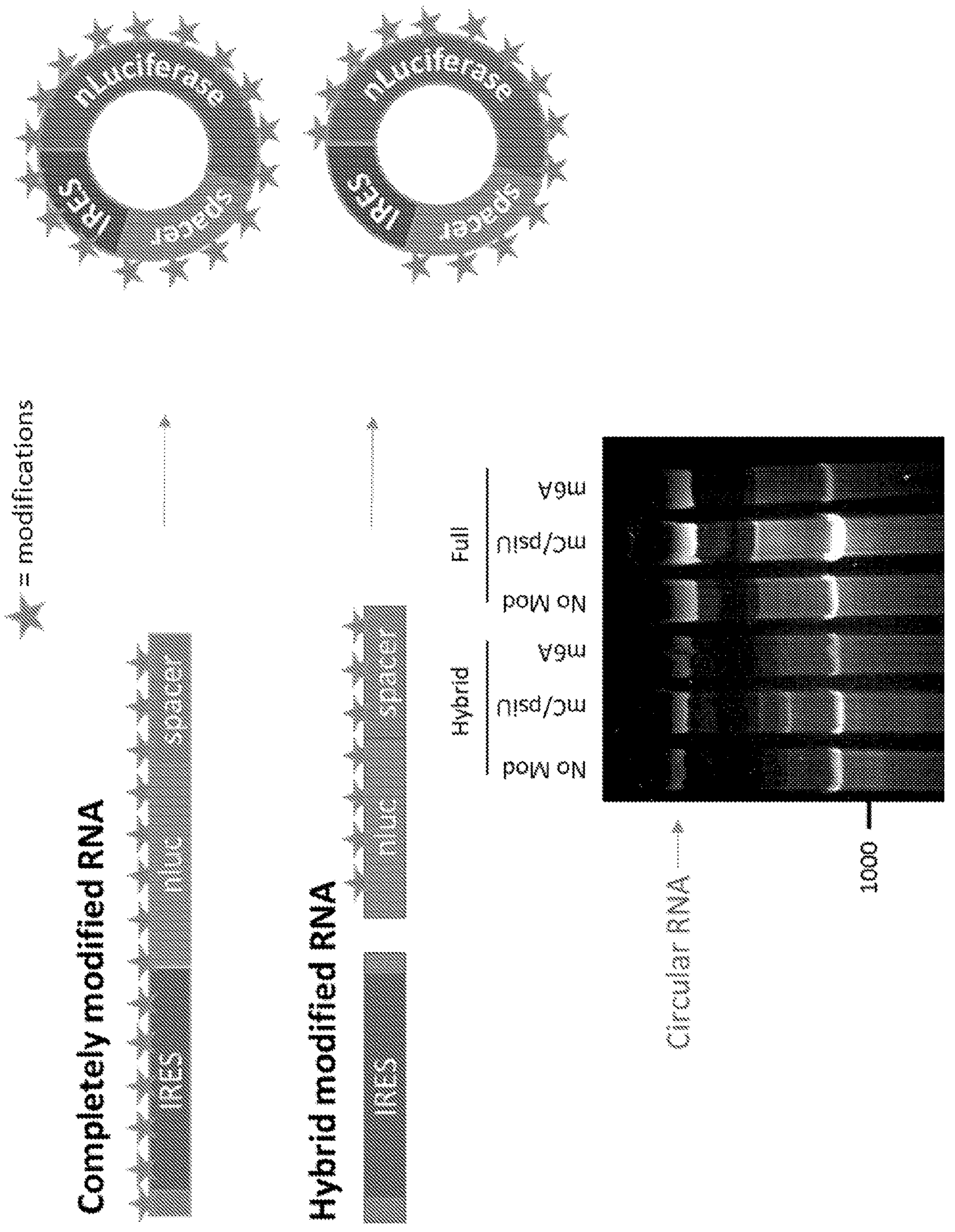
FIGS. 1A, 1B, and 1C show that the modified circular RNAs were translated in cells.

This invention relates generally to pharmaceutical compositions and preparations of circular polyribonucleotides and uses thereof. In some embodiments, the circular polyribonucleotide comprises at least one modified polyribonucleotide and a first portion of contiguous unmodified nucleotides. In some embodiments, the modified circular polyribonucleotide is delivered to a subject.

The present disclosure provides a method of reducing or decreasing immunogenicity of a circular polyribonucleotide in a subject comprising providing a hybrid modified circular polyribonucleotide, wherein the hybrid modified circular polyribonucleotide comprises at least one modified polyribonucleotide and a first portion of contiguous nucleotides having no more than 5% modified nucleotides, administering the hybrid modified circular polyribonucleotide to the subject, and obtaining decreased immunogenicity for the hybrid modified circular polyribonucleotide compared to a corresponding unmodified circular polyribonucleotide in a cell or tissue of the subject. In some embodiments, a method of decreasing or reducing immunogenicity of a circular polyribonucleotide in a subject comprises: providing a hybrid modified circular polyribonucleotide, wherein the hybrid modified circular polyribonucleotide comprises at least one modified nucleotide and a first portion comprising at least about 5 to 1000 contiguous nucleotides having no more than 5% modified nucleotides; administering the hybrid modified circular polyribonucleotide to the subject; and obtaining decreased immunogenicity for the hybrid modified circular polyribonucleotide compared to a corresponding unmodified circular polyribonucleotide in a cell or tissue of the subject. In some embodiments, a method of reducing or decreasing immunogenicity of a circular polyribonucleotide in a subject comprises providing a hybrid modified circular polyribonucleotide, wherein the hybrid modified circular polyribonucleotide comprises at least one modified polyribonucleotide and a first portion of contiguous unmodified nucleotides, administering the hybrid modified circular polyribonucleotide to the subject, and obtaining decreased immunogenicity for the hybrid modified circular polyribonucleotide compared to a corresponding unmodified circular polyribonucleotide. in a cell or tissue of the subject. In some embodiments, the first portion comprises an IRES. In some embodiments, the first portion comprises at least about 5 to 1000 contiguous unmodified nucleotides. In some embodiments, the first portion lacks 5'-methylcytidine or pseudouridine. In some embodiments, no more than 5% of nucleotides in the first portion are modified nucleotides.

The present disclosure provides a method of expressing one or more expression sequences in a subject comprising providing a hybrid modified circular polyribonucleotide comprising at least one modified polyribonucleotide, a first portion of contiguous nucleotides having no more than 5% modified nucleotides, and the one or more expression sequences, administering the hybrid modified circular polyribonucleotide to the subject, and obtaining increased expression of the one or more expression sequences compared to expression of a corresponding one or more expression sequences in a fully modified circular polyribonucleotide in a cell or tissue of the subject. In some embodiments, a method of expressing one or more expression sequences in a subject comprises: providing a hybrid modified circular polyribonucleotide, wherein the hybrid modified circular polyribonucleotide comprises at least one modified nucleotide and a first portion comprising at least about 5 to 1000 contiguous nucleotides having no more than 5% modified nucleotides; administering the hybrid modified circular polyribonucleotide to the subject, and obtaining increased expression of the one or more expression sequences compared to expression of a one or more expression sequences in a fully modified circular polyribonucleotide counterpart in a cell or tissue of the subject. In some embodiments, a method of expressing one or more expression sequences in a subject comprises providing a hybrid modified circular polyribonucleotide comprising at least one modified polyribonucleotide, a first portion of contiguous unmodified nucleotides, and the one or more expression sequences, administering the hybrid modified circular polyribonucleotide to the subject, and obtaining increased expression of the one or more expression sequences compared to expression of a corresponding one or more expression sequences in a fully modified circular polyribonucleotide in a cell or tissue of the subject. In some embodiments, the first portion comprises an IRES. In some embodiments, the first portion comprises at least about 5 to 1000 contiguous unmodified nucleotides. In some embodiments, the first portion lacks 5'-methylcytidine or pseudouridine. In some embodiments, no more than 5% of nucleotides in the first portion are modified nucleotides.

The present disclosure provides a method of increasing stability of a circular polyribonucleotide in a subject comprising providing a hybrid circular polyribonucleotide, wherein the hybrid modified circular polyribonucleotide comprises at least one modified polyribonucleotide and a first portion of contiguous nucleotides having no more than 5% modified nucleotides, administering the hybrid modified circular polyribonucleotide to the subject, and obtaining increased stability for the hybrid modified circular polyribonucleotide compared to a corresponding unmodified circular polyribonucleotide. in a cell or tissue of the subject. In some embodiments, a method of increasing stability of a circular polyribonucleotide in a subject comprises: providing a hybrid modified circular polyribonucleotide, wherein the hybrid modified circular polyribonucleotide comprises at least one modified nucleotide and a first portion comprising at least about 5 to 1000 contiguous nucleotides having no more than 5% modified nucleotides; administering the hybrid modified circular polyribonucleotide to the subject, and obtaining increased stability for the hybrid modified circular polyribonucleotide compared to a corresponding unmodified circular polyribonucleotide. in a cell or tissue of the subject. In some embodiments, a method of increasing stability of a circular polyribonucleotide in a subject comprises providing a hybrid circular polyribonucleotide, wherein the hybrid modified circular polyribonucleotide comprises at least one modified polyribonucleotide and a first portion of contiguous unmodified nucleotides, administering the hybrid modified circular polyribonucleotide to the subject, and obtaining increased stability for the hybrid modified circular polyribonucleotide compared to a corresponding unmodified circular polyribonucleotide. in a cell or tissue of the subject. In some embodiments, the first portion comprises an IRES. In some embodiments, the first portion comprises at least about 5 to 1000 contiguous unmodified nucleotides. In some embodiments, the first portion lacks 5'-methylcytidine or pseudouridine. In some embodiments, no more than 5% of nucleotides in the first portion are modified nucleotides.

Methods of Using Modified Circular Polyribonucleotides

In some aspects, the invention described herein comprises methods of using compositions of hybrid modified circular polyribonucleotides and delivery of hybrid modified circular polyribonucleotides. In some embodiments, the hybrid modified circular polyribonucleotide is delivered to a subject. Compared to a corresponding unmodified circular polyribonucleotide, administration of a hybrid modified circular polyribonucleotide as described herein to a subject can result in reduced or decreased immunogenicity, increased translation efficiency (e.g., increased expression of one or more expression sequences in the hybrid modified circular polyribonucleotide), or increased stability in a cell or tissue of the subject. Compared to a fully modified circular polyribonucleotide counterpart, administration of a hybrid modified circular polyribonucleotide as described herein to a subject can result in increased translation efficiency (e.g., increased expression of one or more expression sequences in the hybrid modified circular polyribonucleotide) in a cell or tissue of the subject. In some embodiments, the hybrid modified circular polyribonucleotide comprises at least one modified polyribonucleotide and a first portion of contiguous unmodified nucleotides. In some embodiments, the present disclosure provides a method of using a hybrid modified circular polyribonucleotide, wherein the hybrid modified circular polyribonucleotide comprises at least one modified nucleotide and a first portion, and wherein the first portion comprises at least about 5 contiguous unmodified nucleotides. In some embodiments, the hybrid circular polyribonucleotide comprises one or more expression sequences.

In some embodiments, the first portion comprises at least about 5 to 1000 contiguous nucleotides having no more than 5% modified nucleotides. In some embodiments, the first portion comprises at least about 5 to 1000 contiguous unmodified nucleotides. In some embodiments, the first portion lacks 5'-methylcytidine, pseudouridine, or N1-methyl-pseudouridine. In some embodiments, no more than 5% of nucleotides in the first portion are modified. In some embodiments, no more than 0%, 1%, 2%, 3%, 4%, or 5% of nucleotides in the first portion are modified. In some embodiments, no nucleotides in the first portion are modified. In some embodiments, the first portion is an IRES. In some embodiments, the first portion is an IRES comprising no more than 5% modified nucleotides. In some embodiments, the first portion is an IRES comprising no modified nucleotides (e.g., only unmodified nucleotides). In some embodiments, the first portion is an IRES consisting of unmodified nucleotides. In some embodiments, a first portion comprises a binding site configured to bind to a protein, peptide, biomolecule, DNA, RNA, or a cell target, consisting of unmodified nucleotides. In some embodiments, the hybrid modified circular polyribonucleotide is translationally competent. In some embodiments, the hybrid modified circular polyribonucleotide is in a pharmaceutical composition, which further comprises a pharmaceutically acceptable carrier or excipient.

A hybrid modified circular polyribonucleotide can comprise at least one modified nucleotide and first portion comprising contiguous unmodified nucleotides. A modified nucleotide is outside the first portion. A modified polyribonucleotide of a hybrid modified circular polyribonucleotide can be an analog or derivative that has one or more chemical modifications to the chemical composition of an unmodified natural ribonucleotide, such as a natural unmodified nucleotide adenosine (A), uridine (U), guaninie (G), cytidine (C) as shown by the chemical formulae in TABLE 1, and monophosphate. The chemical modifications of the modified ribonucleotide can be modifications to any one or more functional groups of the ribonucleotide, such as, the sugar the nucleobase, or the internucleoside linkage (e.g. to a linking phosphate/to a phosphodiester linkage/to the phosphodiester backbone). In some embodiments, a modified nucleotide of a modified circular polyribonucleotide (e.g., a fully modified circular polyribonucleotide or a hybrid circular polyribonucleotide) can be any modification known by a person of skill in the art, such as those identified in or such as in Gilbert, W. V., et al. *Science.* 2016 Jun. 17; 352(6292): 1408-1412, which is herein incorporated by reference. For example, a modification can be as described in TABLE 2.

TABLE 1

Unmodified Natural Ribonucleosides

| Ribo-nucleoside | IUPAC name | Chemical Formula |
|---|---|---|
| Adenosine | (2R,3R,4S,5R)-2-(6-amino-9H-purin-9-yl)-5-(hydroxymethyl) oxolane-3,4-diol | 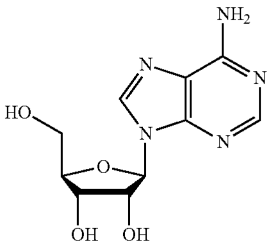 $C_{10}H_{13}N_5O_4$ |
| Uridine | 1-[(3R,4S,5R)-3,4-dihydroxy-5-(hydroxymethyl) oxolan-2-yl]pyrimidine-2,4-dione | 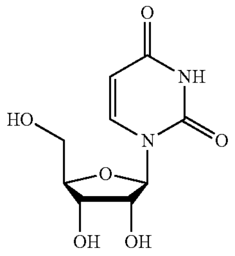 $C_9H_{12}N_2O_6$ |
| Guanine | 2-amino-9H-purin-6(1H)-one | 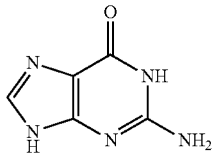 $C_5H_5N_5O$ |

TABLE 1-continued

| Unmodified Natural Ribonucleosides | | |
|---|---|---|
| Ribo-nucleoside | IUPAC name | Chemical Formula |
| Cytidine | 4-amino-1-[(2R,3R,4S,5R)-3,4-dihydroxy-5-(hydroxymethyl)oxolan-2-yl]pyrimidin-2(1H)-one | 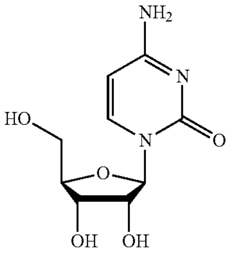 $C_9H_{13}N_3O_5$ |

TABLE 2

| Exemplary Nucleotide Modifications | | | | |
|---|---|---|---|---|
| | ATP | CTP | GTP | UTP |
| Sugar modifications | 2'OMe ATP<br>2'F ATP | 2'OMe CTP<br>2'F CTP | 2'OMe GTP<br>2'F GTP | 2'OMe UTP<br>2'F UTP |
| Base modifications | N1 methyl ATP<br>N6 methyl ATP<br>2 amino ATP | 5 hydroxy methyl CTP<br>m5CTP | | pseudoU<br>N1 ethyl pseudoU<br>N1 methyl pseudoU<br>2 thio U<br>5 carboxy methyl ester U<br>5 methoxy U<br>5 methyl U |

In some embodiments, a modified nucleotide is selected from the group consisting of: N(6)methyladenosine (m6A), 5'-methylcytidine (5 mC), pseudouridine, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, a modified nucleotide is any modified nucleotide known by a person of skill in the art, such as those identified in or such as in Gilbert, W. V., et al. *Science.* 2016 Jun. 17; 352(6292): 1408-1412, which is herein incorporated by reference.

The first portion of the hybrid modified circular polyribonucleotide as described herein comprises at least about 5 to 1000 contiguous nucleotide. In some embodiments, the first portion comprises at least about 5 to 1000, 10 to 1000, 20 to 1000, 50 to 1000, 100 to 1000, 200 to 1000, 300 to 1000, 400 to 1000, 500 to 1000, 600 to 1000, 700 to 1000, 800 to 1000, 900 to 1000, or 900 to 2000 contiguous nucleotide. The first portion of the hybrid modified circular polyribonucleotide as described herein can comprise contiguous nucleotides having no more than 5% modified nucleotides. In some embodiments, the first portion comprises contiguous nucleotides comprises no more than 0%, 1%, 2%, 3%, 4%, or 5% of modified nucleotides. In some embodiments, the first portion is an IRES. In some embodiments, the first portion is an IRES comprising no more than 5% modified nucleotides. In some embodiments, the first portion is an IRES comprising no modified nucleotides (e.g., only unmodified nucleotides). In some embodiments, the first portion is an IRES consisting of unmodified nucleotides. The first portion of the hybrid modified circular polyribonucleotide as described herein can comprise contiguous unmodified nucleotides. The first portion can comprise at least about 5 contiguous unmodified nucleotides. In some embodiments, the first portion comprises at least about 5 to 1000 contiguous unmodified nucleotide. In some embodiments, the first portion comprises at least about 5 to 1000, 10 to 1000, 20 to 1000, 50 to 1000, 100 to 1000, 200 to 1000, 300 to 1000, 400 to 1000, 500 to 1000, 600 to 1000, 700 to 1000, 800 to 1000, 900 to 1000, or 900 to 2000 contiguous unmodified nucleotide. In some embodiments, the first portion comprises at least about 5, 10, 20, 50, 100, 200, 300, 400, 500, 600, 700, 800, 900, or 1000, or any number therebetween, contiguous unmodified nucleotide. In some embodiments, the first portion comprises 5, 10, 20, 50, 100, 200, 300, 400, 500, 600, 700, 800, 900, 1000, or any number therebetween, contiguous unmodified nucleotide. The first portion can comprise an IRES. In some embodiments, the first portion lacks 5'-methylcytidine, pseudouridine, or N1-methyl-pseudouridine. In some embodiments, the first portion lacks a modified selected from the group consisting of: N(6)methyladenosine (m6A), 5'-methylcytidine (5 mC), pseudouridine, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, the first portion lacks a nucleotide modification known by a person of skill in the art, such as those identified in or such as in Gilbert, W. V., et al. *Science.* 2016 Jun. 17; 352(6292): 1408-1412, which is herein incorporated by reference.

A hybrid modified circular polyribonucleotide as described herein can comprise a 5'-methylcytidine, a pseudouridine, or a combination thereof outside the first portion. The hybrid modified circular polyribonucleotide can comprise a modified selected from the group consisting of: N(6)methyladenosine (m6A), 5'-methylcytidine (5 mC), pseudouridine, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite, wherein the modified nucleotide is outside of the first portion. In some embodiments, the modified nucleotide outside of the first portion is any modified nucleotide known by a person of skill in the art, such as those identified in or such as in Gilbert, W. V., et al. *Science*. 2016 Jun. 17; 352(6292): 1408-1412, which is herein incorporated by reference.

Reduced Immunogenicity

A method of reducing or decreasing immunogenicity of a circular polyribonucleotide in a subject can comprise providing a hybrid circular polyribonucleotide, wherein the hybrid modified circular polyribonucleotide comprises at least one modified polyribonucleotide and a first portion of contiguous unmodified nucleotides, administering the hybrid modified circular polyribonucleotide to the subject, and obtaining reduced or decreased immunogenicity for the modified circular polyribonucleotide compared to a corresponding unmodified circular polyribonucleotide in a cell or tissue of the subject. In some embodiments, the first portion comprises at least about 5, 10, 20, 50, 100, 200, 300, 400, 500, 600, 700, 800, 900, or 1000 contiguous unmodified nucleotides. In some embodiments, no more than 5% of nucleotides in the first portion are modified. In some embodiments, no more than 1%, 2%, 3%, 4%, or 5% of nucleotides in the first portion are modified. In some embodiments, no nucleotides in the first portion are modified. In some embodiments, the first portion is an IRES. In some embodiments, a first portion comprises a binding site configured to bind to a protein, peptide, biomolecule, DNA, RNA, or a cell target, consisting of unmodified nucleotides. In some embodiments, the first portion is an IRES comprising no more than 5% modified nucleotides. In some embodiments, the first portion is an IRES comprising no modified nucleotides. In some embodiments, the first portion is an IRES consisting of unmodified nucleotides. In some embodiments, the reduced or decreased immunogenicity for the modified circular polyribonucleotide is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower compared to a corresponding unmodified circular polyribonucleotide in a cell or tissue of the subject.

In some embodiments, the hybrid modified circular polyribonucleotide as disclosed herein has a reduced or decreased immunogenicity compared to a corresponding unmodified circular polyribonucleotide after administration to a subject. In some embodiments, the hybrid modified circular polyribonucleotide as disclosed herein has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide after administration to a subject. In some embodiments, the immunogenicity as described herein is assessed by the level of expression or signaling or activation of at least one of RIG-I, TLR-3, TLR-7, TLR-8, MDA-5, LGP-2, OAS, OASL, PKR, and IFN-beta after administration of the hybrid modified circular polyribonucleotide to a subject.

Increased Translation Efficiency

The present disclosure provides a method of expressing one or more expression sequences in a subject comprising providing a hybrid modified circular polyribonucleotide comprising at least one modified polyribonucleotide, a first portion of contiguous unmodified nucleotides, and the one or more expression sequences, administering the hybrid modified circular polyribonucleotide to the subject, and obtaining increased expression of the one or more expression sequences compared to expression of corresponding one or more expression sequences of a fully modified circular polyribonucleotide counterpart in a cell or tissue of the subject. In some embodiments, the first portion comprises at least about 5, 10, 20, 50, 100, 200, 300, 400, 500, 600, 700, 800, 900, or 1000 contiguous unmodified nucleotides. In some embodiments, no more than 5% of nucleotides in the first portion are modified. In some embodiments, no more than 1%, 2%, 3%, 4%, or 5% of nucleotides in the first portion are modified. In some embodiments, no nucleotides in the first portion are modified. In some embodiments, the first portion is an IRES. In some embodiments, a first portion comprises a binding site configured to bind to a protein, peptide, biomolecule, DNA, RNA, or a cell target, consisting of unmodified nucleotides. In some embodiments, the first portion is an IRES comprising no more than 5% modified nucleotides. In some embodiments, the first portion is an IRES comprising no modified nucleotides. In some embodiments, the first portion is an IRES consisting of unmodified nucleotides. In some embodiments, the hybrid modified circular polyribonucleotide comprises one or more expression sequences.

In some embodiments, the increased expression of the one or more expression sequences of the hybrid modified circular polyribonucleotide is similar to or higher than one or more expression sequences of a fully modified circular polyribonucleotide counterpart. In some embodiments, increased expression of the one or more expression sequences of the hybrid modified circular polyribonucleotide is at least about 0.7, 0.8, 0.9, 1.0, 1.1, 1.2, 1.3, 1.5, 1.6, 1.8, 2, 2.2, 2.5, 2.8, or 3 fold higher than one or more expression sequences of a fully modified circular polyribonucleotide counterpart. In some embodiments, the increased expression of the expression of the one or more expression sequences of the hybrid modified circular polyribonucleotide is similar to or higher than a corresponding unmodified circular polyribonucleotide. In some embodiments, the increased expression of the one or more expression sequences of the hybrid modified circular polyribonucleotide is at least about 0.7, 0.8, 0.9, 1.0, 1.1, 1.2, 1.3, 1.5, 1.6, 1.8, 2, 2.2, 2.5, 2.8, or 3 fold higher than a corresponding unmodified circular polyribonucleotide.

In some embodiments, the increased expression of the expression of the one or more sequences of the hybrid modified circular polyribonucleotide is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than a fully modified circular polyribonucleotide counterpart. In some embodiments, the increased expression of the expression of the one or more sequences of the hybrid modified circular polyribonucleotide is at least about 10% than a fully modified circular polyribonucleotide counterpart. In some embodiments, the increased expression of the expression of the one or more sequences of the hybrid modified circular polyribonucleotide is at least about 20% than a fully modified circular polyribonucleotide counterpart. In some embodiments, the increased expression of the expression of the one or more sequences of the hybrid modified circular polyribonucleotide is at least about 50% than a fully modified circular polyribonucleotide counterpart. In some embodiments, the increased expression of the expression of the one or more sequences of the hybrid modified circular polyribonucleotide is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than that of a corresponding unmodified circular polyribonucleotide. In some embodiments, the increased expression of the expression of the one or more sequences of the hybrid modified circular polyribonucleotide is at least about 10% than that of corresponding unmodified circular polyribonucleotide. In some embodiments, the increased expression of the expression of the one or more sequences of the hybrid modified circular polyribonucleotide is at least about 20% than that of corresponding unmodified circular polyribonucleotide. In some embodiments, the increased expression of the expression of the one or more sequences of the hybrid modified circular polyribonucleotide is at least about 50% than that of corresponding unmodified circular polyribonucleotide. In some embodiments, the increased expression of the expression of the one or more sequences of the hybrid modified circular polyribonucleotide is at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject.

In some embodiments, the expression of the one or more expression sequences of the hybrid modified circular polyribonucleotide has a translation efficiency similar to or higher than one or more expression sequences of a fully modified circular polyribonucleotide counterpart after administration to a subject. In some embodiments, the one or more expression sequences of the hybrid modified circular polyribonucleotide have a translation efficiency that is at least about 0.7, 0.8, 0.9, 1.0, 1.1, 1.2, 1.3, 1.5, 1.6, 1.8, 2, 2.2, 2.5, 2.8, or 3 fold higher than one or more expression sequences of a fully modified circular polyribonucleotide counterpart after administration to a subject. In some embodiments, the expression of the one or more expression sequences of the hybrid modified circular polyribonucleotide has a translation efficiency similar to or higher than a corresponding unmodified circular polyribonucleotide after administration to a subject. In some embodiments, the one or more expression sequences of the hybrid modified circular polyribonucleotide have a translation efficiency that is at least about 0.7, 0.8, 0.9, 1.0, 1.1, 1.2, 1.3, 1.5, 1.6, 1.8, 2, 2.2, 2.5, 2.8, or 3 fold higher than a corresponding unmodified circular polyribonucleotide after administration to a subject.

In some embodiments, the expression of the one or more expression sequences of the hybrid modified circular polyribonucleotide has a translation efficiency similar to or higher than one or more expression sequences of a fully modified circular polyribonucleotide counterpart at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the one or more expression sequences of the hybrid modified circular polyribonucleotide have a translation efficiency that is at least about 0.7, 0.8, 0.9, 1.0, 1.1, 1.2, 1.3, 1.5, 1.6, 1.8, 2, 2.2, 2.5, 2.8, or 3 fold higher than one or more expression sequences of a fully modified circular polyribonucleotide counterpart at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the expression of the one or more expression sequences of the hybrid modified circular polyribonucleotide has a translation efficiency similar to or higher than a corresponding unmodified circular polyribonucleotide after administration to a subject. In some embodiments, the one or more expression sequences of the hybrid modified circular polyribonucleotide have a translation efficiency that is at least about 0.7, 0.8, 0.9, 1.0, 1.1, 1.2, 1.3, 1.5, 1.6, 1.8, 2, 2.2, 2.5, 2.8, or 3 fold higher than a corresponding unmodified circular polyribonucleotide at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject.

In some embodiments, the increased expression of the one or more expression sequences of the hybrid modified circular polyribonucleotide is similar to or higher than a fully modified circular polyribonucleotide counterpart having a first portion comprising more than 5%, or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the increased expression of the one or more expression sequences of the hybrid modified circular polyribonucleotide is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a fully modified circular polyribonucleotide counterpart having a first portion comprising more than 5%, or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject.

In some embodiments, the increased expression of the one or more expression sequences of the hybrid modified circular polyribonucleotide is similar to or higher than a fully modified circular polyribonucleotide counterpart having a first portion comprising more than 5%, or at least 10%, 20%, 30%, 40%, 50%, 60%, 70%, 80%, 90%, or 100% modified nucleotides. In some embodiments, the increased expression of the one or more expression sequences of the hybrid modified circular polyribonucleotide is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a fully modified circular polyribonucleotide counterpart having a first portion comprising more than 5%, or at least 10%, 20%, 30%, 40%, 50%, 60%, 70%, 80%, 90%, or 100% modified nucleotides.

In some embodiments, the increased expression of the one or more expression sequences of the hybrid modified circular polyribonucleotide is similar to or higher than a fully modified circular polyribonucleotide counterpart having a first portion comprising more than 5%, or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the increased expression of the one or more expression sequences of the hybrid modified circular polyribonucleotide is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a fully modified circular polyribonucleotide counterpart having a first portion comprising more than 5%, or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject.

In some embodiments the increased expression of the expression the one or more sequences of the hybrid modified circular polyribonucleotide is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than that of a fully modified circular polyribonucleotide counterpart having a first portion comprising more than 5%, or at least 10%, 20%, 30%, 40%, 50%, 60%, 70%, 80%, 90%, or 100% modified nucleotides, at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the increased expression of the expression the one or more sequences of the hybrid modified circular polyribonucleotide is at least about 10% than that of a fully modified circular polyribonucleotide counterpart having a first portion comprising more than 5% or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the increased expression of the expression the one or more sequences of the hybrid modified circular polyribonucleotide is at least about 20% than that of a fully modified circular polyribonucleotide counterpart having a first portion comprising more than 5%, or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the increased expression of the expression the one or more sequences of the hybrid modified circular polyribonucleotide is at least about 50% than that of a fully modified circular polyribonucleotide counterpart having a first portion comprising more than 5%, or at least 10%, 20%, 30%, 40%, 50%, 60%, 70%, 80%, 90%, or 100% modified nucleotides at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject.

As described herein, in some embodiments, the translation efficiency or increased expression is measured either in a cell comprising the hybrid modified circular polyribonucleotide or the corresponding unmodified circular polyribonucleotide or the fully modified circular polyribonucleotide counterpart, or in an in vitro translation system (e.g., rabbit reticulocyte lysate).

Increased Stability

The present disclosure provides a method of increasing stability of a circular polyribonucleotide in a subject comprising providing a hybrid modified circular polyribonucleotide, wherein the hybrid modified circular polyribonucleotide comprises at least one modified polyribonucleotide and a first portion of contiguous unmodified nucleotides, administering the hybrid modified circular polyribonucleotide to the subject, and obtaining increased stability for the hybrid modified circular polyribonucleotide compared to a corresponding unmodified circular polyribonucleotide. in a cell or tissue of the subject. In some embodiments, the first portion comprises at least about 5, 10, 20, 50, 100, 200, 300, 400, 500, 600, 700, 800, 900, or 1000 contiguous unmodified nucleotides. In some embodiments, no more than 5% of nucleotides in the first portion are modified. In some embodiments, no more than 1%, 2%, 3%, 4%, or 5% of nucleotides in the first portion are modified. In some embodiments, no nucleotides in the first portion are modified. In some embodiments, the first portion is an IRES. In some embodiments, a first portion comprises a binding site configured to bind to a protein, peptide, biomolecule, DNA, RNA, or a cell target, consisting of unmodified nucleotides. In some embodiments, the first portion is an IRES comprising no more than 5% modified nucleotides. In some embodiments, the first portion is an IRES comprising no modified nucleotides. In some embodiments, the first portion is an IRES consisting of unmodified nucleotides. In some embodiments, the increased stability of the hybrid modified circular polyribonucleotide is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher compared to a corresponding unmodified circular polyribonucleotide in a cell or tissue of the subject.

In some embodiments, the hybrid modified circular polyribonucleotide as disclosed herein has increased stability compared to a corresponding unmodified circular polyribonucleotide after administration to a subject. In some embodiments, the hybrid modified circular polyribonucleotide as disclosed has increased stability that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide after administration to a subject.

In some embodiments, the hybrid modified circular polyribonucleotide as disclosed herein has increased stability compared to a corresponding unmodified circular polyribonucleotide at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the hybrid modified circular polyribonucleotide as disclosed herein has increased stability compared to a corresponding unmodified circular polyribonucleotide at 14 days after administration to a subject. In some embodiments, the hybrid modified circular polyribonucleotide as disclosed has increased stability that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, or longer, or any day therebetween, after administration to a subject. In some embodiments, the hybrid modified circular polyribonucleotide as disclosed has increased stability that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide at 14 days after administration to a subject.

In some embodiments, the hybrid modified circular polyribonucleotide has a higher half-life than a corresponding unmodified circular polyribonucleotide after administration to a subject. In some embodiments, the hybrid modified circular polyribonucleotide has a half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide after administration to a subject. In some embodiments, the half-life is measured by introducing the hybrid modified circular polyribonucleotide or the corresponding unmodified circular polyribonucleotide into a cell and measuring a level of the introduced hybrid modified circular polyribonucleotide or corresponding unmodified circular polyribonucleotide inside the cell.

In some embodiments, the hybrid modified circular polyribonucleotide has a half-life of at least that of a corresponding unmodified circular polyribonucleotide after administration to a subject. In some embodiments, the hybrid modified circular polyribonucleotide has a half-life that is increased over that of a corresponding unmodified circular polyribonucleotide after administration to a subject. In some embodiments, the half-life is increased by about 5%, 10%, 15%, 20%, 25%, 30%, 35%, 40%, 45%, 50%, or greater after administration to a subject. In some embodiments, the hybrid modified circular polyribonucleotide has a half-life or persistence in a cell for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween after administration to a subject. In certain embodiments, the hybrid modified circular polyribonucleotide has a half-life or persistence in a cell for no more than about 10 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween after administration to a subject. In some embodiments, the hybrid modified circular polyribonucleotide has a half-life or persistence in a cell while the cell is dividing after administration to a subject. In some embodiments, the hybrid modified circular polyribonucleotide has a half-life or persistence in a cell post division after administration to a subject. In certain embodiments, the hybrid modified circular polyribonucleotide has a half-life or persistence in a dividing cell for greater than about about 10 minutes to about 30 days, or at least about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween after administration to a subject.

In some embodiments, the hybrid modified circular polyribonucleotide persists in a cell during cell division after administration to a subject. In some embodiments, the hybrid modified circular polyribonucleotide persists in daughter cells after mitosis after administration to a subject. In some embodiments, the hybrid modified circular polyribonucleotide is replicated within a cell and is passed to daughter cells after administration to a subject. In some embodiments, a cell passes at least one hybrid modified circular polyribonucleotide to daughter cells with an efficiency of at least 25%, 50%, 60%, 70%, 80%, 85%, 90%, 95%, or 99% after administration to a subject. In some embodiments, cell undergoing meiosis passes the hybrid modified circular polyribonucleotide to daughter cells with an efficiency of at least 25%, 50%, 60%, 70%, 80%, 85%, 90%, 95%, or 99% after administration to a subject. In some embodiments, a cell undergoing mitosis passes the hybrid modified circular polyribonucleotide to daughter cells with an efficiency of at least 25%, 50%, 60%, 70%, 80%, 85%, 90%, 95%, or 99% after administration to a subject.

Modified Circular Polyribonucleotides

The modified circular polyribonucleotide (e.g., a fully modified circular polyribonucleotide or a hybrid modified circular polyribonucleotide) is used in the methods described herein. In some embodiments, the hybrid modified circular polyribonucleotide comprises at least one modified polyribonucleotide and a first portion of contiguous unmodified nucleotides. In some embodiments, a hybrid modified circular polyribonucleotide as described herein comprises comprises at least one modified nucleotide and a first portion, and wherein the first portion comprises at least about 5, 10, 20, 50, 100, 200, 300, 400, 500, 600, 700, 800, 900, or 1000 contiguous unmodified nucleotides. In some embodiments, no more than 5% of nucleotides in the first portion are modified. In some embodiments, no more than 0%, 1%, 2%, 3%, 4%, or 5% of nucleotides in the first portion are modified. In some embodiments, no nucleotides in the first portion are modified. In some embodiments, the first portion is an IRES. In some embodiments, the first portion is an IRES comprising no more than 5% modified nucleotides. In some embodiments, the first portion is an IRES comprising no modified nucleotides. In some embodiments, the first portion is an IRES consisting of unmodified nucleotides. In some embodiments, a first portion comprises a binding site configured to bind to a protein, peptide, biomolecule, DNA, RNA, or a cell target, consisting of unmodified nucleotides. In some embodiments, the first portion lacks 5'-methylcytidine, pseudouridine, or N1-methyl-pseudouridine. In some embodiments, the hybrid modified circular polyribonucleotide is in pharmaceutical composition, which further comprises a pharmaceutically acceptable carrier or excipient. In some embodiments, the hybrid modified circular polyribonucleotide is delivered to a subject. The hybrid modified circular polyribonucleotide as described herein can have reduced or decreased immunogenicity, increased translation efficiency (e.g., increased expression of one or more expression sequences in the hybrid modified circular polyribonucleotide), or increased stability compared to a fully modified circular polyribonucleotide counterpart.

The first portion comprises contiguous nucleotides having no more than 5% modified nucleotides in the hybrid modified circular polyribonucleotide. In some embodiments, no more than 0%, 1%, 2%, 3%, 4%, or 5% of the contiguous nucleotides in the first portion are modified. The first portion comprises contiguous unmodified nucleotides in the hybrid modified circular polyribonucleotide. The first portion can comprise at least about 5 contiguous unmodified nucleotides. In some embodiments, the first portion comprises at least about 5, 10, 20, 50, 100, 200, 300, 400, 500, 600, 700, 800, 900, or 1000 contiguous nucleotide having no more than 0%, 1%, 2%, 3%, 4%, or 5% modified nucleotides. In some embodiments, the first portion comprises at least about 5 to 1000 contiguous nucleotide having no more than 0%, 1%, 2%, 3%, 4%, or 5% modified nucleotides. In some embodiments, the first portion comprises at least about 5 to 1000, 10 to 1000, 20 to 1000, 50 to 1000, 100 to 1000, 200 to 1000, 300 to 1000, 400 to 1000, 500 to 1000, 600 to 1000, 700 to 1000, 800 to 1000, 900 to 1000, or 900 to 2000 contiguous nucleotide having no more than 0%, 1%, 2%, 3%, 4%, or 5% modified nucleotides. In some embodiments, the first portion comprises at least about 5, 10, 20, 50, 100, 200, 300, 400, 500, 600, 700, 800, 900, or 1000 contiguous unmodified nucleotide. In some embodiments, the first portion comprises at least about 5 to 1000 contiguous unmodified nucleotide. In some embodiments, the first portion comprises at least about 5 to 1000, 10 to 1000, 20 to 1000, 50 to 1000, 100 to 1000, 200 to 1000, 300 to 1000, 400 to 1000, 500 to 1000, 600 to 1000, 700 to 1000, 800 to 1000, 900 to 1000, or 900 to 2000 contiguous unmodified nucleotide. In some embodiments, the first portion comprises 5, 10, 20, 50, 100, 200, 300, 400, 500, 600, 700, 800, 900, 1000, or any number therebetween, contiguous unmodified nucleotide. The first portion can comprise an IRES. In some embodiments, the first portion comprises a binding site. In some embodiments, the first portion comprises a binding site configured to bind a peptide, protein, biomolecule, DNA, RNA, or a cell target.

In some embodiments, the hybrid modified circular polyribonucleotide has modified nucleotides, e.g., 5' methylcytidine and pseudouridine, throughout the circular polyribonucleotide except the IRES element or a binding site configured to bind a protein, DNA, RNA, or cell target In these cases, the hybrid modified circular polyribonucleotide has a lower immunogenicity as compared to a corresponding unmodified circular polyribonucleotide. In these cases, the hybrid modified circular polyribonucleotide has a lower immunogenicity as compared to a corresponding circular polyribonucleotide that does not comprise 5' methylcytidine and pseudouridine. In some embodiments, the hybrid modified circular polyribonucleotide has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide. In some embodiments, the immunogenicity as described herein is assessed by expression or signaling or activation of at least one of RIG-I, TLR-3, TLR-7, TLR-8, MDA-5, LGP-2, OAS, OASL, PKR, and IFN-beta. In some embodiments, the hybrid modified circular polyribonucleotide has a higher half-life than a corresponding unmodified circular polyribonucleotide, e.g., a corresponding circular polyribonucleotide that does not comprise 5' methylcytidine and pseudouridine. In some embodiments, the hybrid modified circular polyribonucleotide has a higher half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide. In some embodiments, the half-life is measured by introducing the hybrid modified circular polyribonucleotide or the corresponding circular polyribonucleotide into a cell and measuring a level of the introduced hybrid modified circular polyribonucleotide or corresponding circular polyribonucleotide inside the cell.

A modified circular polyribonucleotide (e.g., a fully modified circular polyribonucleotide or a hybrid modified circular polyribonucleotide) can comprise at least one modified nucleotide. The hybrid modified circular polyribonucleotide as described herein can comprise first portion comprising contiguous unmodified nucleotides and at least one modified nucleotide. A modified nucleotide is outside the first portion. A modified polyribonucleotide of a modified circular polyribonucleotide (e.g., a fully modified circular polyribonucleotide or a hybrid modified circular polyribonucleotide) can be an analog or derivative that has one or more chemical modifications to the chemical composition of an unmodified natural ribonucleotide, such as a natural unmodified nucleotide adenosine (A), uridine (U), guaninie (G), cytidine (C) as shown as described herein. The chemical modifications of the modified ribonucleotide can be modifications to any one or more functional groups of the ribonucleotide, such as, the sugar the nucleobase, or the internucleoside linkage (e.g., to a linking phosphate/to a phosphodiester linkage/to the phosphodiester backbone).

In some embodiments, the modified circular polyribonucleotide (e.g., a fully modified circular polyribonucleotide or a hybrid modified circular polyribonucleotide) includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The one or more post-transcriptional modifications can be any post-transcriptional modification, such as any of the more than one hundred different nucleoside modifications that have been identified in RNA (Rozenski, J, Crain, P, and McCloskey, J. (1999). *The RNA Modification Database:* 1999 *update. Nucl Acids Res* 27: 196-197). In some embodiments, the modified circular polyribonucleotide (e.g., a fully modified circular polyribonucleotide or a hybrid modified circular polyribonucleotide) comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the modified circular polyribonucleotide comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-i-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the modified circular polyribonucleotide comprises at least one nucleoside selected from the group consisting of 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyl adenosine, N6,N6-dimethyladenosine, 7-methyladenine, 2-methylthioadenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the modified circular polyribonucleotide (e.g., a fully modified circular polyribonucleotide or a hybrid modified circular polyribonucleotide) comprises at least one modified nucleotide selected from the group consisting of: N(6)methyladenosine (m6A), 5'-methylcytidine (5 mC), pseudouridine, or N1-methyl-pseudouridine, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, the modified circular polyribonucleotide (e.g., a fully modified circular polyribonucleotide or a hybrid modified circular polyribonucleotide) comprises a nucleotide modification known by a person of skill in the art, such as those identified in or such as in Gilbert, W. V., et al. *Science*. 2016 Jun. 17; 352(6292): 1408-1412, which is herein incorporated by reference.

The modified circular polyribonucleotide (e.g., a fully modified circular polyribonucleotide or a hybrid modified circular polyribonucleotide) may include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modified circular polyribonucleotide (e.g., a fully modified circular polyribonucleotide or a hybrid modified circular polyribonucleotide) includes at least one N(6)methyladenosine (m6A) modification to increase translation efficiency. In some embodiments, the N(6)methyladenosine (m6A) modification can reduce or decrease immunogenicity of the modified circular polyribonucleotide (e.g., a fully modified circular polyribonucleotide or a hybrid modified circular polyribonucleotide).

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat Reviews Mol Cell Biol, 2017, 18:202-210.

"Pseudouridine" refers, in another embodiment, to $m^1acp^3\Psi$ (1-methyl-3-(3-amino-3-carboxypropyl) pseudouridine. In another embodiment, the term refers to $m^1\Psi$ (1-methylpseudouridine). In another embodiment, the term refers to Ψm (2'-O-methylpseudouridine. In another embodiment, the term refers to m5D (5-methyldihydrouridine). In another embodiment, the term refers to $m^3P$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

In some embodiments, chemical modifications to the ribonucleotides of the circular polyribonucleotide may enhance immune evasion. The modified circular polyribonucleotide (e.g., a fully modified circular polyribonucleotide or a hybrid modified circular polyribonucleotide) may be synthesized and/or modified by methods well established in the art, such as those described in "Current protocols in nucleic acid chemistry," Beaucage, S. L. et al. (Eds.), John Wiley & Sons, Inc., New York, NY, USA, which is hereby incorporated herein by reference. Modifications include, for example, end modifications, e.g., 5' end modifications (phosphorylation (mono-, di- and tri-), conjugation, inverted linkages, etc.), 3' end modifications (conjugation, DNA nucleotides, inverted linkages, etc.), base modifications (e.g., replacement with stabilizing bases, destabilizing bases, or bases that base pair with an expanded repertoire of partners), removal of bases (abasic nucleotides), or conjugated bases. The modified ribonucleotide bases may also include 5-methylcytidine and pseudouridine. In some embodiments, base modifications may modulate expression, immune response, stability, subcellular localization, to name a few functional effects, of the circular polyribonucleotide. In some embodiments, the modification includes a bi-orthogonal nucleotides, e.g., an unnatural base. See for example, Kimoto et al, Chem Commun (Camb), 2017, 53:12309, DOI: 10.1039/c7cc06661a, which is hereby incorporated by reference.

In some embodiments, sugar modifications (e.g., at the 2' position or 4' position) or replacement of the sugar one or more ribonucleotides of the circular polyribonucleotide may, as well as backbone modifications, include modification or replacement of the phosphodiester linkages. Specific examples of modified circular polyribonucleotide (e.g., a fully modified circular polyribonucleotide or a hybrid modified circular polyribonucleotide) include, but are not limited to circular polyribonucleotide including modified backbones or no natural internucleoside linkages such as internucleoside modifications, including modification or replacement of the phosphodiester linkages. Modified circular polyribonucleotides (e.g., a fully modified circular polyribonucleotide or a hybrid modified circular polyribonucleotide) having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, the modified circular polyribonucleotide (e.g., a fully modified circular polyribonucleotide or a hybrid modified circular polyribonucleotide) will include ribonucleotides with a phosphorus atom in its internucleoside backbone.

Modified circular polyribonucleotide (e.g., a fully modified circular polyribonucleotide or a hybrid modified circular polyribonucleotide) backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the circular polyribonucleotide may be negatively or positively charged.

The modified nucleotides, which may be incorporated into the modified circular polyribonucleotide (e.g., a fully modified circular polyribonucleotide or a hybrid modified circular polyribonucleotide), can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The a-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked to the circular polyribonucleotide is expected to reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein.

In some embodiments, the modified circular polyribonucleotide (e.g., a fully modified circular polyribonucleotide or a hybrid modified circular polyribonucleotide) may include one or more cytotoxic nucleosides. For example, cytotoxic nucleosides may be incorporated into circular polyribonucleotide, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

The modified circular polyribonucleotide (e.g., a fully modified circular polyribonucleotide or a hybrid modified circular polyribonucleotide) may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the circular polyribonucleotide (e.g., a fully modified circular polyribonucleotide or a hybrid modified circular polyribonucleotide), or in a given predetermined sequence region thereof. In some embodiments, the modified circular polyribonucleotide (e.g., a fully modified circular polyribonucleotide or a hybrid modified circular polyribonucleotide) includes a pseudouridine. In some embodiments, the modified circular polyribonucleotide (e.g., a fully modified circular polyribonucleotide or a hybrid modified circular polyribonucleotide) includes an inosine, which may aid in the immune system characterizing the circular polyribonucleotide as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

In some embodiments, all nucleotides in the hybrid modified circular polyribonucleotide in a given sequence region thereof (e.g., not the first portion or unmodified portion) are modified. In some embodiments, the modification may include an m6A, which may augment expression and/or may attenuate an immune response; an inosine, which may attenuate an immune response; pseudouridine, which may increase RNA stability, or translational readthrough (stagger element), an m5C, which may increase stability and/or may attenuate an immune response; and a 2,2,7-trimethylguanosine, which aids subcellular translocation (e.g., nuclear localization).

Different sugar modifications, nucleotide modifications, and/or internucleoside linkages (e.g., backbone structures) may exist at various positions in the circular polyribonucleotide. One of ordinary skill in the art will appreciate that the nucleotide analogs or other modification(s) may be located at any position(s) of the modified circular polyribonucleotide (e.g., a fully modified circular polyribonucleotide or a hybrid modified circular polyribonucleotide), such that the function of the modified circular polyribonucleotide is not substantially decreased. A modification may also be a non-coding region modification. The modified circular polyribonucleotide (e.g., a fully modified circular polyribonucleotide or a hybrid modified circular polyribonucleotide) may include from about 1% to about 100% modified nucleotides (either in relation to overall nucleotide content, or in relation to one or more types of nucleotide, i.e., any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, a circular polyribonucleotide is a completely modified circular polyribonucleotide or fully modified circular polyribonucleotide and comprises all or substantially all modified adenosine residues, all or substantially all modified uridine residues, all or substantially all modified guanine residues, all or substantially all modified cytidine residues, or any combination thereof. In some embodiments, a circRNA can comprise at least 10%, 20%, 30%, 40%, 50%, 60%, 70%, or 80% modified nucleotides. In some embodiments, a fully modified circRNA comprises substantially all (e.g., greater than 80%, 85%, 90%, 95%, 97%, 98%, or 99%, or about 100%) modified nucleotides. In some embodiments, the modified circular polyribonucleotide provided herein is a hybrid modified circular polyribonucleotide. A hybrid modified circular polyribonucleotide can have at least one modified nucleotide and can have a portion of contiguous unmodified nucleotides (e.g., a first portion/unmodified portion). This unmodified portion of the hybrid modified circular polyribonucleotide can have at least about 5, 10, 15, or 20 contiguous unmodified nucleotides, or any number therebetween. In some embodiments, the unmodified portion of the hybrid modified circular polyribonucleotide has at least about 30, 40, 40, 60, 70, 80, 90, 100, 110, 120, 130, 140, 150, 160, 180, 200, 220, 250, 280, 300, 320, 350, 380, 400, 420, 450, 500, 550, 600, 650, 700, 750, 800, 850, 900, or 1000 contiguous unmodified nucleotides, or any number therebetween. In some embodiments, the hybrid modified circular polyribonucleotide has 1, 2, 3, 4, 5, 6, 7, 8, 9, 10, or more unmodified portions. In some embodiments, the hybrid modified circular polyribonucleotide has at least 1, 2, 3, 4, 5, 6, 7, 8, 9, 10, 12, 15, 20, 30, 40, 50, 70, 80, 100, 120, 150, 200, 250, 300, 400, 500, 600, 700, 800, 900, 1000, or more modified nucleotides. In some embodiments, the hybrid modified circular polyribonucleotide has at least 1%, 2%, 5%, 7%, 8%, 10%, 12%, 15%, 18%, 20%, 25%, 30%, 35%, 40%, 45%, 50%, 55%, 60%, 65%, 70%, 80%, 90%, 95%, or 99% but less than 100% nucleotides that are modified. In some embodiments, the unmodified portion comprises a binding site. In some embodiments, the unmodified portion comprises a binding site configured to bind a peptide, protein, biomolecule, DNA, RNA, or a cell target. In some embodiments, the unmodified portion comprises an IRES.

In some cases, the hybrid modified circular polyribonucleotide as described herein has similar immunogenicity as compared to a corresponding circular polyribonucleotide that is otherwise the same but completely modified. For instance, a hybrid modified circular polyribonucleotide that has 5' methylcytidine and pseudouridine throughout except its IRES element can have similar immunogenicity or lower immunogenicity as compared to a corresponding circular polyribonucleotide that is otherwise the same but has 5' methylcytidine and pseudouridine throughout and no unmodified cytidine and uridine. In some embodiments, the hybrid modified circular polyribonucleotide that has 5' methylcytidine and pseudouridine throughout except its IRES element has translation efficiency that is similar to or higher than the translation efficiency of a corresponding circular polyribonucleotide that is otherwise the same but has 5' methylcytidine and pseudouridine throughout and no unmodified cytidine and uridine.

In some embodiments, the hybrid modified circular polyribonucleotide has a binding site that is unmodified, e.g., having no modified nucleotides. In some embodiments, the hybrid modified circular polyribonucleotide has a binding site configured to bind to a protein, DNA, RNA, or cell target that is unmodified, e.g., having no modified nucleotides. In some embodiments, the hybrid modified circular polyribonucleotide has an internal ribosome entry site (IRES) that is unmodified, e.g., having no modified nucleotides. In some embodiments, the hybrid modified circular polyribonucleotide has no more than 5% of the nucleotides in the internal ribosome entry site (IRES) that are modified nucleotides. In some embodiments, no nucleotides in IRES are modified. In some embodiments, no more than 0%, 1%, 2%, 3%, 4%, or 5% of nucleotides in the IRES are modified. In some embodiments, a hybrid modified circular polyribonucleotide has modified nucleotides throughout except the binding site. In some embodiments, a hybrid modified circular polyribonucleotide has modified nucleotides throughout except the binding site configured to bind a peptide, protein, biomolecule, DNA, RNA, or a cell target. In some embodiments, a hybrid modified circular polyribonucleotide has modified nucleotides throughout except the IRES element. In other embodiments, the hybrid modified circular polyribonucleotide has modified nucleotides throughout except the IRES element and one or more other portions. Without wishing to be bound by a certain theory, the unmodified IRES element renders the hybrid modified circular polyribonucleotide translation competent, e.g., having a translation efficiency for the one or more expression sequences that is similar to or higher than a corresponding circular polyribonucleotide that does not have any modified nucleotides.

In some embodiments, the modified circular polyribonucleotide (e.g., a fully modified circular polyribonucleotide or a hybrid modified circular polyribonucleotide) has a half-life of at least that of a linear counterpart, e.g., linear expression sequence, or linear circular polyribonucleotide. In some embodiments, the modified circular polyribonucleotide (e.g., a fully modified circular polyribonucleotide or a hybrid modified circular polyribonucleotide) has a half-life that is increased over that of a linear counterpart. In some embodiments, the half-life is increased by about 5%, 10%, 15%, 20%, 25%, 30%, 35%, 40%, 45%, 50%, or greater. In some embodiments, the modified circular polyribonucleotide (e.g., a fully modified circular polyribonucleotide or a hybrid modified circular polyribonucleotide) has a half-life or persistence in a cell for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the modified circular polyribonucleotide (e.g., a fully modified circular polyribonucleotide or a hybrid modified circular polyribonucleotide) has a half-life or persistence in a cell for no more than about 10 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween. In some embodiments, the modified circular polyribonucleotide (e.g., a fully modified circular polyribonucleotide or a hybrid modified circular polyribonucleotide) has a half-life or persistence in a cell while the cell is dividing. In some embodiments, the modified circular polyribonucleotide (e.g., a fully modified circular polyribonucleotide or a hybrid modified circular polyribonucleotide) has a half-life or persistence in a cell post division. In certain embodiments, the modified circular polyribonucleotide (e.g., a fully modified circular polyribonucleotide or a hybrid modified circular polyribonucleotide) has a half-life or persistence in a dividing cell for greater than about about 10 minutes to about 30 days, or at least about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

In some embodiments, the modified circular polyribonucleotide (e.g., a fully modified circular polyribonucleotide or a hybrid modified circular polyribonucleotide) comprises one or more expression sequences and is configured for persistent expression in a cell of a subject in vivo. In some embodiments, the modified circular polyribonucleotide (e.g., a fully modified circular polyribonucleotide or a hybrid modified circular polyribonucleotide) is configured such that expression of the one or more expression sequences in the cell at a later time point is equal to or higher than an earlier time point. In such embodiments, the expression of the one or more expression sequences can be either maintained at a relatively stable level or can increase over time. The expression of the expression sequences can be relatively stable for an extended period of time. For instance, in some cases, the expression of the one or more expression sequences in the cell over a time period of at least 7, 8, 9, 10, 12, 14, 16, 18, 20, 22, 23, or more days does not decrease by 50%, 45%, 40%, 35%, 30%, 25%, 20%, 15%, 10%, or 5%. In some cases, in some cases, the expression of the one or more expression sequences in the cell is maintained at a level that does not vary by more than 50%, 45%, 40%, 35%, 30%, 25%, 20%, 15%, 10%, or 5% for at least 7, 8, 9, 10, 12, 14, 16, 18, 20, 22, 23, or more days.

In some embodiments, the modified circular polyribonucleotide (e.g., a fully modified circular polyribonucleotide or a hybrid modified circular polyribonucleotide) is non-immunogenic in a mammal, e.g., a human. In some embodiments, the modified circular polyribonucleotide (e.g., a fully modified circular polyribonucleotide or a hybrid modified circular polyribonucleotide) is capable of replicating or replicates in a cell from an aquaculture animal (fish, crabs, shrimp, oysters, etc.), a mammalian cell, e.g., a cell from a pet or zoo animal (cats, dogs, lizards, birds, lions, tigers, bears, etc.), a cell from a farm or working animal (horses, cows, pigs, chickens, etc.), a human cell, cultured cells, primary cells or cell lines, stem cells, progenitor cells, differentiated cells, germ cells, cancer cells (e.g., tumorigenic, metastic), non-tumorigenic cells (normal cells), fetal cells, embryonic cells, adult cells, mitotic cells, non-mitotic cells, or any combination thereof. In some embodiments, the invention includes a cell comprising the modified circular polyribonucleotide (e.g., a fully modified circular polyribonucleotide or a hybrid modified circular polyribonucleotide) described herein, wherein the cell is a cell from an aquaculture animal (fish, crabs, shrimp, oysters, etc.), a mammalian cell, e.g., a cell from a pet or zoo animal (cats, dogs, lizards, birds, lions, tigers, bears, etc.), a cell from a farm or working animal (horses, cows, pigs, chickens, etc.), a human cell, a cultured cell, a primary cell or a cell line, a stem cell, a progenitor cell, a differentiated cell, a germ cell, a cancer cell (e.g., tumorigenic, metastic), a non-tumorigenic cell (normal cells), a fetal cell, an embryonic cell, an adult cell, a mitotic cell, a non-mitotic cell, or any combination thereof. In some embodiments, the cell is modified to comprise the modified circular polyribonucleotide (e.g., a fully modified circular polyribonucleotide or a hybrid modified circular polyribonucleotide).

In some embodiments, the modified circular polyribonucleotide (e.g., a fully modified circular polyribonucleotide or a hybrid modified circular polyribonucleotide) modulates a cellular function, e.g., transiently or long term. In certain embodiments, the cellular function is stably altered, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the cellular function is transiently altered, e.g., such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, the modified circular polyribonucleotide (e.g., a fully modified circular polyribonucleotide or a hybrid modified circular polyribonucleotide) is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides. In some embodiments, the modified circular polyribonucleotide (e.g., a fully modified circular polyribonucleotide or a hybrid modified circular polyribonucleotide) may be of a sufficient size to accommodate a binding site for a ribosome. One of skill in the art can appreciate that the maximum size of a modified circular polyribonucleotide (e.g., a fully modified circular polyribonucleotide or a hybrid modified circular polyribonucleotide) can be as large as is within the technical constraints of producing a modified circular polyribonucleotide (e.g., a fully modified circular polyribonucleotide or a hybrid modified circular polyribonucleotide), and/or using the modified circular polyribonucleotide (e.g., a fully modified circular polyribonucleotide or a hybrid modified circular polyribonucleotide). While not being bound by theory, it is possible that multiple segments of RNA may be produced from DNA and their 5' and 3' free ends annealed to produce a "string" of RNA, which ultimately may be circularized when only one 5' and one 3' free end remains. In some embodiments, the maximum size of a modified circular polyribonucleotide (e.g., a fully modified circular polyribonucleotide or a hybrid modified circular polyribonucleotide)

may be limited by the ability of packaging and delivering the RNA to a target. In some embodiments, the size of a modified circular polyribonucleotide (e.g., a fully modified circular polyribonucleotide or a hybrid modified circular polyribonucleotide) is a length sufficient to encode useful polypeptides, and thus, lengths of at least 20,000 nucleotides, at least 15,000 nucleotides, at least 10,000 nucleotides, at least 7,500 nucleotides, or at least 5,000 nucleotides, at least 4,000 nucleotides, at least 3,000 nucleotides, at least 2,000 nucleotides, at least 1,000 nucleotides, at least 500 nucleotides, at least t 400 nucleotides, at least 300 nucleotides, at least 200 nucleotides, at least 100 nucleotides may be useful.

In some embodiments, the modified circular polyribonucleotide (e.g., a fully modified circular polyribonucleotide or a hybrid modified circular polyribonucleotide) comprises one or more elements described elsewhere herein. In some embodiments, the elements may be separated from one another by a spacer sequence or linker. In some embodiments, the elements may be separated from one another by 1 ribonucleotide, 2 nucleotides, about 5 nucleotides, about 10 nucleotides, about 15 nucleotides, about 20 nucleotides, about 30 nucleotides, about 40 nucleotides, about 50 nucleotides, about 60 nucleotides, about 80 nucleotides, about 100 nucleotides, about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1,000 nucleotides, up to about 1 kb, at least about 1,000 nucleotides, any amount of nucleotides therebetween. In some embodiments, one or more elements are contiguous with one another, e.g., lacking a spacer element. In some embodiments, one or more elements in the modified circular polyribonucleotide is conformationally flexible. In some embodiments, the conformational flexibility is due to the sequence being substantially free of a secondary structure. In some embodiments, the modified circular polyribonucleotide (e.g., a fully modified circular polyribonucleotide or a hybrid modified circular polyribonucleotide) comprises a secondary or tertiary structure that accommodates one or more desired functions or characteristics described herein, e.g., accommodate a binding site for a ribosome, e.g., translation, e.g., rolling circle translation.

In some embodiments, the modified circular polyribonucleotide (e.g., a fully modified circular polyribonucleotide or a hybrid modified circular polyribonucleotide) comprises particular sequence characteristics. For example, the modified circular polyribonucleotide (e.g., a fully modified circular polyribonucleotide or a hybrid modified circular polyribonucleotide) may comprise a particular nucleotide composition. In some such embodiments, the modified circular polyribonucleotide (e.g., a fully modified circular polyribonucleotide or a hybrid modified circular polyribonucleotide) may include one or more purine rich regions (adenine or guanosine). In some such embodiments, the modified circular polyribonucleotide (e.g., a fully modified circular polyribonucleotide or a hybrid modified circular polyribonucleotide) may include one or more purine rich regions (adenine or guanosine). In some embodiments, the modified circular polyribonucleotide (e.g., a fully modified circular polyribonucleotide or a hybrid modified circular polyribonucleotide) may include one or more AU rich regions or elements (AREs). In some embodiments, the modified circular polyribonucleotide (e.g., a fully modified circular polyribonucleotide or a hybrid modified circular polyribonucleotide) may include one or more adenine rich regions.

In some embodiments, the modified circular polyribonucleotide (e.g., a fully modified circular polyribonucleotide or a hybrid modified circular polyribonucleotide) may include one or more repetitive elements described elsewhere herein.

In some embodiments, the modified circular polyribonucleotide (e.g., a fully modified circular polyribonucleotide or a hybrid modified circular polyribonucleotide) comprises one or more modifications described elsewhere herein.

The modified circular polyribonucleotide (e.g., a fully modified circular polyribonucleotide or a hybrid modified circular polyribonucleotide) may include one or more substitutions, insertions and/or additions, deletions, and covalent modifications with respect to reference sequences, in particular, the parent polyribonucleotide, are included within the scope of this invention.

Expression Sequences

Peptides or Polypeptides

In some embodiments, the modified circular polyribonucleotide (e.g., a fully modified circular polyribonucleotide or a hybrid modified circular polyribonucleotide) comprises at least one expression sequence that encodes a peptide or polypeptide. Such peptide may include, but is not limited to, small peptide, peptidomimetic (e.g., peptoid), amino acids, and amino acid analogs. The peptide may be linear or branched. Such peptide may have a molecular weight less than about 5,000 grams per mole, a molecular weight less than about 2,000 grams per mole, a molecular weight less than about 1,000 grams per mole, a molecular weight less than about 500 grams per mole, and salts, esters, and other pharmaceutically acceptable forms of such compounds. Such peptide may include, but is not limited to, a neurotransmitter, a hormone, a drug, a toxin, a viral or microbial particle, a synthetic molecule, and agonists or antagonists thereof.

The polypeptide may be linear or branched. The polypeptide may have a length from about 5 to about 40,000 amino acids, about 15 to about 35,000 amino acids, about 20 to about 30,000 amino acids, about 25 to about 25,000 amino acids, about 50 to about 20,000 amino acids, about 100 to about 15,000 amino acids, about 200 to about 10,000 amino acids, about 500 to about 5,000 amino acids, about 1,000 to about 2,500 amino acids, or any range therebetween. In some embodiments, the polypeptide has a length of less than about 40,000 amino acids, less than about 35,000 amino acids, less than about 30,000 amino acids, less than about 25,000 amino acids, less than about 20,000 amino acids, less than about 15,000 amino acids, less than about 10,000 amino acids, less than about 9,000 amino acids, less than about 8,000 amino acids, less than about 7,000 amino acids, less than about 6,000 amino acids, less than about 5,000 amino acids, less than about 4,000 amino acids, less than about 3,000 amino acids, less than about 2,500 amino acids, less than about 2,000 amino acids, less than about 1,500 amino acids, less than about 1,000 amino acids, less than about 900 amino acids, less than about 800 amino acids, less than about 700 amino acids, less than about 600 amino acids, less than about 500 amino acids, less than about 400 amino acids, less than about 300 amino acids, or less may be useful.

Some examples of a peptide or polypeptide include, but are not limited to, fluorescent tag or marker, antigen, peptide therapeutic, synthetic or analog peptide from naturally-bioactive peptide, agonist or antagonist peptide, anti-microbial peptide, pore-forming peptide, a bicyclic peptide, a targeting or cytotoxic peptide, a degradation or self-destruction peptide, and degradation or self-destruction peptides. Peptides useful in the invention described herein also include antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today: 21(7):1076-113). Such antigen binding peptides may bind a cytosolic antigen, a nuclear antigen, an intra-organellar antigen.

In some embodiments, the modified circular polyribonucleotide (e.g., a fully modified circular polyribonucleotide or a hybrid modified circular polyribonucleotide) comprises one or more RNA expression sequences, each of which may encode a polypeptide. The polypeptide may be produced in substantial amounts. As such, the polypeptide may be any proteinaceous molecule that can be produced. A polypeptide can be a polypeptide that can be secreted from a cell, or localized to the cytoplasm, nucleus or membrane compartment of a cell. Some polypeptides include, but are not limited to, at least a portion of a viral envelope protein, metabolic regulatory enzymes (e.g., that regulate lipid or steroid production), an antigen, a toleragen, a cytokine, a toxin, enzymes whose absence is associated with a disease, and polypeptides that are not active in an animal until cleaved (e.g., in the gut of an animal), and a hormone.

In some embodiments, the modified circular polyribonucleotide (e.g., a fully modified circular polyribonucleotide or a hybrid modified circular polyribonucleotide) includes an expression sequence encoding a protein, e.g., a therapeutic protein. In some embodiments, therapeutic proteins that can be expressed from the modified circular polyribonucleotide (e.g., a fully modified circular polyribonucleotide or a hybrid modified circular polyribonucleotide) disclosed herein have antioxidant activity, binding, cargo receptor activity, catalytic activity, molecular carrier activity, molecular function regulator, molecular transducer activity, nutrient reservoir activity, protein tag, structural molecule activity, toxin activity, transcription regulator activity, translation regulator activity, or transporter activity. Some examples of therapeutic proteins may include, but are not limited to, an enzyme replacement protein, a protein for supplementation, a protein vaccination, antigens (e.g., tumor antigens, viral, bacterial), hormones, cytokines, antibodies, immunotherapy (e.g., cancer), cellular reprogramming/transdifferentiation factor, transcription factors, chimeric antigen receptor, transposase or nuclease, immune effector (e.g., influences susceptibility to an immune response/signal), a regulated death effector protein (e.g., an inducer of apoptosis or necrosis), a non-lytic inhibitor of a tumor (e.g., an inhibitor of an oncoprotein), an epigenetic modifying agent, epigenetic enzyme, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis effector or inhibitor, a nuclease, a protein fragment or domain, a ligand or a receptor, and a CRISPR system or component thereof.

In some embodiments, exemplary proteins that can be expressed from the modified circular polyribonucleotide (e.g., a fully modified circular polyribonucleotide or a hybrid modified circular polyribonucleotide) disclosed herein include human proteins, for instance, receptor binding protein, hormone, growth factor, growth factor receptor modulator, and regenerative protein (e.g., proteins implicated in proliferation and differentiation, e.g., therapeutic protein, for wound healing). In some embodiments, exemplary proteins that can be expressed from the modified circular polyribonucleotide (e.g., a fully modified circular polyribonucleotide or a hybrid modified circular polyribonucleotide) disclosed herein include EGF (epithelial growth factor). In some embodiments, exemplary proteins that can be expressed from the modified circular polyribonucleotide (e.g., a fully modified circular polyribonucleotide or a hybrid modified circular polyribonucleotide) disclosed herein include enzymes, for instance, oxidoreductase enzymes, metabolic enzymes, mitochondrial enzymes, oxygenases, dehydrogenases, ATP-independent enzyme, and desaturases. In some embodiments, exemplary proteins that can be expressed from the modified circular polyribonucleotide (e.g., a fully modified circular polyribonucleotide or a hybrid modified circular polyribonucleotide) disclosed herein include an intracellular protein or cytosolic protein. In some embodiments, the modified circular polyribonucleotide (e.g., a fully modified circular polyribonucleotide or a hybrid modified circular polyribonucleotide) expresses a NanoLuc® luciferase (nLuc). In some embodiments, exemplary proteins that can be expressed from the modified circular polyribonucleotide (e.g., a fully modified circular polyribonucleotide or a hybrid modified circular polyribonucleotide) disclosed herein include a secretary protein, for instance, a secretary enzyme. In some cases, the modified circular polyribonucleotide (e.g., a fully modified circular polyribonucleotide or a hybrid modified circular polyribonucleotide) expresses a secretary protein that can have a short half-life therapeutic in the blood, or can be a protein with a subcellular localization signal, or protein with secretory signal peptide. In some embodiments, the modified circular polyribonucleotide (e.g., a fully modified circular polyribonucleotide or a hybrid modified circular polyribonucleotide) expresses a *Gaussia* Luciferase (gLuc). In some cases, the modified circular polyribonucleotide (e.g., a fully modified circular polyribonucleotide or a hybrid modified circular polyribonucleotide) expresses a non-human protein, for instance, a fluorescent protein, an energy-transfer acceptor, or a protein-tag like Flag, Myc, or His. In some embodiments, exemplary proteins that can be expressed from the modified circular polyribonucleotide (e.g., a fully modified circular polyribonucleotide or a hybrid modified circular polyribonucleotide) include a GFP. In some embodiments, the modified circular polyribonucleotide (e.g., a fully modified circular polyribonucleotide or a hybrid modified circular polyribonucleotide) expresses tagged proteins, e.g., fusion proteins or engineered proteins containing a protein tage, e.g., chitin binding protein (CBP), maltose binding protein (MBP), Fc tag, glutathione-S-transferase (GST), AviTag (GLNDIFEAQKIEWHE (SEQ ID NO: 86)), Calmodulin-tag (KRRWKKNFIAVSAANRFKKISSSGAL (SEQ ID NO: 87)); polyglutamate tag (EEEEEE (SEQ ID NO: 88)); E-tag (GAPVPYPDPLEPR (SEQ ID NO: 89)); FLAG-tag (DYKDDDDK (SEQ ID NO: 90)), HA-tag (YPYDVPDYA (SEQ ID NO: 91)); His-tag (HHHHHH (SEQ ID NO: 92)); Myc-tag (EQKLISEEDL (SEQ ID NO: 93)); NE-tag (TKENPRSNQEESYDDNES (SEQ ID NO: 94)); S-tag (KETAAAKFERQHMDS (SEQ ID NO: 95)); SBP-tag (MDEKTTGWRGGHVVEGLAGELEQLRARLEHHPQGQREP (SEQ ID NO: 96)); Softag 1 (SLAELLNAGLGGS (SEQ IDN O: 97)); Softag 3 (TQDPSRVG (SEQ ID NO: 98)); Spot-tag (PDRVRAVSHWSS (SEQ ID NO: 99)); Strep-tag (Strep-tag II: WSHPQFEK (SEQ ID NO: 100)); TC tag (CCPGCC (SEQ ID NO: 101)); Ty tag (EVHTNQDPLD (SEQ ID NO: 102)); V5 tag (GKPIPNPLLGLDST (SEQ ID NO: 103)); VSV-tag (YTDIEMNRLGK (SEQ ID NO: 104)); or Xpress tag (DLYDDDDK (SEQ ID NO: 105)).

In some embodiments, the modified circular polyribonucleotide (e.g., a fully modified circular polyribonucleotide or a hybrid modified circular polyribonucleotide) expresses an antibody, e.g., an antibody fragment, or a portion thereof. In some embodiments, the antibody expressed by the modified circular polyribonucleotide (e.g., a fully modified circular polyribonucleotide or a hybrid modified circular polyribonucleotide) can be of any isotype, such as IgA, IgD, IgE, IgG, IgM. In some embodiments, the modified circular polyribonucleotide (e.g., a fully modified circular polyribonucleotide or a hybrid modified circular polyribonucleotide) expresses a portion of an antibody, such as a light chain, a heavy chain, a Fc fragment, a CDR (complementary determining region), a Fv fragment, or a Fab fragment, a further portion thereof. In some embodiments, the modified circular polyribonucleotide (e.g., a fully modified circular polyribonucleotide or a hybrid modified circular polyribonucleotide) expresses one or more portions of an antibody. For instance, the modified circular polyribonucleotide (e.g., a fully modified circular polyribonucleotide or a hybrid modified circular polyribonucleotide) can comprise more than one expression sequence, each of which expresses a portion of an antibody, and the sum of which can constitute the antibody. In some cases, the modified circular polyribonucleotide (e.g., a fully modified circular polyribonucleotide or a hybrid modified circular polyribonucleotide) comprises one expression sequence coding for the heavy chain of an antibody, and another expression sequence coding for the light chain of the antibody. In some cases, when the modified circular polyribonucleotide (e.g., a fully modified circular polyribonucleotide or a hybrid modified circular polyribonucleotide) is expressed in a cell or a a cell-free environment, the light chain and heavy chain can be subject to appropriate modification, folding, or other post-translation modification to form a functional antibody.

Regulatory Elements

In some embodiments, the modified circular polyribonucleotide (e.g., a fully modified circular polyribonucleotide or a hybrid modified circular polyribonucleotide) comprises a regulatory element, e.g., a sequence that modifies expression of an expression sequence within the modified circular polyribonucleotide.

A regulatory element may include a sequence that is located adjacent to an expression sequence that encodes an expression product. A regulatory element may be linked operatively to the adjacent sequence. A regulatory element may increase an amount of product expressed as compared to an amount of the expressed product when no regulatory element exists. In addition, one regulatory element can increase an amount of products expressed for multiple expression sequences attached in tandem. Hence, one regulatory element can enhance the expression of one or more expression sequences. Multiple regulatory element are well-known to persons of ordinary skill in the art.

A regulatory element as provided herein can include a selective translation sequence. As used herein, the term "selective translation sequence" can refer to a nucleic acid sequence that selectively initiates or activates translation of an expression sequence in the modified circular polyribonucleotide, for instance, certain riboswtich aptazymes. A regulatory element can also include a selective degradation sequence. As used herein, the term "selective degradation sequence" can refer to a nucleic acid sequence that initiates degradation of the modified circular polyribonucleotide, or an expression product of the modified circular polyribonucleotide. Exemplary selective degradation sequence can include riboswitch aptazymes and miRNA binding sites.

In some embodiments, the regulatory element is a translation modulator. A translation modulator can modulate translation of the expression sequence in the modified circular polyribonucleotide. A translation modulator can be a translation enhancer or suppressor. In some embodiments, the modified circular polyribonucleotide (e.g., a fully modified circular polyribonucleotide or a hybrid modified circular polyribonucleotide) includes at least one translation modulator adjacent to at least one expression sequence. In some embodiments, the modified circular polyribonucleotide (e.g., a fully modified circular polyribonucleotide or a hybrid modified circular polyribonucleotide) includes a translation modulator adjacent each expression sequence. In some embodiments, the translation modulator is present on one or both sides of each expression sequence, leading to separation of the expression products, e.g., peptide(s) and or polypeptide(s).

In some embodiments, a translation initiation sequence can function as a regulatory element. In some embodiments, a translation initiation sequence comprises an AUG codon. In some embodiments, a translation initiation sequence comprises any eukaryotic start codon such as AUG, CUG, GUG, UUG, ACG, AUC, AUU, AAG, AUA, or AGG. In some embodiments, a translation initiation sequence comprises a Kozak sequence. In some embodiments, translation begins at an alternative translation initiation sequence, e.g., translation initiation sequence other than AUG codon, under selective conditions, e.g., stress induced conditions. As a non-limiting example, the translation of the modified circular polyribonucleotide (e.g., a fully modified circular polyribonucleotide or a hybrid modified circular polyribonucleotide) may begin at alternative translation initiation sequence, such as ACG. As another non-limiting example, the modified circular polyribonucleotide (e.g., a fully modified circular polyribonucleotide or a hybrid modified circular polyribonucleotide) translation may begin at alternative translation initiation sequence, CTG/CUG. As yet another non-limiting example, the modified circular polyribonucleotide (e.g., a fully modified circular polyribonucleotide or a hybrid modified circular polyribonucleotide) translation may begin at alternative translation initiation sequence, GTG/GUG. As yet another non-limiting example, the modified circular polyribonucleotide (e.g., a fully modified circular polyribonucleotide or a hybrid modified circular polyribonucleotide) may begin translation at a repeat-associated non-AUG (RAN) sequence, such as an alternative translation initiation sequence that includes short stretches of repetitive RNA, e.g., CGG, GGGGCC, CAG, CTG.

Nucleotides flanking a codon that initiates translation, such as, but not limited to, a start codon or an alternative start codon, are known to affect the translation efficiency, the length and/or the structure of the modified circular polyribonucleotide. (See e.g., Matsuda and Mauro PLoS ONE, 2010 5: 11; the contents of which are herein incorporated by reference in its entirety). Masking any of the nucleotides flanking a codon that initiates translation may be used to alter the position of translation initiation, translation efficiency, length and/or structure of the modified circular polyribonucleotide.

In one embodiment, a masking agent may be used near the start codon or alternative start codon in order to mask or hide the codon to reduce the probability of translation initiation at the masked start codon or alternative start codon. Non-limiting examples of masking agents include antisense locked nucleic acids (LNA) oligonucleotides and exon-junction complexes (EJCs). (See e.g., Matsuda and Mauro describing masking agents LNA oligonucleotides and EJCs (PLoS ONE, 2010 5: 11); the contents of which are herein incorporated by reference in its entirety). In another embodiment, a masking agent may be used to mask a start codon of the modified circular polyribonucleotide (e.g., a fully modified circular polyribonucleotide or a hybrid modified circular polyribonucleotide) in order to increase the likelihood that translation will initiate at an alternative start codon.

In some embodiments, translation is initiated under selective conditions, such as but not limited to viral induced selection in the presence of GRSF-1 and the modified circular polyribonucleotide (e.g., a fully modified circular polyribonucleotide or a hybrid modified circular polyribonucleotide) includes GRSF-1 binding sites, see for example, Kash et al. J Virol 76:20, 10417-10426 (2002).

Translation Initiation Sequence

In some embodiments, the modified circular polyribonucleotide (e.g., a fully modified circular polyribonucleotide or a hybrid modified circular polyribonucleotide) encodes a polypeptide and may comprise a translation initiation sequence, e.g, a start codon. In some embodiments, the translation initiation sequence includes a Kozak or Shine-Dalgarno sequence. In some embodiments, the modified circular polyribonucleotide (e.g., a fully modified circular polyribonucleotide or a hybrid modified circular polyribonucleotide) includes the translation initiation sequence, e.g., Kozak sequence, adjacent to an expression sequence. In some embodiments, the translation initiation sequence is a non-coding start codon. In some embodiments, the translation initiation sequence, e.g., Kozak sequence, is present on one or both sides of each expression sequence, leading to separation of the expression products. In some embodiments, the modified circular polyribonucleotide (e.g., a fully modified circular polyribonucleotide or a hybrid modified circular polyribonucleotide) includes at least one translation initiation sequence adjacent to an expression sequence. In some embodiments, the translation initiation sequence provides conformational flexibility to the modified circular polyribonucleotide. In some embodiments, the translation initiation sequence is within a substantially single stranded region of the modified circular polyribonucleotide.

The modified circular polyribonucleotide (e.g., a fully modified circular polyribonucleotide or a hybrid modified circular polyribonucleotide) may include more than 1 start codon such as, but not limited to, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 50, at least 60 or more than 60 start codons. Translation may initiate on the first start codon or may initiate downstream of the first start codon.

In some embodiments, the modified circular polyribonucleotide (e.g., a fully modified circular polyribonucleotide or a hybrid modified circular polyribonucleotide) may initiate at a codon which is not the first start codon, e.g., AUG. Translation of the modified circular polyribonucleotide (e.g., a fully modified circular polyribonucleotide or a hybrid modified circular polyribonucleotide) may initiate at an alternative translation initiation sequence, such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5: 11; the contents of each of which are herein incorporated by reference in their entireties). In some embodiments, translation begins at an alternative translation initiation sequence under selective conditions, e.g., stress induced conditions. As a non-limiting example, the translation of the modified circular polyribonucleotide (e.g., a fully modified circular polyribonucleotide or a hybrid modified circular polyribonucleotide) may begin at alternative translation initiation sequence, such as ACG. As another non-limiting example, the modified circular polyribonucleotide (e.g., a fully modified circular polyribonucleotide or a hybrid modified circular polyribonucleotide) translation may begin at alternative translation initiation sequence, CTG/CUG. As yet another non-limiting example, the modified circular polyribonucleotide (e.g., a fully modified circular polyribonucleotide or a hybrid modified circular polyribonucleotide) translation may begin at alternative translation initiation sequence, GTG/GUG. As yet another non-limiting example, the modified circular polyribonucleotide (e.g., a fully modified circular polyribonucleotide or a hybrid modified circular polyribonucleotide) may begin translation at a repeat-associated non-AUG (RAN) sequence, such as an alternative translation initiation sequence that includes short stretches of repetitive RNA e.g. CGG, GGGGCC, CAG, CTG.

In some embodiments, translation is initiated by eukaryotic initiation factor 4A (eIF4A) treatment with Rocaglates (translation is repressed by blocking 43S scanning, leading to premature, upstream translation initiation and reduced protein expression from transcripts bearing the RocA-eIF4A target sequence, see for example, Iwasaki et al. *Nature* 534, 558-561 (2016).

IRES

In some embodiments, the modified circular polyribonucleotide (e.g., a fully modified circular polyribonucleotide or a hybrid modified circular polyribonucleotide) described herein comprises an internal ribosome entry site (IRES) element. A suitable IRES element to include in a modified circular polyribonucleotide (e.g., a fully modified circular polyribonucleotide or a hybrid modified circular polyribonucleotide) comprises an RNA sequence capable of engaging an eukaryotic ribosome. In some embodiments, the IRES element is at least about 5 nt, at least about 8 nt, at least about 9 nt, at least about 10 nt, at least about 15 nt, at least about 20 nt, at least about 25 nt, at least about 30 nt, at least about 40 nt, at least about 50 nt, at least about 100 nt, at least about 200 nt, at least about 250 nt, at least about 350 nt, or at least about 500 nt. In one embodiment, the IRES element is derived from the DNA of an organism including, but not limited to, a virus, a mammal, and a *Drosophila*. Such viral DNA may be derived from, but is not limited to, picornavirus complementary DNA (cDNA), with encephalomyocarditis virus (EMCV) cDNA and poliovirus cDNA. In one embodiment, *Drosophila* DNA from which an IRES element is derived includes, but is not limited to, an Antennapedia gene from *Drosophila melanogaster.*

In some embodiments, the IRES element is at least partially derived from a virus, for instance, it can be derived from a viral IRES element, such as ABPV_IGRpred, AEV, ALPV_IGRpred, BQCV_IGRpred, BVDV1_1-385, BVDV1_29-391, CrPV_5NCR, CrPV_IGR, crTMV_IREScp, crTMV_IRESmp75, crTMV_IRESmp228, crTMV_IREScp, crTMV_IREScp, CSFV, CVB3, DCV_IGR, EMCV-R, EoPV_5NTR, ERAV_245-961, ERBV_162-920, EV71_1-748, FeLV-Notch2, FMDV_type_C, GBV-A, GBV-B, GBV-C, gypsy_env, gypsyD5, gypsyD2, HAV_HM175, HCV_type_1a, HiPV_IGRpred, HIV-1, HoCV1_IGRpred, HRV-2, IAPV_IGRpred, idefix, KBV_IGRpred, LINE-1_ORFI_-101_to_-1, LINE-1_ORF1_-302_to_-202, LINE-1_ORF2_-138_to_-86, LINE-1_ORF1_-44_to_-1, PSIV_IGR, PV_typel_Mahoney, PV_type3_Leon, REV-A, RhPV_5NCR, RhPV_IGR, SINV1_IGRpred, SV40_661-830, TMEV, TMV_UI_IRESmp228, TRV_5NTR, TrV_IGR, or TSV_IGR. In some embodiments, the IRES element is at least partially derived from a cellular IRES, such as AML1/RUNX1, Antp-D, Antp-DE, Antp-CDE, Apaf-1, Apaf-1, AQP4, AT1R_varl, AT1R_var2, AT1R_var3, AT1R_var4, BAG1_p36delta236 nt, BAG1_p36, BCL2, BiP_-222-3, c-IAP1_285-1399, c-IAP1_1313-1462, c-jun, c-myc, Cat-1_224, CCND1, DAP5, eIF4G, eIF4GI-ext, eIF4GII, eIF4GII-long, ELG1, ELH, FGF1A, FMR1, Gtx-133-141, Gtx-1-166, Gtx-1-120, Gtx-1-196, hairless, HAP4, HIF1a, hSNMI, Hsp101, hsp70, hsp70, Hsp90, IGF2_leader2, Kv1.4_1.2, L-myc, LamB1_-335_-1, LEF1, MNT_75-267, MNT_36-160, MTG8a, MYB, MYT2_997-1152, n-MYC, NDST1, NDST2, NDST3, NDST4L, NDST4S, NRF_-653_-17, NtHSF1, ODC1, p27kip1, p53_128-269, PDGF2/c-sis, Pim-1, PITSLRE_p58, Rbm3, reaper, Scamper, TFIID, TIF4631, Ubx_1-966, Ubx_373-961, UNR, Ure2, UtrA, VEGF-A_-133-1, XIAP_5-464, XIAP_305-466, or YAP1. In some embodiments, the IRES element comprises a synthetic IRES, for instance, (GAAA)16, (PPT19)4, KMI1, KMI1, KMI2, KMI2, KMIX, X1, or X2.

In some embodiments, the modified circular polyribonucleotide (e.g., a fully modified circular polyribonucleotide or a hybrid modified circular polyribonucleotide) includes at least one IRES flanking at least one (e.g., 2, 3, 4, 5, or more) expression sequence. In some embodiments, the IRES flanks both sides of at least one (e.g., 2, 3, 4, 5, or more) expression sequence. In some embodiments, the modified circular polyribonucleotide (e.g., a fully modified circular polyribonucleotide or a hybrid modified circular polyribonucleotide) includes one or more IRES sequences on one or both sides of each expression sequence, leading to separation of the resulting peptide(s) and or polypeptide(s).

Termination Element

In some embodiments, the modified circular polyribonucleotide (e.g., a fully modified circular polyribonucleotide or a hybrid modified circular polyribonucleotide) includes one or more expression sequences and each expression sequence may or may not have a termination element. In some embodiments, the modified circular polyribonucleotide (e.g., a fully modified circular polyribonucleotide or a hybrid modified circular polyribonucleotide) includes one or more expression sequences and the expression sequences lack a termination element, such that the modified circular polyribonucleotide (e.g., a fully modified circular polyribonucleotide or a hybrid modified circular polyribonucleotide) is continuously translated. Exclusion of a termination element may result in rolling circle translation or continuous expression of expression product, e.g., peptides or polypeptides, due to lack of ribosome stalling or fall-off. In such an embodiment, rolling circle translation expresses a continuous expression product through each expression sequence. In some other embodiments, a termination element of an expression sequence can be part of a stagger element. In some embodiments, one or more expression sequences in the modified circular polyribonucleotide (e.g., a fully modified circular polyribonucleotide or a hybrid modified circular polyribonucleotide) comprises a termination element. However, rolling circle translation or expression of a succeeding (e.g., second, third, fourth, fifth, etc.) expression sequence in the modified circular polyribonucleotide (e.g., a fully modified circular polyribonucleotide or a hybrid modified circular polyribonucleotide) is performed. In such instances, the expression product may fall off the ribosome when the ribosome encounters the termination element, e.g., a stop codon, and terminates translation. In some embodiments, translation is terminated while the ribosome, e.g., at least one subunit of the ribosome, remains in contact with the modified circular polyribonucleotide.

In some embodiments, the modified circular polyribonucleotide (e.g., a fully modified circular polyribonucleotide or a hybrid modified circular polyribonucleotide) includes a termination element at the end of one or more expression sequences. In some embodiments, one or more expression sequences comprises two or more termination elements in succession. In such embodiments, translation is terminated and rolling circle translation is terminated. In some embodiments, the ribosome completely disengages with the modified circular polyribonucleotide. In some such embodiments, production of a succeeding (e.g., second, third, fourth, fifth, etc.) expression sequence in the modified circular polyribonucleotide (e.g., a fully modified circular polyribonucleotide or a hybrid modified circular polyribonucleotide) may require the ribosome to reengage with the modified circular polyribonucleotide (e.g., a fully modified circular polyribonucleotide or a hybrid modified circular polyribonucleotide) prior to initiation of translation. Generally, termination elements include an in-frame nucleotide triplet that signals termination of translation, e.g., UAA, UGA, UAG. In some embodiments, one or more termination elements in the modified circular polyribonucleotide (e.g., a fully modified circular polyribonucleotide or a hybrid modified circular polyribonucleotide) are frame-shifted termination elements, such as but not limited to, off-frame or −1 and +1 shifted reading frames (e.g., hidden stop) that may terminate translation. Frame-shifted termination elements include nucleotide triples, TAA, TAG, and TGA that appear in the second and third reading frames of an expression sequence. Frame-shifted termination elements may be important in preventing misreads of mRNA, which is often detrimental to the cell.

Stagger Element

In some embodiments, the modified circular polyribonucleotide (e.g., a fully modified circular polyribonucleotide or a hybrid modified circular polyribonucleotide) includes at least one stagger element adjacent to an expression sequence. In some embodiments, the modified circular polyribonucleotide (e.g., a fully modified circular polyribonucleotide or a hybrid modified circular polyribonucleotide) includes a stagger element adjacent to each expression sequence. In some embodiments, the stagger element is present on one or both sides of each expression sequence, leading to separation of the expression products, e.g., peptide(s) and or polypeptide(s). In some embodiments, the stagger element is a portion of the one or more expression sequences. In some embodiments, the modified circular polyribonucleotide (e.g., a fully modified circular polyribonucleotide or a hybrid modified circular polyribonucleotide) comprises one or more expression sequences, and each of the one or more expression sequences is separated from a succeeding expression sequence by a stagger element on the modified circular polyribonucleotide. In some embodiments, the stagger element prevents generation of a single polypeptide (a) from two rounds of translation of a single expression sequence or (b) from one or more rounds of translation of two or more expression sequences. In some embodiments, the stagger element is a sequence separate from the one or more expression sequences. In some embodiments, the stagger element comprises a portion of an expression sequence of the one or more expression sequences.

In some embodiments, the modified circular polyribonucleotide (e.g., a fully modified circular polyribonucleotide or a hybrid modified circular polyribonucleotide) includes a stagger element. To avoid production of a continuous expression product, e.g., peptide or polypeptide, while maintaining rolling circle translation, a stagger element may be included to induce ribosomal pausing during translation. In some embodiments, the stagger element is at 3' end of at least one of the one or more expression sequences. The stagger element can be configured to stall a ribosome during rolling circle translation of the modified circular polyribonucleotide. The stagger element may include, but is not limited to a 2A-like, or CHYSEL (cis-acting hydrolase element) sequence. In some embodiments, the stagger element encodes a sequence with a C-terminal consensus sequence that is $X_1X_2X_3EX_5NPGP$, where $X_1$ is absent or G or H, $X_2$ is absent or D or G, $X_3$ is D or V or I or S or M, and $X_5$ is any amino acid (SEQ ID NO: 108). In some embodiments, this sequence comprises a non-conserved sequence of amino-acids with a strong alpha-helical propensity followed by the consensus sequence -D(V/I)ExNPG P, where x=any amino acid (SEQ ID NO: 65). Some nonlimiting examples of stagger elements includes GDVESNPGP (SEQ ID NO: 67), GDIEENPGP (SEQ ID NO: 68), VEPNPGP (SEQ ID NO: 69), IETNPGP (SEQ ID NO: 70), GDIESNPGP (SEQ ID NO: 71), GDVELNPGP (SEQ ID NO: 72), GDIETNPGP (SEQ ID NO: 73), GDVENPGP (SEQ ID NO: 74), GDVEENPGP (SEQ ID NO: 75), GDVEQNPGP (SEQ ID NO: 76), IESNPGP (SEQ ID NO: 77), GDIELNPGP (SEQ ID NO: 78), HDIETNPGP (SEQ ID NO: 79), HDVETNPGP (SEQ ID NO: 80), HDVEMNPGP (SEQ ID NO: 81), GDMESNPGP (SEQ ID NO: 82), GDVETNPGP (SEQ ID NO: 83), GDIEQNPGP (SEQ ID NO: 84), and DSEFNPGP (SEQ ID NO: 85).

In some embodiments, the stagger element described herein cleaves an expression product, such as between G and P of the consensus sequence described herein. As one non-limiting example, the modified circular polyribonucleotide (e.g., a fully modified circular polyribonucleotide or a hybrid modified circular polyribonucleotide) includes at least one stagger element to cleave the expression product. In some embodiments, the modified circular polyribonucleotide (e.g., a fully modified circular polyribonucleotide or a hybrid modified circular polyribonucleotide) includes a stagger element adjacent to at least one expression sequence. In some embodiments, the modified circular polyribonucleotide (e.g., a fully modified circular polyribonucleotide or a hybrid modified circular polyribonucleotide) includes a stagger element after each expression sequence. In some embodiments, the modified circular polyribonucleotide (e.g., a fully modified circular polyribonucleotide or a hybrid modified circular polyribonucleotide) includes a stagger element is present on one or both sides of each expression sequence, leading to translation of individual peptide(s) and or polypeptide(s) from each expression sequence.

In some embodiments, a stagger element comprises one or more modified nucleotides or unnatural nucleotides that induce ribosomal pausing during translation. Unnatural nucleotides may include peptide nucleic acid (PNA), Morpholino and locked nucleic acid (LNA), as well as glycol nucleic acid (GNA) and threose nucleic acid (TNA). Examples such as these are distinguished from naturally occurring DNA or RNA by changes to the backbone of the molecule. Exemplary modifications can include any modification to the sugar, the nucleobase, the internucleoside linkage (e.g. to a linking phosphate/to a phosphodiester linkage/to the phosphodiester backbone), and any combination thereof that can induce ribosomal pausing during translation. Some of the exemplary modifications provided herein are described elsewhere herein.

In some embodiments, the stagger element is present in the modified circular polyribonucleotide (e.g., a fully modified circular polyribonucleotide or a hybrid modified circular polyribonucleotide) in other forms. For example, in some exemplary modified circular polyribonucleotides, a stagger element comprises a termination element of a first expression sequence in the modified circular polyribonucleotide, and a nucleotide spacer sequence that separates the termination element from a first translation initiation sequence of an expression succeeding the first expression sequence. In some examples, the first stagger element of the first expression sequence is upstream of (5' to) a first translation initiation sequence of the expression succeeding the first expression sequence in the modified circular polyribonucleotide. In some cases, the first expression sequence and the expression sequence succeeding the first expression sequence are two separate expression sequences in the modified circular polyribonucleotide. The distance between the first stagger element and the first translation initiation sequence can enable continuous translation of the first expression sequence and its succeeding expression sequence. In some embodiments, the first stagger element comprises a termination element and separates an expression product of the first expression sequence from an expression product of its succeeding expression sequences, thereby creating discrete expression products. In some cases, the modified circular polyribonucleotide (e.g., a fully modified circular polyribonucleotide or a hybrid modified circular polyribonucleotide) comprising the first stagger element upstream of the first translation initiation sequence of the succeeding sequence in the modified circular polyribonucleotide (e.g., a fully modified circular polyribonucleotide or a hybrid modified circular polyribonucleotide) is continuously translated, while a corresponding modified circular polyribonucleotide (e.g., a fully modified circular polyribonucleotide or a hybrid modified circular polyribonucleotide) comprising a stagger element of a second expression sequence that is upstream of a second translation initiation sequence of an expression sequence succeeding the second expression sequence is not continuously translated. In some cases, there is only one expression sequence in the modified circular polyribonucleotide, and the first expression sequence and its succeeding expression sequence are the same expression sequence. In some exemplary modified circular polyribonucleotides, a stagger element comprises a first termination element of a first expression sequence in the modified circular polyribonucleotide, and a nucleotide spacer sequence that separates the termination element from a downstreamn translation initiation sequence. In some such examples, the first stagger element is upstream of (5' to) a first translation initiation sequence of the first expression sequence in the modified circular polyribonucleotide. In some cases, the distance between the first stagger element and the first translation initiation sequence enables continuous translation of the first expression sequence and any succeeding expression sequences. In some embodiments, the first stagger element separates one round expression product of the first expression sequence from the next round expression product of the first expression sequences, thereby creating discrete expression products. In some cases, the modified circular polyribonucleotide (e.g., a fully modified circular polyribonucleotide or a hybrid modified circular polyribonucleotide) comprising the first stagger element upstream of the first translation initiation sequence of the first expression sequence in the modified circular polyribonucleotide (e.g., a fully modified circular polyribonucleotide or a hybrid modified circular polyribonucleotide) is continuously translated, while a corresponding modified circular polyribonucleotide (e.g., a fully modified circular polyribonucleotide or a hybrid modified circular polyribonucleotide) comprising a stagger element upstream of a second translation initiation sequence of a second expression sequence in the corresponding modified circular polyribonucleotide (e.g., a fully modified circular polyribonucleotide or a hybrid modified circular polyribonucleotide) is not continuously translated. In some cases, the distance between the second stagger element and the second translation initiation sequence is at least 2×, 3×, 4×, 5×, 6×, 7×, 8×, 9×, or 10× greater in the corresponding modified circular polyribonucleotide (e.g., a fully modified circular polyribonucleotide or a hybrid modified circular polyribonucleotide) than a distance between the first stagger element and the first translation initiation in the modified circular polyribonucleotide. In some cases, the distance between the first stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater. In some embodiments, the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the first stagger element and the first translation initiation. In some embodiments, the modified circular polyribonucleotide (e.g., a fully modified circular polyribonucleotide or a hybrid modified circular polyribonucleotide) comprises more than one expression sequence.

Regulatory Nucleic Acids

In some embodiments, the modified circular polyribonucleotide (e.g., a fully modified circular polyribonucleotide or a hybrid modified circular polyribonucleotide) comprises one or more expression sequences that encode regulatory nucleic acid, e.g., that modifies expression of an endogenous gene and/or an exogenous gene. In some embodiments, the expression sequence of a modified circular polyribonucleotide (e.g., a fully modified circular polyribonucleotide or a hybrid modified circular polyribonucleotide) as provided herein can comprise a sequence that is antisense to a regulatory nucleic acid like a non-coding RNA, such as, but not limited to, tRNA, lncRNA, miRNA, rRNA, snRNA, microRNA, siRNA, piRNA, snoRNA, snRNA, exRNA, scaRNA, Y RNA, and hnRNA.

In one embodiment, the regulatory nucleic acid targets a host gene. The regulatory nucleic acids may include, any of the regulatory nucleic acids described in [0177] and [0181]-[0189] of International Patent Publication No. WO2019118919A1, which is incorporated herein by reference in its entirety.

In some embodiments, the modified circular polyribonucleotide (e.g., a fully modified circular polyribonucleotide or a hybrid modified circular polyribonucleotide) comprises a regulatory nucleic acid, such as a guide RNA (gRNA). In some embodiments, the modified circular polyribonucleotide (e.g., a fully modified circular polyribonucleotide or a hybrid modified circular polyribonucleotide) comprises a guide RNA or encodes the guide RNA. A gRNA short synthetic RNA composed of a "scaffold" sequence necessary for binding to the incomplete effector moiety and a user-defined ~20 nucleotide targeting sequence for a genomic target. In practice, guide RNA sequences are generally designed to have a length of between 17-24 nucleotides (e.g., 19, 20, or 21 nucleotides) and complementary to the targeted nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991.

The gRNA may recognize specific DNA sequences (e.g., sequences adjacent to or within a promoter, enhancer, silencer, or repressor of a gene).

In one embodiment, the gRNA is used as part of a CRISPR system for gene editing. For the purposes of gene editing, the modified circular polyribonucleotide (e.g., a fully modified circular polyribonucleotide or a hybrid modified circular polyribonucleotide) may be designed to include one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence are required by Cas9 for DNA cleavage to occur; for Cpf1 at least about 16 nucleotides of gRNA sequence is needed to achieve detectable DNA cleavage.

The modified circular polyribonucleotide (e.g., a fully modified circular polyribonucleotide or a hybrid modified circular polyribonucleotide) may modulate expression of RNA encoded by a gene. Because multiple genes can share some degree of sequence homology with each other, in some embodiments, the modified circular polyribonucleotide (e.g., a fully modified circular polyribonucleotide or a hybrid modified circular polyribonucleotide) can be designed to target a class of genes with sufficient sequence homology. In some embodiments, the modified circular polyribonucleotide (e.g., a fully modified circular polyribonucleotide or a hybrid modified circular polyribonucleotide) can contain a sequence that has complementarity to sequences that are shared amongst different gene targets or are unique for a specific gene target. In some embodiments, the modified circular polyribonucleotide (e.g., a fully modified circular polyribonucleotide or a hybrid modified circular polyribonucleotide) can be designed to target conserved regions of an RNA sequence having homology between several genes thereby targeting several genes in a gene family (e.g., different gene isoforms, splice variants, mutant genes, etc.). In some embodiments, the modified circular polyribonucleotide (e.g., a fully modified circular polyribonucleotide or a hybrid modified circular polyribonucleotide) can be designed to target a sequence that is unique to a specific RNA sequence of a single gene.

In some embodiments, the expression sequence has a length less than 5000 bps (e.g., less than about 5000 bps, 4000 bps, 3000 bps, 2000 bps, 1000 bps, 900 bps, 800 bps, 700 bps, 600 bps, 500 bps, 400 bps, 300 bps, 200 bps, 100 bps, 50 bps, 40 bps, 30 bps, 20 bps, 10 bps, or less). In some embodiments, the expression sequence has, independently or in addition to, a length greater than 10 bps (e.g., at least about 10 bps, 20 bps, 30 bps, 40 bps, 50 bps, 60 bps, 70 bps, 80 bps, 90 bps, 100 bps, 200 bps, 300 bps, 400 bps, 500 bps, 600 bps, 700 bps, 800 bps, 900 bps, 1000 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4 kb, 4.1 kb, 4.2 kb, 4.3 kb, 4.4 kb, 4.5 kb, 4.6 kb, 4.7 kb, 4.8 kb, 4.9 kb, 5 kb, or greater).

In some embodiments, the expression sequence comprises one or more of the features described herein, e.g., a sequence encoding one or more peptides or proteins, one or more regulatory element, one or more regulatory nucleic acids, e.g., one or more non-coding RNAs, other expression sequences, and any combination thereof.

Translation Efficiency

In some embodiments, the translation efficiency of a modified circular polyribonucleotide (e.g., a fully modified circular polyribonucleotide or a hybrid modified circular polyribonucleotide) as provided herein is greater than a reference, e.g., a linear counterpart, a linear expression sequence, a linear modified circular polyribonucleotide, or a fully modified circular polyribonucleotide counterpart. In some embodiments, a modified circular polyribonucleotide (e.g., a fully modified circular polyribonucleotide or a hybrid modified circular polyribonucleotide) as provided herein has the translation efficiency that is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than that of a reference. In some embodiments, a modified circular polyribonucleotide (e.g., a fully modified circular polyribonucleotide or a hybrid modified circular polyribonucleotide) has a translation efficiency 10% greater than that of a linear counterpart. In some embodiments, a modified circular polyribonucleotide (e.g., a fully modified circular polyribonucleotide or a hybrid modified circular polyribonucleotide) has a translation efficiency 300% greater than that of a linear counterpart. In some embodiments, a hybrid modified circular polyribonucleotide has a translation efficiency 10% greater than that of a fully modified circular polyribonucleotide counterpart. In some embodiments, a hybrid modified circular polyribonucleotide has a translation efficiency 300% greater than that of a fully modified circular polyribonucleotide counterpart. In some embodiments, a hybrid modified circular polyribonucleotide has a translation efficiency that is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than that of a corresponding circular polyribonucleotide. In some embodiments, a hybrid modified circular polyribonucleotide has a translation efficiency that is at least about 10% than that of a corresponding circular polyribonucleotide. In some embodiments, a hybrid modified circular polyribonucleotide has a translation efficiency that is at least about 20% than that of a corresponding circular polyribonucleotide. In some embodiments, a hybrid modified circular polyribonucleotide has a translation efficiency that is at least about 50% than that of a corresponding circular polyribonucleotide.

In some embodiments, the modified circular polyribonucleotide (e.g., a fully modified circular polyribonucleotide or a hybrid modified circular polyribonucleotide) produces stoichiometric ratios of expression products. Rolling circle translation continuously produces expression products at substantially equivalent ratios. In some embodiments, the modified circular polyribonucleotide (e.g., a fully modified circular polyribonucleotide or a hybrid modified circular polyribonucleotide) has a stoichiometric translation efficiency, such that expression products are produced at substantially equivalent ratios. In some embodiments, the modified circular polyribonucleotide (e.g., a fully modified circular polyribonucleotide or a hybrid modified circular polyribonucleotide) has a stoichiometric translation efficiency of multiple expression products, e.g., products from 2, 3, 4, 5, 6, 7, 8, 9, 10, 11, 12, or more expression sequences.

Rolling Circle Translation

In some embodiments, once translation of the modified circular polyribonucleotide (e.g., a fully modified circular polyribonucleotide or a hybrid modified circular polyribonucleotide) is initiated, the ribosome bound to the modified circular polyribonucleotide (e.g., a fully modified circular polyribonucleotide or a hybrid modified circular polyribonucleotide) does not disengage from the modified circular polyribonucleotide (e.g., a fully modified circular polyribonucleotide or a hybrid modified circular polyribonucleotide) before finishing at least one round of translation of the modified circular polyribonucleotide. In some embodiments, the modified circular polyribonucleotide (e.g., a fully modified circular polyribonucleotide or a hybrid modified circular polyribonucleotide) as described herein is competent for rolling circle translation. In some embodiments, during rolling circle translation, once translation of the modified circular polyribonucleotide (e.g., a fully modified circular polyribonucleotide or a hybrid modified circular polyribonucleotide) is initiated, the ribosome bound to the modified circular polyribonucleotide (e.g., a fully modified circular polyribonucleotide or a hybrid modified circular polyribonucleotide) does not disengage from the modified circular polyribonucleotide (e.g., a fully modified circular polyribonucleotide or a hybrid modified circular polyribonucleotide) before finishing at least 2 rounds, at least 3 rounds, at least 4 rounds, at least 5 rounds, at least 6 rounds, at least 7 rounds, at least 8 rounds, at least 9 rounds, at least 10 rounds, at least 11 rounds, at least 12 rounds, at least 13 rounds, at least 14 rounds, at least 15 rounds, at least 20 rounds, at least 30 rounds, at least 40 rounds, at least 50 rounds, at least 60 rounds, at least 70 rounds, at least 80 rounds, at least 90 rounds, at least 100 rounds, at least 150 rounds, at least 200 rounds, at least 250 rounds, at least 500 rounds, at least 1000 rounds, at least 1500 rounds, at least 2000 rounds, at least 5000 rounds, at least 10000 rounds, at least $10^5$ rounds, or at least $10^6$ rounds of translation of the modified circular polyribonucleotide.

In some embodiments, the rolling circle translation of the modified circular polyribonucleotide (e.g., a fully modified circular polyribonucleotide or a hybrid modified circular polyribonucleotide) leads to generation of polypeptide product that is translated from more than one round of translation of the modified circular polyribonucleotide (e.g., a fully modified circular polyribonucleotide or a hybrid modified circular polyribonucleotide) ("continuous" expression product). In some embodiments, the modified circular polyribonucleotide (e.g., a fully modified circular polyribonucleotide or a hybrid modified circular polyribonucleotide) comprises a stagger element, and rolling circle translation of the modified circular polyribonucleotide (e.g., a fully modified circular polyribonucleotide or a hybrid modified circular polyribonucleotide) leads to generation of polypeptide product that is generated from a single round of translation or less than a single round of translation of the modified circular polyribonucleotide (e.g., a fully modified circular polyribonucleotide or a hybrid modified circular polyribonucleotide) ("discrete" expression product). In some embodiments, the modified circular polyribonucleotide (e.g., a fully modified circular polyribonucleotide or a hybrid modified circular polyribonucleotide) is configured such that at least 10%, 20%, 30%, 40%, 50%, at least 60%, at least 70%, at least 80%, at least 90%, at least 95%, at least 96%, at least 97%, at least 98%, at least 99%, or 100% of total polypeptides (molar/molar) generated during the rolling circle translation of the modified circular polyribonucleotide (e.g., a fully modified circular polyribonucleotide or a hybrid modified circular polyribonucleotide) are discrete polypeptides. In some embodiments, the amount ratio of the discrete products over the total polypeptides is tested in an in vitro translation system. In some embodiments, the in vitro translation system used for the test of amount ratio comprises rabbit reticulocyte lysate. In some embodiments, the amount ratio is tested in an in vivo translation system, such as a eukaryotic cell or a prokaryotic cell, a cultured cell or a cell in an organism.

Untranslated Regions

In some embodiments, the modified circular polyribonucleotide (e.g., a fully modified circular polyribonucleotide or a hybrid modified circular polyribonucleotide) comprises untranslated regions (UTRs). UTRs of a genomic region comprising a gene may be transcribed but not translated. In some embodiments, a UTR may be included upstream of the translation initiation sequence of an expression sequence described herein. In some embodiments, a UTR may be included downstream of an expression sequence described herein. In some instances, one UTR for first expression sequence is the same as or continuous with or overlapping with another UTR for a second expression sequence. In some embodiments, the intron is a human intron. In some embodiments, the intron is a full length human intron, e.g., ZKSCAN1.

In some embodiments, the modified circular polyribonucleotide (e.g., a fully modified circular polyribonucleotide or a hybrid modified circular polyribonucleotide) comprises a UTR with one or more stretches of Adenosines and Uridines embedded within. These AU rich signatures are may increase turnover rates of the expression product.

Introduction, removal, or modification of UTR AU rich elements (AREs) may be useful to modulate the stability or immunogenicity of the modified circular polyribonucleotide. When engineering specific modified circular polyribonucleotides, one or more copies of an ARE may be introduced to the modified circular polyribonucleotide (e.g., a fully modified circular polyribonucleotide or a hybrid modified circular polyribonucleotide) and the copies of an ARE may modulate translation and/or production of an expression product. Likewise, AREs may be identified and removed or engineered into the modified circular polyribonucleotide (e.g., a fully modified circular polyribonucleotide or a hybrid modified circular polyribonucleotide) to modulate the intracellular stability and thus affect translation and production of the resultant protein.

It should be understood that any UTR from any gene may be incorporated into the respective flanking regions of the modified circular polyribonucleotide. Exemplary UTRs that can be used in a modified circular polyribonucleotide (e.g., a fully modified circular polyribonucleotide or a hybrid modified circular polyribonucleotide) provided herein include those described in [0200]-[0201] of International Patent Publication No. WO2019118919A1, which is incorporated herein by reference in its entirety.

PolyA Sequence

In some embodiments, the modified circular polyribonucleotide (e.g., a fully modified circular polyribonucleotide or a hybrid modified circular polyribonucleotide) may include a poly-A sequence. In some embodiments, the length of a poly-A sequence is greater than 10 nucleotides in length. In one embodiment, the poly-A sequence is greater than 15 nucleotides in length (e.g., at least or greater than about 10, 15, 20, 25, 30, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the poly-A sequence is designed according to the descriptions of the poly-A sequence in [0202]-[0204] of International Patent Publication No. WO2019118919A1, which is incorporated herein by reference in its entirety.

In some embodiments, the modified circular polyribonucleotide (e.g., a fully modified circular polyribonucleotide or a hybrid modified circular polyribonucleotide) comprises a polyA, lacks a polyA, or has a modified polyA to modulate one or more characteristics of the modified circular polyribonucleotide. In some embodiments, the modified circular polyribonucleotide (e.g., a fully modified circular polyribonucleotide or a hybrid modified circular polyribonucleotide) lacking a polyA or having modified polyA improves one or more functional characteristics, e.g., immunogenicity, half-life, expression efficiency, etc.

RNA-Binding

In some embodiments, the modified circular polyribonucleotide (e.g., a fully modified circular polyribonucleotide or a hybrid modified circular polyribonucleotide) comprises one or more RNA binding sites. microRNAs (or miRNA) are short noncoding RNAs that bind to the 3'UTR of nucleic acid molecules and down-regulate gene expression either by reducing nucleic acid molecule stability or by inhibiting translation. The modified circular polyribonucleotide (e.g., a fully modified circular polyribonucleotide or a hybrid modified circular polyribonucleotide) may comprise one or more microRNA target sequences, microRNA sequences, or microRNA seeds. Such sequences may correspond to any known microRNA, such as those taught in US Publication US2005/0261218, US Publication US2005/0059005, and [0207]-[0215] of International Patent Publication No. WO2019118919A1, the contents of which are incorporated herein by reference in their entirety.

Protein-Binding

In some embodiments, the modified circular polyribonucleotide (e.g., a fully modified circular polyribonucleotide or a hybrid modified circular polyribonucleotide) includes one or more protein binding sites that enable a protein, e.g., a ribosome, to bind to an internal site in the RNA sequence. By engineering protein binding sites, e.g., ribosome binding sites, into the modified circular polyribonucleotide, the modified circular polyribonucleotide (e.g., a fully modified circular polyribonucleotide or a hybrid modified circular polyribonucleotide) may evade or have reduced detection by the host's immune system, have modulated degradation, or modulated translation, by masking the modified circular polyribonucleotide (e.g., a fully modified circular polyribonucleotide or a hybrid modified circular polyribonucleotide) from components of the host's immune system.

In some embodiments, the modified circular polyribonucleotide (e.g., a fully modified circular polyribonucleotide or a hybrid modified circular polyribonucleotide) comprises at least one immunoprotein binding site, for example to evade immune responses, e.g., CTL (cytotoxic T lymphocyte) responses. In some embodiments, the immunoprotein binding site is a nucleotide sequence that binds to an immunoprotein and aids in masking the modified circular polyribonucleotide (e.g., a fully modified circular polyribonucleotide or a hybrid modified circular polyribonucleotide) as exogenous. In some embodiments, the immunoprotein binding site is a nucleotide sequence that binds to an immunoprotein and aids in hiding the modified circular polyribonucleotide (e.g., a fully modified circular polyribonucleotide or a hybrid modified circular polyribonucleotide) as exogenous or foreign.

Traditional mechanisms of ribosome engagement to linear RNA involve ribosome binding to the capped 5' end of an RNA. From the 5' end, the ribosome migrates to an initiation codon, whereupon the first peptide bond is formed. According to the present invention, internal initiation (i.e., cap-independent) of translation of the modified circular polyribonucleotide (e.g., a fully modified circular polyribonucleotide or a hybrid modified circular polyribonucleotide) does not require a free end or a capped end. Rather, a ribosome binds to a non-capped internal site, whereby the ribosome begins polypeptide elongation at an initiation codon. In some embodiments, the modified circular polyribonucleotide (e.g., a fully modified circular polyribonucleotide or a hybrid modified circular polyribonucleotide) includes one or more RNA sequences comprising a ribosome binding site, e.g., an initiation codon.

Natural 5'UTRs bear features which play roles in for translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5 'UTR also have been known to form secondary structures which are involved in elongation factor binding.

In some embodiments, the modified circular polyribonucleotide (e.g., a fully modified circular polyribonucleotide or a hybrid modified circular polyribonucleotide) encodes a protein binding sequence that binds to a protein. In some embodiments, the protein binding sequence targets or localizes the modified circular polyribonucleotide (e.g., a fully modified circular polyribonucleotide or a hybrid modified circular polyribonucleotide) to a specific target. In some embodiments, the protein binding sequence specifically binds an arginine-rich region of a protein.

In some embodiments, the protein binding site includes, but is not limited to, a binding site to the protein such as ACIN1, AGO, APOBEC3F, APOBEC3G, ATXN2, AUH, BCCIP, CAPRIN1, CELF2, CPSF1, CPSF2, CPSF6, CPSF7, CSTF2, CSTF2T, CTCF, DDX21, DDX3, DDX3X, DDX42, DGCR8, EIF3A, EIF4A3, EIF4G2, ELAVL1, ELAVL3, FAM120A, FBL, FIP1L1, FKBP4, FMR1, FUS, FXR1, FXR2, GNL3, GTF2F1, HNRNPA1, HNRNPA2B1, HNRNPC, HNRNPK, HNRNPL, HNRNPM, HNRNPU, HNRNPUL1, IGF2BP1, IGF2BP2, IGF2BP3, ILF3, KHDRBS1, LARP7, LIN28A, LIN28B, m6A, MBNL2, METTL3, MOV10, MSI1, MSI2, NONO, NONO–, NOP58, NPM1, NUDT21, PCBP2, POLR2A, PRPF8, PTBP1, RBFOX2, RBM10, RBM22, RBM27, RBM47, RNPS1, SAFB2, SBDS, SF3A3, SF3B4, SIRT7, SLBP, SLTM, SMNDC1, SND1, SRRM4, SRSF1, SRSF3, SRSF7, SRSF9, TAF15, TARDBP, TIA1, TNRC6A, TOP3B, TRA2A, TRA2B, U2AF1, U2AF2, UNK, UPF1, WDR33, XRN2, YBX1, YTHDC1, YTHDF1, YTHDF2, YWHAG, ZC3H7B, PDK1, AKT1, and any other protein that binds RNA.

Encryptogen

As described herein, the modified circular polyribonucleotide (e.g., a fully modified circular polyribonucleotide or a hybrid modified circular polyribonucleotide) comprises an encryptogen to reduce, evade or avoid the innate immune response of a cell. In one aspect, provided herein are modified circular polyribonucleotide (e.g., a fully modified circular polyribonucleotide or a hybrid modified circular polyribonucleotide) which when delivered to cells, results in a reduced immune response from the host as compared to the response triggered by a reference compound, e.g. a linear polynucleotide corresponding to the described modified circular polyribonucleotide (e.g., a fully modified circular polyribonucleotide or a hybrid modified circular polyribonucleotide), a corresponding unmodified circular polyribonucleotide, a modified circular polyribonucleotide lacking an encryptogen. In some embodiments, the modified circular polyribonucleotide (e.g., a fully modified circular polyribonucleotide or a hybrid modified circular polyribonucleotide) has less immunogenicity than a counterpart lacking an encryptogen.

In some embodiments, an encryptogen enhances stability. There is growing body of evidence about the regulatory roles played by the UTRs in terms of stability of a nucleic acid molecule and translation. The regulatory features of a UTR may be included in the encryptogen to enhance the stability of the modified circular polyribonucleotide.

In some embodiments, 5' or 3'UTRs can constitute encryptogens in a modified circular polyribonucleotide. For example, removal or modification of UTR AU rich elements (AREs) may be useful to modulate the stability or immunogenicity of the modified circular polyribonucleotide.

In some embodiments, removal of modification of AU rich elements (AREs) in expression sequence, e.g., translatable regions, can be useful to modulate the stability or immunogenicity of the modified circular polyribonucleotide In some embodiments, an encryptogen comprises miRNA binding site or binding site to any other non-coding RNAs. For example, incorporation of miR-142 sites into the modified circular polyribonucleotide (e.g., a fully modified circular polyribonucleotide or a hybrid modified circular polyribonucleotide) described herein may not only modulate expression in hematopoietic cells, but also reduce or abolish immune responses to a protein encoded in the modified circular polyribonucleotide.

In some embodiments, an encyptogen comprises one or more protein binding sites that enable a protein, e.g., an immunoprotein, to bind to the RNA sequence. By engineering protein binding sites into the modified circular polyribonucleotide, the modified circular polyribonucleotide (e.g., a fully modified circular polyribonucleotide or a hybrid modified circular polyribonucleotide) may evade or have reduced detection by the host's immune system, have modulated degradation, or modulated translation, by masking the modified circular polyribonucleotide (e.g., a fully modified circular polyribonucleotide or a hybrid modified circular polyribonucleotide) from components of the host's immune system. In some embodiments, the modified circular polyribonucleotide (e.g., a fully modified circular polyribonucleotide or a hybrid modified circular polyribonucleotide) comprises at least one immunoprotein binding site, for example to evade immune responses, e.g., CTL responses. In some embodiments, the immunoprotein binding site is a nucleotide sequence that binds to an immunoprotein and aids in masking the modified circular polyribonucleotide (e.g., a fully modified circular polyribonucleotide or a hybrid modified circular polyribonucleotide) as exogenous.

In some embodiments, an encryptogen comprises one or more modified nucleotides. Exemplary modifications can include any modification to the sugar, the nucleobase, the internucleoside linkage (e.g. to a linking phosphate/to a phosphodiester linkage/to the phosphodiester backbone), and any combination thereof that can prevent or reduce immune response against the modified circular polyribonucleotide. Some of the exemplary modifications provided herein are described in details below.

In some embodiments, the modified circular polyribonucleotide (e.g., a fully modified circular polyribonucleotide or a hybrid modified circular polyribonucleotide) includes one or more modifications as described elsewhere herein to reduce an immune response from the host as compared to the response triggered by a reference compound, e.g. a modified circular polyribonucleotide (e.g., a fully modified circular polyribonucleotide or a hybrid modified circular polyribonucleotide) lacking the modifications. In particular, the addition of one or more inosine has been shown to discriminate RNA as endogenous versus viral. See for example, Yu, Z. et al. (2015) RNA editing by ADAR1 marks dsRNA as “self”. Cell Res. 25, 1283-1284, which is incorporated by reference in its entirety.

In some embodiments, the modified circular polyribonucleotide (e.g., a fully modified circular polyribonucleotide or a hybrid modified circular polyribonucleotide) includes one or more expression sequences for shRNA or an RNA sequence that can be processed into siRNA, and the shRNA or siRNA targets RIG-1 and reduces expression of RIG-1. RIG-1 can sense foreign circular RNA and leads to degradation of foreign circular RNA. Therefore, a circular polynucleotide harboring sequences for RIG-1-targeting shRNA, siRNA or any other regulatory nucleic acids can reduce immunity, e.g., host cell immunity, against the modified circular polyribonucleotide.

In some embodiments, the modified circular polyribonucleotide (e.g., a fully modified circular polyribonucleotide or a hybrid modified circular polyribonucleotide) lacks a sequence, element or structure, that aids the modified circular polyribonucleotide (e.g., a fully modified circular polyribonucleotide or a hybrid modified circular polyribonucleotide) in reducing, evading or avoiding an innate immune response of a cell. In some such embodiments, the modified circular polyribonucleotide (e.g., a fully modified circular polyribonucleotide or a hybrid modified circular polyribonucleotide) may lack a polyA sequence, a 5' end, a 3' end, phosphate group, hydroxyl group, or any combination thereof.

Riboswitches

In some embodiments, the modified circular polyribonucleotide (e.g., a fully modified circular polyribonucleotide or a hybrid modified circular polyribonucleotide) comprises one or more riboswitches.

A riboswitch is typically considered a part of the modified circular polyribonucleotide (e.g., a fully modified circular polyribonucleotide or a hybrid modified circular polyribonucleotide) that can directly bind a small target molecule, and whose binding of the target affects RNA translation, the expression product stability and activity (Tucker B J, Breaker R R (2005), Curr Opin Struct Biol 15 (3): 342-8). Thus, the modified circular polyribonucleotide (e.g., a fully modified circular polyribonucleotide or a hybrid modified circular polyribonucleotide) that includes a riboswitch is directly involved in regulating its own activity, depending on the presence or absence of its target molecule. In some embodiments, a riboswitch has a region of aptamer-like affinity for a separate molecule. Thus, in the broader context of the instant invention, any aptamer included within a non-coding nucleic acid could be used for sequestration of molecules from bulk volumes. Downstream reporting of the event via “(ribo)switch” activity may be especially advantageous.

In some embodiments, the riboswitch may have an effect on gene expression including, but not limited to, transcriptional termination, inhibition of translation initiation, mRNA self-cleavage, and in eukaryotes, alteration of splicing pathways. The riboswitch may function to control gene expression through the binding or removal of a trigger molecule. Thus, subjecting a modified circular polyribonucleotide (e.g., a fully modified circular polyribonucleotide or a hybrid modified circular polyribonucleotide) that includes the riboswitch to conditions that activate, deactivate or block the riboswitch to alter expression. Expression can be altered as a result of, for example, termination of transcription or blocking of ribosome binding to the RNA.

Binding of a trigger molecule or an analog thereof can, depending on the nature of the riboswitch, reduce or prevent expression of the RNA molecule or promote or increase expression of the RNA molecule. Some examples of riboswitches are described herein.

a cyclic di-GMP riboswitches, a FMN riboswitch (also RFN-element), a glmS riboswitch, a Glutamine riboswitches, a Glycine riboswitch, a Lysine riboswitch (also L-box), a PreQI riboswitch (e.g., PreQI-1 riboswitches and PreQI-11 riboswitches), a Purine riboswitch, a SAH riboswitch, a SAM riboswitch, a SAM-SAH riboswitch, a Tetrahydrofolate riboswitch, a theophylline binding riboswitch, a thymine pyrophosphate binding riboswitch, a *T. tengcongensis* glmS catalytic riboswitch, a TPP riboswitch (also THI-box), a Moco riboswitch, or a Adenine sensing add-A riboswitch, each of which is described in [0235]-[0252] of International Patent Publication No. WO2019118919A1, which is incorporated herein by reference in its entirety.

Aptazyme

In some embodiments, the modified circular polyribonucleotide (e.g., a fully modified circular polyribonucleotide or a hybrid modified circular polyribonucleotide) comprises an aptazyme. Aptazyme is a switch for conditional expression in which an aptamer region is used as an allosteric control element and coupled to a region of catalytic RNA (a “ribozyme” as described below). In some embodiments, the aptazyme is active in cell type specific translation. In some embodiments, the aptazyme is active under cell state specific translation, e.g., virally infected cells or in the presence of viral nucleic acids or viral proteins.

A ribozyme (from ribonucleic acid enzyme, also called RNA enzyme or catalytic RNA) is a RNA molecule that catalyzes a chemical reaction.

Some nonlimiting examples of ribozymes include hammerhead ribozyme, VL ribozyme, leadzyme, hairpin ribozyme, and other ribozymes described in [0254]-[0259] of International Patent Publication No. WO2019118919A1, which is incorporated herein by reference in its entirety.

In some embodiments, modified circRNA described herein can be used for transcription and replication of RNA. For example, circRNA can be used to encode non-coding RNA, lncRNA, miRNA, tRNA, rRNA, snoRNA, ncRNA, siRNA, or shRNA. In some embodiments, circRNA can include anti-sense miRNA and a transcriptional element. After transcription, such circRNA can produce functional, linear miRNAs. Non-limiting examples of circRNA expression and modulation applications are listed in TABLE 3.

TABLE 3

| Process | MOA (example) |
|---|---|
| Combinational therapy of inhibition & translation | Inhibition of one protein and supplementation of another (or same) |

"ATTN. CWU: Shading has been verified to be removed

Target Binding

In some embodiments, modified circRNA (e.g., a fully modified circular polyribonucleotide or a hybrid modified circular polyribonucleotide) binds one or more targets. In one embodiment, circRNA binds both a DNA target and a protein target and e.g., mediates transcription. In another embodiment, circRNA (e.g., a fully modified circular polyribonucleotide or a hybrid modified circular polyribonucleotide) brings together a protein complex and e.g., mediates signal transduction. In another embodiment, circRNA (e.g., a fully modified circular polyribonucleotide or a hybrid modified circular polyribonucleotide) binds two or more different targets, such as proteins, and e.g., shuttles these proteins to the cytoplasm. In some embodiments, a pharmaceutical composition comprises a hybrid modified circular polyribonucleotide, wherein the hybrid modified circular polyribonucleotide comprises: at least one modified nucleotide; a first portion comprising a first binding site configured to bind a first binding moiety of a first target, e.g., a RNA, DNA, protein, or a cell target, wherein the first binding moiety is a first circular polyribonucleotide (circRNA)-binding motif consisting of unmodified nucleotides; wherein the first target and the hybrid modified circular polyribonucleotide form a complex. In some embodiments, a pharmaceutical composition comprises a hybrid modified circular polyribonucleotide, wherein the hybrid modified circular polyribonucleotide comprises: at least one modified nucleotide; a first portion comprising a first binding site configured to bind a first binding moiety of a first target, e.g., a RNA, DNA, protein, or a cell target, wherein the first binding moiety is a first circular polyribonucleotide (circRNA)-binding motif consisting of unmodified nucleotides; and a second binding site configured to bind a second binding moiety of a second target, wherein the second binding moiety is a second circRNA-binding motif, wherein the first binding moiety is different than the second binding moiety, wherein the first target, the second target, and the hybrid modified circular polyribonucleotide form a complex, and wherein the first target or the second target is a not a microRNA. In some embodiments, a pharmaceutical composition comprising a hybrid modified circular polyribonucleotide, wherein the hybrid modified circular polyribonucleotide comprises: at least one modified nucleotide; a first portion comprising a first binding site configured to bind a first binding moiety of a first target, wherein the first binding moiety is a first circular polyribonucleotide (circRNA)-binding motif; and a second binding site configured to bind a second binding moiety of a second target, wherein the second binding moiety is a second circRNA-binding motif, wherein the first binding moiety is different than the second binding moiety, and wherein the first target and the second target are both a microRNA. In some embodiments, the hybrid modified circular polyribonucleotide comprises a first portion comprising a binding site configured to bind to a protein, peptide, biomolecule, DNA, RNA, or a cell target, consisting of unmodified nucleotides. In some embodiments, a first portion as described herein comprises a binding site configured to bind to a protein, peptide, biomolecule, DNA, RNA, or a cell target, consisting of unmodified nucleotides.

In some embodiments, modified circRNA (e.g., a fully modified circular polyribonucleotide or a hybrid modified circular polyribonucleotide) binds at least one of DNA, RNA, and proteins and thereby regulates cellular processes (e.g., alter protein expression). In some embodiments, synthetic modified circRNA (e.g., a fully modified circular polyribonucleotide or a hybrid modified circular polyribonucleotide) includes binding sites for interaction with at least one moiety, e.g., a binding moiety, of DNA, RNA or proteins of choice to thereby compete in binding with the endogenous counterpart.

In one embodiment, synthetic modified circRNA (e.g., a fully modified circular polyribonucleotide or a hybrid modified circular polyribonucleotide) binds and/or sequesters miRNAs. In another embodiment, synthetic modified circRNA (e.g., a fully modified circular polyribonucleotide or a hybrid modified circular polyribonucleotide) binds and/or sequesters proteins. In another embodiment, synthetic modified circRNA binds and/or sequesters mRNA. In another embodiment, synthetic modified circRNA (e.g., a fully modified circular polyribonucleotide or a hybrid modified circular polyribonucleotide) binds and/or sequesters ribosomes. In another embodiment, synthetic modified circRNA (e.g., a fully modified circular polyribonucleotide or a hybrid modified circular polyribonucleotide) binds and/or sequesters modified circRNA. In another embodiment, synthetic modified circRNA binds and/or sequesters long-noncoding RNA (lncRNA) or any other non-coding RNA, e.g., miRNA, tRNA, rRNA, snoRNA, ncRNA, siRNA, long-noncoding RNA, shRNA. Besides binding and/or sequestration sites, the modified circRNA may include a degradation element, which will result in degradation of the bound and/or sequestered RNA and/or protein.

In one embodiment, a modified circRNA (e.g., a fully modified circular polyribonucleotide or a hybrid modified circular polyribonucleotide) comprises a lncRNA or a sequence of a lncRNA, e.g., a modified circRNA comprises a sequence of a naturally occurring, non-circular lncRNA or a fragment thereof. In one embodiment, a lncRNA or a sequence of a lncRNA is circularized, with or without a spacer sequence, to form a synthetic modified circRNA (e.g., a fully modified circular polyribonucleotide or a hybrid modified circular polyribonucleotide).

In one embodiment, a modified circRNA (e.g., a fully modified circular polyribonucleotide or a hybrid modified circular polyribonucleotide) has ribozyme activity. In one embodiment, a modified circRNA (e.g., a fully modified circular polyribonucleotide or a hybrid modified circular polyribonucleotide) can be used to act as a ribozyme and cleave pathogenic or endogenous RNA, DNA, small molecules or protein. In one embodiment, a modified circRNA (e.g., a fully modified circular polyribonucleotide or a hybrid modified circular polyribonucleotide) has enzymatic activity. In one embodiment, synthetic modified circRNA (e.g., a fully modified circular polyribonucleotide or a hybrid modified circular polyribonucleotide) is able to specifically recognize and cleave RNA (e.g., viral RNA). In another embodiment modified circRNA (e.g., a fully modified circular polyribonucleotide or a hybrid modified circular polyribonucleotide) is able to specifically recognize and cleave proteins. In another embodiment modified circRNA (e.g., a fully modified circular polyribonucleotide or a hybrid modified circular polyribonucleotide) is able to specifically recognize and degrade small molecules.

In one embodiment, a modified circRNA (e.g., a fully modified circular polyribonucleotide or a hybrid modified circular polyribonucleotide) is an immolating or self-cleaving or cleavable modified circRNA. In one embodiment, a modified circRNA (e.g., a fully modified circular polyribonucleotide or a hybrid modified circular polyribonucleotide) can be used to deliver RNA, e.g., miRNA, tRNA, rRNA, snoRNA, ncRNA, siRNA, long-noncoding RNA, shRNA. In one embodiment, synthetic modified circRNA (e.g., a fully modified circular polyribonucleotide or a hybrid modified circular polyribonucleotide) is made up of microRNAs separated by (1) self-cleavable elements (e.g., hammerhead, splicing element), (2) cleavage recruitment sites (e.g., ADAR), (3) a degradable linker (glycerol), (4) a chemical linker, and/or (5) a spacer sequence. In another embodiment, synthetic modified circRNA is made up of siRNAs separated by (1) self-cleavable elements (e.g., hammerhead, splicing element), (2) cleavage recruitment sites (e.g., ADAR), (3) a degradable linker (glycerol), (4), chemical linker, and/or (5) a spacer sequence.

In one embodiment, a modified circRNA is a transcriptionally/replication competent modified circRNA. This modified circRNA (e.g., a fully modified circular polyribonucleotide or a hybrid modified circular polyribonucleotide) can encode any type of RNA. In one embodiment, a synthetic modified circRNA has an anti-sense miRNA and a transcriptional element. In one embodiment, after transcription, linear functional miRNAs are generated from a modified circRNA (e.g., a fully modified circular polyribonucleotide or a hybrid modified circular polyribonucleotide).

In one embodiment, a modified circRNA (e.g., a fully modified circular polyribonucleotide or a hybrid modified circular polyribonucleotide) has one or more of the above attributes in combination with a translating element.

Targets

A modified circRNA (e.g., a fully modified circular polyribonucleotide or a hybrid modified circular polyribonucleotide) comprises at least one binding site for a binding moiety of a target. Targets include, but are not limited to, nucleic acids (e.g., RNAs, DNAs, RNA-DNA hybrids), small molecules (e.g., drugs), aptamers, polypeptides, proteins, lipids, carbohydrates, antibodies, viruses, virus particles, membranes, multi-component complexes, cells, other cellular moieties, any fragments thereof, and any combination thereof. (See, e.g., Fredriksson et al., (2002) Nat Biotech 20:473-77; Gullberg et al., (2004) PNAS, 101:8420-24). For example, a target is a single-stranded RNA, a double-stranded RNA, a single-stranded DNA, a double-stranded DNA, a DNA or RNA comprising one or more double stranded regions and one or more single stranded regions, an RNA-DNA hybrid, a small molecule, an aptamer, a polypeptide, a protein, a lipid, a carbohydrate, an antibody, an antibody fragment, a mixture of antibodies, a virus particle, a membrane, a multi-component complex, a cell, a cellular moiety, any fragment thereof, or any combination thereof.

In some embodiments, a target is a polypeptide, a protein, or any fragment thereof. For example, a target can be a purified polypeptide, an isolated polypeptide, a fusion tagged polypeptide, a polypeptide attached to or spanning the membrane of a cell or a virus or virion, a cytoplasmic protein, an intracellular protein, an extracellular protein, a kinase, a phosphatase, an aromatase, a helicase, a protease, an oxidoreductase, a reductase, a transferase, a hydrolase, a lyase, an isomerase, a glycosylase, a extracellular matrix protein, a ligase, an ion transporter, a channel, a pore, an apoptotic protein, a cell adhesion protein, a pathogenic protein, an aberrantly expressed protein, an transcription factor, a transcription regulator, a translation protein, a chaperone, a secreted protein, a ligand, a hormone, a cytokine, a chemokine, a nuclear protein, a receptor, a transmembrane receptor, a signal transducer, an antibody, a membrane protein, an integral membrane protein, a peripheral membrane protein, a cell wall protein, a globular protein, a fibrous protein, a glycoprotein, a lipoprotein, a chromosomal protein, any fragment thereof, or any combination thereof. In some embodiments, a target is a heterologous polypeptide. In some embodiments, a target is a protein overexpressed in a cell using molecular techniques, such as transfection. In some embodiments, a target is a recombinant polypeptide. For example, a target is in a sample produced from bacterial (e.g., *E. coli*), yeast, mammalian, or insect cells (e.g., proteins overexpressed by the organisms). In some embodiments, a target is a polypeptide with a mutation, insertion, deletion, or polymorphism. In some embodiments, a target is an antigen, such as a polypeptide used to immunize an organism or to generate an immune response in an organism, such as for antibody production.

In some embodiments, a target is an antibody. An antibody can specifically bind to a particular spatial and polar organization of another molecule. An antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. A naturally occurring antibody can be a protein comprising at least two heavy (H) chains and two light (L) chains inter-connected by disulfide bonds. Each heavy chain can be comprised of a heavy chain variable region ($V_H$) and a heavy chain constant region. The heavy chain constant region can be comprised of three domains, $C_{H1}$, $C_{H2}$ and $C_{H3}$. Each light chain can be comprised of a light chain variable region ($V_L$) and a light chain constant region. The light chain constant region can be comprised of one domain, $C_L$. The $V_H$ and $V_L$ regions can be further subdivided into regions of hypervariability, termed complementary determining regions (CDR), interspersed with regions that are more conserved, termed framework regions (FR). Each $V_H$ and $V_L$ can be composed of three CDRs and four FRs arranged from amino-terminus to carboxy-terminus in the following order: $FR_1$, $CDR_1$, $FR_2$, $CDR_2$, $FR_3$, $CDR_3$, and FR4. The constant regions of the antibodies may mediate the binding of the immunoglobulin to host tissues or factors, including various cells of the immune system (e.g., effector cells) and the first component (C1 q) of the classical complement system. The antibodies can be of any isotype (e.g., IgG, IgE, IgM, IgD, IgA and IgY), class (e.g., $lgG_1$, $lgG_2$, $lgG_3$, $lgG_4$, $lgA_1$ and $lgA_2$), subclass or modified version thereof. Antibodies may include a complete immunoglobulin or fragments thereof. An antibody fragment can refer to one or more fragments of an antibody that retain the ability to specifically bind to a binding moiety, such as an antigen. In addition, aggregates, polymers, and conjugates of immunoglobulins or their fragments are also included so long as binding affinity for a particular molecule is maintained. Examples of antibody fragments include a Fab fragment, a monovalent fragment consisting of the $V_L$, $V_H$, $C_L$ and $C_{H1}$ domains; a $F(ab)_2$ fragment, a bivalent fragment comprising two Fab fragments linked by a disulfide bridge at the hinge region; an Fd fragment consisting of the $V_H$ and $C_{H1}$ domains; an Fv fragment consisting of the $V_L$ and $V_H$ domains of a single arm of an antibody; a single domain antibody (dAb) fragment (Ward et al., (1989) Nature 341:544-46), which consists of a $V_H$ domain; and an isolated CDR and a single chain Fragment (scFv) in which the $V_L$ and $V_H$ regions pair to form monovalent molecules (known as single chain Fv (scFv); see, e.g., Bird et al., (1988) Science 242:423-26; and Huston et al., (1988) PNAS 85:5879-83). Thus, antibody fragments include Fab, $F(ab)_2$, scFv, Fv, dAb, and the like. Although the two domains $V_L$ and $V_H$ are coded for by separate genes, they can be joined, using recombinant methods, by an artificial peptide linker that enables them to be made as a single protein chain. Such single chain antibodies include one or more antigen binding moieties. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

In some embodiments, a target is a polymeric form of ribonucleotides and/or deoxyribonucleotides (adenine, guanine, thymine, or cytosine), such as DNA or RNA (e.g., mRNA). DNA includes double-stranded DNA found in linear DNA molecules (e.g., restriction fragments), viruses, plasmids, and chromosomes. In some embodiments, a polynucleotide target is single-stranded, double stranded, small interfering RNA (siRNA), messenger RNA (mRNA), transfer RNA (tRNA), a chromosome, a gene, a noncoding genomic sequence, genomic DNA (e.g., fragmented genomic DNA), a purified polynucleotide, an isolated polynucleotide, a hybridized polynucleotide, a transcription factor binding site, mitochondrial DNA, ribosomal RNA, a eukaryotic polynucleotide, a prokaryotic polynucleotide, a synthesized polynucleotide, a ligated polynucleotide, a recombinant polynucleotide, a polynucleotide containing a nucleic acid analogue, a methylated polynucleotide, a demethylated polynucleotide, any fragment thereof, or any combination thereof. In some embodiments, a target is a recombinant polynucleotide. In some embodiments, a target is a heterologous polynucleotide. For example, a target is a polynucleotide produced from bacterial (e.g., *E. coli*), yeast, mammalian, or insect cells (e.g., polynucleotides heterologous to the organisms). In some embodiments, a target is a polynucleotide with a mutation, insertion, deletion, or polymorphism.

In some embodiments, a target is an aptamer. An aptamer is an isolated nucleic acid molecule that binds with high specificity and affinity to a binding moiety, such as a protein. An aptamer is a three dimensional structure held in certain conformation(s) that provides chemical contacts to specifically bind its given target. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the specific binding of a target molecule, is not entirely dependent on a conserved linear base sequence (a non-coding sequence), but rather a particular secondary/tertiary/quaternary structure. Any coding potential that an aptamer may possess is entirely fortuitous and plays no role whatsoever in the binding of an aptamer to its cognate target. Aptamers must also be differentiated from the naturally occurring nucleic acid sequences that bind to certain proteins. These latter sequences are naturally occurring sequences embedded within the genome of the organism that bind to a specialized sub-group of proteins that are involved in the transcription, translation, and transportation of naturally occurring nucleic acids (e.g., nucleic acid-binding proteins). Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can bind virtually any protein (not just nucleic acid-binding proteins) as well as almost any partner of interest including small molecules, carbohydrates, peptides, etc. For most partners, even proteins, a naturally occurring nucleic acid sequence to which it binds does not exist. For those partners that do have such a sequence, e.g., nucleic acid-binding proteins, such sequences will differ from aptamers as a result of the relatively low binding affinity used in nature as compared to tightly binding aptamers. Aptamers are capable of specifically binding to selected partners and modulating the partner's activity or binding interactions, e.g., through binding, aptamers may block their partner's ability to function. The functional property of specific binding to a partner is an inherent property an aptamer. A typical aptamer is 6-35 kDa in size (20-100 nucleotides), binds its partner with micromolar to sub-nanomolar affinity, and may discriminate against closely related targets (e.g., aptamers may selectively bind related proteins from the same gene family). Aptamers are capable of using commonly seen intermolecular interactions such as hydrogen bonding, electrostatic complementarities, hydrophobic contacts, and steric exclusion to bind with a specific partner. Aptamers have a number of desirable characteristics for use as therapeutics and diagnostics including high specificity and affinity, low immunogenicity, biological efficacy, and excellent pharmacokinetic properties. An aptamer can comprise a molecular stem and loop structure formed from the hybridization of complementary polynucleotides that are covalently linked (e.g., a hairpin loop structure). The stem comprises the hybridized polynucleotides and the loop is the region that covalently links the two complementary polynucleotides.

In some embodiments, a target is a small molecule. For example, a small molecule can be a macrocyclic molecule, an inhibitor, a drug, or chemical compound. In some embodiments, a small molecule contains no more than five hydrogen bond donors. In some embodiments, a small molecule contains no more than ten hydrogen bond acceptors. In some embodiments, a small molecule has a molecular weight of 500 Daltons or less. In some embodiments, a small molecule has a molecular weight of from about 180 to 500 Daltons. In some embodiments, a small molecule contains an octanol-water partition coefficient lop P of no more than five. In some embodiments, a small molecule has a partition coefficient log P of from −0.4 to 5.6. In some embodiments, a small molecule has a molar refractivity of from 40 to 130. In some embodiments, a small molecule contains from about 20 to about 70 atoms. In some embodiments, a small molecule has a polar surface area of 140 $Angstroms^2$ or less.

In some embodiments, a target is a cell. For example, a target is an intact cell, a cell treated with a compound (e.g., a drug), a fixed cell, a lysed cell, or any combination thereof. In some embodiments, a target is a single cell. In some embodiments, a target is a plurality of cells.

In some embodiments, a single target or a plurality of (e.g., two or more) targets have a plurality of binding moieties. In one embodiment, the single target may have 2, 3, 4, 5, 6, 7, 8, 9, 10, or more binding moieties. In one embodiment, two or more targets are in a sample, such as a mixture or library of targets, and the sample comprises two or more binding moieties. In some embodiments, a single target or a plurality of targets comprise a plurality of different binding moieties. For example, a plurality may include at least about 2, 3, 4, 5, 6, 7, 8, 9, 10, 15, 20, 30, 40, 50, 60, 70, 80, 90, 100, 200, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, or 30,000 binding moieties.

A target can comprise a plurality of binding moieties comprising at least 2 different binding moieties. For example, a binding moiety can comprise a plurality of binding moieties comprising at least 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, or 25,000 different binding moieties.

Binding Sites and Binding Moieties

In some instances, a modified circRNA (e.g., a fully modified circular polyribonucleotide or a hybrid modified circular polyribonucleotide) comprises one binding site. In some embodiments, a first portion comprises a binding site configured to bind to a protein, peptide, biomolecule, DNA, RNA, or a cell target, consisting of unmodified nucleotides. In some embodiments, a first portion comprises one or more binding sites configured to bind to a protein, peptide, biomolecule, DNA, RNA, or a cell target, or combination thereof, consisting of unmodified nucleotides. In some instances, a modified circRNA (e.g., a fully modified circular polyribonucleotide or a hybrid modified circular polyribonucleotide) comprises at least two binding sites. For example, a modified circRNA can comprise 2, 3, 4, 5, 6, 7, 8, 9, 10, 11, 12, 13, 14, 15, 16, 17, 18, 19, 20, or more binding sites. In some embodiments, modified circRNA (e.g., a fully modified circular polyribonucleotide or a hybrid modified circular polyribonucleotide) described herein is a molecular scaffold that binds one or more binding moieties of one or more targets. Each target may be, but is not limited to, a different or the same nucleic acids (e.g., RNAs, DNAs, RNA-DNA hybrids), small molecules (e.g., drugs), aptamers, polypeptides, proteins, lipids, carbohydrates, antibodies, viruses, virus particles, membranes, multi-component complexes, cells, cellular moieties, any fragments thereof, and any combination thereof. In some embodiments, the one or more binding sites bind to one or more binding moieties of the same target. In some embodiments, the one or more binding sites bind to one or more binding moieties of different targets. In some embodiments, modified circRNA act as scaffolds for one or more binding moieties of one or more targets. In some embodiments, modified circRNA (e.g., a fully modified circular polyribonucleotide or a hybrid modified circular polyribonucleotide) modulate cellular processes by specifically binding to one or more binding moieties of one or more targets. In some embodiments, modified circRNA (e.g., a fully modified circular polyribonucleotide or a hybrid modified circular polyribonucleotide) described herein includes binding sites for one or more specific targets of interest. In some embodiments, modified circRNA (e.g., a fully modified circular polyribonucleotide or a hybrid modified circular polyribonucleotide) includes multiple binding sites or a combination of binding sites for each binding moiety of interest. For example, a modified circRNA (e.g., a fully modified circular polyribonucleotide or a hybrid modified circular polyribonucleotide) includes a binding site for a polynucleotide target, such as a DNA or RNA. For example, a modified circRNA (e.g., a fully modified circular polyribonucleotide or a hybrid modified circular polyribonucleotide) includes a binding site for an mRNA target. For example, a modified circRNA (e.g., a fully modified circular polyribonucleotide or a hybrid modified circular polyribonucleotide) includes a binding site for an rRNA target. For example, a modified circRNA includes a binding site for a tRNA target. For example, a modified circRNA (e.g., a fully modified circular polyribonucleotide or a hybrid modified circular polyribonucleotide) includes a binding site for genomic DNA target.

In some instances, a modified circRNA (e.g., a fully modified circular polyribonucleotide or a hybrid modified circular polyribonucleotide) comprises a binding site for a binding moiety on a single-stranded DNA. In some instances, a modified circRNA (e.g., a fully modified circular polyribonucleotide or a hybrid modified circular polyribonucleotide) comprises a binding site for a binding moiety on a double-stranded DNA. In some instances, a modified circRNA (e.g., a fully modified circular polyribonucleotide or a hybrid modified circular polyribonucleotide) comprises a binding site for a binding moiety on an antibody. In some instances, a modified circRNA (e.g., a fully modified circular polyribonucleotide or a hybrid modified circular polyribonucleotide) comprises a binding site for a binding moiety on a virus particle. In some instances, a modified circRNA (e.g., a fully modified circular polyribonucleotide or a hybrid modified circular polyribonucleotide) comprises a binding site for a binding moiety on a small molecule. In some instances, a modified circRNA (e.g., a fully modified circular polyribonucleotide or a hybrid modified circular polyribonucleotide) comprises a binding site for a binding moiety in or on a cell. In some instances, a modified circRNA (e.g., a fully modified circular polyribonucleotide or a hybrid modified circular polyribonucleotide) comprises a binding site for a binding moiety on a RNA-DNA hybrid. In some instances, a modified circRNA (e.g., a fully modified circular polyribonucleotide or a hybrid modified circular polyribonucleotide) comprises a binding site for a binding moiety on a methylated polynucleotide. In some instances, a modified circRNA (e.g., a fully modified circular polyribonucleotide or a hybrid modified circular polyribonucleotide) comprises a binding site for a binding moiety on an unmethylated polynucleotide. In some instances, a modified circRNA (e.g., a fully modified circular polyribonucleotide or a hybrid modified circular polyribonucleotide) comprises a binding site for a binding moiety on an aptamer. In some instances, a modified circRNA (e.g., a fully modified circular polyribonucleotide or a hybrid modified circular polyribonucleotide) comprises a binding site for a binding moiety on a polypeptide. In some instances, a modified circRNA (e.g., a fully modified circular polyribonucleotide or a hybrid modified circular polyribonucleotide) comprises a binding site for a binding moiety on a polypeptide, a protein, a protein fragment, a tagged protein, an antibody, an antibody fragment, a small molecule, a virus particle (e.g., a virus particle comprising a transmembrane protein), or a cell.

In some instances, a binding moiety comprises at least two amide bonds. In some instances, a binding moiety does not comprise a phosphodiester linkage. In some instances, a binding moiety is not DNA or RNA.

The modified circRNAs (e.g., a fully modified circular polyribonucleotides or a hybrid modified circular polyribonucleotides) provided herein can include one or more binding sites for binding moieties on a complex. The modified circRNAs (e.g., a fully modified circular polyribonucleotides or a hybrid modified circular polyribonucleotides) provided herein can include one or more binding sites for targets to form a complex. The modified circRNAs (e.g., a fully modified circular polyribonucleotides or a hybrid modified circular polyribonucleotides) provided herein can form a complex between a modified circRNA (e.g., a fully modified circular polyribonucleotide or a hybrid modified circular polyribonucleotide) and a target. In some embodiments, a modified circRNA (e.g., a fully modified circular polyribonucleotide or a hybrid modified circular polyribonucleotide) forms a complex with a single target. In some embodiments, a modified circRNA (e.g., a fully modified circular polyribonucleotide or a hybrid modified circular polyribonucleotide) forms a complex with a complex of two or more targets. In some embodiments, a modified circRNA (e.g., a fully modified circular polyribonucleotide or a hybrid modified circular polyribonucleotide) forms a complex with a complex of three or more targets. In some embodiments, two or more modified circRNAs (e.g., a fully modified circular polyribonucleotides or a hybrid modified circular polyribonucleotides) form a complex with a single target. In some embodiments, two or more modified circRNAs (e.g., a fully modified circular polyribonucleotides or a hybrid modified circular polyribonucleotides) form a complex with two or more targets. In some embodiments, a first modified circRNA (e.g., a fully modified circular polyribonucleotide or a hybrid modified circular polyribonucleotide) forms a complex with a first binding moiety of a first target and a second different binding moiety of a second target. In some embodiments, a first modified circRNA (e.g., a fully modified circular polyribonucleotide or a hybrid modified circular polyribonucleotide) forms a complex with a first binding moiety of a first target and a second modified circRNA (e.g., a fully modified circular polyribonucleotide or a hybrid modified circular polyribonucleotide) forms a complex with a second binding moiety of a second target.

In some embodiments, a modified circRNA (e.g., a fully modified circular polyribonucleotide or a hybrid modified circular polyribonucleotide) can include a binding site for one or more binding moieties on one or more antibody-polypeptide complexes, polypeptide-polypeptide complexes, polypeptide-DNA complexes, polypeptide-RNA complexes, polypeptide-aptamer complexes, virus particle-antibody complexes, virus particle-polypeptide complexes, virus particle-DNA complexes, virus particle-RNA complexes, virus particle-aptamer complexes, cell-antibody complexes, cell-polypeptide complexes, cell-DNA complexes, cell-RNA complexes, cell-aptamer complexes, small molecule-polypeptide complexes, small molecule-DNA complexes, small molecule-aptamer complexes, small molecule-cell complexes, small molecule-virus particle complexes, and combinations thereof.

In some instances, a binding moiety is on a polypeptide, protein, or fragment thereof. In some embodiments, a binding moiety comprises a domain, a fragment, an epitope, a region, or a portion of a polypeptide, protein, or fragment thereof. For example, a binding moiety comprises a domain, a fragment, an epitope, a region, or a portion of an isolated polypeptide, a polypeptide of a cell, a purified polypeptide, or a recombinant polypeptide. For example, a binding moiety comprises a domain, a fragment, an epitope, a region, or a portion of an antibody or fragment thereof. For example, a binding moiety comprises a domain, a fragment, an epitope, a region, or a portion of a transcription factor. For example, a binding moiety comprises a domain, a fragment, an epitope, a region, or a portion of a receptor. For example, a binding moiety comprises a domain, a fragment, an epitope, a region, or a portion of a transmembrane receptor. Binding moieties may be on or comprise a domain, a fragment, an epitope, a region, or a portion of isolated, purified, and/or recombinant polypeptides. Binding moieties include binding moieties on or a domain, a fragment, an epitope, a region, or a portion of a mixture of analytes (e.g., a lysate). For example, binding moieties are on or comprise a domain, a fragment, an epitope, a region, or a portion of from a plurality of cells or from a lysate of a single cell.

In some instances, a binding moiety is on or comprises a domain, a fragment, an epitope, a region, or a portion of a small molecule. For example, a binding moiety is on or comprises a domain, a fragment, an epitope, a region, or a portion of a drug. For example, a binding moiety is on or comprises a domain, a fragment, an epitope, a region, or a portion of a compound. For example, a binding moiety is on or comprises a domain, a fragment, an epitope, a region, or a portion of an organic compound. In some instances, a binding moiety is on or comprises a domain, a fragment, an epitope, a region, or a portion of a small molecule with a molecular weight of 900 Daltons or less. In some instances, a binding moiety is on or comprises a domain, a fragment, an epitope, a region, or a portion of a small molecule with a molecular weight of 500 Daltons or more. Binding moieties may be obtained, for example, from a library of naturally occurring or synthetic molecules, including a library of compounds produced through combinatorial means, i.e. a compound diversity combinatorial library. Combinatorial libraries, as well as methods for their production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; and 5,223,409, the disclosures of which are herein incorporated by reference.

A binding moiety can be on or comprise a domain, a fragment, an epitope, a region, or a portion of a member of a specific binding pair (e.g., a ligand). A binding moiety can be on or comprise a domain, a fragment, an epitope, a region, or a portion of monovalent (monoepitopic) or polyvalent (polyepitopic). A binding moiety can be antigenic or haptenic. A binding moiety can be on or comprise a domain, a fragment, an epitope, a region, or a portion of a single molecule or a plurality of molecules that share at least one common epitope or determinant site. A binding moiety can be on or comprise a domain, a fragment, an epitope, a region, or a portion of a part of a cell (e.g., a bacteria cell, a plant cell, or an animal cell). A binding moiety can be either in a natural environment (e.g., tissue), a cultured cell, or a microorganism (e.g., a bacterium, fungus, protozoan, or virus), or a lysed cell. A binding moiety can be modified (e.g., chemically), to provide one or more additional binding sites such as, but not limited to, a dye (e.g., a fluorescent dye), a polypeptide modifying moiety such as a phosphate group, a carbohydrate group, and the like, or a polynucleotide modifying moiety such as a methyl group.

In some instances, a binding moiety is on or comprises a domain, a fragment, an epitope, a region, or a portion of a molecule found in a sample from a host. A sample from a host includes a body fluid (e.g., urine, blood, plasma, serum, saliva, semen, stool, sputum, cerebral spinal fluid, tears, mucus, and the like). A sample can be examined directly or may be pretreated to render a binding moiety more readily detectible. Samples include a quantity of a substance from a living thing or formerly living things. A sample can be natural, recombinant, synthetic, or not naturally occurring. A binding moiety can be any of the above that is expressed from a cell naturally or recombinantly, in a cell lysate or cell culture medium, an in vitro translated sample, or an immunoprecipitation from a sample (e.g., a cell lysate).

In some instances, a binding moiety of a target is expressed in a cell-free system or in vitro. For example, a binding moiety of a target is in a cell extract. In some instances, a binding moiety of a target is in a cell extract with a DNA template, and reagents for transcription and translation. Exemplary sources of cell extracts that can be used include wheat germ, *Escherichia coli*, rabbit reticulocyte, hyperthermophiles, hybridomas, *Xenopus* oocytes, insect cells, and mammalian cells (e.g., human cells). Exemplary cell-free methods that can be used to express target polypeptides (e.g., to produce target polypeptides on an array) include Protein in situ arrays (PISA), Multiple spotting technique (MIST), Self-assembled mRNA translation, Nucleic acid programmable protein array (NAPPA), nanowell NAPPA, DNA array to protein array (DAPA), membrane-free DAPA, nanowell copying and μIP-microintaglio printing, and pMAC-protein microarray copying (See Kilb et al., *Eng. Life Sci.* 2014, 14, 352-364).

In some instances, a binding moiety of a target is synthesized in situ (e.g., on a solid substrate of an array) from a DNA template. In some instances, a plurality of binding moieties is synthesized in situ from a plurality of corresponding DNA templates in parallel or in a single reaction. Exemplary methods for in situ target polypeptide expression include those described in Stevens, Structure 8(9): R177-R185 (2000); Katzen et al., *Trends Biotechnol.* 23(3):150-6. (2005); He et al., *Curr. Opin. Biotechnol.* 19(1):4-9. (2008); Ramachandran et al., *Science* 305(5680):86-90. (2004); He et al., *Nucleic Acids Res.* 29(15):E73-3 (2001); Angenendt et al., *Mol. Cell* Proteomics 5(9): 1658-66 (2006); Tao et al, *Nat Biotechnol* 24(10):1253-4 (2006); Angenendt et al., *Anal. Chem.* 76(7):1844-9 (2004); Kinpara et al., *J. Biochem.* 136(2):149-54 (2004); Takulapalli et al., *J. Proteome Res.* 11(8):4382-91 (2012); He et al., *Nat. Methods* 5(2):175-7 (2008); Chatterjee and J. LaBaer, *Curr Opin Biotech* 17(4):334-336 (2006); He and Wang, *Biomol Eng* 24(4):375-80 (2007); and He and Taussig, *J. Immunol. Methods* 274(1-2):265-70 (2003).

In some instances, a binding moiety of a nucleic acid target comprises a span of at least 6 nucleotides, for example, least 8, 9, 10, 12, 15, 20, 25, 30, 40, 50, or 100 nucleotides. In some instances, a binding moiety of a protein target comprises a contiguous stretch of nucleotides. In some instances, a binding moiety of a protein target comprises a non-contiguous stretch of nucleotides. In some instances, a binding moiety of a nucleic acid target comprises a site of a mutation or functional mutation, including a deletion, addition, swap, or truncation of the nucleotides in a nucleic acid sequence.

In some instances, a binding moiety of a protein target comprises a span of at least 6 amino acids, for example, least 8, 9, 10, 12, 15, 20, 25, 30, 40, 50, or 100 amino acids. In some instances, a binding moiety of a protein target comprises a contiguous stretch of amino acids. In some instances, a binding moiety of a protein target comprises a non-contiguous stretch of amino acids. In some instances, a binding moiety of a protein target comprises a site of a mutation or functional mutation, including a deletion, addition, swap, or truncation of the amino acids in a polypeptide sequence.

In some embodiments, a binding moiety is on or comprises a domain, a fragment, an epitope, a region, or a portion of a membrane bound protein. Exemplary membrane bound proteins include, but are not limited to, GPCRs (e.g., adrenergic receptors, angiotensin receptors, cholecystokinin receptors, muscarinic acetylcholine receptors, neurotensin receptors, galanin receptors, dopamine receptors, opioid receptors, erotonin receptors, somatostatin receptors, etc.), ion channels (e.g., nicotinic acetylcholine receptors, sodium channels, potassium channels, etc.), receptor tyrosine kinases, receptor serine/threonine kinases, receptor guanylate cyclases, growth factor and hormone receptors (e.g., epidermal growth factor (EGF) receptor), and others. The binding moiety may also be on or comprise a domain, a fragment, an epitope, a region, or a portion of a mutant or modified variants of membrane-bound proteins. For example, some single or multiple point mutations of GPCRs retain function and are involved in disease (See, e.g., Stadel et al., (1997) *Trends in Pharmacological Review* 18:430-37).

In some embodiments, modified circRNA (e.g., a fully modified circular polyribonucleotide or a hybrid modified circular polyribonucleotide) can include other binding motifs for binding other intracellular molecules. Non-limiting examples of modified circRNA (e.g., a fully modified circular polyribonucleotide or a hybrid modified circular polyribonucleotide) applications are listed in TABLE 4.

TABLE 4

| Process | MOA (example) |
|---|---|
| Directed Transcription | DNA-circRNA-Protein (pol, TF) |
| Epigenetic Remodeling | DNA-circRNA-Protein (SWI/SNF) |
| Transcriptional interference | circRNA-DNA |
| Translational interference | circRNA-mRNA or ribosome |
| Protein interaction inhibitor | circRNA-Protein |
| Protein Degradation | Protein- circRNA-Protein (ubiq) |
| RNA Degradation | RNA-circRNA-RNA (RNAse to RNA) |
| DNA Degradation | DNA-circRNA-Protein (DNA to DNAse) |
| Artificial Receptor | Cell Surface-circRNA-Substrate |
| Protein Translocation | Protein-circRNA-Protein/RNA |
| Cellular Fusion | Cell Surface-circRNA-Cell Surface |
| Complex Disassembly | Protein-circRNA-Protein/RNA |
| Receptor inhibition | Protein-circRNA-Substrate |
| Signal Transduction | Protein-circRNA-Protein (caspase) |
| Multi-Enzyme Acceleration | Multiple Enzymes-circRNA |
| Induction of receptor | circRNA-receptor |

RNA Binding Sites

In some embodiments, the modified circular polyribonucleotide (e.g., a fully modified circular polyribonucleotide or a hybrid modified circular polyribonucleotide) comprises one or more RNA binding sites. In some embodiments, a first portion comprises one or more RNA binding sites, consisting of unmodified nucleotides. In some embodiments, the modified circular polyribonucleotide (e.g., a fully modified circular polyribonucleotide or a hybrid modified circular polyribonucleotide) includes RNA binding sites that modify expression of an endogenous gene and/or an exogenous gene. In some embodiments, the RNA binding site modulates expression of a host gene. The RNA binding site can include a sequence that hybridizes to an endogenous gene (e.g., a sequence for a miRNA, siRNA, mRNA, lncRNA, RNA, DNA, an antisense RNA, gRNA as described herein), a sequence that hybridizes to an exogenous nucleic acid such as a viral DNA or RNA, a sequence that hybridizes to an RNA, a sequence that interferes with gene transcription, a sequence that interferes with RNA translation, a sequence that stabilizes RNA or destabilizes RNA such as through targeting for degradation, or a sequence that modulates a DNA- or RNA-binding factor.

In some embodiments, the RNA binding site can be one of a tRNA, lncRNA, lincRNA, miRNA, rRNA, snRNA, microRNA, siRNA, piRNA, snoRNA, snRNA, exRNA, scaRNA, Y RNA, and hnRNA binding site. RNA binding sites are well-known to persons of ordinary skill in the art.

Certain RNA binding sites can inhibit gene expression through the biological process of RNA interference (RNAi). In some embodiments, the modified circular polyribonucleotides comprises an RNAi molecule with RNA or RNA-like structures typically having 15-50 base pairs (such as about18-25 base pairs) and having a nucleobase sequence identical (complementary) or nearly identical (substantially complementary) to a coding sequence in an expressed target gene within the cell. RNAi molecules include, but are not limited to: short interfering RNA (siRNA), double-strand RNA (dsRNA), microRNA (miRNA), short hairpin RNA (shRNA), meroduplexes, and dicer substrates.

In some embodiments, the RNA binding site comprises an siRNA or an shRNA. siRNA and shRNA resemble intermediates in the processing pathway of the endogenous miRNA genes. In some embodiments, siRNA can function as miRNA and vice versa. MicroRNA, like siRNA, can use RISC to downregulate target genes, but unlike siRNA, most animal miRNA do not cleave the mRNA. Instead, miRNA reduce protein output through translational suppression or polyA removal and mRNA degradation. Known miRNA binding sites are within mRNA 3'-UTRs; miRNA seem to target sites with near-perfect complementarity to nucleotides 2-8 from the miRNA's 5' end. This region is known as the seed region. Because siRNA and miRNA are interchangeable, exogenous siRNA can downregulate mRNA with seed complementarity to the siRNA. Multiple target sites within a 3'-UTR can give stronger downregulation.

MicroRNA (miRNA) are short noncoding RNA that bind to the 3'-UTR of nucleic acid molecules and down-regulate gene expression either by reducing nucleic acid molecule stability or by inhibiting translation. The modified circular polyribonucleotide (e.g., a fully modified circular polyribonucleotide or a hybrid modified circular polyribonucleotide) can comprise one or more miRNA target sequences, miRNA sequences, or miRNA seeds. Such sequences can correspond to any miRNA.

A miRNA sequence comprises a "seed" region, i.e., a sequence in the region of positions 2-8 of the mature miRNA, which sequence has Watson-Crick complementarity to the miRNA target sequence. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA target is flanked by an adenine (A) opposed to miRNA position 1. In some embodiments, a miRNA seed can comprise 6 nucleotides (e.g., nucleotides 2-7 of the mature miRNA), wherein the seed-complementary site in the corresponding miRNA target is flanked by an adenine (A) opposed to miRNA at position 1.

The bases of the miRNA seed can be substantially complementary with the target sequence. By engineering miRNA target sequences into the modified circular polyribonucleotide, the modified circular polyribonucleotide (e.g., a fully modified circular polyribonucleotide or a hybrid modified circular polyribonucleotide) can evade or be detected by the host's immune system, have modulated degradation, or modulated translation. This process can reduce the hazard of off target effects upon modified circular polyribonucleotide (e.g., a fully modified circular polyribonucleotide or a hybrid modified circular polyribonucleotide) delivery.

The modified circular polyribonucleotide (e.g., a fully modified circular polyribonucleotide or a hybrid modified circular polyribonucleotide) can include an miRNA sequence identical to about 5 to about 25 contiguous nucleotides of a target gene. In some embodiments, the miRNA sequence targets a mRNA and commences with the dinucleotide AA, comprises a GC-content of about 30%-70%, about 30%-60%, about 40%-60%, or about 45%-55%, and does not have a high percentage identity to any nucleotide sequence other than the target in the genome of the mammal in which it is to be introduced, for example, as determined by standard BLAST search.

Conversely, miRNA binding sites can be engineered out of (i.e. removed from) the modified circular polyribonucleotide (e.g., a fully modified circular polyribonucleotide or a hybrid modified circular polyribonucleotide) to modulate protein expression in specific tissues. Regulation of expression in multiple tissues can be accomplished through introduction or removal or one or several miRNA binding sites.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126). MiRNA can also regulate complex biological processes, such as angiogenesis (miR-132). In the modified circular polyribonucleotides described herein, binding sites for miRNA that are involved in such processes can be removed or introduced, in order to tailor the expression from the modified circular polyribonucleotide (e.g., a fully modified circular polyribonucleotide or a hybrid modified circular polyribonucleotide) to biologically relevant cell types or to the context of relevant biological processes. In some embodiments, the miRNA binding site includes, e.g., miR-7.

Through an understanding of the expression patterns of miRNA in different cell types, the modified circular polyribonucleotide (e.g., a fully modified circular polyribonucleotide or a hybrid modified circular polyribonucleotide) described herein can be engineered for more targeted expression in specific cell types or only under specific biological conditions. Through introduction of tissue-specific miRNA binding sites, the modified circular polyribonucleotide (e.g., a fully modified circular polyribonucleotide or a hybrid modified circular polyribonucleotide) can be designed for optimal protein expression in a tissue or in the context of a biological condition.

In addition, miRNA seed sites can be incorporated into the modified circular polyribonucleotide (e.g., a fully modified circular polyribonucleotide or a hybrid modified circular polyribonucleotide) to modulate expression in certain cells which results in a biological improvement. An example of this is incorporation of miR-142 sites. Incorporation of miR-142 sites into the modified circular polyribonucleotide (e.g., a fully modified circular polyribonucleotide or a hybrid modified circular polyribonucleotide) described herein can modulate expression in hematopoietic cells, but also reduce or abolish immune responses to a protein encoded in the modified circular polyribonucleotide.

In some embodiments, the modified circular polyribonucleotide comprises at least one miRNA, e.g., 2, 3, 4, 5, 6, or more. In some embodiments, the modified circular polyribonucleotide (e.g., a fully modified circular polyribonucleotide or a hybrid modified circular polyribonucleotide) comprises an miRNA having at least about 75%, about 80%, about 85%, about 90%, about 95%, about 96%, about 97%, about 98%, about 99%, or 100% nucleotide sequence identity to any one of the nucleotide sequences or a sequence that is complementary to a target sequence.

Lists of known miRNA sequences can be found in databases maintained by research organizations, for example, Wellcome Trust Sanger Institute, Penn Center for Bioinformatics, Memorial Sloan Kettering Cancer Center, and European Molecule Biology Laboratory. RNAi molecules can be readily designed and produced by technologies known in the art. In addition, computational tools can be used to determine effective and specific sequence motifs.

In some embodiments, a modified circular polyribonucleotide (e.g., a fully modified circular polyribonucleotide or a hybrid modified circular polyribonucleotide) comprises a long non-coding RNA. Long non-coding RNA (lncRNA) include non-protein coding transcripts longer than 100 nucleotides. The longer length distinguishes lncRNA from small regulatory RNA, such as miRNA, siRNA, and other short RNA. In general, the majority (~78%) of lncRNA are characterized as tissue-specific. Divergent lncRNA that are transcribed in the opposite direction to nearby protein-coding genes (comprise a significant proportion ~20% of total lncRNA in mammalian genomes) can regulate the transcription of the nearby gene.

The length of the RNA binding site may be between about 5 to 30 nucleotides, between about 10 to 30 nucleotides, or about 11, 12, 13, 14, 15, 16, 17, 18, 19, 20, 21, 22, 23, 24, 25, 26, 27, 28, 29, 30, or more nucleotides. The degree of identity of the RNA binding site to a target of interest can be at least 75%, at least 80%, at least 85%, at least 90%, or at least 95%.

In some embodiments, the modified circular polyribonucleotide (e.g., a fully modified circular polyribonucleotide or a hybrid modified circular polyribonucleotide) includes one or more large intergenic non-coding RNA (lincRNA) binding sites. LincRNA make up most of the long non-coding RNA. LincRNA are non-coding transcripts and, in some embodiments, are more than about 200 nucleotides long. In some embodiments, lincRNA have an exon-intron-exon structure, similar to protein-coding genes, but do not encompass open-reading frames and do not code for proteins. LincRNA expression can be strikingly tissue-specific compared to coding genes. LincRNA are typically co-expressed with their neighboring genes to a similar extent to that of pairs of neighboring protein-coding genes. In some embodiments, the modified circular polyribonucleotide (e.g., a fully modified circular polyribonucleotide or a hybrid modified circular polyribonucleotide) comprises a circularized lincRNA.

In some embodiments, the modified circular polyribonucleotides disclosed herein include one or more lincRNA, for example, FIRRE, LINC00969, PVT1, LINC01608, JPX, LINC01572, LINC00355, C1orf132, C3orf35, RP11-734, LINCO1608, CC-499B15.5, CASC15, LINC00937, and RP11-191.

Lists of known lincRNA and lncRNA sequences can be found in databases maintained by research organizations, for example, Institute of Genomics and Integrative Biology, Diamantina Institute at the University of Queensland, Ghent University, and Sun Yat-sen University. LincRNA and lncRNA molecules can be readily designed and produced by technologies known in the art. In addition, computational tools can be used to determine effective and specific sequence motifs.

The RNA binding site can comprise a sequence that is substantially complementary, or fully complementary, to all or a fragment of an endogenous gene or gene product (e.g., mRNA). The complementary sequence can complement sequences at the boundary between introns and exons to prevent the maturation of newly-generated nuclear RNA transcripts of specific genes into mRNA for transcription. The complementary sequence may be specific to genes by hybridizing with the mRNA for that gene and prevent its translation. The RNA binding site can comprise a sequence that is antisense or substantially antisense to all or a fragment of an endogenous gene or gene product, such as DNA, RNA, or a derivative or hybrid thereof.

In some embodiments, the modified circular polyribonucleotide (e.g., a fully modified circular polyribonucleotide or a hybrid modified circular polyribonucleotide) comprises a RNA binding site that has an RNA or RNA-like structure typically between about 5-5000 base pairs (depending on the specific RNA structure, e.g., miRNA 5-30 bps, lncRNA 200-500 bps) and has a nucleobase sequence identical (complementary) or nearly identical (substantially complementary) to a coding sequence in an expressed target gene within the cell.

DNA Binding Sites

In some embodiments, the modified circular polyribonucleotide (e.g., a fully modified circular polyribonucleotide or a hybrid modified circular polyribonucleotide) comprises a DNA binding site, such as a sequence for a guide RNA (gRNA). In some embodiments, a first portion comprises one or more DNA binding sites, consisting of unmodified nucleotides. In some embodiments, the modified circular polyribonucleotide (e.g., a fully modified circular polyribonucleotide or a hybrid modified circular polyribonucleotide) comprises a guide RNA or a complement to a gRNA sequence. A gRNA short synthetic RNA composed of a "scaffold" sequence necessary for binding to the incomplete effector moiety and a user-defined ~20 nucleotide targeting sequence for a genomic target. Guide RNA sequences can have a length of between 17-24 nucleotides (e.g., 19, 20, or 21 nucleotides) and complementary to the targeted nucleic acid sequence. Custom gRNA generators and algorithms can be used in the design of effective guide RNA. Gene editing can be achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNA can be effective in genome editing.

The gRNA can recognize specific DNA sequences (e.g., sequences adjacent to or within a promoter, enhancer, silencer, or repressor of a gene).

In some embodiments, the gRNA is part of a CRISPR system for gene editing. For gene editing, the modified circular polyribonucleotide (e.g., a fully modified circular polyribonucleotide or a hybrid modified circular polyribonucleotide) can be designed to include one or multiple guide RNA sequences corresponding to a desired target DNA sequence. The gRNA sequences may include at least 10, 11, 12, 13, 14, 15, 16, 17, 18, 19, 20, 21, 22, 23, 24, 25, 26, 27, 28, 29, 30, or more nucleotides for interaction with Cas9 or other exonuclease to cleave DNA, e.g., Cpf1 interacts with at least about 16 nucleotides of gRNA sequence for detectable DNA cleavage.

In some embodiments, the modified circular polyribonucleotide (e.g., a fully modified circular polyribonucleotide or a hybrid modified circular polyribonucleotide) includes sequences that bind a major groove of in duplex DNA. In one such instance, the specificity and stability of a triplex structure created by the modified circular polyribonucleotide (e.g., a fully modified circular polyribonucleotide or a hybrid modified circular polyribonucleotide) and duplex DNA is afforded via Hoogsteen hydrogen bonds, which are different from those formed in classical Watson-Crick base pairing in duplex DNA. In one instance, the modified circular polyribonucleotide (e.g., a fully modified circular polyribonucleotide or a hybrid modified circular polyribonucleotide) binds to the purine-rich strand of a target duplex through the major groove.

In some embodiments, triplex formation occurs in two motifs, distinguished by the orientation of the modified circular polyribonucleotide (e.g., a fully modified circular polyribonucleotide or a hybrid modified circular polyribonucleotide) with respect to the purine-rich strand of the target duplex. In some instances, polypyrimidine sequence stretches in a modified circular polyribonucleotides bind to the polypurine sequence stretches of a duplex DNA via Hoogsteen hydrogen bonding in a parallel fashion (i.e. in the same 5' to 3', orientation as the purine-rich strand of the duplex), whereas the polypurine stretches (R) bind in an antiparallel fashion to the purine strand of the duplex via reverse-Hoogsteen hydrogen bonds. In the antiparallel, a purine motif comprises triplets of G:G–C, A:A–T, or T:A–T; whereas in the parallel, a pyrimidine motif comprises canonical triples of C+:G–C or T:A–T triplets (where C+represents a protonated cytosine on the N3 position). Antiparallel GA and GT sequences in a modified circular polyribonucleotide (e.g., a fully modified circular polyribonucleotide or a hybrid modified circular polyribonucleotide) may form stable triplexes at neutral pH, while parallel CT sequences in a modified circular polyribonucleotide (e.g., a fully modified circular polyribonucleotide or a hybrid modified circular polyribonucleotide) may bind at acidic pH. N3 on cytosine in the modified circular polyribonucleotide (e.g., a fully modified circular polyribonucleotide or a hybrid modified circular polyribonucleotide) may be protonated. Substitution of C with 5-methyl-C may permit binding of CT sequences in the modified circular polyribonucleotide (e.g., a fully modified circular polyribonucleotide or a hybrid modified circular polyribonucleotide) at physiological pH as 5-methyl-C has a higher pK than does cytosine. For both purine and pyrimidine motifs, contiguous homopurine-homopyrimidine sequence stretches of at least 10 base pairs aid modified circular polyribonucleotide (e.g., a fully modified circular polyribonucleotide or a hybrid modified circular polyribonucleotide) binding to duplex DNA, since shorter triplexes may be unstable under physiological conditions, and interruptions in sequences can destabilize the triplex structure. In some embodiments, the DNA duplex target for triplex formation includes consecutive purine bases in one strand. In some embodiments, a target for triplex formation comprises a homopurine sequence in one strand of the DNA duplex and a homopyrimidine sequence in the complementary strand.

In some embodiments, a triplex comprising a modified circular polyribonucleotide (e.g., a fully modified circular polyribonucleotide or a hybrid modified circular polyribonucleotide) is a stable structure. In some embodiments, a triplex comprising a modified circular polyribonucleotide (e.g., a fully modified circular polyribonucleotide or a hybrid modified circular polyribonucleotide) exhibits an increased half-life, e.g., increased by about 5%, 10%, 15%, 20%, 25%, 30%, 35%, 40%, 45%, 50%, or greater, e.g., persistence for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time there between.

Protein Binding Sites

In some embodiments, the modified circular polyribonucleotide (e.g., a fully modified circular polyribonucleotide or a hybrid modified circular polyribonucleotide) includes one or more protein binding sites. In some embodiments, a first portion comprises one or more protein binding sites, consisting of unmodified nucleotides. In one embodiment, the modified circular polyribonucleotide (e.g., a fully modified circular polyribonucleotide or a hybrid modified circular polyribonucleotide) includes a protein binding site to reduce an immune response from the host as compared to the response triggered by a reference compound, e.g., a modified circular polyribonucleotide (e.g., a fully modified circular polyribonucleotide or a hybrid modified circular polyribonucleotide) lacking the protein binding site, e.g., linear RNA.

In some embodiments, modified circular polyribonucleotides disclosed herein include one or more protein binding sites to bind a protein, e.g., a ribosome. By engineering protein binding sites, e.g., ribosome binding sites, into the modified circular polyribonucleotide (e.g., a fully modified circular polyribonucleotide or a hybrid modified circular polyribonucleotide), the modified circular polyribonucleotide (e.g., a fully modified circular polyribonucleotide or a hybrid modified circular polyribonucleotide) can evade or have reduced detection by the host's immune system, have modulated degradation, or modulated translation.

In some embodiments, the modified circular polyribonucleotide (e.g., a fully modified circular polyribonucleotide or a hybrid modified circular polyribonucleotide) comprises at least one immunoprotein binding site, for example, to mask the modified circular polyribonucleotide (e.g., a fully modified circular polyribonucleotide or a hybrid modified circular polyribonucleotide) from components of the host's immune system, e.g., evade CTL responses. In some embodiments, the immunoprotein binding site is a nucleotide sequence that binds to an immunoprotein and aids in masking the modified circular polyribonucleotide (e.g., a fully modified circular polyribonucleotide or a hybrid modified circular polyribonucleotide) as non-endogenous.

Traditional mechanisms of ribosome engagement to linear RNA involve ribosome binding to the capped 5' end of an RNA. From the 5' end, the ribosome migrates to an initiation codon, whereupon the first peptide bond is formed. According to the present invention, internal initiation (i.e., cap-independent) or translation of the modified circular polyribonucleotide (e.g., a fully modified circular polyribonucleotide or a hybrid modified circular polyribonucleotide) does not require a free end or a capped end. Rather, a ribosome binds to a non-capped internal site, whereby the ribosome begins polypeptide elongation at an initiation codon. In some embodiments, the modified circular polyribonucleotide (e.g., a fully modified circular polyribonucleotide or a hybrid modified circular polyribonucleotide) includes one or more RNA sequences comprising a ribosome binding site, e.g., an initiation codon.

In some embodiments, modified circular polyribonucleotides disclosed herein comprise a protein binding sequence that binds to a protein. In some embodiments, the protein binding sequence targets or localizes a modified circular polyribonucleotide (e.g., a fully modified circular polyribonucleotide or a hybrid modified circular polyribonucleotide) to a specific target. In some embodiments, the protein binding sequence specifically binds an arginine-rich region of a protein.

In some embodiments, the protein binding site includes, but is not limited to, a binding site to the protein, such as ACIN1, AGO, APOBEC3F, APOBEC3G, ATXN2, AUH, BCCIP, CAPRIN1, CELF2, CPSF1, CPSF2, CPSF6, CPSF7, CSTF2, CSTF2T, CTCF, DDX21, DDX3, DDX3X, DDX42, DGCR8, EIF3A, EIF4A3, EIF4G2, ELAVL1, ELAVL3, FAM120A, FBL, FIP1L1, FKBP4, FMR1, FUS, FXR1, FXR2, GNL3, GTF2F1, HNRNPA1, HNRNPA2B1, HNRNPC, HNRNPK, HNRNPL, HNRNPM, HNRNPU, HNRNPUL1, IGF2BP1, IGF2BP2, IGF2BP3, ILF3, KHDRBS1, LARP7, LIN28A, LIN28B, m6A, MBNL2, METTL3, MOV10, MSI1, MSI2, NONO, NONO−, NOP58, NPM1, NUDT21, PCBP2, POLR2A, PRPF8, PTBP1, RBFOX2, RBM10, RBM22, RBM27, RBM47, RNPS1, SAFB2, SBDS, SF3A3, SF3B4, SIRT7, SLBP, SLTM, SMNDC1, SND1, SRRM4, SRSF1, SRSF3, SRSF7, SRSF9, TAF15, TARDBP, TIA1, TNRC6A, TOP3B, TRA2A, TRA2B, U2AF1, U2AF2, UNK, UPF1, WDR33, XRN2, YBX1, YTHDC1, YTHDF1, YTHDF2, YWHAG, ZC3H7B, PDK1, AKT1, and any other protein that binds RNA.

Other Binding Sites

In some embodiments, the modified circular polyribonucleotide (e.g., a fully modified circular polyribonucleotide or a hybrid modified circular polyribonucleotide) comprises one or more binding sites to a non-RNA or non-DNA target. In some embodiments, a first portion comprises one or more binding sites to a non-RNA or non-DNA target, consisting of unmodified nucleotides. In some embodiments, the binding site can be one of a small molecule, an aptamer, a lipid, a carbohydrate, a virus particle, a membrane, a multi-component complex, a cell, a cellular moiety, or any fragment thereof binding site. In some embodiments, the modified circular polyribonucleotide (e.g., a fully modified circular polyribonucleotide or a hybrid modified circular polyribonucleotide) comprises one or more binding sites to a lipid. In some embodiments, the modified circular polyribonucleotide (e.g., a fully modified circular polyribonucleotide or a hybrid modified circular polyribonucleotide) comprises one or more binding sites to a carbohydrate. In some embodiments, the modified circular polyribonucleotide (e.g., a fully modified circular polyribonucleotide or a hybrid modified circular polyribonucleotide) comprises one or more binding sites to a carbohydrate. In some embodiments, the modified circular polyribonucleotide (e.g., a fully modified circular polyribonucleotide or a hybrid modified circular polyribonucleotide) comprises one or more binding sites to a membrane. In some embodiments, the modified circular polyribonucleotide (e.g., a fully modified circular polyribonucleotide or a hybrid modified circular polyribonucleotide) comprises one or more binding sites to a multi-component complex, e.g., ribosome, nucleosome, transcription machinery, etc.

Sequestration

In some embodiments, modified circRNA (e.g., a fully modified circular polyribonucleotide or a hybrid modified circular polyribonucleotide) described herein sequesters a target, e.g., DNA, RNA, proteins, and other cellular components to regulate cellular processes. Modified circRNA (e.g., a fully modified circular polyribonucleotide or a hybrid modified circular polyribonucleotide) with binding sites for a target of interest can compete with binding of the target with an endogenous binding partner. In some embodiments, modified circRNA (e.g., a fully modified circular polyribonucleotide or a hybrid modified circular polyribonucleotide) described herein sequesters miRNA. In some embodiments, modified circRNA (e.g., a fully modified circular polyribonucleotide or a hybrid modified circular polyribonucleotide) described herein sequesters mRNA. In some embodiments, modified circRNA (e.g., a fully modified circular polyribonucleotide or a hybrid modified circular polyribonucleotide) described herein sequesters proteins. In some embodiments, modified circRNA (e.g., a fully modified circular polyribonucleotide or a hybrid modified circular polyribonucleotide) described herein sequesters ribosomes. In some embodiments, modified circRNA (e.g., a fully modified circular polyribonucleotide or a hybrid modified circular polyribonucleotide) described herein sequesters other modified circRNA. In some embodiments, modified circRNA described herein sequesters non-coding RNA, lncRNA, miRNA, tRNA, rRNA, snoRNA, ncRNA, siRNA, or shRNA. In some embodiments, modified circRNA (e.g., a fully modified circular polyribonucleotide or a hybrid modified circular polyribonucleotide) described herein includes a degradation element that degrades a sequestered target, e.g., DNA, RNA, protein, or other cellular component bound to the modified circRNA. Non-limiting examples of modified circRNA (e.g., a fully modified circular polyribonucleotide or a hybrid modified circular polyribonucleotide) sequestration applications are listed in TABLE 5.

TABLE 5

| Process | MOA (example) |
|---|---|
| Transcriptional interference | circRNA-DNA |
| Translational interference | circRNA-mRNA or ribosome |
| Protein interaction inhibitor | circRNA-Protein |
| microRNA sequester | circRNA-RNA (antisense) |
| circRNA sequester (endogenous circRNA) | circRNA-circRNA (antisense) |

In some embodiments, any of the methods of using modified circRNA (e.g., a fully modified circular polyribonucleotide or a hybrid modified circular polyribonucleotide) described herein can be in combination with a translating element. Modified circRNA described herein that contain a translating element can translate RNA into proteins.

Cleavage Sequences

In some embodiments, the modified circular polyribonucleotide (e.g., a fully modified circular polyribonucleotide or a hybrid modified circular polyribonucleotide) includes at least one cleavage sequence. In some embodiments, the cleavage sequence is adjacent to an expression sequence. In some embodiments, the modified circular polyribonucleotide (e.g., a fully modified circular polyribonucleotide or a hybrid modified circular polyribonucleotide) includes a cleavage sequence, such as in an immolating modified circRNA or cleavable modified circRNA or self-cleaving modified circRNA. In some embodiments, the modified circular polyribonucleotide (e.g., a fully modified circular polyribonucleotide or a hybrid modified circular polyribonucleotide) comprises two or more cleavage sequences, leading to separation of the modified circular polyribonucleotide (e.g., a fully modified circular polyribonucleotide or a hybrid modified circular polyribonucleotide) into multiple products, e.g., miRNAs, linear RNAs, smaller modified circular polyribonucleotide, etc.

In some embodiments, the cleavage sequence includes a ribozyme RNA sequence. A ribozyme (from ribonucleic acid enzyme, also called RNA enzyme or catalytic RNA) is a RNA molecule that catalyzes a chemical reaction. Many natural ribozymes catalyze either the hydrolysis of one of their own phosphodiester bonds, or the hydrolysis of bonds in other RNA, but they have also been found to catalyze the aminotransferase activity of the ribosome. Catalytic RNA can be “evolved” by in vitro methods. Similar to riboswitch activity discussed above, ribozymes and their reaction products can regulate gene expression. In some embodiments, a catalytic RNA or ribozyme can be placed within a larger non-coding RNA such that the ribozyme is present at many copies within the cell for the purposes of chemical transformation of a molecule from a bulk volume. In some embodiments, aptamers and ribozymes can both be encoded in the same non-coding RNA.

Immolating Sequence

In some embodiments, modified circRNA (e.g., a fully modified circular polyribonucleotide or a hybrid modified circular polyribonucleotide) described herein comprises immolating modified circRNA or cleavable modified circRNA or self-cleaving modified circRNA. Modified circRNA can deliver cellular components including, for example, RNA, lncRNA, lincRNA, miRNA, tRNA, rRNA, snoRNA, ncRNA, siRNA, or shRNA. In some embodiments, modified circRNA (e.g., a fully modified circular polyribonucleotide or a hybrid modified circular polyribonucleotide) includes miRNA separated by (i) self-cleavable elements; (ii) cleavage recruitment sites; (iii) degradable linkers; (iv) chemical linkers; and/or (v) spacer sequences. In some embodiments, modified circRNA includes siRNA separated by (i) self-cleavable elements; (ii) cleavage recruitment sites (e.g., ADAR); (iii) degradable linkers (e.g., glycerol); (iv) chemical linkers; and/or (v) spacer sequences. Non-limiting examples of self-cleavable elements include hammerhead, splicing element, hairpin, hepatitis delta virus (HDV), Varkud Satellite (VS), and glmS ribozymes. Non-limiting examples of modified circRNA (e.g., a fully modified circular polyribonucleotide or a hybrid modified circular polyribonucleotide) immodulation applications are listed in TABLE 6.

TABLE 6

| Process | MOA (example) |
|---|---|
| miRNA delivery | microRNAs in a circular form with self cleavage element (e.g. hammerhead), cleavage recruitment (e.g. ADAR) or degradable linker (glycerol) |
| siRNA delivery | siRNAs in a circular form with self cleavage element (e.g. hammerhead), cleavage recruitment (e.g. ADAR) or degradable linker (glycerol) |

Circularization

In one embodiment, a linear modified polyribonucleotide may be cyclized, or concatemerized. In some embodiments, a linear unmodified polyribonucleotide molecule is ligated to a linear modified polyribonucleotide molecule to produce a linear hybrid modified polyribonucleotide molecule that may be cyclized or concatemerized to produce the hybrid modified circular polyribonucleotide as described herein. In some embodiments, a linear polyribonucleotide molecule comprises a first portion having a sequence of polyribonucleotides that are not modified when the nucleotides outside of the first are modified, which may then be cyclized or concatemerized to produce the hybrid modified circular polyribonucleotide as described herein. In some embodiments, the linear hybrid modified polyribonucleotide may be cyclized in vitro prior to formulation and/or delivery. In some embodiments, the linear modified polyribonucleotide (e.g., a linear fully modified polyribonucleotide or a linear hybrid modified linear polyribonucleotide) may be cyclized within a cell.

Extracellular Circularization

In some embodiments, the linear modified polyribonucleotide (e.g., a linear fully modified polyribonucleotide or a linear hybrid modified polyribonucleotide) is cyclized, or concatemerized using a chemical method to form a modified circular polyribonucleotide. In some chemical methods, the 5'-end and the 3'-end of the nucleic acid (e.g., a linear modified circular polyribonucleotide) includes chemically reactive groups that, when close together, may form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a linear RNA molecule will undergo a nucleophilic attack on the 5'-NHS-ester moiety forming a new 5'-/3'-amide bond.

In one embodiment, a DNA or RNA ligase may be used to enzymatically link a 5'-phosphorylated nucleic acid molecule (e.g., a linear modified polyribonucleotide or linear hybrid modified polyribonucleotide) to the 3'-hydroxyl group of a nucleic acid (e.g., a linear nucleic acid) forming a new phosphorodiester linkage. In an example reaction, a linear modified polyribonucleotide (e.g., a linear fully modified polyribonucleotide or a linear hybrid modified polyribonucleotide) is incubated at 37° C. for 1 hour with 1-10 units of T4 RNA ligase (New England Biolabs, Ipswich, MA) according to the manufacturer's protocol. The ligation reaction may occur in the presence of a linear nucleic acid capable of base-pairing with both the 5'- and 3'-region in juxtaposition to assist the enzymatic ligation reaction. In one embodiment, the ligation is splint ligation. For example, a splint ligase, like SplintR® ligase, can be used for splint ligation. For splint ligation, a single stranded polynucleotide (splint), like a single stranded RNA, can be designed to hybridize with both termini of a linear polyribonucleotide, so that the two termini can be juxtaposed upon hybridization with the single-stranded splint. Splint ligase can thus catalyze the ligation of the juxtaposed two termini of the linear modified polyribonucleotide, generating a modified circular polyribonucleotide, or catalyze the ligation of the juxtaposed two termini of the linear hybrid modified polyribonucleotide, generating a hybrid modified circular polyribonucleotide.

In one embodiment, a DNA or RNA ligase may be used in the synthesis of the modified circular polynucleotides (e.g., a fully modified circular polyribonucleotide or a hybrid modified circular polyribonucleotide). As a non-limiting example, the ligase may be a circ ligase or circular ligase.

In one embodiment, either the 5'- or 3'-end of the linear modified polyribonucleotide (e.g., a linear fully modified polyribonucleotide or a linear hybrid modified polyribonucleotide) can encode a ligase ribozyme sequence such that during in vitro transcription, the resultant linear modified polyribonucleotide (e.g., a linear fully modified polyribonucleotide or a linear hybrid modified polyribonucleotide) includes an active ribozyme sequence capable of ligating the 5'-end of the linear modified polyribonucleotide (e.g., a linear fully modified polyribonucleotide or a linear hybrid modified polyribonucleotide) to the 3'-end of the linear modified polyribonucleotide (e.g., a linear fully modified polyribonucleotide or a linear hybrid modified polyribonucleotide). The ligase ribozyme may be derived from the Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0° C. and 37° C.

In one embodiment, a linear modified polyribonucleotide (e.g., a linear fully modified polyribonucleotide or a linear hybrid modified polyribonucleotide) may be cyclized or concatemerized by using at least one non-nucleic acid moiety. In one aspect, the at least one non-nucleic acid moiety may react with regions or features near the 5' terminus and/or near the 3' terminus of the linear modified circular polyribonucleotide in order to cyclize or concatemerized the linear modified circular polyribonucleotide. In another aspect, the at least one non-nucleic acid moiety may be located in or linked to or near the 5' terminus and/or the 3' terminus of the linear modified circular polyribonucleotide. The non-nucleic acid moieties contemplated may be homologous or heterologous. As a non-limiting example, the non-nucleic acid moiety may be a linkage such as a hydrophobic linkage, ionic linkage, a biodegradable linkage and/or a cleavable linkage. As another non-limiting example, the non-nucleic acid moiety is a ligation moiety. As yet another non-limiting example, the non-nucleic acid moiety may be an oligonucleotide or a peptide moiety, such as an aptamer or a non-nucleic acid linker as described herein.

In one embodiment, a linear modified polyribonucleotide (e.g., a linear fully modified polyribonucleotide or a linear hybrid modified polyribonucleotide) may be cyclized or concatemerized due to a non-nucleic acid moiety that causes an attraction between atoms, molecular surfaces at, near or linked to the 5' and 3' ends of the linear modified polyribonucleotide (e.g., a linear fully modified polyribonucleotide or a linear hybrid modified polyribonucleotide). As a non-limiting example, one or more linear modified polyribonucleotides (e.g., a linear fully modified polyribonucleotide or a linear hybrid modified polyribonucleotide) may be cyclized or concatermized by intermolecular forces or intramolecular forces. Non-limiting examples of intermolecular forces include dipole-dipole forces, dipole-induced dipole forces, induced dipole-induced dipole forces, Van der Waals forces, and London dispersion forces. Non-limiting examples of intramolecular forces include covalent bonds, metallic bonds, ionic bonds, resonant bonds, agnostic bonds, dipolar bonds, conjugation, hyperconjugation and antibonding.

In one embodiment, the linear modified polyribonucleotide (e.g., a linear fully modified polyribonucleotide or a linear hybrid modified polyribonucleotide) may comprise a ribozyme RNA sequence near the 5' terminus and near the 3' terminus. The ribozyme RNA sequence may covalently link to a peptide when the sequence is exposed to the remainder of the ribozyme. In one aspect, the peptides covalently linked to the ribozyme RNA sequence near the 5' terminus and the 3'terminus may associate with each other causing a linear modified polyribonucleotide (e.g., a linear fully modified polyribonucleotide or a linear hybrid modified polyribonucleotide) to cyclize or concatemerize. In another aspect, the peptides covalently linked to the ribozyme RNA near the 5' terminus and the 3' terminus may cause the linear primary construct or linear mRNA to cyclize or concatemerize after being subjected to ligated using various methods known in the art such as, but not limited to, protein ligation. Non-limiting examples of ribozymes for use in the linear primary constructs or linear RNA of the present invention or a non-exhaustive listing of methods to incorporate and/or covalently link peptides are described in US Patent Publication No. US20030082768, the contents of which is here in incorporated by reference in its entirety.

In some embodiments, the linear modified polyribonucleotide (e.g., a linear fully modified polyribonucleotide or a linear hybrid modified polyribonucleotide) may include a 5' triphosphate of the nucleic acid converted into a 5' monophosphate, e.g., by contacting the 5' triphosphate with RNA 5' pyrophosphohydrolase (RppH) or an ATP diphosphohydrolase (apyrase). Alternately, converting the 5' triphosphate of the linear modified polyribonucleotide (e.g., a linear fully modified polyribonucleotide or a linear hybrid modified polyribonucleotide) into a 5' monophosphate may occur by a two-step reaction comprising: (a) contacting the 5' nucleotide of the linear modified polyribonucleotide (e.g., a linear fully modified polyribonucleotide or a linear hybrid modified polyribonucleotide) with a phosphatase (e.g., Antarctic Phosphatase, Shrimp Alkaline Phosphatase, or Calf Intestinal Phosphatase) to remove all three phosphates; and (b) contacting the 5' nucleotide after step (a) with a kinase (e.g., Polynucleotide Kinase) that adds a single phosphate.

In some embodiments, the circularization efficiency of the circularization methods provided herein is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or 100%. In some embodiments, the circularization efficiency of the circularization methods provided herein is at least about 40%.

Splicing Element

In some embodiment, the modified circular polyribonucleotide (e.g., a fully modified circular polyribonucleotide or a hybrid modified circular polyribonucleotide) includes at least one splicing element. In a modified circular polyribonucleotide (e.g., a fully modified circular polyribonucleotide or a hybrid modified circular polyribonucleotide) as provided herein, a splicing element can be a complete splicing element that can mediate splicing of the modified circular polyribonucleotide. Alternatively, the spicing element can also be a residual splicing element from a completed splicing event. For instance, in some cases, a splicing element of a linear polyribonucleotide can mediate a splicing event that results in circularization of the linear polyribonucleotide, thereby the resultant modified circular polyribonucleotide (e.g., a fully modified circular polyribonucleotide or a hybrid modified circular polyribonucleotide) comprises a residual splicing element from such splicing-mediated circularization event. In some cases, the residual splicing element is not able to mediate any splicing. In other cases, the residual splicing element can still mediate splicing under certain circumstances. In some embodiments, the splicing element is adjacent to at least one expression sequence. In some embodiments, the modified circular polyribonucleotide (e.g., a fully modified circular polyribonucleotide or a hybrid modified circular polyribonucleotide) includes a splicing element adjacent each expression sequence. In some embodiments, the splicing element is on one or both sides of each expression sequence, leading to separation of the expression products, e.g., peptide(s) and or polypeptide(s).

In some embodiments, the modified circular polyribonucleotide (e.g., a fully modified circular polyribonucleotide or a hybrid modified circular polyribonucleotide) includes an internal splicing element that when replicated the spliced ends are joined together. Some examples may include miniature introns (<100 nt) with splice site sequences and short inverted repeats (30-40 nt) such as AluSq2, AluJr, and AluSz, inverted sequences in flanking introns, Alu elements in flanking introns, and motifs found in (suptable4 enriched motifs) cis-sequence elements proximal to backsplice events such as sequences in the 200 bp preceding (upstream of) or following (downstream from) a backsplice site with flanking exons. In some embodiments, the modified circular polyribonucleotide (e.g., a fully modified circular polyribonucleotide or a hybrid modified circular polyribonucleotide) includes at least one repetitive nucleotide sequence described elsewhere herein as an internal splicing element.

In such embodiments, the repetitive nucleotide sequence may include repeated sequences from the Alu family of introns. In some embodiments, a splicing-related ribosome binding protein can regulate modified circular polyribonucleotide (e.g., a fully modified circular polyribonucleotide or a hybrid modified circular polyribonucleotide) biogenesis (e.g., the Muscleblind and Quaking (QKI) splicing factors).

In some embodiments, the modified circular polyribonucleotide (e.g., a fully modified circular polyribonucleotide or a hybrid modified circular polyribonucleotide) may include canonical splice sites that flank head-to-tail junctions of the modified circular polyribonucleotide.

In some embodiments, the modified circular polyribonucleotide (e.g., a fully modified circular polyribonucleotide or a hybrid modified circular polyribonucleotide) may include a bulge-helix-bulge motif, comprising a 4-base pair stem flanked by two 3-nucleotide bulges. Cleavage occurs at a site in the bulge region, generating characteristic fragments with terminal 5'-hydroxyl group and 2', 3'-cyclic phosphate. Circularization proceeds by nucleophilic attack of the 5'—OH group onto the 2', 3'-cyclic phosphate of the same molecule forming a 3', 5'-phosphodiester bridge.

In some embodiments, the modified circular polyribonucleotide (e.g., a fully modified circular polyribonucleotide or a hybrid modified circular polyribonucleotide) may include a multimeric repeating RNA sequence that harbors a HPR element. The HPR comprises a 2',3'-cyclic phosphate and a 5'-OH termini. The HPR element self-processes the 5'- and 3'-ends of the linear circular polyribonucleotide modified circular polyribonucleotide, thereby ligating the ends together.

In some embodiments, the modified circular polyribonucleotide (e.g., a fully modified circular polyribonucleotide or a hybrid modified circular polyribonucleotide) may include a sequence that mediates self-ligation. In one embodiment, the modified circular polyribonucleotide (e.g., a fully modified circular polyribonucleotide or a hybrid modified circular polyribonucleotide) may include a HDV sequence (e.g., HDV replication domain conserved sequence, GGCUCAUCUCGACAAGAGGCGGCAGUC-CUCAGUACUCUUACUCUUUUCUGUAAAG AGGA-GACUGCUGGACUCGCCGCCCAAGUUCGAG-CAUGAGCC (SEQ ID NO: 109) or GGCUAGAGGCGGCAGUCCUCAGUACUCUUACUC-UUUUCUGUAAAGAGGAGACUG CUGGA-CUCGCCGCCCGAGCC (SEQ ID NO: 110)) to self-ligate. In one embodiment, the modified circular polyribonucleotide (e.g., a fully modified circular polyribonucleotide or a hybrid modified circular polyribonucleotide) may include loop E sequence (e.g., in PSTVd) to self-ligate. In another embodiment, the modified circular polyribonucleotide (e.g., a fully modified circular polyribonucleotide or a hybrid modified circular polyribonucleotide) may include a self-circularizing intron, e.g., a 5' and 3' slice junction, or a self-circularizing catalytic intron such as a Group I, Group II, or Group III Introns. Nonlimiting examples of group I intron self-splicing sequences may include self-splicing permuted intron-exon sequences derived from T4 bacteriophage gene td, and the intervening sequence (IVS) rRNA of Tetrahymena.

Other Circularization Methods

In some embodiments, linear modified circular polyribonucleotides may include complementary sequences, including either repetitive or nonrepetitive nucleic acid sequences within individual introns or across flanking introns. Repetitive nucleic acid sequence are sequences that occur within a segment of the modified circular polyribonucleotide. In some embodiments, the modified circular polyribonucleotide (e.g., a fully modified circular polyribonucleotide or a hybrid modified circular polyribonucleotide) includes a repetitive nucleic acid sequence. In some embodiments, the repetitive nucleotide sequence includes poly CA or poly UG sequences. In some embodiments, the modified circular polyribonucleotide (e.g., a fully modified circular polyribonucleotide or a hybrid modified circular polyribonucleotide) includes at least one repetitive nucleic acid sequence that hybridizes to a complementary repetitive nucleic acid sequence in another segment of the modified circular polyribonucleotide, with the hybridized segment forming an internal double strand. In some embodiments, repetitive nucleic acid sequences and complementary repetitive nucleic acid sequences from two separate modified circular polyribonucleotides hybridize to generate a single circularized polyribonucleotide, with the hybridized segments forming internal double strands. In some embodiments, the complementary sequences are found at the 5' and 3' ends of the linear modified circular polyribonucleotides. In some embodiments, the complementary sequences include about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more paired nucleotides.

In some embodiments, chemical methods of circularization may be used to generate the modified circular polyribonucleotide. Such methods may include, but are not limited to click chemistry (e.g., alkyne and azide based methods, or clickable bases), olefin metathesis, phosphoramidate ligation, hemiaminal-imine crosslinking, base modification, and any combination thereof.

In some embodiments, enzymatic methods of circularization may be used to generate the modified circular polyribonucleotide (e.g., a fully modified circular polyribonucleotide or a hybrid modified circular polyribonucleotide). In some embodiments, a ligation enzyme, e.g., DNA or RNA ligase, may be used to generate a template of the circular polyribonuclease or complement, a complementary strand of the circular polyribonuclease, or the circular polyribonuclease.

Circularization of the modified circular polyribonucleotide (e.g., a fully modified circular polyribonucleotide or a hybrid modified circular polyribonucleotide) may be accomplished by methods known in the art, for example, those described in "RNA circularization strategies in vivo and in vitro" by Petkovic and Muller from Nucleic Acids Res, 2015, 43(4): 2454-2465, and "In vitro circularization of RNA" by Muller and Appel, from RNA Biol, 2017, 14(8): 1018-1027.

Replication Element

The modified circular polyribonucleotide (e.g., a fully modified circular polyribonucleotide or a hybrid modified circular polyribonucleotide) may encode a sequence and/or motifs useful for replication. Replication of a modified circular polyribonucleotide (e.g., a fully modified circular polyribonucleotide or a hybrid modified circular polyribonucleotide) may occur by generating a complement modified circular polyribonucleotide. In some embodiments, the modified circular polyribonucleotide (e.g., a fully modified circular polyribonucleotide or a hybrid modified circular polyribonucleotide) includes a motif to initiate transcription, where transcription is driven by either endogenous cellular machinery (DNA-dependent RNA polymerase) or an RNA-depended RNA polymerase encoded by the modified circular polyribonucleotide. The product of rolling-circle transcriptional event may be cut by a ribozyme to generate either complementary or propagated modified circular polyribonucleotide (e.g., a fully modified circular polyribonucleotide or a hybrid modified circular polyribonucleotide) at unit length. The ribozymes may be encoded by the modified circular polyribonucleotide, its complement, or by an RNA sequence in trans. In some embodiments, the encoded ribozymes may include a sequence or motif that regulates (inhibits or promotes) activity of the ribozyme to control circular RNA propagation. In some embodiments, unit-length sequences may be ligated into a circular form by a cellular RNA ligase. In some embodiments, the modified circular polyribonucleotide (e.g., a fully modified circular polyribonucleotide or a hybrid modified circular polyribonucleotide) includes a replication element that aids in self amplification. Examples of such replication elements include, those described in [0280]-[0282] of International Patent Publication No. WO2019118919A1, which is incorporated herein by reference in its entirety. In another embodiment, the modified circular polyribonucleotide (e.g., a fully modified circular polyribonucleotide or a hybrid modified circular polyribonucleotide) includes at least one ribozyme sequence to cleave long transcripts replicated from the modified circular polyribonucleotide (e.g., a fully modified circular polyribonucleotide or a hybrid modified circular polyribonucleotide) to a specific length, where another encoded ribozyme cuts the transcripts at the ribozyme sequence. Circularization forms a complement to the modified circular polyribonucleotide.

In some embodiments, the modified circular polyribonucleotide (e.g., a fully modified circular polyribonucleotide or a hybrid modified circular polyribonucleotide) is substantially resistant to degradation, e.g., by exonucleases.

In some embodiments, the modified circular polyribonucleotide (e.g., a fully modified circular polyribonucleotide or a hybrid modified circular polyribonucleotide) replicates within a cell. In some embodiments, the modified circular polyribonucleotide (e.g., a fully modified circular polyribonucleotide or a hybrid modified circular polyribonucleotide) replicates within in a cell at a rate of between about 10%-20%, 20%-30%, 30%-40%, 40%-50%, 50%-60%, 60%-70%, 70%-75%, 75%-80%, 80%-85%, 85%-90%, 90%-95%, 95%-99%, or any percentage therebetween. In some embodiments, the modified circular polyribonucleotide (e.g., a fully modified circular polyribonucleotide or a hybrid modified circular polyribonucleotide) is replicated within a cell and is passed to daughter cells. In some embodiments, a cell passes at least one modified circular polyribonucleotide (e.g., a fully modified circular polyribonucleotide or a hybrid modified circular polyribonucleotide) to daughter cells with an efficiency of at least 25%, 50%, 60%, 70%, 80%, 85%, 90%, 95%, or 99%. In some embodiments, cell undergoing meiosis passes the modified circular polyribonucleotide (e.g., a fully modified circular polyribonucleotide or a hybrid modified circular polyribonucleotide) to daughter cells with an efficiency of at least 25%, 50%, 60%, 70%, 80%, 85%, 90%, 95%, or 99%. In some embodiments, a cell undergoing mitosis passes the modified circular polyribonucleotide hybrid modified circular polyri (e.g., a fully modified circular polyribonucleotide or a hybrid modified circular polyribonucleotide) bonucleotide to daughter cells with an efficiency of at least 25%, 50%, 60%, 70%, 80%, 85%, 90%, 95%, or 99%.

In some embodiments, the modified circular polyribonucleotide (e.g., a fully modified circular polyribonucleotide or a hybrid modified circular polyribonucleotide) replicates within the host cell. In one embodiment, the modified circular polyribonucleotide (e.g., a fully modified circular polyribonucleotide or a hybrid modified circular polyribonucleotide) is capable of replicating in a mammalian cell, e.g., human cell.

While in some embodiments the modified circular polyribonucleotide hybrid modified circular polyribonucleotide replicates in the host cell, the modified circular polyribonucleotide (e.g., a fully modified circular polyribonucleotide or a hybrid modified circular polyribonucleotide) does not integrate into the genome of the host, e.g., with the host's chromosomes. In some embodiments, the modified circular polyribonucleotide (e.g., a fully modified circular polyribonucleotide or a hybrid modified circular polyribonucleotide) has a negligible recombination frequency, e.g., with the host's chromosomes. In some embodiments, the modified circular polyribonucleotide (e.g., a fully modified circular polyribonucleotide or a hybrid modified circular polyribonucleotide) has a recombination frequency, e.g., less than about 1.0 cM/Mb, 0.9 cM/Mb, 0.8 cM/Mb, 0.7 cM/Mb, 0.6 cM/Mb, 0.5 cM/Mb, 0.4 cM/Mb, 0.3 cM/Mb, 0.2 cM/Mb, 0.1 cM/Mb, or less, e.g., with the host's chromosomes.

Other Sequences

In some embodiments, the modified circular polyribonucleotide (e.g., a fully modified circular polyribonucleotide or a hybrid modified circular polyribonucleotide) further includes another nucleic acid sequence. In some embodiments, the modified circular polyribonucleotide (e.g., a fully modified circular polyribonucleotide or a hybrid modified circular polyribonucleotide) may comprise other sequences that include DNA, RNA, or artificial nucleic acids. The other sequences may include, but are not limited to, genomic DNA, cDNA, or sequences that encode tRNA, mRNA, rRNA, miRNA, gRNA, siRNA, or other RNAi molecules. In one embodiment, the modified circular polyribonucleotide (e.g., a fully modified circular polyribonucleotide or a hybrid modified circular polyribonucleotide) includes an siRNA to target a different loci of the same gene expression product as the modified circular polyribonucleotide. In one embodiment, the modified circular polyribonucleotide (e.g., a fully modified circular polyribonucleotide or a hybrid modified circular polyribonucleotide) includes an siRNA to target a different gene expression product as the modified circular polyribonucleotide.

In some embodiments, the modified circular polyribonucleotide (e.g., a fully modified circular polyribonucleotide or a hybrid modified circular polyribonucleotide) lacks a 5'-UTR. In some embodiments, the modified circular polyribonucleotide (e.g., a fully modified circular polyribonucleotide or a hybrid modified circular polyribonucleotide) lacks a 3'-UTR. In some embodiments, the modified circular polyribonucleotide (e.g., a fully modified circular polyribonucleotide or a hybrid modified circular polyribonucleotide) lacks a poly-A sequence. In some embodiments, the modified circular polyribonucleotide (e.g., a fully modified circular polyribonucleotide or a hybrid modified circular polyribonucleotide) lacks a termination element. In some embodiments, the modified circular polyribonucleotide (e.g., a fully modified circular polyribonucleotide or a hybrid modified circular polyribonucleotide) lacks an internal ribosomal entry site. In some embodiments, the modified circular polyribonucleotide (e.g., a fully modified circular polyribonucleotide or a hybrid modified circular polyribonucleotide) lacks degradation susceptibility by exonucleases. In some embodiments, the fact that the modified circular polyribonucleotide (e.g., a fully modified circular polyribonucleotide or a hybrid modified circular polyribonucleotide) lacks degradation susceptibility can mean that the modified circular polyribonucleotide (e.g., a fully modified circular polyribonucleotide or a hybrid modified circular polyribonucleotide) is not degraded by an exonuclease, or only degraded in the presence of an exonuclease to a limited extent that is comparable to or similar to in the absence of exonuclease. In some embodiments, the modified circular polyribonucleotide (e.g., a fully modified circular polyribonucleotide or a hybrid modified circular polyribonucleotide) lacks degradation by exonucleases. In some embodiments, the modified circular polyribonucleotide (e.g., a fully modified circular polyribonucleotide or a hybrid modified circular polyribonucleotide) has reduced degradation when exposed to exonuclease. In some embodiments, the modified circular polyribonucleotide (e.g., a fully modified circular polyribonucleotide or a hybrid modified circular polyribonucleotide) lacks binding to a cap-binding protein In some embodiments, the modified circular polyribonucleotide (e.g., a fully modified circular polyribonucleotide or a hybrid modified circular polyribonucleotide) lacks a 5' cap.

In some embodiments, the modified circular polyribonucleotide (e.g., a fully modified circular polyribonucleotide or a hybrid modified circular polyribonucleotide) lacks a 5'-UTR and is competent for protein express from its one or more expression sequences. In some embodiments, the modified circular polyribonucleotide (e.g., a fully modified circular polyribonucleotide or a hybrid modified circular polyribonucleotide) lacks a 3'-UTR and is competent for protein express from its one or more expression sequences. In some embodiments, the modified circular polyribonucleotide (e.g., a fully modified circular polyribonucleotide or a hybrid modified circular polyribonucleotide) lacks a poly-A sequence and is competent for protein express from its one or more expression sequences. In some embodiments, the modified circular polyribonucleotide (e.g., a fully modified circular polyribonucleotide or a hybrid modified circular polyribonucleotide) lacks a termination element and is competent for protein express from its one or more expression sequences. In some embodiments, the modified circular polyribonucleotide (e.g., a fully modified circular polyribonucleotide or a hybrid modified circular polyribonucleotide) lacks an internal ribosomal entry site and is competent for protein express from its one or more expression sequences. In some embodiments, the modified circular polyribonucleotide (e.g., a fully modified circular polyribonucleotide or a hybrid modified circular polyribonucleotide) lacks a cap and is competent for protein express from its one or more expression sequences. In some embodiments, the modified circular polyribonucleotide (e.g., a fully modified circular polyribonucleotide or a hybrid modified circular polyribonucleotide) lacks a 5'-UTR, a 3'-UTR, and an IRES, and is competent for protein express from its one or more expression sequences. In some embodiments, the modified circular polyribonucleotide (e.g., a fully modified circular polyribonucleotide or a hybrid modified circular polyribonucleotide) comprises one or more of the following sequences: a sequence that encodes one or more miRNAs, a sequence that encodes one or more replication proteins, a sequence that encodes an exogenous gene, a sequence that encodes a therapeutic, a regulatory element (e.g., translation modulator, e.g., translation enhancer or suppressor), a translation initiation sequence, one or more regulatory nucleic acids that targets endogenous genes (siRNA, lncRNAs, shRNA), and a sequence that encodes a therapeutic mRNA or protein.

The other sequence may have a length from about 2 to about 10000 nts, about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

As a result of its circularization, the modified circular polyribonucleotide (e.g., a fully modified circular polyribonucleotide or a hybrid modified circular polyribonucleotide) may include certain characteristics that distinguish it from linear RNA. For example, the modified circular polyribonucleotide (e.g., a fully modified circular polyribonucleotide or a hybrid modified circular polyribonucleotide) is less susceptible to degradation by exonuclease as compared to linear RNA. As such, the modified circular polyribonucleotide (e.g., a fully modified circular polyribonucleotide or a hybrid modified circular polyribonucleotide) is more stable than a linear RNA, especially when incubated in the presence of an exonuclease. The increased stability of the modified circular polyribonucleotide (e.g., a fully modified circular polyribonucleotide or a hybrid modified circular polyribonucleotide) compared with linear RNA makes modified circular polyribonucleotide (e.g., a fully modified circular polyribonucleotide or a hybrid modified circular polyribonucleotide) more useful as a cell transforming reagent to produce polypeptides and can be stored more easily and for longer than linear RNA. The stability of the modified circular polyribonucleotide (e.g., a fully modified circular polyribonucleotide or a hybrid modified circular polyribonucleotide) treated with exonuclease can be tested using methods standard in art which determine whether RNA degradation has occurred (e.g., by gel electrophoresis).

Moreover, unlike linear RNA, the modified circular polyribonucleotide (e.g., a fully modified circular polyribonucleotide or a hybrid modified circular polyribonucleotide) is less susceptible to dephosphorylation when the modified circular polyribonucleotide (e.g., a fully modified circular polyribonucleotide or a hybrid modified circular polyribonucleotide) is incubated with phosphatase, such as calf intestine phosphatase.

Nucleotide Spacer Sequences

In some embodiments, the modified circular polyribonucleotide (e.g., a fully modified circular polyribonucleotide or a hybrid modified circular polyribonucleotide) comprises a spacer sequence.

In some embodiments, the modified circular polyribonucleotide (e.g., a fully modified circular polyribonucleotide or a hybrid modified circular polyribonucleotide) comprises at least one spacer sequence. In some embodiments, the modified circular polyribonucleotide (e.g., a fully modified circular polyribonucleotide or a hybrid modified circular polyribonucleotide) comprises 1, 2, 3, 4, 5, 6, 7, or more spacer sequences.

In some embodiments, the modified circular polyribonucleotide (e.g., a fully modified circular polyribonucleotide or a hybrid modified circular polyribonucleotide) comprises one or more spacer sequence configured according to descriptions in [0295]-[0302] of International Patent Publication No. WO2019118919A1, which is incorporated herein by reference in its entirety Non-nucleic acid linkers The modified circular polyribonucleotide (e.g., a fully modified circular polyribonucleotide or a hybrid modified circular polyribonucleotide) described herein may also comprise a non-nucleic acid linker. In some embodiments, the modified circular polyribonucleotide (e.g., a fully modified circular polyribonucleotide or a hybrid modified circular polyribonucleotide) described herein has a non-nucleic acid linker between one or more of the sequences or elements described herein. In one embodiment, one or more sequences or elements described herein are linked with the linker. The non-nucleic acid linker may be a chemical bond, e.g., one or more covalent bonds or non-covalent bonds. In some embodiments, the non-nucleic acid linker is a peptide or protein linker. Such a linker may be between 2-30 amino acids, or longer. The linker includes flexible, rigid or cleavable linkers, such as those described in [0304]-[0307] of International Patent Publication No. WO2019118919A1, which is incorporated herein by reference in its entirety.

Stability/Half-Life

In some embodiments, the modified circular polyribonucleotide (e.g., a fully modified circular polyribonucleotide or a hybrid modified circular polyribonucleotide) provided herein has increased half-life over a reference, e.g., a linear polyribonucleotide having the same nucleotide sequence but is not circularized (linear counterpart) or a corresponding unmodified circular polyribonucleotide. In some embodiments, the modified circular polyribonucleotide (e.g., a fully modified circular polyribonucleotide or a hybrid modified circular polyribonucleotide) is substantially resistant to degradation, e.g., exonuclease. In some embodiments, the modified circular polyribonucleotide (e.g., a fully modified circular polyribonucleotide or a hybrid modified circular polyribonucleotide) is resistant to self-degradation. In some embodiments, the modified circular polyribonucleotide (e.g., a fully modified circular polyribonucleotide or a hybrid modified circular polyribonucleotide) lacks an enzymatic cleavage site, e.g., a dicer cleavage site. In some embodiments, the modified circular polyribonucleotide (e.g., a fully modified circular polyribonucleotide or a hybrid modified circular polyribonucleotide) has a half-life at least about 5%, at least about 10%, at least about 20%, at least about 30%, at least about 40%, at least about 50%, at least about 60%, at least about 70%, at least about 80%, at least about 90%, at least about 100%, at least about 120%, at least about 140%, at least about 150%, at least about 160%, at least about 180%, at least about 200%, at least about 300%, at least about 400%, at least about 500%, at least about 600%, at least about 700% at least about 800%, at least about 900%, at least about 1000% or at least about 10000%, longer than a reference, e.g., a linear counterpart or a corresponding unmodified circular polyribonucleotide.

In some embodiments, the modified circular polyribonucleotide (e.g., a fully modified circular polyribonucleotide or a hybrid modified circular polyribonucleotide) persists in a cell during cell division. In some embodiments, the modified circular polyribonucleotide (e.g., a fully modified circular polyribonucleotide or a hybrid modified circular polyribonucleotide) persists in daughter cells after mitosis. In some embodiments, the modified circular polyribonucleotide (e.g., a fully modified circular polyribonucleotide or a hybrid modified circular polyribonucleotide) is replicated within a cell and is passed to daughter cells. In some embodiments, the modified circular polyribonucleotide (e.g., a fully modified circular polyribonucleotide or a hybrid modified circular polyribonucleotide) comprises a replication element that mediates self-replication of the modified circular polyribonucleotide (e.g., a fully modified circular polyribonucleotide or a hybrid modified circular polyribonucleotide). In some embodiments, the replication element mediates transcription of the modified circular polyribonucleotide (e.g., a fully modified circular polyribonucleotide or a hybrid modified circular polyribonucleotide) into a linear polyribonucleotide that is complementary to the modified circular polyribonucleotide (e.g., a fully modified circular polyribonucleotide or a hybrid modified circular polyribonucleotide) (linear complementary). In some embodiments, the linear complementary polyribonucleotide can be circularized in vivo in cells into a complementary modified circular polyribonucleotide. In some embodiments, the complementary polyribonucleotide can further self-replicate into another modified circular polyribonucleotide, which has the same or similar nucleotide sequence as the starting modified circular polyribonucleotide. One exemplary self-replication element includes HDV replication domain (as described by Beeharry et al, *Virol,* 2014, 450-451:165-173). In some embodiments, a cell passes at least one modified circular polyribonucleotide (e.g., a fully modified circular polyribonucleotide or a hybrid modified circular polyribonucleotide) to daughter cells with an efficiency of at least 25%, 50%, 60%, 70%, 80%, 85%, 90%, 95%, or 99%. In some embodiments, cell undergoing meiosis passes the modified circular polyribonucleotide (e.g., a fully modified circular polyribonucleotide or a hybrid modified circular polyribonucleotide) to daughter cells with an efficiency of at least 25%, 50%, 60%, 70%, 80%, 85%, 90%, 95%, or 99%. In some embodiments, a cell undergoing mitosis passes the modified circular polyribonucleotide (e.g., a fully modified circular polyribonucleotide or a hybrid modified circular polyribonucleotide) to daughter cells with an efficiency of at least 25%, 50%, 60%, 70%, 80%, 85%, 90%, 95%, or 99%.

Structure

In some embodiments, the modified circular polyribonucleotide (e.g., a fully modified circular polyribonucleotide or a hybrid modified circular polyribonucleotide) comprises a higher order structure, e.g., a secondary or tertiary structure. In some embodiments the circular polyribonucleotide is configured to comprise a higher order structure, such as those described in International Patent Publication No. WO2019118919A1, which is incorporated herein by reference in its entirety.

Pharmaceutical Compositions

The present invention includes compositions in combination with one or more pharmaceutically acceptable excipients. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g., non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product.

Delivery

The modified circular polyribonucleotide (e.g., a fully modified circular polyribonucleotide or a hybrid modified circular polyribonucleotide) described herein may be included in pharmaceutical compositions comprising a pharmaceutically acceptable carrier or excipient. The modified circular polyribonucleotide (e.g., a fully modified circular polyribonucleotide or a hybrid modified circular polyribonucleotide) described herein may be included in pharmaceutical compositions with a delivery carrier. In some embodiments, the modified circular polyribonucleotide (e.g., a fully modified circular polyribonucleotide or a hybrid modified circular polyribonucleotide) as described herein may be included in a pharmaceutical compositions free of any carrier. In some embodiments, the modified circular polyribonucleotide (e.g., a fully modified circular polyribonucleotide or a hybrid modified circular polyribonucleotide) as described herein may be included in a pharmaceutical compositions comprising a parenterally acceptable diluent. In some embodiments, the modified circular polyribonucleotide (e.g., a fully modified circular polyribonucleotide or a hybrid modified circular polyribonucleotide) as described herein may be included in a pharmaceutical compositions comprising ethanol. Methods as disclosed herein include a method of in vivo delivery of a modified circular polyribonucleotide (e.g., a fully modified circular polyribonucleotide or a hybrid modified circular polyribonucleotide) as disclosed herein, composition as disclosed herein, or a pharmaceutical composition as disclosed herein comprising parenterally administering the modified circular polyribonucleotide (e.g., a fully modified circular polyribonucleotide or a hybrid modified circular polyribonucleotide), composition, or a pharmaceutical composition to the cell or tissue of a subject, or to a subject.

Pharmaceutical compositions described herein may be formulated for example to include a pharmaceutical excipient or carrier. A pharmaceutical carrier can be a membrane, lipid biylar, and/or a polymeric carrier, e.g., a liposome, such as a nanoparticle, e.g., a lipid nanoparticle, and delivered by known methods, such as via partial or full encapsulation of the modified circular polyribonucleotide, to a subject in need thereof (e.g., a human or non-human agricultural or domestic animal, e.g., cattle, dog, cat, horse, poultry). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof. Methods of delivery are also described, e.g., in Gori et al., Delivery and Specificity of CRISPR/Cas9 Genome Editing Technologies for Human Gene Therapy. Human Gene Therapy. July 2015, 26(7): 443-451. doi: 10.1089/hum.2015.074; and Zuris et al. Cationic lipid-mediated delivery of proteins enables efficient protein-based genome editing in vitro and in vivo. Nat Biotechnol. 2014 Oct. 30; 33(1):73-80.

In some embodiments, the modified circular polyribonucleotide (e.g., a fully modified circular polyribonucleotide or a hybrid modified circular polyribonucleotide) or a pharmaceutical composition can be delivered as a naked delivery formulation. A naked delivery formulation delivers a circular polyribonucleotide (e.g., a hybrid modified circular polyribonucleotide as described herein) to a cell without the aid of a carrier and without covalent modification or partial or complete encapsulation of the circular polyribonucleotide.

A naked delivery formulation is a formulation that is free from a carrier and wherein the circular polyribonucleotide (e.g., a hybrid modified circular polyribonucleotide as described herein) is without a covalent modification that binds a moiety that aids in delivery to a cell or without partial or complete encapsulation of the circular polyribonucleotide. In some embodiments, a hybrid modified circular polyribonucleotide without covalent modification bound to a moiety that aids in delivery to a cell is not covalently bound to a protein, small molecule, a particle, a polymer, or a biopolymer that aids in delivery to a cell.

In some embodiments, a naked delivery formulation may be free of any or all of: transfection reagents, cationic carriers, carbohydrate carriers, nanoparticle carriers, or protein carriers. For example, a naked delivery formulation may be free from phtoglycogen octenyl succinate, phytoglycogen beta-dextrin, anhydride-modified phytoglycogen beta-dextrin, lipofectamine, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N\N'-Dimethylaminoethane)-carbamoyl]Cholesterol Hydrochloride (DC-Cholesterol HCl), diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride (DODAC), human serum albumin (HSA), low-density lipoprotein (LDL), high-density lipoprotein (HDL), or globulin.

A naked delivery formulation may comprise a non-carrier excipient. In some embodiments, a non-carrier excipient may comprise an inactive ingredient. In some embodiments, a non-carrier excipient may comprise a buffer, for example PBS. In some embodiments, a non-carrier excipient may be a solvent, a non-aqueous solvent, a diluent (e.g., a parenterally acceptable diluent), a suspension aid, a surface active agent, an isotonic agent, a thickening agent, an emulsifying agent, a preservative, a polymer, a peptide, a protein, a cell, a hyaluronidase, a dispersing agent, a granulating agent, a disintegrating agent, a binding agent, a buffering agent, a lubricating agent, or an oil.

In some embodiments, a naked delivery formulation may comprise a diluent (e.g., a parenterally acceptable diluent). A diluent may be a liquid diluent or a solid diluent. In some embodiments, a diluent may be an RNA solubilizing agent, a buffer, or an isotonic agent. Examples of an RNA solubilizing agent include water, ethanol, methanol, acetone, formamide, and 2-propanol. Examples of a buffer include 2-(N-morpholino)ethanesulfonic acid (MES), Bis-Tris, 2-[(2-amino-2-oxoethyl)-(carboxymethyl)amino]acetic acid (ADA), N-(2-Acetamido)-2-aminoethanesulfonic acid (ACES), piperazine-N,N'-bis(2-ethanesulfonic acid) (PIPES), 2-[[1,3-dihydroxy-2-(hydroxymethyl)propan-2-yl] amino]ethanesulfonic acid (TES), 3-(N-morpholino)propanesulfonic acid (MOPS), 4-(2-hydroxyethyl)-1-piperazineethanesulfonic acid (HEPES), Tris, Tricine, Gly-Gly, Bicine, or phosphate. Examples of an isotonic agent include glycerin, mannitol, polyethylene glycol, propylene glycol, trehalose, or sucrose.

The invention is further directed to a host or host cell comprising the hybrid modified circular polyribonucleotide described herein. In some embodiments, the host or host cell is a plant, insect, bacteria, fungus, vertebrate, mammal (e.g., human), or other organism or cell.

In some embodiments, the modified circular polyribonucleotide (e.g., a fully modified circular polyribonucleotide or a hybrid modified circular polyribonucleotide) is non-immunogenic in the host. In some embodiments, the modified circular polyribonucleotide (e.g., a fully modified circular polyribonucleotide or a hybrid modified circular polyribonucleotide) has a decreased or fails to produce a response by the host's immune system as compared to the response triggered by a reference compound, e.g., a linear polynucleotide corresponding to the described modified circular polyribonucleotide (e.g., a fully modified circular polyribonucleotide or a hybrid modified circular polyribonucleotide) or a modified circular polyribonucleotide lacking an encryptogen. Some immune responses include, but are not limited to, humoral immune responses (e.g., production of antigen-specific antibodies) and cell-mediated immune responses (e.g., lymphocyte proliferation).

In some embodiments, a host or a host cell is contacted with (e.g., delivered to or administered to) the modified circular polyribonucleotide (e.g., a fully modified circular polyribonucleotide or a hybrid modified circular polyribonucleotide). In some embodiments, the host is a mammal, such as a human. The amount of the modified circular polyribonucleotide (e.g., a fully modified circular polyribonucleotide or a hybrid modified circular polyribonucleotide), expression product, or both in the host can be measured at any time after administration. In certain embodiments, a time course of host growth in a culture is determined. If the growth is increased or reduced in the presence of the modified circular polyribonucleotide, the modified circular polyribonucleotide (e.g., a fully modified circular polyribonucleotide or a hybrid modified circular polyribonucleotide) or expression product or both is identified as being effective in increasing or reducing the growth of the host.

Methods of Delivery

A method of delivering a modified circular polyribonucleotide molecule (e.g., a fully modified circular polyribonucleotide or a hybrid modified circular polyribonucleotide) as described herein to a cell, tissue or subject, comprises administering the pharmaceutical composition as described herein to the cell, tissue, or subject.

In some embodiments, the method of delivering is an in vivo method. For example, a method of delivering a modified circular polyribonucleotide (e.g., a fully modified circular polyribonucleotide or a hybrid modified circular polyribonucleotide) as described herein comprises parenterally administering to a subject in need thereof, the pharmaceutical composition as described herein to the subject in need thereof. As another example, a method of delivering a modified circular polyribonucleotide (e.g., a fully modified circular polyribonucleotide or a hybrid modified circular polyribonucleotide) to a cell or tissue of a subject, comprises administering parenterally to the cell or tissue the pharmaceutical composition as described herein. In some embodiments, the modified circular polyribonucleotide (e.g., a fully modified circular polyribonucleotide or a hybrid modified circular polyribonucleotide) is in an amount effective to elicit a biological response in the subject. In some embodiments, the modified circular polyribonucleotide (e.g., a fully modified circular polyribonucleotide or a hybrid modified circular polyribonucleotide) is an amount effective to have a biological effect on the cell or tissue in the subject. In some embodiments, the pharmaceutical composition as described herein comprises a carrier. In some embodiments the pharmaceutical composition as described herein comprises a diluent and is free of any carrier. In some embodiments, parenteral administration is intravenously, intramuscularly, ophthalmically, or topically.

In some embodiments, the pharmaceutical composition is administered orally. In some embodiments the pharmaceutical composition is administered nasally. In some embodiments, the pharmaceutical composition is administered by inhalation. In some embodiments the pharmaceutical composition is administered topically. In some embodiments the pharmaceutical composition is administered ophthalmically. In some embodiments the pharmaceutical composition is administered rectally. In some embodiments the pharmaceutical composition is administered by injection. The administration can be systemic administration or local administration. In some embodiments the pharmaceutical composition is administered parenterally. In some embodiments the pharmaceutical composition is administered intravenously, intraarterially, intraperitoneally, intradermally, intracranially, intrathecally, intralymphatically, subcutaneously, or intramuscularly. In some embodiments, the pharmaceutical composition is administered via intraocular administration, intracochlear (inner ear) administration, or intratracheal administration. In some embodiments, any of the methods of delivery as described herein are performed with a carrier. In some embodiments, any methods of delivery as described herein are performed without the aid of a carrier or cell penetrating agent.

Cell and Vesicle-Based Carriers

A modified circular RNA (e.g., a fully modified circular polyribonucleotide or a hybrid modified circular polyribonucleotide) composition or preparation described herein can be administered to a cell in a vesicle or other membrane-based carrier.

In embodiments, a modified circular RNA (e.g., a fully modified circular polyribonucleotide or a hybrid modified circular polyribonucleotide) in a pharmaceutical composition described herein is administered in or via a cell, vesicle or other membrane-based carrier. In one embodiment, the pharmaceutical composition comprising the modified circRNA can be formulated in liposomes or other similar vesicles. Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

Lipid nanoparticles are another example of a carrier that provides a biocompatible and biodegradable delivery system for the modified circular RNA composition (e.g., a fully modified circular polyribonucleotide or a hybrid modified circular polyribonucleotide) or preparation described herein. Nanostructured lipid carriers (NLCs) are modified solid lipid nanoparticles (SLNs) that retain the characteristics of the SLN, improve drug stability and loading capacity, and prevent drug leakage. Polymer nanoparticles (PNPs) are an important component of drug delivery. These nanoparticles can effectively direct drug delivery to specific targets and improve drug stability and controlled drug release. Lipid-polymer nanoparticles (PLNs), a new type of carrier that combines liposomes and polymers, may also be employed. These nanoparticles possess the complementary advantages of PNPs and liposomes. A PLN is composed of a core-shell structure; the polymer core provides a stable structure, and the phospholipid shell offers good biocompatibility. As such, the two components increase the drug encapsulation efficiency rate, facilitate surface modification, and prevent leakage of water-soluble drugs. For a review, see, e.g., Li et al. 2017, Nanomaterials 7, 122; doi:10.3390/nano7060122.

Additional non-limiting examples of carriers include carbohydrate carriers (e.g., an anhydride-modified phytoglycogen or glycogen-type material), protein carriers (e.g., a protein covalently linked to the circular polyribonucleotide), or cationic carriers (e.g., a cationic lipopolymer or transfection reagent). Non-limiting examples of carbohydrate carriers include phtoglycogen octenyl succinate, phytoglycogen beta-dextrin, and anhydride-modified phytoglycogen beta-dextrin. Non-limiting examples of cationic carriers include lipofectamine, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly (lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy) ethyl]-2-oleyl-3-(2-hydroxyethyl)imidazolinium chloride (DOTIM), 2,3-dioleyloxy-N-[2(sperminecarboxamido) ethyl]-N,N-dimethyl-1-propanaminium trifluoroacetate (DOSPA), 3B—[N—(N\N'-Dimethylaminoethane)-carbamoyl]Cholesterol Hydrochloride (DC-Cholesterol HCl), diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), and N,N-dioleyl-N,N-dimethylammonium chloride (DODAC). Non-limiting examples of protein carriers include human serum albumin (HSA), low-density lipoprotein (LDL), high-density lipoprotein (HDL), or globulin.

Exosomes can also be used as drug delivery vehicles for a circular RNA composition or preparation described herein. For a review, see Ha et al. July 2016. Acta Pharmaceutica Sinica B. Volume 6, Issue 4, Pages 287-296.

Ex vivo differentiated red blood cells can also be used as a carrier for a circular RNA composition or preparation described herein. See, e.g., WO2015073587; WO2017123646; WO2017123644; WO2018102740; WO2016183482; WO2015153102; WO2018151829; WO2018009838; Shi et al. 2014. Proc Natl Acad Sci USA. 111(28): 10131-10136; U.S. Pat. No. 9,644,180; Huang et al. 2017. Nature Communications 8: 423; Shi et al. 2014. Proc Natl Acad Sci USA. 111(28): 10131-10136.

Fusosome compositions, e.g., as described in WO2018208728, can also be used as carriers to deliver the modified circular RNA (e.g., a fully modified circular polyribonucleotide or a hybrid modified circular polyribonucleotide) or pharmaceutical compostions thereof as described herein.

Virosomes and virus-like particles (VLPs) can also be used as carriers to deliver a modified circular RNA or pharmaceutical composition thereof as described herein to targeted cells.

Plant nanovesicles and plant messenger packs (PMPs), e.g., as described in International Patent Publication Nos. WO2011097480, WO2013070324, WO2017004526, or WO2020041784 can also be used as carriers to deliver the circular RNA or pharmaceutical composition thereof as described herein.

Methods of Production

In some embodiments, the modified circular polyribonucleotide (e.g., a fully modified circular polyribonucleotide or a hybrid modified circular polyribonucleotide) includes a deoxyribonucleic acid sequence that is non-naturally occurring and can be produced using recombinant technology (methods described in detail below; e.g., derived in vitro using a DNA plasmid) or chemical synthesis.

It is within the scope of the invention that a DNA molecule used to produce an RNA circle can comprise a DNA sequence of a naturally-occurring original nucleic acid sequence, a modified version thereof, or a DNA sequence encoding a synthetic polypeptide not normally found in nature (e.g., chimeric molecules or fusion proteins). DNA and RNA molecules can be modified using a variety of techniques including, but not limited to, classic mutagenesis techniques and recombinant techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof.

The modified circular polyribonucleotide (e.g., a fully modified circular polyribonucleotide or a hybrid modified circular polyribonucleotide) may be prepared according to any available technique including, but not limited to chemical synthesis and enzymatic synthesis. In some embodiments, a linear primary construct or linear mRNA may be cyclized, or concatemerized to create a modified circular polyribonucleotide (e.g., a fully modified circular polyribonucleotide or a hybrid modified circular polyribonucleotide) described herein. The mechanism of cyclization or concatemerization may occur through methods such as, but not limited to, chemical, enzymatic, splint ligation), or ribozyme catalyzed methods. The newly formed 5'-/3'-linkage may be an intramolecular linkage or an intermolecular linkage.

Methods of making the modified circular polyribonucleotides described herein are described in, for example, Khudyakov & Fields, Artificial DNA: Methods and Applications, CRC Press (2002); in Zhao, Synthetic Biology: Tools and Applications, (First Edition), Academic Press (2013); and Egli & Herdewijn, Chemistry and Biology of Artificial Nucleic Acids, (First Edition), Wiley-VCH (2012).

Various methods of synthesizing modified circular polyribonucleotides are also described in the art (see, e.g., U.S. Pat. Nos. 6,210,931, 5,773,244, US Patent No. U.S. Pat. Nos. 5,766,903, 5,712,128, 5,426,180, US Publication No. US20100137407, International Publication No. WO1992001813 and International Publication No. WO2010084371; the contents of each of which are herein incorporated by reference in their entireties).

In some embodiments, the modified circular polyribonucleotides may be cleaned up after production to remove production impurities, e.g., free ribonucleic acids, linear or nicked RNA, DNA, proteins, etc. In some embodiments, the modified circular polyribonucleotides may be purified by any known method commonly used in the art. Examples of nonlimiting purification methods include, column chromatography, gel excision, size exclusion, etc.

Methods of Expression

The present invention includes a method for protein expression, comprising translating at least a region of the modified circular polyribonucleotide (e.g., a fully modified circular polyribonucleotide or a hybrid modified circular polyribonucleotide) provided herein.

In some embodiments, the methods for protein expression comprises translation of at least 10%, at least 20%, at least 30%, at least 40%, at least 50%, at least 60%, at least 70%, at least 80%, at least 90%, or at least 95% of the total length of the modified circular polyribonucleotide (e.g., a fully modified circular polyribonucleotide or a hybrid modified circular polyribonucleotide) into polypeptides. In some embodiments, the methods for protein expression comprises translation of the modified circular polyribonucleotide (e.g., a fully modified circular polyribonucleotide or a hybrid modified circular polyribonucleotide) into polypeptides of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids. In some embodiments, the methods for protein expression comprises translation of the modified circular polyribonucleotide (e.g., a fully modified circular polyribonucleotide or a hybrid modified circular polyribonucleotide) into polypeptides of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, or about 1000 amino acids. In some embodiments, the methods comprise translation of the modified circular polyribonucleotide (e.g., a fully modified circular polyribonucleotide or a hybrid modified circular polyribonucleotide) into continuous polypeptides as provided herein, discrete polypeptides as provided herein, or both.

In some embodiments, the translation of the at least a region of the modified circular polyribonucleotide (e.g., a fully modified circular polyribonucleotide or a hybrid modified circular polyribonucleotide) takes place in vitro, such as rabbit reticulocyte lysate. In some embodiments, the translation of the at least a region of the modified circular polyribonucleotide (e.g., a fully modified circular polyribonucleotide or a hybrid modified circular polyribonucleotide) takes place in vivo, for instance, after transfection of a eukaryotic cell, or transformation of a prokaryotic cell such as a bacteria.

In some aspects, the present disclosure provides methods of in vivo expression of one or more expression sequences in a subject, comprising: administering a modified circular polyribonucleotide (e.g., a fully modified circular polyribonucleotide or a hybrid modified circular polyribonucleotide) to a cell of the subject wherein the modified circular polyribonucleotide (e.g., a fully modified circular polyribonucleotide or a hybrid modified circular polyribonucleotide) comprises the one or more expression sequences; and expressing the one or more expression sequences from the modified circular polyribonucleotide (e.g., a fully modified circular polyribonucleotide or a hybrid modified circular polyribonucleotide) in the cell. In some embodiments, the modified circular polyribonucleotide (e.g., a fully modified circular polyribonucleotide or a hybrid modified circular polyribonucleotide) is configured such that expression of the one or more expression sequences in the cell at a later time point is equal to or higher than an earlier time point. In some embodiments, the modified circular polyribonucleotide (e.g., a fully modified circular polyribonucleotide or a hybrid modified circular polyribonucleotide) is configured such that expression of the one or more expression sequences in the cell over a time period of at least 7, 8, 9, 10, 12, 14, 16, 18, 20, 22, 23, or more days does not decrease by greater than about 40%. In some embodiments, the modified circular polyribonucleotide (e.g., a fully modified circular polyribonucleotide or a hybrid modified circular polyribonucleotide) is configured such that expression of the one or more expression sequences in the cell is maintained at a level that does not vary by more than about 40% for at least 7, 8, 9, 10, 12, 14, 16, 18, 20, 22, 23, or more days. In some embodiments, the administration of the modified circular polyribonucleotide (e.g., a fully modified circular polyribonucleotide or a hybrid modified circular polyribonucleotide) is conducted using any delivery method described herein. In some embodiments, the modified circular polyribonucleotide (e.g., a fully modified circular polyribonucleotide or a hybrid modified circular polyribonucleotide) is administered to the subject via intravenous injection. In some embodiments, the administration of the modified circular polyribonucleotide (e.g., a fully modified circular polyribonucleotide or a hybrid modified circular polyribonucleotide) includes, but is not limited to, prenatal administration, neonatal administration, postnatal administration, oral, by injection (e.g., intravenous, intraarterial, intraperitoneal, intradermal, subcutaneous and intramuscular), by ophthalmic administration and by intranasal administration.

In some embodiments, the methods for protein expression comprise modification, folding, or other post-translation modification of the translation product. In some embodiments, the methods for protein expression comprise post-translation modification in vivo, e.g., via cellular machinery.

Numbered Embodiments

[1] A pharmaceutical composition comprising a pharmaceutically acceptable carrier or excipient and a modified circular polyribonucleotide, wherein the modified circular polyribonucleotide comprises at least one modified nucleotide and a first portion, and wherein the first portion comprises at least about 5, 10, 20, 50, 100, 200, 300, 400, 500, 600, 700, 800, 900, or 1000 contiguous unmodified nucleotides.

[2] A pharmaceutical composition comprising a pharmaceutically acceptable carrier or excipient and a modified circular polyribonucleotide, wherein the modified circular polyribonucleotide comprises at least one modified nucleotide and a first portion, and wherein the first portion comprises at least about 5, 10, 20, 50, 100, 200, 300, 400, 500, 600, 700, 800, 900, or 1000 contiguous nucleotides and wherein the first portion lacks 5'-methylcytidine or pseudouridine.

[3] The pharmaceutical composition of numbered embodiments [1] or [2], wherein the modified circular polyribonucleotide has a lower immunogenicity than a corresponding unmodified circular polyribonucleotide.

[4] The pharmaceutical composition of any one numbered embodiments [1]-[3], wherein the modified circular polyribonucleotide has a half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide.

[5] The pharmaceutical composition of any one numbered embodiments [1]-[4], wherein the modified circular polyribonucleotide has a higher half-life than a corresponding unmodified circular polyribonucleotide.

[6] The pharmaceutical composition of any one numbered embodiments [1]-[5], wherein the modified circular polyribonucleotide has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide, as assessed by expression or signaling or activation of at least one of RIG-I, TLR-3, TLR-7, TLR-8, MDA-5, LGP-2, OAS, OASL, PKR, and IFN-beta.

[7] The pharmaceutical composition of any one numbered embodiments [1]-[6], wherein the modified circular polyribonucleotide has a higher half-life than a corresponding unmodified circular polyribonucleotide.

[8] The pharmaceutical composition of any one numbered embodiments [1]-[7], wherein the at least one modified nucleotide is selected from the group consisting of: N(6) methyladenosine (m6A), 5'-methylcytidine, and pseudouridine.

[9] The pharmaceutical composition of any one numbered embodiments [1]-[8], wherein the at least one modified nucleic acid is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

[10] The pharmaceutical composition of any one numbered embodiments [1]-[9], wherein at least about 10%, 20%, 30%, 40%, 50%, 60%, 70%, 80%, 90%, 95%, or 99% nucleotides of the modified circular polyribonucleotide are modified nucleotides.

[11] The pharmaceutical composition of any one numbered embodiments [1]-[10], wherein the circular polyribonucleotide comprises a binding site configured to bind to a protein, DNA, RNA, or a cell target, consisting of unmodified nucleotides.

[12] The pharmaceutical composition of numbered embodiment [11], wherein the first portion comprises the binding site.

[13] The pharmaceutical composition of any one numbered embodiments [1]-[12], wherein the modified circular polyribonucleotide comprises an IRES consisting of unmodified nucleotides.

[14] The pharmaceutical composition of any one numbered embodiments [1]-[13], wherein the first portion comprises an IRES.

[15] The pharmaceutical composition of any one numbered embodiments [1]-[14], wherein the modified circular polyribonucleotide comprises one or more expression sequences.

[16] The pharmaceutical composition of any one numbered embodiments [1]-[15], wherein the modified circular polyribonucleotide comprises the one or more expression sequences and the IRES, and wherein the modified circular polyribonucleotide comprises a 5'-methylcytidine, a pseudouridine, or a combination thereof outside the IRES.

[17] The pharmaceutical composition of any one numbered embodiments [1]-[16], wherein one or more expression sequences of the modified circular polyribonucleotide have a higher translation efficiency than a fully modified circular polyribonucleotide counterpart.

[18] The pharmaceutical composition of any one numbered embodiments [1]-[17], wherein one or more expression sequences of the modified circular polyribonucleotide have a translation efficiency of that is at least about 0.7, 0.8, 0.9, 1.0, 1.1, 1.2, 1.3, 1.5, 1.6, 1.8, 2, 2.2, 2.5, 2.8, 3 fold higher than a fully modified circular polyribonucleotide counterpart.

[19] The pharmaceutical composition of any one of numbered embodiments [17] or [18], wherein the fully modified circular polyribonucleotide counterpart comprises at least one modified nucleotide outside a first portion and more than 5% modified nucleotide nucleotides in the first portion.

[20] The pharmaceutical composition of any one numbered embodiments [1]-[19], wherein one or more expression sequences of the modified circular polyribonucleotide have a higher translation efficiency than a corresponding unmodified circular polyribonucleotide.

[21] The pharmaceutical composition of any one numbered embodiments [1]-[20], wherein one or more expression sequences of the modified circular polyribonucleotide have a translation efficiency of that is at least about 0.7, 0.8, 0.9, 1.0, 1.1, 1.2, 1.3, 1.5, 1.6, 1.8, 2, 2.2, 2.5, 2.8, 3 fold higher than a corresponding unmodified circular polyribonucleotide.

[22] The pharmaceutical composition of any one numbered embodiments [1]-[21], wherein one or more expression sequences of the modified circular polyribonucleotide have a higher translation efficiency than a corresponding circular polyribonucleotide having a first portion comprising a modified nucleotide.

[23] The pharmaceutical composition of any one of numbered embodiments [1]-[22], wherein one or more expression sequences of the circular polyribonucleotide have a higher translation efficiency than a corresponding circular polyribonucleotide having a first portion comprising more than 10% modified nucleotides.

[24] The pharmaceutical composition of any one numbered embodiments [1]-[23], wherein one or more expression sequences of the modified circular polyribonucleotide have a translation efficiency that is at least about 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding circular polyribonucleotide having a first portion comprising a modified nucleotide.

[25] The pharmaceutical composition of any one of numbered embodiments [17]-[23], wherein the translation efficiency is measured either in a cell comprising the circular polyribonucleotide or the corresponding circular polyribonucleotide, or in an in vitro translation system (e.g., rabbit reticulocyte lysate).

[26] The pharmaceutical composition of any one numbered embodiments [1]-[25], wherein the modified circular polyribonucleotide is competent for rolling circle translation.

[27] The pharmaceutical composition of any one of numbered embodiments [15]-[26], wherein each of the one or more expression sequences is separated from a succeeding expression sequence by a stagger element on the circular polyribonucleotide, wherein the rolling circle translation of the one or more expression sequences generates at least two polypeptide molecules.

[28] The pharmaceutical composition of any one of numbered embodiments [1]-[27], wherein the pharmaceutically acceptable carrier or excipient is ethanol.

[29] The pharmaceutical composition of numbered embodiment [27], wherein the stagger element prevents generation of a single polypeptide (a) from two rounds of translation of a single expression sequence or (b) from one or more rounds of translation of two or more expression sequences.

[30] The pharmaceutical composition of numbered embodiment [27] or [29], wherein the stagger element is a sequence separate from the one or more expression sequences.

[31] The pharmaceutical composition of numbered embodiment [27] or [29], wherein the stagger element comprises a portion of an expression sequence of the one or more expression sequences.

[32] The pharmaceutical composition of any one of numbered embodiments 1-24, wherein the modified circular polyribonucleotide is competent for rolling circle translation, wherein the modified circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the modified circular polyribonucleotide are discrete polypeptides, and wherein each of the discrete polypeptides is generated from a single round of translation or less than a single round of translation of the one or more expression sequences.

[33] The pharmaceutical composition of numbered embodiment [32], wherein the modified circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the modified circular polyribonucleotide are the discrete polypeptides, and wherein amount ratio of the discrete products over the total polypeptides is tested in an in vitro translation system.

[34] The pharmaceutical composition of numbered embodiment [33], wherein the in vitro translation system comprises rabbit reticulocyte lysate.

[35] The pharmaceutical composition of any one of numbered embodiments [27]-[34], wherein the stagger element is at a 3' end of at least one of the one or more expression sequences, and wherein the stagger element is configured to stall a ribosome during rolling circle translation of the modified circular polyribonucleotide.

[36] The pharmaceutical composition of any one of numbered embodiments [27]-[35], wherein the stagger element encodes a peptide sequence selected from the group consisting of a 2A sequence and a 2A-like sequence.

[37] The pharmaceutical composition of any one of numbered embodiments [27]-[36], wherein the stagger element encodes a sequence with a C-terminal sequence that is GP.

[38] The pharmaceutical composition of any one of numbered embodiments [27]-[37], wherein the stagger element encodes a sequence with a C-terminal consensus sequence that is D(V/I)ExNPGP, where x=any amino acid (SEQ ID NO: 66).

[39] The pharmaceutical composition of any one of numbered embodiments [27]-[38], wherein the stagger element encodes a sequence selected from the group consisting of GDVESNPGP (SEQ ID NO: 67), GDIEENPGP (SEQ ID NO: 68), VEPNPGP (SEQ ID NO: 69), IETNPGP (SEQ ID NO: 70), GDIESNPGP (SEQ ID NO: 71), GDVELNPGP (SEQ ID NO: 72), GDIETNPGP (SEQ ID NO: 73), GDVENPGP (SEQ ID NO: 74), GDVEENPGP (SEQ ID NO: 75), GDVEQNPGP (SEQ ID NO: 76), IESNPGP (SEQ ID NO: 77), GDIELNPGP (SEQ ID NO: 78), HDIETNPGP (SEQ ID NO: 79), HDVETNPGP (SEQ ID NO: 80), HDVEMNPGP (SEQ ID NO: 81), GDMESNPGP (SEQ ID NO: 82), GDVETNPGP (SEQ ID NO: 83), GDIEQNPGP (SEQ ID NO: 84), and DSEFNPGP (SEQ ID NO: 85).

[40] The pharmaceutical composition of any one of numbered embodiments [27]-[39], wherein the stagger element is at 3' end of each of the one or more expression sequences.

[41] The pharmaceutical composition of any one of numbered embodiments [27]-[40], wherein the stagger element of a first expression sequence in the modified circular polyribonucleotide is upstream of (5' to) a first translation initiation sequence of an expression sequence succeeding the first expression sequence in the modified circular polyribonucleotide, and wherein a distance between the stagger element and the first translation initiation sequence enables continuous translation of the first expression sequence and the succeeding expression sequence.

[42] The pharmaceutical composition of any one of numbered embodiments [27]-[40], wherein the stagger element of a first expression sequence in the modified circular polyribonucleotide is upstream of (5' to) a first translation initiation sequence of an expression sequence succeeding the first expression in the circular polyribonucleotide, wherein the circular polyribonucleotide is continuously translated, wherein a corresponding modified circular polyribonucleotide comprising a second stagger element upstream of a second translation initiation sequence of a second expression sequence in the modified corresponding circular polyribonucleotide is not continuously translated, and wherein the second stagger element in the corresponding modified circular polyribonucleotide is at a greater distance from the second translation initiation sequence, e.g., at least 2×, 3×, 4×, 5×, 6×, 7×, 8×, 9×, 10×, than a distance between the stagger element and the first translation initiation in the modified circular polyribonucleotide.

[43] The pharmaceutical composition of numbered embodiment [41] or [42], wherein the distance between the stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater.

[44] The pharmaceutical composition of numbered embodiment [41] or [42], wherein the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the tagger element and the first translation initiation.

[45] The pharmaceutical composition of any one of numbered embodiments [41]-[43], wherein the expression sequence succeeding the first expression sequence on the modified circular polyribonucleotide is an expression sequence other than the first expression sequence.

[46] The pharmaceutical composition of any one of numbered embodiments [41]-[43], wherein the succeeding expression sequence of the first expression sequence on the modified circular polyribonucleotide is the first expression sequence.

[47] The pharmaceutical composition of any previous numbered embodiment, wherein the modified circular polyribonucleotide comprises at least one structural element selected from:

a) an encryptogen;
b) a stagger element;
c) a regulatory element;
d) a replication element; and
f) quasi-double-stranded secondary structure.

[48] The pharmaceutical composition of any previous numbered embodiment, wherein the modified circular polyribonucleotide comprises at least one functional characteristic selected from:

a) greater translation efficiency than a linear counterpart;
b) a stoichiometric translation efficiency of multiple translation products;
c) less immunogenicity than a counterpart lacking an encryptogen;
d) increased half-life over a linear counterpart; and
e) persistence during cell division.

[49] The pharmaceutical composition of any previous numbered embodiment, wherein the modified circular polyribonucleotide has a translation efficiency at least 5%, at least 10%, at least 15%, at least 20%, at least 30%, at least 40%, at least 50%, at least 60%, at least 70%, at least 80%, at least 90%, at least 100%, at least 150%, at least 2 fold, at least 3 fold, at least 4 fold, at least 5 fold, at least 6 fold, at least 7 fold, at least 8 fold, at least 9 fold, at least 10 fold, at least 20 fold, at least 50 fold, or at least 100 fold greater than a linear counterpart.

[50] The pharmaceutical composition of any previous numbered embodiment, wherein the modified circular polyribonucleotide has a translation efficiency at least 5 fold greater than a linear counterpart.

[51] The pharmaceutical composition of any previous numbered embodiment, wherein the modified circular polyribonucleotide lacks at least one of:

a) a 5'-UTR;
b) a 3'-UTR;
c) a poly-A sequence;
d) a 5'-cap;
e) a termination element;
f) degradation susceptibility by exonucleases; and
g) binding to a cap-binding protein.

[52] The pharmaceutical composition of any one of numbered embodiments [26]-[51], wherein the one or more expression sequences comprise a Kozak initiation sequence.

[53] The pharmaceutical composition of any one of numbered embodiments [47]-[52], wherein the quasi-helical structure comprises at least one double-stranded RNA segment with at least one non-double-stranded segment.

[54] The pharmaceutical composition of numbered embodiment [53], wherein the quasi-helical structure comprises a first sequence and a second sequence linked with a repetitive sequence, e.g., an A-rich sequence.

[55] The pharmaceutical composition of any one of numbered embodiments [47]-[54], wherein the encryptogen comprises a splicing element.

[56] The pharmaceutical composition of any previous numbered embodiment, wherein the encryptogen comprises a protein binding site, e.g., ribonucleotide binding protein.

[57] The pharmaceutical composition of any previous numbered embodiment, wherein the encryptogen comprises an immunoprotein binding site, e.g., to evade immune responses, e.g., CTL responses.

[58] The pharmaceutical composition of any previous numbered embodiment, wherein the modified circular polyribonucleotide has at least 2× less immunogenicity than a counterpart lacking the encryptogen, e.g., as assessed by expression or signaling or activation of at least one of RIG-I, TLR-3, TLR-7, TLR-8, MDA-5, LGP-2, OAS, OASL, PKR, and IFN-beta.

[59] The pharmaceutical composition of any previous numbered embodiment, wherein the modified circular polyribonucleotide further comprises a riboswitch.

[60] The pharmaceutical composition of any previous numbered embodiment, wherein the modified circular polyribonucleotide further comprises an aptazyme.

[61] The pharmaceutical composition of any previous numbered embodiment, wherein the modified circular polyribonucleotide comprises a non-canonical translation initiation sequence, e.g., GUG, CUG start codon, e.g., a translation initiation sequence that initiates expression under stress conditions.

[62] The pharmaceutical composition of any previous numbered embodiment, wherein the one or more expression sequences encodes a peptide.

[63] The pharmaceutical composition of any previous numbered embodiment, wherein the modified circular polyribonucleotide comprises a regulatory nucleic acid, e.g., a non-coding RNA.

[64] The pharmaceutical composition of any previous numbered embodiment, wherein the circular polyribonucleotide has a size in the range of about 20 bases to about 20 kb.

[65] The pharmaceutical composition of any previous numbered embodiment, wherein the modified circular polyribonucleotide is synthesized through circularization of a linear polyribonucleotide.

[66] The pharmaceutical composition of any previous numbered embodiment, wherein the modified circular polyribonucleotide comprises a plurality of expression sequences having either a same nucleotide sequence or different nucleotide sequences.

[67] The pharmaceutical composition of any previous numbered embodiment, wherein the modified circular polyribonucleotide is substantially resistant to degradation, e.g., exonuclease.

[68] The pharmaceutical composition of any previous numbered embodiment, wherein the modified circular polyribonucleotide comprises:

a. a modified circular polyribonucleotide comprising:
b. a first binding site configured to bind a first binding moiety of a first target, e.g., a RNA, DNA, protein, membrane of cell etc., wherein the first binding moiety is a first circular polyribonucleotide (circRNA)-binding motif; and
c. a second binding site configured to bind a second binding moiety of a second target, wherein the second binding moiety is a second circRNA-binding motif,
d. wherein the first binding moiety is different than the second binding moiety,
e. wherein the first target, the second target, and the modified circular polyribonucleotide form a complex, and
f. wherein the first target or the second target is a not a microRNA.

[69] The pharmaceutical composition of any previous numbered embodiment, wherein the modified circular polyribonucleotide comprises:

a. a modified circular polyribonucleotide comprising:
a first binding site configured to bind a first binding moiety of a first target, wherein the first binding moiety is a first circular polyribonucleotide (circRNA)-binding motif; and
a second binding site configured to bind a second binding moeity of a second target, wherein the second binding moiety is a second circRNA-binding motif,
b. wherein the first binding moiety is different than the second binding moiety, and
c. wherein the first target and the second target are both a microRNA.

[70] The pharmaceutical composition of numbered embodiment [68] or [69], wherein the first and second targets interact with each other.

[71] The pharmaceutical composition of any one of numbered embodiments [68]-[70], wherein the complex modulates a cellular process.

[72] The pharmaceutical composition of any one of numbered embodiments [68]-[71], wherein the first and second targets are the same, and the first and second binding sites bind different moieties.

[73] The pharmaceutical composition of any one of numbered embodiments [68]-[72], wherein the first and second targets are different.

[74] The pharmaceutical composition of any one of numbered embodiments [68]-[73], wherein the modified circular polyribonucleotide further comprises one or more additional binding sites configured to bind a third or more binding moieties.

[75] The pharmaceutical composition of any one of numbered embodiments [68]-[74], wherein one or more targets are the same and one or more binding sites are configured to bind different moieties.

[76] The pharmaceutical composition of any one of numbered embodiments [68]-[75], wherein formation of the complex modulates a cellular process.

[77] The pharmaceutical composition of any one of numbered embodiments [68]-[76], wherein the modified circular polyribonucleotide modulates a cellular process associated with the first or second target when contacted to the first and second targets.

[78] The pharmaceutical composition of any one of numbered embodiments [68]-[77], wherein the first and second targets interact with each other in the complex.

[79] The pharmaceutical composition of any one of numbered embodiments [68]-[78], wherein the cellular process is associated with pathogenesis of a disease or condition.

[80] The pharmaceutical composition of any one of numbered embodiments [71]-[79], wherein the cellular process is different than translation of the circular polyribonucleic acid.

[81] The pharmaceutical composition of any one of numbered embodiments [71]-[80], wherein the cellular process is associated with pathogenesis of a disease or condition.

[82] The pharmaceutical composition of any one of numbered embodiments [68]-[81], wherein the first target comprises a deoxyribonucleic acid (DNA) molecule, and the second target comprises a protein.

[83] The pharmaceutical composition of any one of numbered embodiments [68]-[82], wherein the complex modulates directed transcription of the DNA molecule, epigenetic remodeling of the DNA molecule, or degradation of the DNA molecule.

[84] The pharmaceutical composition of any one of numbered embodiments [68]-[83], wherein the first target comprises a first protein, and the second target comprises a second protein.

[85] The pharmaceutical composition of any one of numbered embodiments [68]-[84], wherein the complex modulates degradation of the first protein, translocation of the first protein, or signal transduction, or modulates a native protein function, or inhibits formation of a complex formed by direct interaction between the first and second proteins.

[86] The pharmaceutical composition of any one of numbered embodiments [68]-[85], wherein the first target comprises a first ribonucleic acid (RNA) molecule, and the second target comprises a second RNA molecule.

[87] The pharmaceutical composition of numbered embodiment [86], wherein the complex modulates degradation of the first RNA molecule.

[88] The pharmaceutical composition of any one of numbered embodiments [68]-[87], wherein the first target comprises a protein, and the second target comprises a RNA molecule.

[89] The pharmaceutical composition of any one of numbered embodiments [68]-[88], wherein the complex modulates translocation of the protein or inhibits formation of a complex formed by direct interaction between the protein and the RNA molecule.

[90] The pharmaceutical composition of any one of numbered embodiments [68]-[89], wherein the first binding moiety comprises a receptor, and the second binding moiety comprises a substrate of the receptor.

[91] The pharmaceutical composition of any one of numbered embodiments [68]-[90], wherein the complex inhibits activation of the receptor.

[92] The pharmaceutical composition of any previous numbered embodiment, wherein the modified circular polyribonucleotide comprises a binding site configured to bind a binding moiety of a target, wherein the binding moiety is a ribonucleic acid (RNA)-binding motif, wherein the modified circular polyribonucleotide is translation incompetent or translation defective, and wherein the target is not a microRNA.

[93] The pharmaceutical composition of any previous numbered embodiment, wherein the modified circular polyribonucleotide comprises a binding site configured to bind a binding moiety of a target, wherein the binding moiety is a ribonucleic acid (RNA)-binding motif, wherein the modified circular polyribonucleotide is translation incompetent or translation defective, and wherein the target is a microRNA.

[94] The pharmaceutical composition of numbered embodiment [92] or [93], wherein the target comprises a DNA molecule.

[95] The pharmaceutical composition of any one of numbered embodiments [92]-[94], wherein binding of the binding moiety to the modified circular polyribonucleotide modulates interference of transcription of a DNA molecule.

[96] The pharmaceutical composition of any one of numbered embodiments [92]-[95], wherein the target comprises a protein.

[97] The pharmaceutical composition of numbered embodiment [96], wherein binding of the binding moiety to the modified circular polyribonucleotide inhibits interaction of the protein with other molecules.

[98] The pharmaceutical composition of numbered embodiment [96] or [97], wherein the protein is a receptor, and wherein binding of the first binding moiety to the modified circular polyribonucleotide activates the receptor.

[99] The pharmaceutical composition of any one of numbered embodiments [96]-[98], wherein the protein is a first enzyme, wherein the modified circular polyribonucleotide further comprises a second binding site configured to bind to a second enzyme, and wherein binding of the first and second enzymes to the modified circular polyribonucleotide modulates enzymatic activity of the first and second enzymes.

[100] The pharmaceutical composition of any one of numbered embodiments [92]-[99], wherein the target comprises a messenger RNA (mRNA) molecule.

[101] The pharmaceutical composition of numbered embodiment [100], wherein binding of the binding moiety to the modified circular polyribonucleotide modulates interference of translation of the mRNA molecule.

[102] The pharmaceutical composition of any one of numbered embodiments [92]-[101], wherein the target comprises a ribosome.

[103] The pharmaceutical composition of numbered embodiment [102], wherein binding of the binding moiety to the modified circular polyribonucleotide modulates interference of a translation process.

[104] The pharmaceutical composition of any one of numbered embodiments [92]-[103], wherein the target comprises a circular RNA molecule.

[105] The pharmaceutical composition of numbered embodiment [104], wherein binding of the binding moiety to the modified circular polyribonucleotide sequesters the circular RNA molecule.

[106] The pharmaceutical composition of any one of numbered embodiments [92]-[105], wherein binding of the binding moiety to the modified circular polyribonucleotide sequesters the microRNA molecule.

[107] The pharmaceutical composition of any one of the previous numbered embodiment, wherein the modified circular polyribonucleotide comprises a binding site configured to bind a binding moiety on a membrane of a cell target; and wherein the binding moiety is a ribonucleic acid (RNA)-binding motif.

[108] The pharmaceutical composition of any one of the previous numbered embodiments, wherein the modified circular polyribonucleotide further comprises a second binding site configured to bind a second binding moiety on a second cell target, wherein the second binding moiety is a second RNA-binding motif.

[109] The pharmaceutical composition of any one of the previous numbered embodiments, wherein the c modified circular polyribonucleotide is configured to bind to both targets.

[110] The pharmaceutical composition of any one of the previous numbered embodiments, wherein the modified circular polyribonucleotide further comprises a second binding site configured to bind a second binding moiety, and wherein binding of both targets to the circular polyribonucleotide induces a conformational change in the first target, thereby inducing signal transduction downstream of the target.

[111] The pharmaceutical composition of any previous numbered embodiment formulated in a carrier, e.g., membrane or lipid bilayer.

[112] A method of delivering a modified circular polyribonucleotide to a subject comprising administering the pharmaceutical composition of any one of the preceding numbered embodiments to the subject.

[113] A method of decreasing or reducing immunogenicity of a circular polyribonucleotide in a subject comprising:

providing a hybrid circular polyribonucleotide wherein the hybrid modified circular polyribonucleotide comprises at least one modified nucleotide and a first portion comprising at least about 5, 10, 20, 50, 100, 200, 300, 400, 500, 600, 700, 800, 900, or 1000 contiguous unmodified nucleotides;

administering the hybrid modified circular polyribonucleotide to the subject; and obtaining decreased or reduced immunogenicity for the hybrid modified circular polyribonucleotide compared to a corresponding unmodified circular polyribonucleotide in a cell or tissue of the subject.

[114] A method of expressing one or more expression sequences in a subject comprising:

providing a modified circular polyribonucleotide comprising the one or more expression sequences, wherein the hybrid modified circular polyribonucleotide comprises at least one modified nucleotide and a first portion comprising at least about 5, 10, 20, 50, 100, 200, 300, 400, 500, 600, 700, 800, 900, or 1000 contiguous unmodified nucleotides;

administering the hybrid modified circular polyribonucleotide to the subject; and obtaining increased expression of the one or more expression sequences compared to expression of one or more expression sequences in a fully modified circular polyribonucleotide counterpart in a cell or tissue of the subject.

[115] A method of increasing stability of a circular polyribonucleotide in a subject comprising:

providing a hybrid modified circular polyribonucleotide, wherein the hybrid modified circular polyribonucleotide comprises a modified circular polyribonucleotide and a first portion comprising at least about 5, 10, 20, 50, 100, 200, 300, 400, 500, 600, 700, 800, 900, or 1000 contiguous unmodified nucleotides;

administering the hybrid modified circular polyribonucleotide to the subject; and obtaining increased stability for the hybrid modified circular polyribonucleotide compared to a corresponding unmodified circular polyribonucleotide in a cell or tissue of the subject.

[116] A method of treatment, comprising administering the pharmaceutical composition of any previous composition numbered embodiment to a subject with a disease or condition.

[117] A method of producing a pharmaceutical composition, comprising generating the modified circular polyribonucleotide of any previous composition numbered embodiment.

[118] A method of making the modified circular polyribonucleotide of any previous composition numbered embodiment, comprising circularizing a linear polyribonucleotide having a nucleic acid sequence as the modified circular polyribonucleotide.

[119] A method of making a hybrid modified circular polyribonucleotide, comprising ligating an unmodified first portion to a modified linear polyribonucleotide to produce a hybrid linear polyribonucleotide, and circularizing the hybrid linear polyribonucleotide.

[120] An engineered cell comprising the composition of any previous composition numbered embodiment.

[121] A method of decreasing or reducing immunogenicity of a circular polyribonucleotide in a subject comprising:
- providing a hybrid modified circular polyribonucleotide, wherein the hybrid modified circular polyribonucleotide comprises at least one modified nucleotide and a first portion comprising about 5 to 1000 contiguous nucleotides having no more than 5% modified nucleotides;
- administering the hybrid modified circular polyribonucleotide to the subject; and
- obtaining decreased or reduced immunogenicity for the hybrid modified circular polyribonucleotide compared to a corresponding unmodified circular polyribonucleotide in a cell or tissue of the subject.

[122] The method of numbered embodiment [121], wherein the first portion comprises at least about 5, 10, 20, 50, 100, 200, 300, 400, 500, 600, 700, 800, 900, or 1000 contiguous nucleotides.

[123] The method of numbered embodiment [121] or [122], wherein the first portion consists of unmodified nucleotides.

[124] The method of any one of numbered embodiments [121]-[123], wherein the first portion comprises at least about 5, 10, 20, 50, 100, 200, 300, 400, 500, 600, 700, 800, 900, or 1000 contiguous unmodified nucleotides.

[125] The method of any one of numbered embodiments [121]-[124], wherein the first portion lacks 5'-methylcytidine or pseudouridine.

[126] The method of any one of numbered embodiments [121]-[125], wherein the circular polyribonucleotide is translationally competent.

[127] The method of any one of numbered embodiments [121]-[126], wherein the hybrid modified circular polyribonucleotide:
- a. has at least about 0.7, 0.8, 0.9, 1.0, 1.1, 1.2, 1.3, 1.5, 1.6, 1.8, 2, 2.2, 2.5, 2.8, 3 fold higher expression than a corresponding unmodified circular polyribonucleotide;
- b. has a half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide;
- c. has a higher half-life than a corresponding unmodified circular polyribonucleotide; or
- d. has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide, as assessed by expression or signaling or activation of at least one of RIG-I, TLR-3, TLR-7, TLR-8, MDA-5, LGP-2, OAS, OASL, PKR, and IFN-beta.

[128] The method of any one of numbered embodiments [121]-[127], wherein the at least one modified nucleotide is selected from the group consisting of:
- a. N(6)methyladenosine (m6A), 5'-methylcytidine, and pseudouridine;
- b. 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite; or
- c. any modified nucleotide in TABLE 2.

[129] The method of any one of numbered embodiments [121]-[128], wherein at least about 10%, 20%, 30%, 40%, 50%, 60%, 70%, 80%, 90%, 95%, or 99% nucleotides of the hybrid modified circular polyribonucleotide are modified nucleotides.

[130] The method of any one of numbered embodiments [121]-[129], wherein the hybrid modified circular polyribonucleotide comprises a binding site configured to bind to a protein, peptide, biomolecule, DNA, RNA, or a cell target, consisting of unmodified nucleotides.

[131] The method of any one of numbered embodiments [121]-[130], wherein the hybrid modified circular polyribonucleotide comprises one or more expression sequences.

[132] The method of any one of numbered embodiments [121]-[131], wherein the first portion comprises an IRES consisting of unmodified nucleotides or no more than 5% modified nucleotides.

[133] The method of numbered embodiments [131] or [132], wherein one or more expression sequences of the hybrid modified circular polyribonucleotide have:
- a. a higher translation efficiency than a fully modified circular polyribonucleotide counterpart;
- b. a translation efficiency that is at least about 0.7, 0.8, 0.9, 1.0, 1.1, 1.2, 1.3, 1.5, 1.6, 1.8, 2, 2.2, 2.5, 2.8, 3 fold higher than a fully modified circular polyribonucleotide counterpart;
- c. has a higher translation efficiency than a corresponding unmodified circular polyribonucleotide; or
- d. a translation efficiency that is at least about 0.7, 0.8, 0.9, 1.0, 1.1, 1.2, 1.3, 1.5, 1.6, 1.8, 2, 2.2, 2.5, 2.8, 3 fold higher than a corresponding unmodified circular polyribonucleotide.

[134] A method of expressing one or more expression sequences in a subject comprising:
- providing a hybrid modified circular polyribonucleotide comprising one or more expression sequences, wherein the hybrid modified circular polyribonucleotide comprises at least one modified nucleotide and a first portion comprising about 5 to 1000 contiguous nucleotides having no more than 5% modified nucleotides;
- administering the hybrid modified circular polyribonucleotide to the subject; and
- obtaining increased expression of the one or more expression sequences compared to expression of a corresponding one or more expression sequences in a fully modified circular polyribonucleotide counterpart in a cell or tissue of the subject.

[135] A method of increasing stability of a circular polyribonucleotide in a subject comprising:
- providing a hybrid modified circular polyribonucleotide, wherein the hybrid modified circular polyribonucleotide comprises at least one modified nucleotide and a first portion comprising about 5 to 1000 contiguous nucleotides having no more than 5% modified nucleotides;

administering the hybrid modified circular polyribonucleotide to the subject; and obtaining increased stability for the hybrid modified circular polyribonucleotide compared to a corresponding unmodified circular polyribonucleotide in a cell or tissue of the subject.

[136] The method of numbered embodiment [134] or [135], wherein the first portion comprises an IRES.

[137] The method of any one of numbered embodiments [134]-[136], wherein the first portion comprises at least about 5, 10, 20, 50, 100, 200, 300, 400, 500, 600, 700, 800, 900, or 1000 contiguous nucleotides.

[138] The method of any one of numbered embodiments [134]-[137], wherein the first portion consists of unmodified nucleotides.

[139] The method of any one of numbered embodiments [134]-[138], wherein the first portion comprises at least about 5, 10, 20, 50, 100, 200, 300, 400, 500, 600, 700, 800, 900, or 1000 contiguous unmodified nucleotides.

[140] The method of any one of numbered embodiments [134]-[139], wherein the hybrid modified circular polyribonucleotide comprises one or more expression sequences.

[141] The method of any one of numbered embodiments [134]-[140], wherein the circular polyribonucleotide is translationally competent.

[142] The method of any one of numbered embodiments [134]-[141], wherein the at least one modified nucleotide is selected from the group consisting of:

a. N(6)methyladenosine (m6A), 5'-methylcytidine, and pseudouridine;
b. 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite; or
c. any modified nucleotide in TABLE 2.

[143] The method of any one of numbered embodiments [134]-[142], wherein the first portion comprises an IRES consisting of unmodified nucleotides or no more than 5% modified nucleotides.

All references and publications cited herein are hereby incorporated by reference.

The above described embodiments can be combined to achieve the afore-mentioned functional characteristics. This is also illustrated by the below examples which set forth exemplary combinations and functional characteristics achieved. TABLE 7 provides an exemplary overview which shows how different elements described above can be combined and the functional characteristics observed.

TABLE 7

Exemplary Elements in EXAMPLES

| Exemplary function | Elements (e.g. start codon, stagger element, encryptogen, IRES etc.) Replication element Transcription start | Expression sequence Coding for product | Stagger element Ribosomal pausing; rolling circle translation | Regulatory element Expression modifier | Encryptogen Modulating immune response | Quasi-double strand secondary structure | Effect of Circular Polyribo-nucleotide |
|---|---|---|---|---|---|---|---|
| Example 12 | | x | x | | x | | Greater translation efficiency than a linear counterpart |
| Example 13 | | x | x | | x | | Stochiometric translation efficiency of mutliple translation products |
| Example 47 | | x | | | x | | Less immunogenicity than counterpart lacking an encryptogen |
| Example 50 | | | | | | | |
| Example 18 | x | | | | | | |
| Example 21 | | x | x | | | | Increased half-life over a linear counterpart |
| Example 32 | | | | | | | |
| Example 33 | x | x | x | | | | Increased half-life over a linear counterpart |
| Example 41 | x | x | x | | | | Greater translation |

TABLE 7-continued

Exemplary Elements in EXAMPLES

| | Elements (e.g. start codon, stagger element, encryptogen, IRES etc.) | | | | | | |
|---|---|---|---|---|---|---|---|
| Exemplary function | Replication element Transcription start | Expression sequence Coding for product | Stagger element Ribosomal pausing; rolling circle translation | Regulatory element Expression modifier | Encryptogen Modulating immune response | Quasi-double strand secondary structure | Effect of Circular Polyribonucleotide |
| Example 42 | | | | | | | efficiency than a linear counterpart |
| Example 15 | | | | | x | | |
| Example 17 | | | | | | | |
| Example 43 | | | | | | | |
| Example 44 | | | | | | | |
| Example 51 | x | | | | | | Persistence during cell division |
| Example 52 | x | x | | | | | Greater translation efficiency than a linear counterpart |
| Example 1 | x | | | x | | | Less immunogenicity than counterpart lacking an encryptogen |
| Example 53 | x | | | x | | | Greater translation efficiency than a linear counterpart; Increased half-life over a linear counterpart; Less immunogenicity than counterpart lacking an encryptogen |
| Example 54 | | | | | | | |

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used. Examples 5, 6, 9, 14, 15, and 50-52, and their corresponding Figures as described in [0376]-[0392], [0400]-[0415], [0433]-[0440], and [0620]-[0633] of International Patent Publication No. WO2019118919A1, are incorporated herein by reference in their entirety.

Example 1: Circular RNA with Modified Nucleotides was Generated, Translated, and Reduced Immunogenicity of Circular RNA This Example demonstrates the generation of modified circular polyribonucleotide that produced protein product. In addition, this Example demonstrates circular RNA engineered with nucleotide modifications had reduced immunogenicity as compared to a linear RNA.

A non-naturally occurring circular RNA engineered to include one or more desirable properties and with complete or partial incorporation of modified nucleotides was produced. As shown in the following Example, full length modified linear RNA or a hybrid of modified and unmodified linear RNA was circularized and expression of Nanoluciferase (NLuc) was assessed. In addition, modified circular RNA was shown to have reduced activation of immune related genes (q-PCR of MDA5, OAS and IFN-beta expression) in BJ cells, as compared to a non-modified circular RNA.

Circular RNA with a WT EMCV Nluc stop spacer was generated. For complete modification substitution, the modified nucleotides, pseudouridine and methylcytosine or m6A, were added in place of the standard unmodified nucleotides, uridine and cytosine or adenosine, respectively, during the in vitro transcription reaction. For the hybrid construct, the WT EMCV IRES was synthesized separately from the NLuc ORF. The WT EMCV IRES was synthesized using either modified or non-modified nucleotides. In contrast, the NLuc ORF sequence was synthesized using the modified nucleotides, pseudouridine and methylcytosine or m6A, in place of the standard unmodified nucleotides, uridine and cytosine or adenosine, respectively, during the in vitro transcription reaction. Following synthesis of the modified or unmodified IRES and the modified ORF, these two oligonucleotides were ligated together using T4 DNA ligase. As shown in FIG. 1A modified circular RNA was generated.

To measure expression efficiency of NLuc from the fully modified or hybrid modified constructs, 0.1 pmol of linear and circular RNA was transfected into BJ fibroblasts for 6h. nLuc expression was measured at 6 hours, 24 hours, 48 hours, and 72 hours post-transfection.

The level of innate immune response genes was monitored in cells from total RNA isolated from the cells using a phenol-based extraction reagent (Invitrogen). Total RNA (500 ng) was subjected to reverse transcription to generate cDNA. qRT-PCR analysis was performed using a dye-based quantitative PCR mix (BioRad).

Figure 1B:
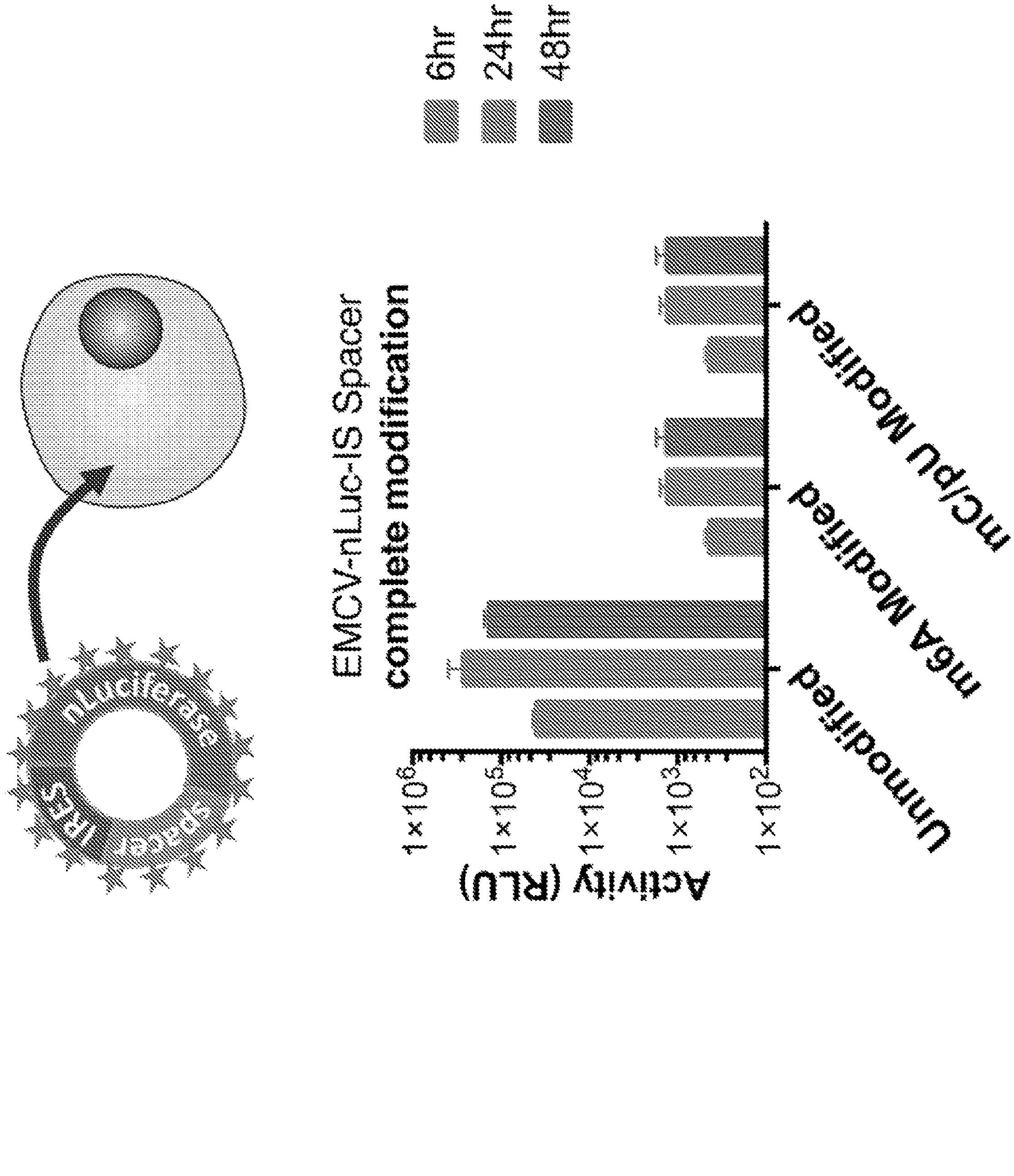
Figure 1C:
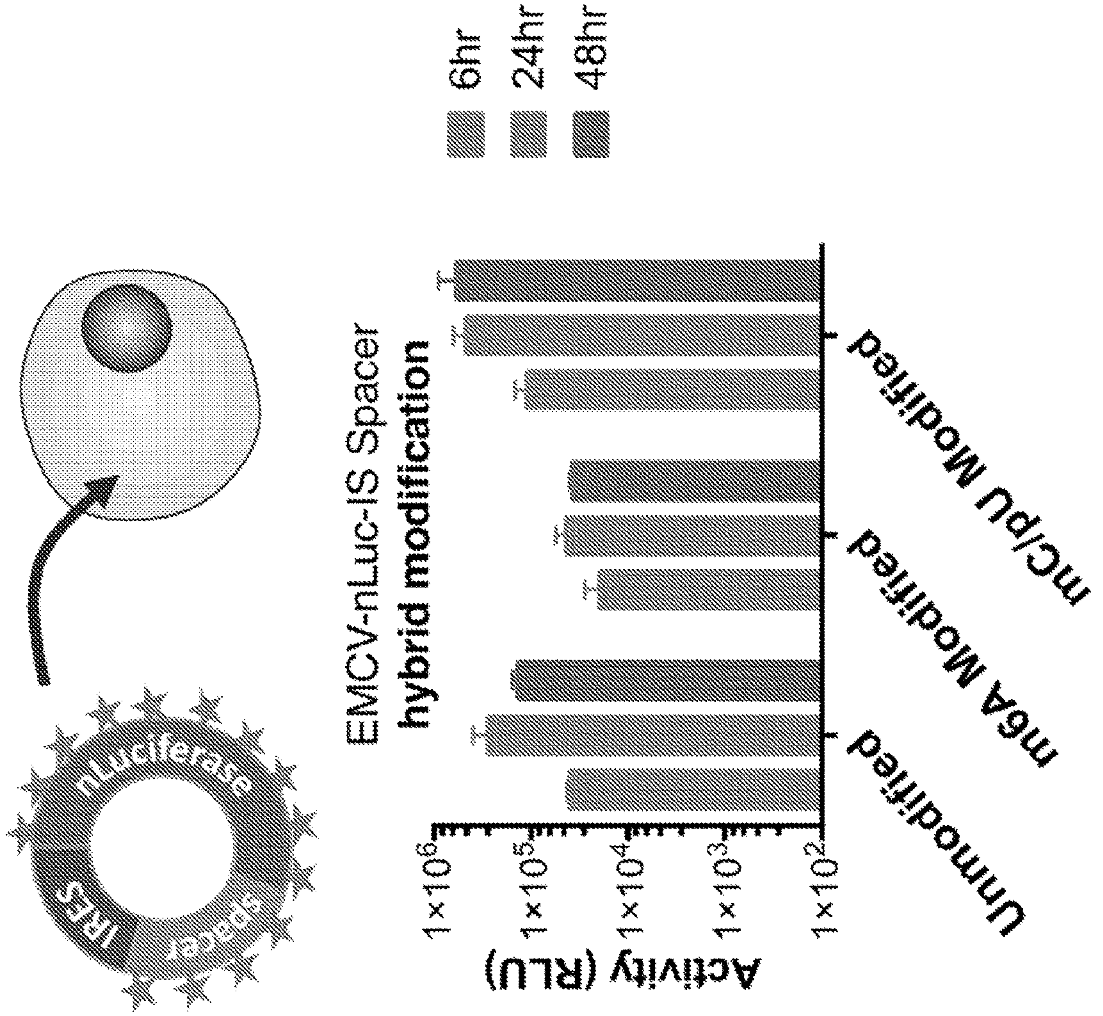
Figure 2A:
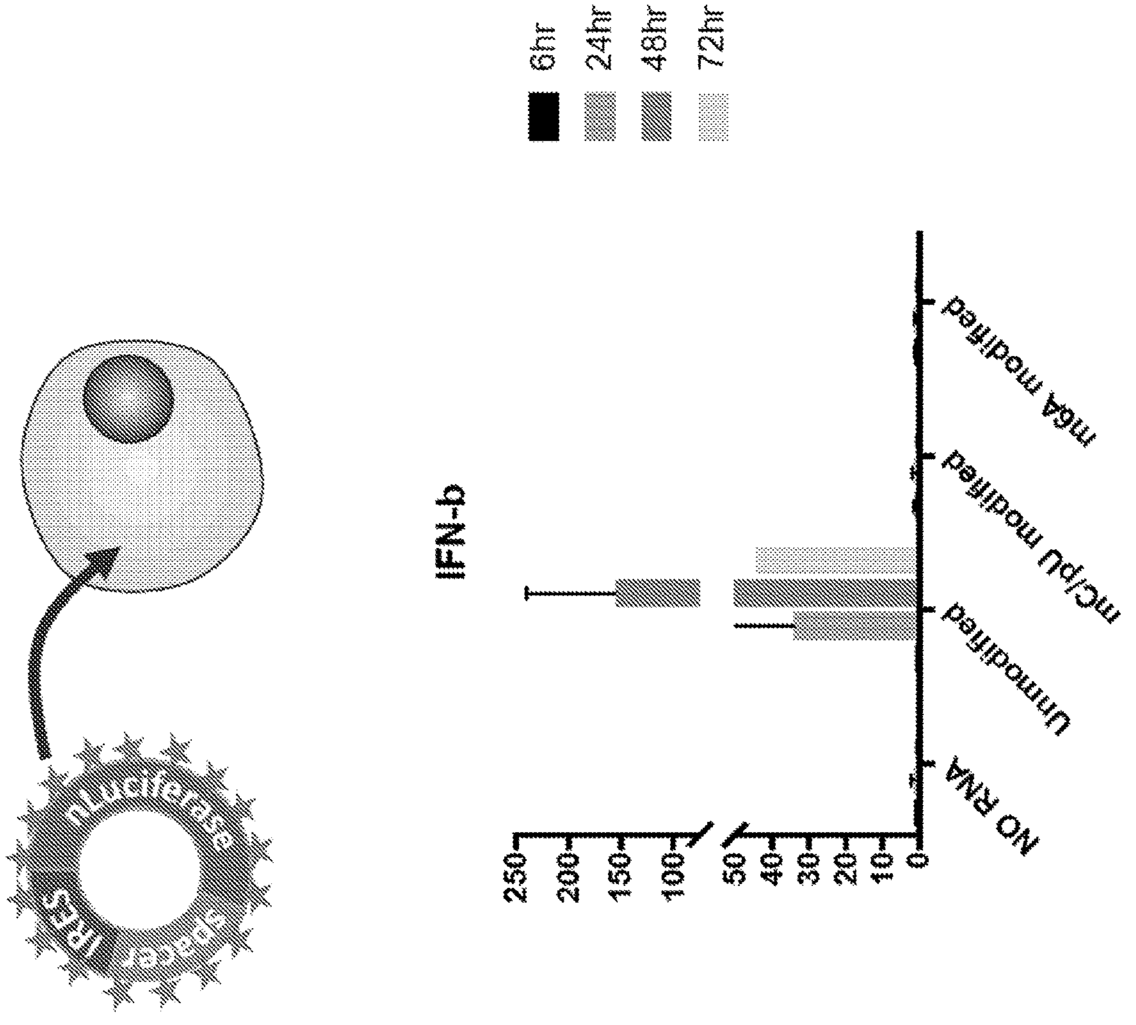
FIGS. 2A, 2B, and 2C show that modified circular RNAs have reduced immunogenicity as compared to unmodified circular RNAs to cells as assessed by MDA5, OAS and IFN-beta expression in the transfected cells.
Figure 2B:
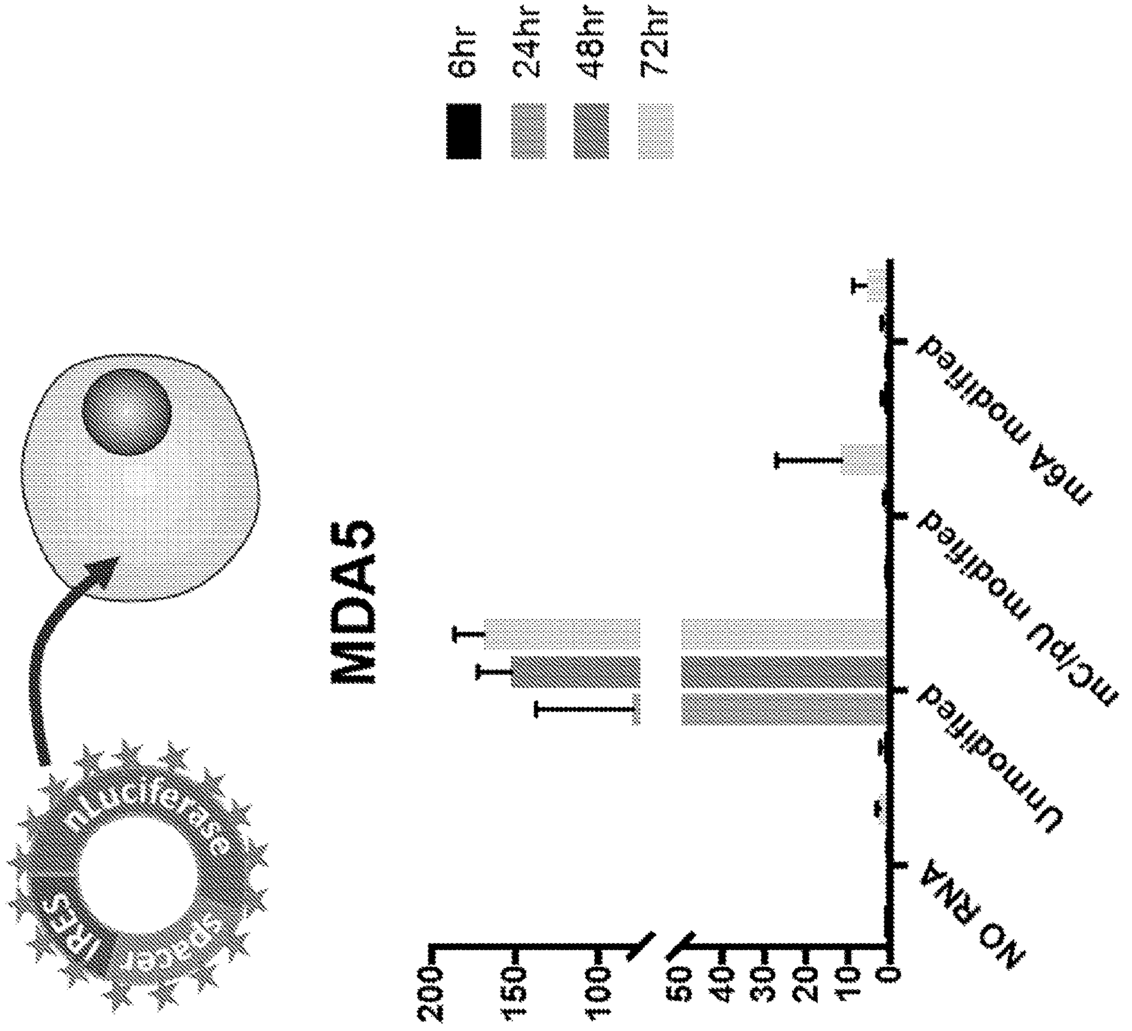
Figure 2C:
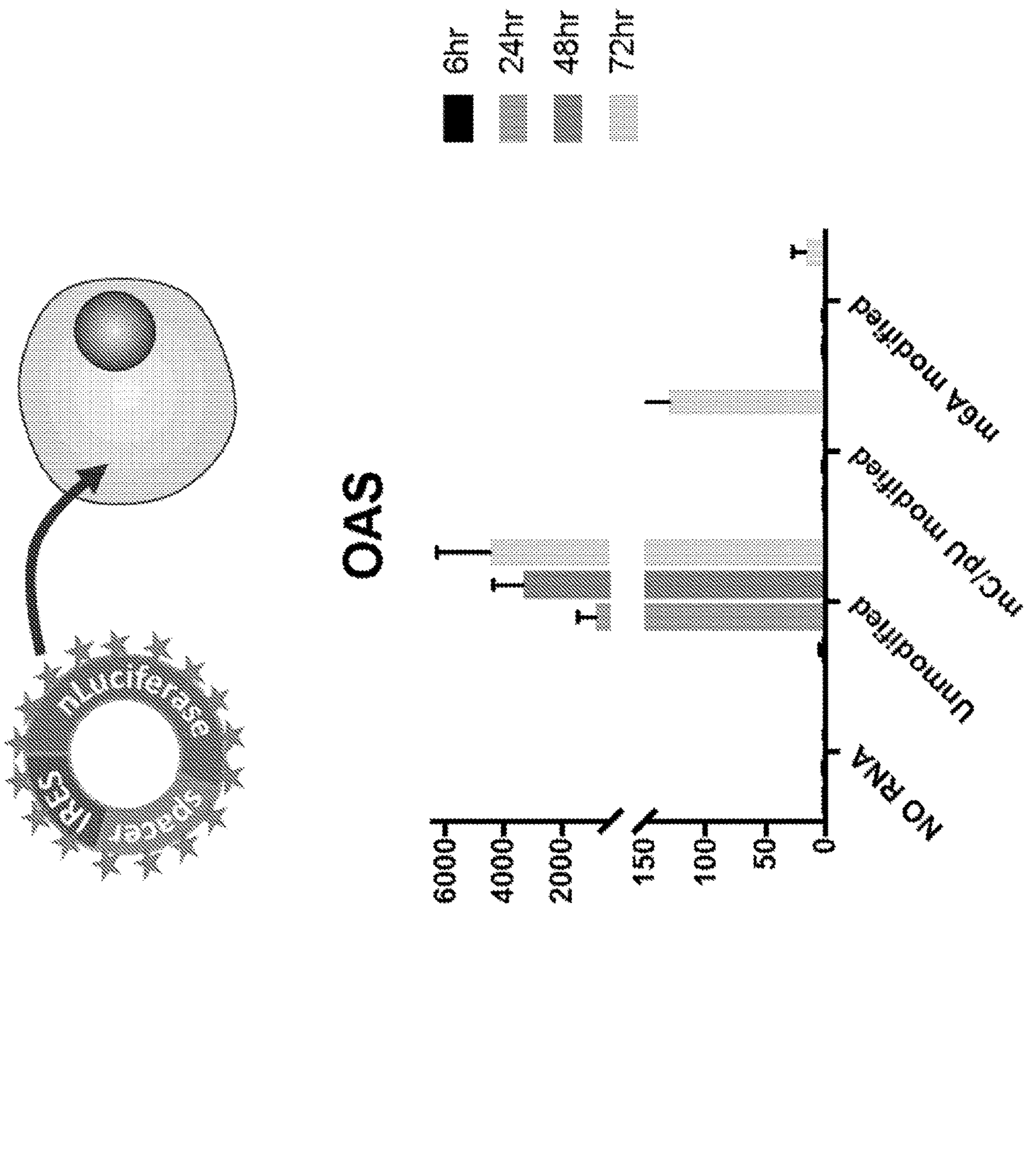

As shown in FIGS. 1B and 1C, modified circular RNA was translated. As shown in FIGS. 2A-C, qRT-PCR levels of immune related genes from BJ cells transfected with circular RNA showed reduction of MDA5, OAS and IFN-beta expression as compared to unmodified circular RNA transfected cells. Thus, induction of immunogenic related genes in recipient cells was reduced in cells transfected with modified circular RNA, as compared to unmodified circular RNA transfected cells.

Example 2: Circular RNA with Modified Nucleotides Reduced Immunogenicity

This Example demonstrates the generation of modified circular polyribonucleotide that produced a protein product. In addition, this Example demonstrates circular RNA engineered with nucleotide modifications had reduced immunogenicity as compared to unmodified RNA.

A non-naturally occurring circular RNA engineered to include one or more desirable properties and with complete or partial incorporation of modified nucleotides was produced. As shown in the following Example, full length modified linear RNA or a hybrid of modified and unmodified linear RNA was circularized and expression of Nanoluciferase (NLuc) was assessed. In addition, modified circular RNA was shown to have reduced activation of immune related genes (q-PCR of MDA5, OAS and IFN-beta expression) in BJ cells, as compared to a non-modified circular RNA.

Figure 3:
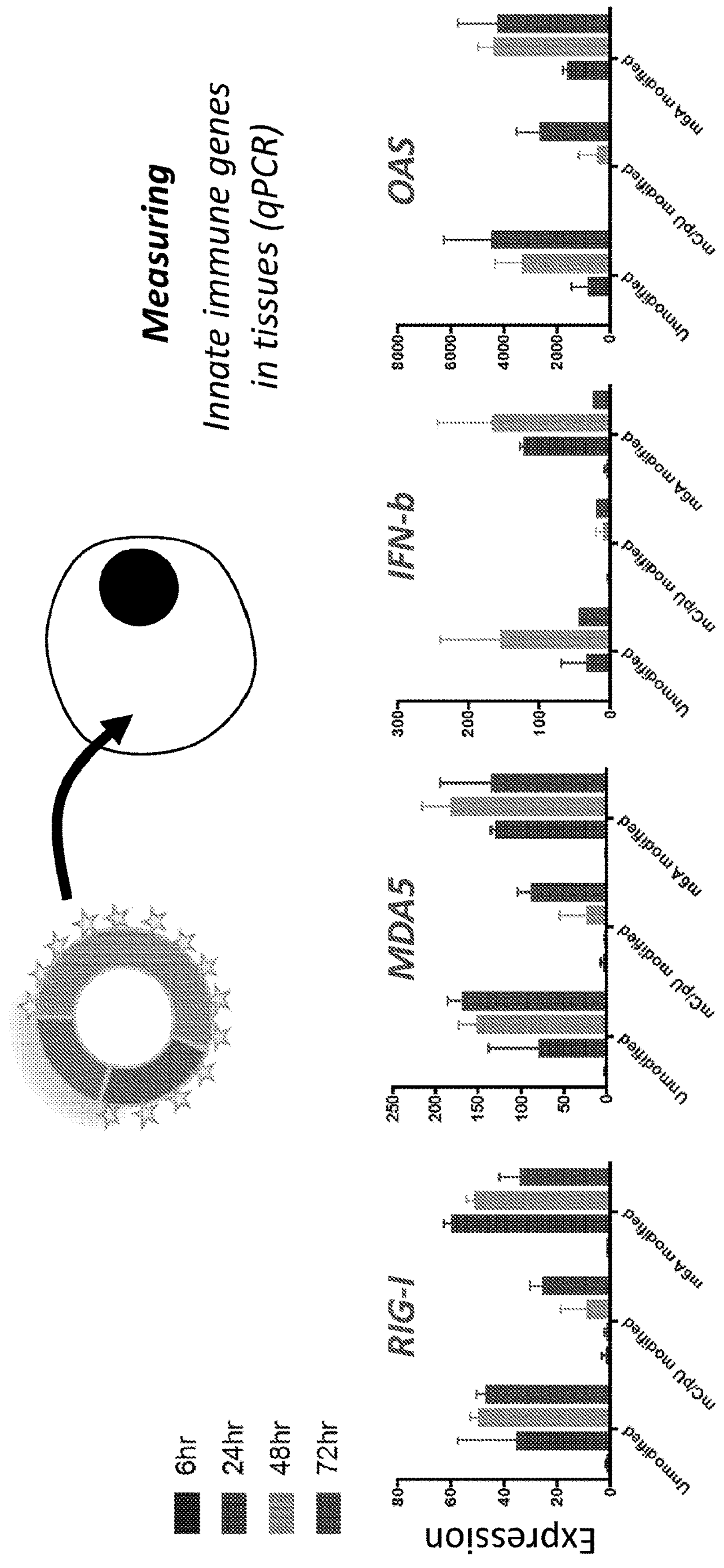
FIG. 3 shows that hybrid modified circular RNAs have reduced immunogenicity as compared to unmodified circular RNAs as assessed by RIG-I, MDA5, IFN-beta, and OAS expression in cells.

Circular RNA with a WT EMCV NLuc stop spacer was generated. For modification substitution, the modified nucleotides, pseudouridine and methylcytosine or m6A, were added in place of the standard unmodified nucleotides, uridine and cytosine or adenosine, respectively, during the in vitro transcription reaction. The WT EMCV IRES was synthesized separately from the nLuc ORF. The WT EMCV IRES was synthesized using either modified (fully modified) or non-modified nucleotides (hybrid modified). In contrast, the nLuc ORF sequence was synthesized using modified nucleotides, pseudouridine and methylcytosine or m6A, in place of the standard unmodified nucleotides, uridine and cytosine or adenosine, respectively, for the entire sequence during the in vitro transcription reaction. Following synthesis of the modified or unmodified IRES and the modified ORF, these two oligonucleotides were ligated together using T4 DNA ligase. As shown in FIG. 3, hybrid modified circular RNAs were generated.

To measure expression efficiency, hybrid modified circular RNA was transfected into cells and expression of immune proteins was measured. Expression levels of innate immune response genes were monitored in BJ cells transfected with unmodified circular RNA, or hybrid modified circular RNAs with either pseudouridine and methylcytosine or m6A modifications. Total RNA was isolated from the cells using a phenol-based extraction reagent (Invitrogen) and subjected to reverse transcription to generate cDNA. qRT-PCR analysis for immune related genes was performed using a dye-based quantitative PCR mix (BioRad).

As shown in FIG. 3, qRT-PCR levels of immune related genes from BJ cells transfected with the hybrid modified circular RNAs, pseudouridine and methylcytosine hybrid modified circular RNAs showed reduced levels of RIG-I, MDA5, IFN-beta and OAS expression as compared to unmodified circular RNA transfected cells, indicating reduced immunogenicity of this hybrid modified circular RNA that activated the immunogenic related genes. Unlike the fully modified circular RNA shown in Example 26, m6A hybrid modified circular RNA showed similar levels of RIG-I, MDA5, IFN-beta and OAS expression as unmodified circular RNA transfected cells. Thus, hybrid modification of circular RNA, as compared to unmodified circular RNA, as well as the level of modification had an impact on activating immunogenic related genes.

Example 3: Circular RNA with Modified Nucleotides was Generated and Selectively Bound Proteins This Example demonstrates the generation of modified circular polyribonucleotide that supported protein binding. In addition, this Example demonstrates circular RNA engineered with nucleotide modifications that selectively interacted with proteins involved in immune system monitoring to have reduced immunogenicity as compared to unmodified RNA.

A non-naturally occurring circular RNA engineered to include complete or partial incorporation of modified nucleotides was produced. As shown in the following Example, full length modified linear RNA or a hybrid of modified and unmodified linear RNA was circularized and protein scaffolding was assessed through measurements of nLuc expression. In addition, selectively modified circular RNA had reduced interactions with proteins that activate immune related genes (q-PCR of MDA5, OAS and IFN-beta expression) in BJ cells, as compared to a unmodified circular RNA.

Circular RNA with a WT EMCV Nluc stop spacer was generated. For modification substitution, the modified nucleotides, pseudouridine and methylcytosine or m6A, were added in place of the standard unmodified nucleotides, uridine and cytosine or adenosine, respectively, during the in vitro transcription reaction. The WT EMCV IRES was synthesized separately from the nLuc ORF. The WT EMCV IRES was synthesized using either modified (completely modified) or unmodified nucleotides (hybrid modified). In contrast, the nLuc ORF sequence was synthesized using modified nucleotides, pseudouridine and methylcytosine or m6A, in place of the standard unmodified nucleotides, uridine and cytosine or adenosine, respectively, for the entire sequence during the in vitro transcription reaction. Following synthesis of the modified or unmodified IRES and the modified ORF, these two oligonucleotides were ligated together using T4 DNA ligase. As shown in FIG. 1A, completely modified (upper construct) or hybrid modified (lower construct) circular RNAs were generated.

To measure protein scaffolding efficiency, expression of nLuc from the completely modified or hybrid modified constructs was measured. After 0.1 pmol of linear and circular RNA was transfected into BJ fibroblasts for 6h, nLuc expression was measured at 6 hours, 24 hours, 48 hours and 72 hours post-transfection.

As shown in FIGS. 1B and 1C, completely modified circular RNA had greatly reduced protein binding capacity, as measured by protein translation output, as compared to unmodified circular RNA. In contrast, hybrid modification demonstrated as much as or increased binding to proteins, e.g., protein translation machinery.

To further measure protein scaffolding efficiency, completely modified circular RNA was transfected into cells and protein scaffolding to immune proteins was measured. The level of protein scaffolding to immune proteins that activate innate immune response genes was monitored in BJ cells transfected with unmodified circular RNA, or completely modified circular RNA with either pseudouridine and methylcytosine or m6A modifications. Total RNA was isolated from the cells using a phenol-based extraction reagent (Invitrogen) and subjected to reverse transcription to generate cDNA. qRT-PCR analysis for immune related genes was performed using a dye-based quantitative PCR mix (BioRad).

As shown in FIGS. 1A-C, qRT-PCR levels of immune related genes from BJ cells transfected with completely modified circular RNAs, both pseudouridine and methylcytosine or m6A completely modified circular RNAs, showed reduced levels of MDA5, OAS and IFN-beta expression as compared to unmodified circular RNA transfected cells, indicating reduced protein scaffolding between modified circular RNAs and immune proteins that activate immunogenic related genes. Thus, modification of circular RNA, as compared to unmodified circular RNA, had an impact on protein scaffolding. Selective modification allowed binding of protein translation machinery, while complete modification reduced binding to proteins that activate immunogenic related genes in transfected recipient cells.

Example 4: CircRNA with an Unmodified IRES but Modified Nucleotides in the ORF has Increased Translation In Vivo Compared to a circRNA with a Modified IRES and Modified Nucleotides in the ORF This example describes that including modified nucleotides in circRNA but no modifications in the IRES increased circRNA translation in vivo, compared to modified circRNA with modifications in the IRES.

To generate circRNA to harbor modified nucleotides in the ORF, two IVT templates are amplified separately. The first section (Sequence #1: 1-686 nts) includes a 5' spacer, EMCV IRES and 38 nucleotides of GLuc ORF. The second section (Sequence #2: 687-1203 nts) harbors remaining ORF region of GLuc and 3' spacer.

First section of RNA is generated from a DNA template via in vitro transcription as linear RNA with either modified nucleotides or unmodified nucleotides. Modified first section is fully substituted with N1-methyl-pseudouridine. Unmodified first section is generated with unmodified nucleotides.

The second section is generated from a DNA template via in vitro transcription and is fully substituted with N1-methyl-pseudouridine.

Each batch of transcribed RNA is purified individually with an RNA cleanup kit (New England Biolabs, T2050) and RppH-treated (NEB, M0356). After a second purification, the following RNA-RNA ligation reactions take place: (1) Unmodified first section+second section; (2) Modified first section+second section.

These ligations are performed using a DNA splint as follows: 2 uM of selected first section RNA, 2 uM of second section RNA, 2.56 uM of splint DNA (5'-GGCTTGGCCTCGGCCACAGCGATGCAGATC-3' (SEQ ID NO: 111)), 50 mM NaCl is combined. This mixture is incubated at 75° C. for 10 min and then slowly cooled down to 37° C. The mixture is further incubated for ligation in the presence of 50 mM Tris-HCl, 10 mM MgCl2, 1 mM ATP, 1 mM DTT, 0.16 U/uL RNase inhibitor (Promega, N2115) and 15 U/uL T4 DNA ligase (NEB, M0202M) for 4 hours. Ligated RNA is purified with Monarch RNA purification column (NEB, T2050). The efficiency of RNA-RNA ligation is monitored by separating on Urea-PAGE and image quantified.

For circularization of ligated RNA, each circularization mixture is independently prepared with 1 uM of ligated RNA, 2 uM of splint DNA (5'-GTTTTTCGGCTATTCCCAATAGCCGTTTTG-3' (SEQ ID NO: 112)), 50 mM Tris-HCl, 2 mM MgCl2 and 400 uM ATP. This mixture is heated at 75° C. for 10 min and slowly cooled down at room temperature over 20 min. After cooling, 0.2 U/uL of T4 RNA ligase 2 (NEB, M0239) and 0.4 U/uL of RNAse inhibitor (Promega, N2115) are added and the reaction is incubated for 4 hour. Ligated RNA is purified with ethanol precipitation. Circular RNA is Urea-PAGE purified, eluted in a buffer (0.5 M Sodium Acetate, 0.1% SDS, 1 mM EDTA), ethanol precipitated and resuspended in RNA storage solution (ThermoFisher Scientific, AM7000).

The (1) hybrid modified circRNA: Unmodified first section+second section; and (2) fully modified circRNA: modified first section+second section are generated.

RNA is formulated with 10% TransIT (MirusBio) and 5% Boost (MirusBio) in PBS. The total volume of the injection is 100 uL for each dose. The final RNA concentration is 0.1 pmol/uL (10 pmol/mouse). Each dose (100 uL) is injected intravenously via the mouse tail vein. Non-injected animals, and animals injected with the vehicle only (no RNA) are used as controls.

Blood samples (50 uL) is collected from the tail-vein of each mouse into EDTA tubes, at 6 hours, 1, 2, 3, 7, 14, 21, 28 and 35 days post-dosing. Plasma is isolated by centrifugation for 25 min at 1300 g at 4° C. and the activity of *Gaussia* Luciferase, a secreted enzyme, is tested using a *Gaussia* Luciferase Flash activity assay (Thermo Scientific Pierce) following manufacturer's instructions. Briefly, 50 μL of 1×GLuc substrate is injected to 5 μL of plasma in a well of a 96 well clear bottom plate to carry out the GLuc luciferase activity assay. Plates are read right after mixing in a luminometer instrument (Promega).

It is expected that blood from mice injected with hybrid modified circRNA shows greater luciferase activity compared to fully modified circ RNA and compared to controls. This example demonstrates that hybrid modified circRNA expresses greater amounts of *Gaussia* luciferase compared to fully modified circRNA and compared to controls.

This Example demonstrates that an circRNA with an unmodified IRES but modified nucleotides elsewhere (hybrid modified circRNA) shows greater expression in vivo compared fully modified circRNA.

Example 5: CircRNA with an Unmodified IRES but Modified Nucleotides in the ORF has Increased RNA Translation In Vivo Compared to Fully Unmodified circRNA This example demonstrates that including modified nucleotides in circRNA increases circRNA expression in vivo.

In this example, circRNA was designed with an ORF encoding a *Gaussia* Luciferase (GLuc), EMCV IRES as translation element, and 5' and 3' spacer region.

To generate circRNA to harbor modified nucleotides in the ORF, two IVT templates were amplified separately. The first section (Sequence #1: 1-686 nts) included a 5' spacer, EMCV IRES and 38 nucleotides of GLuc ORF. The second section (Sequence #2: 687-1203 nts) harbored the remaining ORF region of GLuc and 3' spacer. First section of RNA was generated from a DNA template via in vitro transcription as linear RNA with unmodified nucleotides. The second section was generated from a DNA template via in vitro transcription under three different conditions; (1) with unmodified nucleotides (2) fully substituted with Pseudo-Uridine and 5-Methyl-Cytidine (3) fully substituted with N1-Methyl-Pseudouridine.

Each batch of transcribed RNA was purified individually with an RNA cleanup kit (New England Biolabs, T2050) and RppH-treated (NEB, M0356). After a second purification, each batch of RNA were subjected to RNA-RNA ligation. First section of RNA (containing the IRES) and each of the versions of the second section of RNA were annealed using a DNA splint.

Each reaction was performed as follows: 2 uM of first section RNA, 2 uM of selected second section RNA, 2.56 uM of splint DNA (5'-GGCTTGGCCTCGGCCACAGC-GATGCAGATC-3' (SEQ ID NO: 111)), 50 mM NaCl was combined. This mixture was incubated at 75° C. for 10 min and then slowly cooled down to 37° C. The mixture was further incubated for ligation in the presence of 50 mM Tris-HCl, 10 mM MgCl2, 1 mM ATP, 1 mM DTT, 0.16 U/uL RNase inhibitor (Promega, N2115) and 15 U/uL T4 DNA ligase (NEB, M0202M) for 4 hours. Ligated RNA was purified with Monarch RNA purification column (NEB, T2050). The efficiency of RNA-RNA ligation was monitored by separating on Urea-PAGE and image quantified.

RNA-RNA ligated material was:

(1) Ligated RNA Unmod.: First section+Second section with unmodified nucleotides (2) Ligated RNA pU/5 mC: First section+Second section fully substituted with Pseudo-Uridine and 5-Methyl-Cytidine (3) Ligated RNA N1mΨ: First section+Second section fully substituted with N1-Methyl-Pseudouridine.

For circularization of ligated RNA, each circularization mixture was independently prepared with 1 uM of ligated RNA, 2 uM of splint DNA (5'-GTTTTTCGGCTATTCC-CAATAGCCGTTTTG-3' (SEQ ID NO: 112)), 50 mM Tris-HCl, 2 mM MgCl2 and 400 uM ATP. This mixture was heated at 75° C. for 10 min and slowly cooled down at room temperature over 20 min. After cooling, 0.2 U/uL of T4 RNA ligase 2 (NEB, M0239) and 0.4 U/uL of RNAse inhibitor (Promega, N2115) were added and the reaction was incubated for 4 hour. Ligated RNA was purified with ethanol precipitation. Circular RNA was Urea-PAGE purified, eluted in a buffer (0.5 M Sodium Acetate, 0.1% SDS, 1 mM EDTA), ethanol precipitated and resuspended in RNA storage solution (ThermoFisher Scientific, AM7000).

Additionally, mRNA encoding GLuc (fully substituted with Pseudo-Uridine and 5-Methyl-C) was purchased from Trilink Biotechnologies. A second mRNA control encoding GLuc and human alpha globin 5' and 3' UTRs was generated in-house by in vitro transcription with co-transcriptional capping with CleanCap™ AG. The in-house synthesized mRNA was purified with Monarch RNA purification column (NEB, T2050), and subjected to gel elution as described above.

RNA is formulated with 10% TransIT (MirusBio) and 5% Boost (MirusBio) in PBS. The total volume of the injection is 100 uL for each dose. The final RNA concentration is 0.1 pmol/uL (10 pmol/mouse). Each dose (100 uL) is injected intravenously via the mouse tail vein. Non-injected animals, and animals injected with the vehicle only (no RNA) are used as controls. Blood samples (50 uL) is collected from the tail-vein of each mouse into EDTA tubes, at 6 hours, 1, 2, 3, 7, 14, 21, 28 and 35 days post-dosing. Plasma is isolated by centrifugation for 25 min at 1300 g at 4° C. and the activity of *Gaussia* Luciferase, a secreted enzyme, is tested using a *Gaussia* Luciferase Flash activity assay (Thermo Scientific Pierce) following manufacturer's instructions. Briefly, 50 μL of 1×GLuc substrate is injected to 5 μL of plasma in a well of a 96 well clear bottom plate to carry out the GLuc luciferase activity assay. Plates are read right after mixing in a luminometer instrument (Promega).

It is expected that blood from mice injected with circRNA generated from ligated RNA pU/5 mC and circRNA generated from ligated RNA N1mΨ show greater luciferase activity compared to circRNA generated from ligated RNA Unmod, and greater luciferase activity compared to both modified and unmodified mRNA. This example describes that circRNA generated from ligated RNA pU/5 mC and circRNA generated from ligated RNA N1mΨ express greater amounts of *Gaussia* luciferase compared to circRNA generated from ligated RNA Unmod, and greater luciferase activity compared to both modified and unmodified mRNA. This example also describes that circRNA generated from ligated RNA pU/5 mC and circRNA generated from ligated RNA N1mΨ express *Gaussia* Luciferase for a increased period of time compared to circRNA generated from ligated RNA Unmod, and greater luciferase activity compared to both modified and unmodified mRNA.

This Example describes that a circRNA with an unmodified IRES but modified nucleotides elsewhere shows longer and increased expression compared to its unmodified counterpart.

This Example describes that a circRNA with an unmodified IRES but modified nucleotides elsewhere shows longer and increased expression compared to modified mRNA and unmodified mRNA.

Example 6: CircRNA with an Unmodified IRES but Modified Nucleotides in the ORF has Increased RNA Stability In Vivo Compared to a Corresponding Unmodified circRNA This Example demonstrates that including modified nucleotides in circRNA increases circRNA stability in vivo.

In this example, circRNA was designed with an ORF encoding a *Gaussia* Luciferase (GLuc), EMCV IRES as translation element, and 5' and 3' spacer region.

To generate circRNA to harbor modified nucleotides in the ORF, two IVT templates were amplified separately. The first section (Sequence #1: 1-686 nts) includes includes 5' spacer, EMCV IRES and 38 nucleotides of GLuc ORF. The second section (Sequence #2: 687-1203 nts) harbors remaining ORF region of GLuc and 3' spacer. First section of RNA was generated from a DNA template via in vitro transcription as linear RNA with unmodified nucleotides. The second section was generated from a DNA template via in vitro transcription under three different conditions; (1) with unmodified nucleotides (2) fully substituted with Pseudo-Uridine and 5-Methyl-Cytidine (3) fully substituted with N1-Methyl-Pseudouridine.

Each batch of transcribed RNA was purified individually with an RNA cleanup kit (New England Biolabs, T2050) and RppH-treated (NEB, M0356). After a second purification, each batch of RNA were subjected to RNA-RNA ligation. First section of RNA (containing the IRES) and each of the versions of the second section of RNA were annealed using a DNA splint.

Each reaction was performed as follows: 2 uM of first section RNA, 2 uM of selected second section RNA, 2.56 uM of splint DNA (5'-GGCTTGGCCTCGGCCACAGC-GATGCAGATC-3'(SEQ ID NO: 111)), 50 mM NaCl was combined. This mixture was incubated at 75° C. for 10 min and then slowly cooled down to 37° C. The mixture was further incubated for ligation in the presence of 50 mM Tris-HCl, 10 mM MgCl2, 1 mM ATP, 1 mM DTT, 0.16 U/uL RNase inhibitor (Promega, N2115) and 15 U/uL T4 DNA ligase (NEB, M0202M) for 4 hours. Ligated RNA was purified with Monarch RNA purification column (NEB, T2050). The efficiency of RNA-RNA ligation was monitored by separating on Urea-PAGE and image quantified.

RNA-RNA ligated material was:

(1) Ligated RNA Unmod.: First section+Second section with unmodified nucleotides (2) Ligated RNA pU/5 mC: First section+Second section fully substituted with Pseudo-Uridine and 5-Methyl-Cytidine (3) Ligated RNA N1mΨ: First section+Second section fully substituted with N1-Methyl-Pseudouridine.

For circularization of ligated RNA, each circularization mixture was independently prepared with 1 uM of ligated RNA, 2 uM of splint DNA (5'-GTTTTTCGGCTATTCC-CAATAGCCGTTTTG-3' (SEQ ID NO: 112)), 50 mM Tris-HCl, 2 mM MgCl2 and 400 uM ATP. This mixture was heated at 75° C. for 10 min and slowly cooled down at room temperature over 20 min. After cooling, 0.2 U/uL of T4 RNA ligase 2 (NEB, M0239) and 0.4 U/uL of RNAse inhibitor (Promega, N2115) were added and the reaction was incubated for 4 hour. Ligated RNA was purified with ethanol precipitation. Circular RNA was Urea-PAGE purified, eluted in a buffer (0.5 M Sodium Acetate, 0.1% SDS, 1 mM EDTA), ethanol precipitated and resuspended in RNA storage solution (ThermoFisher Scientific, AM7000).

Additionally, mRNA encoding GLuc (fully substituted with Pseudo-Uridine and 5-Methyl-C) was purchased from Trilink Biotechnologies. A second mRNA control encoding GLuc and human alpha globin 5' and 3' UTRs was generated in-house by in vitro transcription with co-transcriptional capping with CleanCap™ AG. The in-house synthesized mRNA was purified with Monarch RNA purification column (NEB, T2050), and subjected to gel elution as described above.

RNA is formulated with 10% TransIT (MirusBio) and 5% Boost (MirusBio) in PBS. The total volume of the injection is 100 uL for each dose. The final RNA concentration is 0.1 pmol/uL (10 pmol/mouse). Each dose (100 uL) is injected intravenously via the mouse tail vein. Non-injected animals, and animals injected with the vehicle only (no RNA) are used as controls.

Liver and spleen tissues is collected from mice at 6 hours and 7 days after injection and stored in RNAlater (ThermoFisher Scientific). Tissues are homogenized in Trizol and RNA was extracted using Zymo miniprep plus kits (Zymo Research, D4068). RNA stability is measured by RT-qPCR. GLuc ORF and 18S rRNA are measured by qPCR, using the Luna® Universal One-Step RT-qPCR system (New England Biolabs) in triplicate using a Bio-rad CFX384 Thermal Cycler. Relative values are calculated using the Pffal method.

It is expected that liver and spleen tissue from mice injected with circRNA generated from ligated RNA pU/5 mC and circRNA generated from ligated RNA N1mΨ show increased quantities of GLuc ORF compared to circRNA generated from ligated RNA Unmod, and greater luciferase activity compared to both modified and unmodified mRNA at 7 days post injection.

This Example describes that an circRNA with an unmodified IRES but modified nucleotides elsewhere shows greater persistence and stability compared to its unmodified counterpart.

This Example describes that an circRNA with an unmodified IRES but modified nucleotides elsewhere shows greater persistence and stability compared to modified mRNA and unmodified mRNA.

Example 7: CircRNA with an Unmodified IRES but Modified Nucleotides in the ORF has Increased RNA Translation and Increased Stability In Vivo This Example describes that including modified nucleotides in circRNA increases circRNA expression and stability in vivo.

In this example, circRNA was designed with an ORF encoding a *Gaussia* Luciferase (GLuc), Gtx as translation element, and 5' and 3' spacer region.

To generate circRNA to harbor modified nucleotides in the ORF, but not in the IRES, an IRES was designed to be substantially free of uridines, for example Gtx (sequence: CCGGCGGAA). RNA is generated from a DNA template via in vitro transcription as linear RNA with (1) with unmodified nucleotides (2) fully substituted with Pseudo-Uridine and (3) fully substituted with N1-Methyl-Pseudouridine.

Each batch of transcribed RNA is purified individually with an RNA cleanup kit (New England Biolabs, T2050) and RppH-treated (NEB, M0356).

For circularization of the RNA, each circularization mixture is independently prepared with 1 uM of ligated RNA, 2 uM of splint DNA (5'-GTTTTTCGGCTATTCC-CAATAGCCGTTTTG-3' (SEQ ID NO: 112)), 50 mM Tris-HCl, 2 mM MgCl2 and 400 uM ATP. This mixture is heated at 75° C. for 10 min and slowly cooled down at room temperature over 20 min. After cooling, 0.2 U/uL of T4 RNA ligase 2 (NEB, M0239) and 0.4 U/uL of RNAse inhibitor (Promega, N2115) are added and the reaction is incubated for 4 hour. Ligated RNA is purified with ethanol precipitation. CircRNA is Urea-PAGE purified, eluted in a buffer (0.5 M Sodium Acetate, 0.1% SDS, 1 mM EDTA), ethanol precipitated and resuspended in RNA storage solution (ThermoFisher Scientific, AM7000).

Additionally, mRNA encoding GLuc (fully substituted with Pseudo-Uridine or N1-Methyl-Pseudouridine) is purchased from Trilink Biotechnologies. A second mRNA control encoding GLuc and human alpha globin 5' and 3' UTRs is generated in-house by in vitro transcription with co-transcriptional capping with CleanCap™ AG. The in-house synthesized mRNA is purified with Monarch RNA purification column (NEB, T2050), and subjected to gel elution as described above.

RNA is formulated with 10% TransIT (MirusBio) and 5% Boost (MirusBio) in PBS. The total volume of the injection is 100 uL for each dose. The final RNA concentration is 0.1 pmol/uL (10 pmol/mouse). Each dose (100 uL) is injected intravenously via the mouse tail vein. Non-injected animals, and animals injected with the vehicle only (no RNA) are used as controls.

Liver and spleen tissues is collected from mice at 6 hours and 7 days after injection and stored in RNAlater (ThermoFisher Scientific). Tissues are homogenized in Trizol and RNA was extracted using Zymo miniprep plus kits (Zymo Research, D4068). RNA stability is measured by RT-qPCR. GLuc ORF and 18S rRNA are measured by qPCR, using the Luna® Universal One-Step RT-qPCR system (New England Biolabs) in triplicate using a Bio-rad CFX384 Thermal Cycler. Relative values are calculated using the Pffa1 method.

It is expected that liver and spleen tissue from mice injected with circRNA generated with pU modifications and circRNA generated from N1mΨ modifications show increased quantities of GLuc ORF compared to circRNA generated from unmodified RNA, and greater luciferase activity compared to both modified and unmodified mRNA at 7 days post injection.

This Example describes that an circRNA with an unmodified IRES but modified nucleotides elsewhere shows greater persistence and stability compared to its corresponding unmodified circRNA.

This Example describes that a circRNA with an unmodified IRES but modified nucleotides elsewhere shows greater expression, persistence, and stability compared to modified mRNA and unmodified mRNA.

Example 8: Circular RNA Containing Modified Nucleotides has Reduced Immunogenicity In Vivo Compared Circular RNA Generated with Unmodified Nucleotides Only This Example demonstrates that including modified nucleotides in circular RNA reduces circular RNA immunogenicity in vivo.

In this example, circular RNA includes an ORF encoding *Gaussia* Luciferase (GLuc) and 5' and 3' human alpha-globin UTRs.

Circular RNA, lacking an IRES (translation incompetent) was generated in vitro either with fully unmodified nucleotides or with substitutions of Uracil to Pseudo-Uridine and Cytosine to 5-Methyl-Cytidine. To this end, linear RNA with fully unmodified nucleotides or with modified Uracil and Cytosine substitutions was transcribed in vitro from a DNA template including all the motifs listed above, as well as a T7 RNA polymerase promoter to drive transcription. Transcribed RNA was purified with an RNA cleanup kit (New England Biolabs, T2050), treated with RNA 5'phosphohydrolase (RppH) (New England Biolabs, M0356) following the manufacturer's instructions, and purified again with an RNA purification column (New England Biolabs, T2050). RppH-treated linear RNA was circularized using a splint DNA (5'-GACCAGAAGAGTCCCTGCTGCC-CACTCAGA-3' (SEQ ID NO: 113)) and T4 RNA ligase 2 (New England Biolabs, M0239). Circular RNA was Urea-PAGE purified, eluted in a buffer (0.5 M Sodium Acetate, 0.1% SDS, 1 mM EDTA), ethanol precipitated and resuspended in RNA storage solution (ThermoFisher Scientific, AM7000).

RNA was formulated with 15% TransIT (MirusBio) and 7.5% Boost (MirusBio) in PBS. The total volume of the injection was 100 uL for each dose. The final RNA concentration of 0.1 pmol/uL. (10 pmol/mouse). Each dose (100 uL) was injected intravenously via the mouse tail vein. Non-injected animals, and animals injected with the vehicle only (no RNA) were used as controls. Liver and spleen were harvested at 1 and 2 days after injection and stored in RNAlater (ThermoFisher Scientific).

Tissues were homogenized in Trizol and RNA was extracted using Zymo Miniprep Plus kits. Immune response genes including RIG-I, MDA5, INFa, IFNB, IFNg, TNFa and IL6, as well as housekeeping gene 18S rRNA were measured by qPCR, using the Luna® Universal One-Step RT-qPCR system (New England Biolabs) in triplicate using a Bio-rad CFX384 Thermal Cycler. Relative values were calculated using the Pffafl method (Pfaffl *Nucleic Acids Res* 2001).

Figure 49:
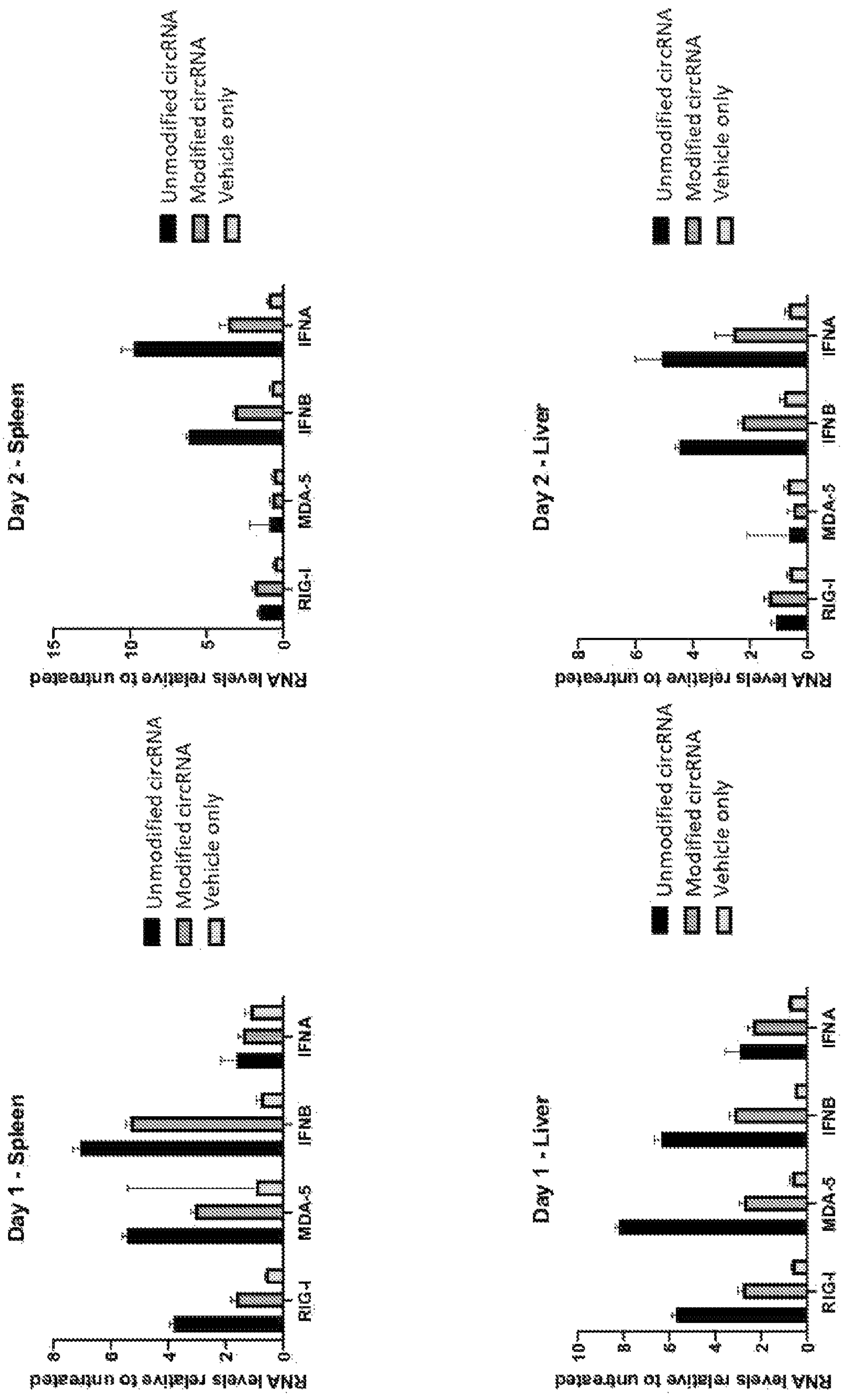
FIG. 49 shows a circular RNA containing modified nucleotides has reduced immunogenicity in vivo compared to modified mRNA and compared to circular RNA generated with unmodified nucleotides only.

When circular RNA containing modified nucleotides was used, mice exhibited substantially lower expression of immune markers (RIG-I, MDA5, INFa, IFNb, INFg, TNFa and IL6) compared to its circular RNA counterpart that did not contain modified nucleotides; and to its modified mRNA counterpart (FIG. 49).

This Example demonstrates that circular RNA containing modified nucleotides induced less immunogenicity when injected into animals compared with circular RNA that contained only unmodified nucleotides.

Example 9: Circular RNA Containing Modified Nucleotides has Increased Stability In Vivo Compared to its Fully Unmodified Circular RNA Counterpart and Modified mRNA This Example demonstrates that including modified nucleotides in circular RNA increases circular RNA stability in vivo.

In this example, circular RNA includes an ORF encoding *Gaussia* Luciferase (GLuc) and 5' and 3' human alpha-globin UTRs.

Circular RNA, lacking an IRES (translation incompetent) was generated in vitro either with fully unmodified nucleotides or with substitutions of Uracil to Pseudo-Uridine and Cytosine to 5-Methyl-Cytidine. To this end, linear RNA with fully unmodified nucleotides or with modified Uracil and Cytosine substitutions was transcribed in vitro from a DNA template including all the motifs listed above, as well as a T7 RNA polymerase promoter to drive transcription. Transcribed RNA was purified with an RNA cleanup kit (New England Biolabs, T2050), treated with RNA 5'phosphohydrolase (RppH) (New England Biolabs, M0356) following the manufacturer's instructions, and purified again with an RNA purification column (New England Biolabs, T2050). RppH-treated linear RNA was circularized using a splint DNA (5'-GACCAGAAGAGTCCCTGCTGCC-CACTCAGA-3' (SEQ ID NO: 113)) and T4 RNA ligase 2 (New England Biolabs, M0239). Circular RNA was Urea-PAGE purified, eluted in a buffer (0.5 M Sodium Acetate, 0.1% SDS, 1 mM EDTA), ethanol precipitated and resuspended in RNA storage solution (ThermoFisher Scientific, AM7000).

As a control, linear RNA was generated fully substituted with Pseudo-Uridine and 5-Methyl-Cytidine, capped with a cap analog, and was Urea-PAGE purified as described above.

RNA was formulated with 15% TransIT (MirusBio) and 7.5% Boost (MirusBio) in PBS. The total volume of the injection was 100 uL for each dose. The final RNA concentration of 0.1 pmol/uL.10 pmol/mouse). Each dose (100 uL) was injected intravenously via the mouse tail vein. Non-injected animals, and animals injected with the vehicle only (no RNA) were used as controls. Liver and spleen were harvested at 1, 2, 7 and 14 day after injection and stored in RNAlater (ThermoFisher Scientific).

Tissues were homogenized in Trizol and RNA was extracted using Zymo Miniprep Plus kits. Circular RNA and linear RNA were detected by RT-qPCR Luna® Universal One-Step RT-qPCR system (New England Biolabs) in triplicate using a Bio-rad CFX384 Thermal Cycler. As a control, 18S rRNA was measured. Relative values were calculated using the Pffafl method (Pfaffl *Nucleic Acids Res* 2001).

Figure 50:
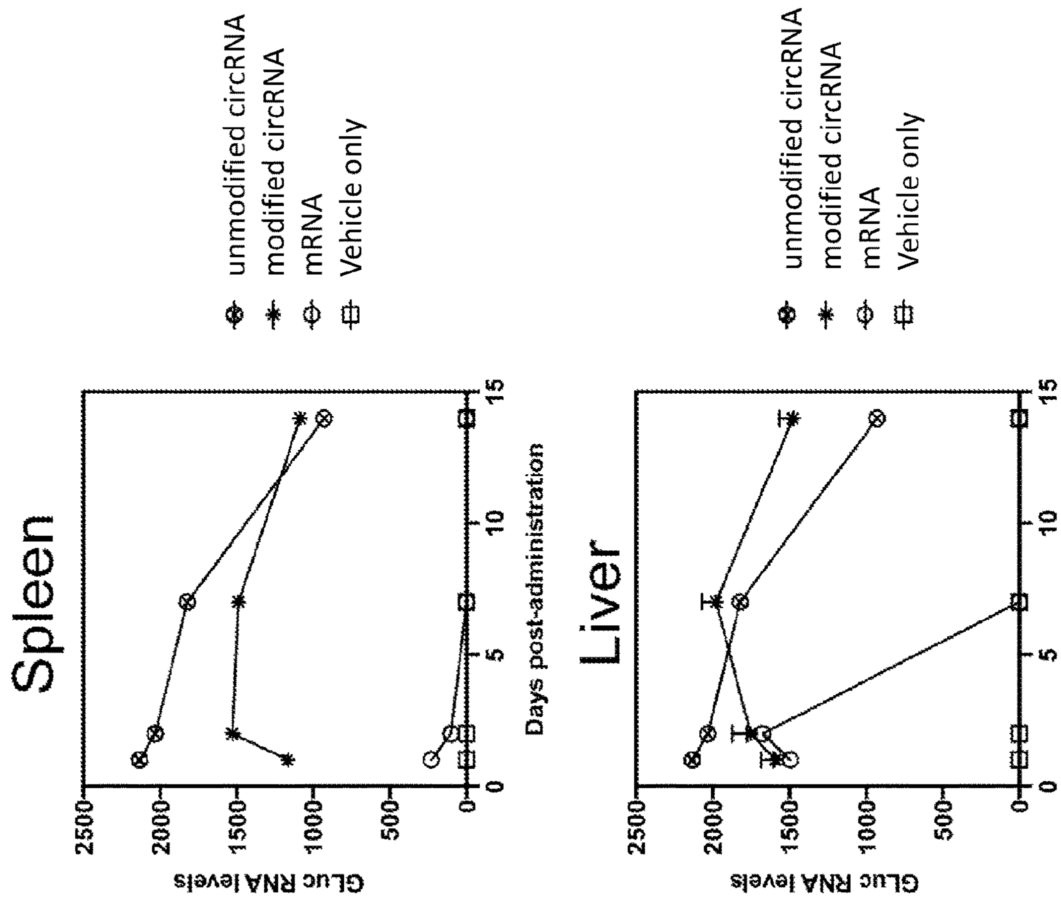
FIG. 50 shows a circular RNA containing modified nucleotides has increased stability in vivo than its fully unmodified counterpart and modified mRNA.

In this example, circular RNA containing modified nucleotide was present in liver and spleen over a longer period of time than circular RNA that did not contain modified nucleotides (unmodified nucleotides only); and present in liver and spleen over a longer period of time than modified mRNA (FIG. 50).

This Example demonstrates that circular RNA generated with modified nucleotide is more stable at 14 days post-injection when compared with circular RNA generated with unmodified nucleotides and compared with modified mRNA.

Example 10: In Vitro Circular RNA Production

This example demonstrates in vitro production of a circular RNA.

Figure 4:
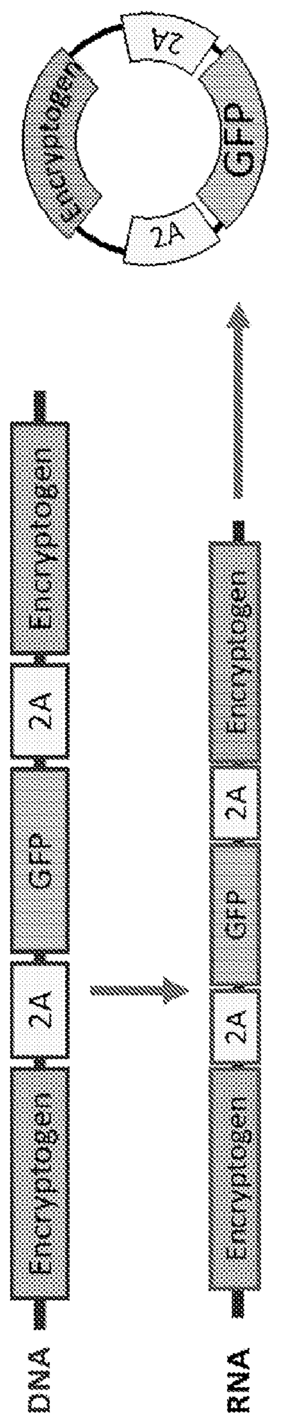
FIG. 4 shows a schematic of an exemplary in vitro production process of a circular RNA that contains a start-codon, an ORF (open reading frame) coding for GFP, a stagger element (2A), an encryptogen, and an IRES (internal ribosome entry site).

A circular RNA is designed with a start-codon (SEQ ID NO:1), ORF(s) (SEQ ID NO:2), stagger element(s) (SEQ ID NO:3), encryptogen(s) (SEQ ID NO:4), and an IRES (SEQ ID NO:5), shown in FIG. 4. Circularization enables rolling circle translation, multiple open reading frames (ORFs) with alternating stagger elements for discrete ORF expression and controlled protein stoichiometry, encryptogen(s) to attenuate or mitigate RNA immunogenicity, and an optional IRES that targets RNA for ribosomal entry without poly-A sequence.

In this Example, the circular RNA is generated as follows. Unmodified linear RNA is synthesized by in vitro transcription using T7 RNA polymerase from a DNA segment having 5'- and 3'-ZKSCAN1 introns and an ORF encoding GFP linked to 2A sequences. Transcribed RNA is purified with an RNA purification system (QIAGEN), treated with alkaline phosphatase (ThermoFisher Scientific, EF0652) following the manufacturer's instructions, and purified again with the RNA purification system.

Splint ligation circular RNA is generated by treatment of the transcribed linear RNA and a DNA splint using T4 DNA ligase (New England Bio, Inc., M0202M), and the circular RNA is isolated following enrichment with RNase R treatment. RNA quality is assessed by agarose gel or through automated electrophoresis (Agilent).

Example 11: In Vivo Circular RNA Production, Cell Culture

This example demonstrates in vivo production of a circular RNA.

Figure 5:
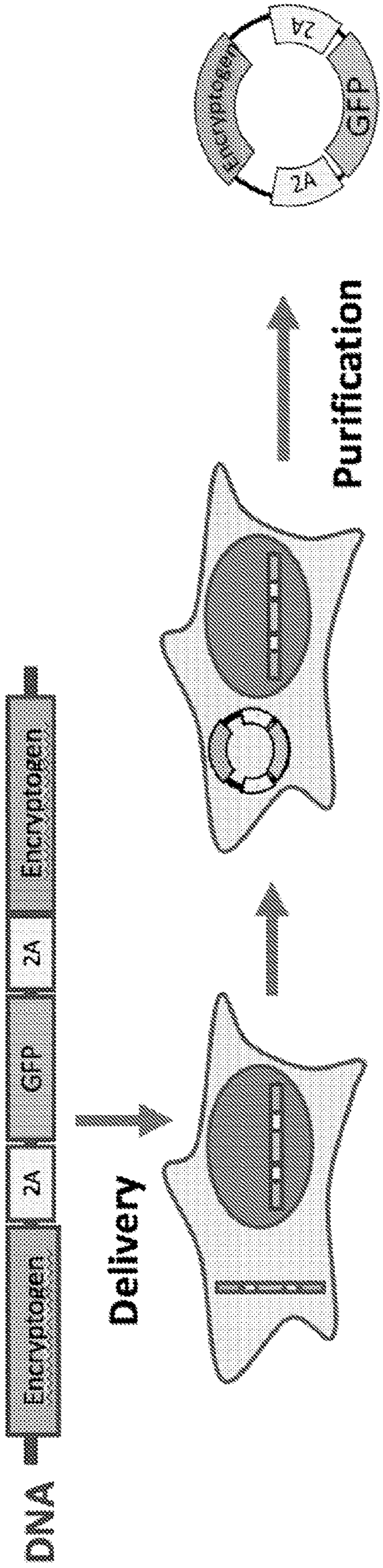
FIG. 5 shows a schematic of an exemplary in vivo production process of a circular RNA.

GFP (SEQ ID NO: 2) is cloned into an expression vector, e.g. pcDNA3.1(+) (Addgene) (SEQ ID NO: 6). This vector is mutagenized to induce circular RNA production in cells (SEQ ID NO: 6 and described by Kramer et al 2015), shown in FIG. 5.

HeLa cells are grown at 37° C. and 5% $CO_2$ in Dulbecco's modified Eagle's medium (DMEM) with high glucose (Life Technologies), supplemented with penicillin-streptomycin and 10% fetal bovine serum. One microgram of the above described expression plasmid is transfected using lipid transfection reagent (Life Technologies), and total RNA from the transfected cells is isolated using a phenol-based RNA isolation reagent (Life Technologies) as per the manufacturer's instructions between 1 hour and 20 days after transfection.

To measure GFP circular RNA and mRNA levels, qPCR reverse transcription using random hexamers is performed. In short, for RT-qPCR Hela cells' total RNA and RNase R-digested RNA from the same source are used as templates for the RT-PCR. To prepare the cDNAs of GFP mRNAs and circular GFP RNAs, the reverse transcription reactions are performed with a reverse transcriptase (Super-Script II: RNase H; Invitrogen) and random hexamers in accordance with the manufacturer's instruction. The amplified PCR products are analyzed using a 6% PAGE and visualized by ethidium bromide staining. To estimate the enrichment factor, the PCR products are quantified by densitometry (ImageQuant; Molecular Dynamics) and the concentrations of total RNA samples are measured by UV absorbance.

An additional RNA measurement is performed with northern blot analysis. Briefly, whole cell extract was obtained using a phenol based reagent (TRIzol) or nuclear and cytoplasmic protein extracts are obtained by fractionation of the cells with a commercial kit (CelLytic NuCLEAR Extraction Kit, Sigma). To inhibit RNA polymerase II transcription, cells are treated with flavopiridol (1 mM final concentration; Sigma) for 0-6 h at 37° C. For RNase R treatments, 10 mg of total RNA is treated with 20 U of RNase R (Epicentre) for 1 h at 37° C.

Northern blots using oligonucleotide probes are performed as follows. Oligonucleotide probes, PCR primers are designed using standard primer designing tools. T7 promoter sequence is added to the reverse primer to obtain an antisense probe in in vitro transcription reaction. In vitro transcription is performed using T7 RNA polymerase with a DIG-RNA labeling mix according to manufacturer's instruction. DNA templates are removed by DNAs I digestion and RNA probes purified by phenol chloroform extraction and subsequent precipitation. Probes are used at 50 ng/ml. Total RNA (2 g-10 g) is denatured using Glyoxal load dye (Ambion) and resolved on 1.2% agarose gel in MOPS buffer. The gel is soaked in 1×TBE for 20 min and transferred to a Hybond-N+membrane (GE Healthcare) for 1 h (15 V) using a semi-dry blotting system (Bio-Rad). Membranes are dried and UV-crosslinked (at 265 nm) 1× at 120,000 J cm-2. Pre-hybridization is done at 68° C. for 1 h and DIG-labelled in-vitro transcribed RNA probes are hybridized overnight. The membranes are washed three times in 2×SSC, 0.1% SDS at 68° C. for 30 min, followed by three 30 min washes in 0.2×SSC, 0.1% SDS at 68° C. The immunodetection is performed with anti-DIG directly-conjugated with alkaline phosphatase antibodies. Immunoreactive bands are visualized using chemiluminescent alkaline phosphatase substrate (CDP star reagent) and an image detection and quantification system (LAS-4000 detection system).

Example 12: Preparation of Circular RNA and In Vitro Translation

This example demonstrates gene expression and detection of the gene product from a circular RNA.

Figure 6:
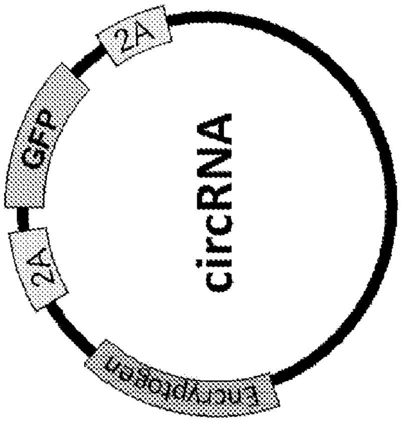
FIG. 6 shows design of an exemplary circular RNA that comprises a start-codon, an ORF coding for GFP, a stagger element (2A), and an encryptogen.

In this Example, the circular RNA is designed with a start-codon (SEQ ID NO:1), a GFP ORF (SEQ ID NO:2), stagger element(s) (SEQ ID NO:3), human-derived encryptogen(s) (SEQ ID NO:4), and with or without an IRES (SEQ ID NO:5), see FIG. 6. In this Example, the circular RNA is generated either in vitro or in cells as described in Example 10 and 11.

The circular RNA is incubated for 5 h or overnight in rabbit reticulocyte lysate (Promega, Fitchburg, WI, USA) at 30° C. The final composition of the reaction mixture includes 70% rabbit reticulocyte lysate, 10 M methionine and leucine, 20 M amino acids other than methionine and leucine, and 0.8 U/μL RNase inhibitor (Toyobo, Osaka, Japan). Aliquots are taken from the mixture and separated on 10-20% gradient polyacrylamide/sodium dodecyl sulfate (SDS) gels (Atto, Tokyo, Japan). The supernatant is removed and the pellet is dissolved in 2×SDS sample buffer (0.125 M Tris-HCl, pH 6.8, 4% SDS, 30% glycerol, 5% 2-mercaptoethanol, 0.01% bromophenol blue) at 70° C. for 15 min. The hemoglobin protein is removed during this process whereas proteins other than hemoglobin are concentrated.

After centrifugation at 1,400×g for 5 min, the supernatant is analyzed on 10-20% gradient polyacrylamide/SDS gels. A commercially available standard (BioRad) is used as the size marker. After being electrotransferred to a polyvinylidene fluoride (PVDF) membrane (Millipore) using a semi-dry method, the blot is visualized using a chemiluminescent kit (Rockland).

It is expected that the GFP protein is visualized in cell lysates and is detected in higher quantities in circular RNA than linear RNA, as a result of rolling circle translation.

Example 13: Stoichiometric Protein Expression from Circular RNA

This example demonstrates the ability of circular RNA to stoichiometrically express of proteins.

Figure 7:
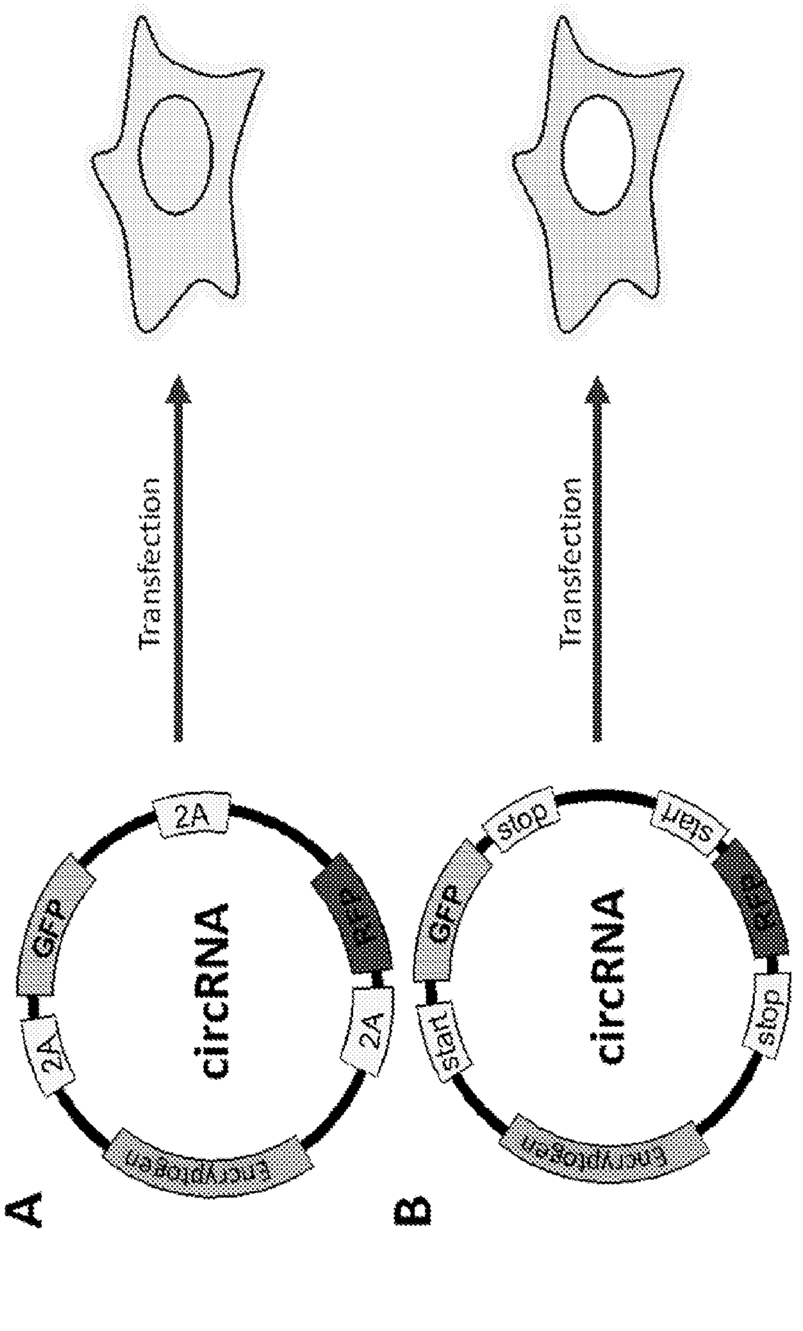
FIG. 7 shows schematics (A and B) demonstrating in vivo stoichiometric protein expression of two different circular RNAs.

In this Example, one circular RNA is designed to include encryptogens (SEQ ID NO:4) and an ORF encoding GFP (SEQ ID NO: 2) and an ORF encoding RFP (SEQ ID NO:8) with stagger elements (SEQ ID NO: 3) flanking the GFP and RFP ORFs, see FIG. 7. Another circular RNA is designed similarly, however instead of flanking 2A sequences it will have a Stop and Start codon in between the GFP and RFP ORFs. The circular RNAs are generated either in vitro or in cells as described in Example 10 and 11.

The circular RNAs are incubated for 5 h or overnight in rabbit reticulocyte lysate (Promega, Fitchburg, WI, USA) at 30° C. The final composition of the reaction mixture includes 70% rabbit reticulocyte lysate, 10 M methionine and leucine, 20 M amino acids other than methionine and leucine, and 0.8 U/μL RNase inhibitor (Toyobo, Osaka, Japan). Aliquots are taken from the mixture and separated on 10-20% gradient polyacrylamide/sodium dodecyl sulfate (SDS) gels (Atto, Tokyo, Japan). The supernatant is removed and the pellet is dissolved in 2×SDS sample buffer (0.125 M Tris-HCl, pH 6.8, 4% SDS, 30% glycerol, 5% 2-mercaptoethanol, 0.01% bromophenol blue) at 70° C. for 15 min. The hemoglobin protein is removed during this process whereas proteins other than hemoglobin are concentrated.

After centrifugation at 1,400×g for 5 min, the supernatant is analyzed on 10-20% gradient polyacrylamide/SDS gels. A commercially available standard (BioRad) is used as the size marker. After being electrotransferred to a polyvinylidene fluoride (PVDF) membrane (Millipore) using a semi-dry method, the blot is visualized using a chemiluminescent kit (Rockland).

It is expected that circular RNA with GFP and RFP ORFs not separated by a Stop and start codon will have equal amounts of either protein, while cells treated with the circular RNA including the start and stop codon in between the ORFs will have different amounts of either protein.

Example 14: In Vivo Expression

This example demonstrates the ability to express protein from a circular RNA in vivo.

Figure 8:
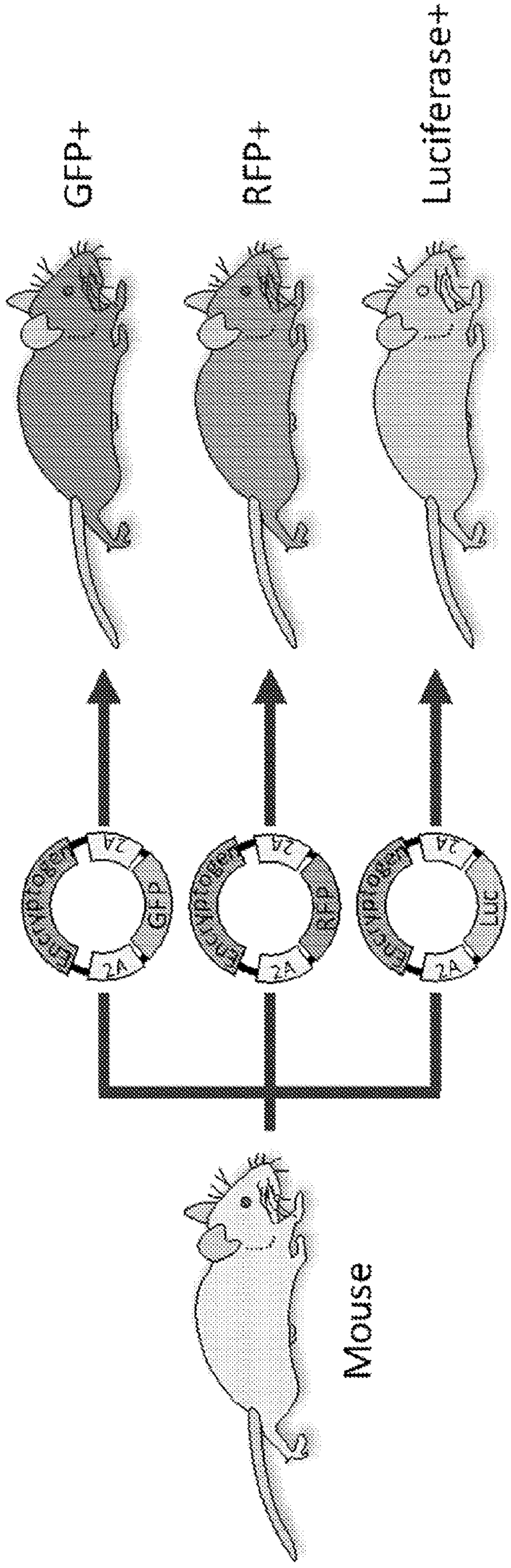
FIG. 8 is a schematic demonstrating in vivo protein expression in mouse model from exemplary circular RNAs.

For this Example, circular RNAs designed to include including encryptogen(s) (SEQ ID NO:4) and an ORF encoding GFP (SEQ ID NO:2) or RFP (SEQ ID NO:8) or Luciferase (SEQ ID NO:10) with stagger elements (SEQ ID NO:3) flanking the GFP, RFP or Luciferase ORF, see FIG. 8. The circular RNA is generated either in vitro or in cells as described in Example 10 and 11.

Male BALB/c mice 6-8 weeks old receive 300 mg/kg (6 mg) circular RNA (50 uL vol) with GFP, RFP, or luciferase ORFs, as described herein, or linear RNA as a control, via intradermal (ID), intramuscular (IM), oral (PO), intraperitoneal (IP), or intravenous (IV) administration. Animals receive a single dose or three injections (day 1, day 3, day 5).

Blood, heart, lung, spleen, kidney, liver, and skin injection sites are collected from non-dosed control mice and at 2, 4, 8, 24, 48, 72, 96 120, 168, and 264 hr post-dosing (n=4 mice/time point). Blood samples are collected from jugular venipuncture at study termination.

Circular RNA quantification for both serum and tissues is performed using quantification of branched DNA (bDNA) (Panomics/Affymetrix). A standard curve on each plate of known amounts of RNA (added to untreated tissue samples) is used to quantitate the RNA in treated tissues. The calculated amount in picograms (pg) is normalized to the amount of weighed tissue in the lysate applied to the plate. Protein expression (RFP or GFP) is evaluated by FACS or western blot in each tissue as described in a previous Example.

A separate group of mice dosed with luciferase circular RNA are injected with 3 mg luciferin at 6, 24, 48, 72, and 96 hr post-dosing and the animals are imaged on an in vivo imaging system (IVIS Spectrum, PerkinElmer). At 6 hr post-dosing, three animals are sacrificed and dissected, and the muscle, skin, draining lymph nodes, liver, and spleen are imaged ex vivo.

It is expected that mice express GFP, RFP, or luciferase in treated tissues.

Example 15: Circular RNA Includes at Least One Double-Stranded RNA Segment

This example demonstrates that circular RNA includes at least one double-stranded RNA segment.

Figure 9:
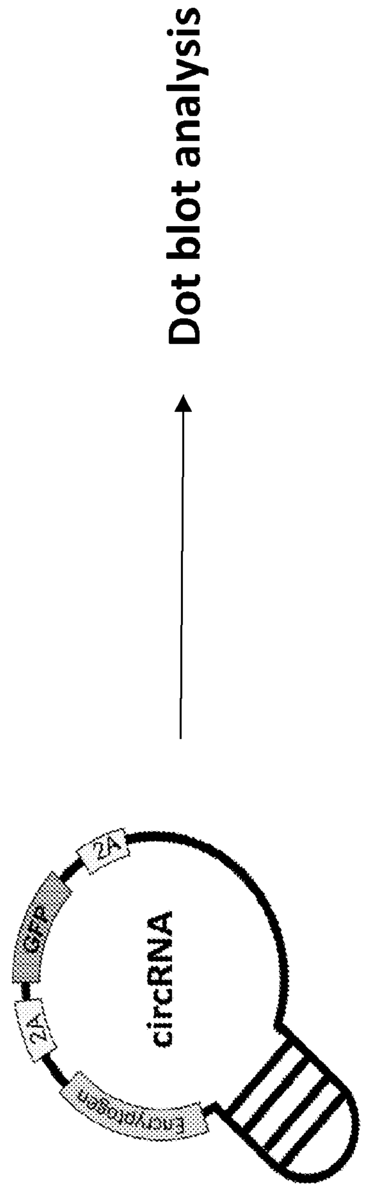
FIG. 9 shows a schematic of an exemplary circular RNA that has one double-stranded RNA segment, which can be subject to dot blot analysis for its structural information.

In this Example, circular RNA is synthesized through one of the methods described previously, to include a GFP ORF and an IRES, see FIG. 9. Dot blot assays with J2 and K1 monoclonal antibodies will be utilized to measure double stranded RNA structures of at least 40 bp in length. Circular RNA (200 ng) is blotted onto a nylon membrane (super charged Nytran), dried, blocked with 5% non-fat dried milk in TBS-T buffer (50 mM Tris-HCl, 150 mM NaCl, 0.05% Tween-20, pH 7.4), and incubated with dsRNA-specific mAb J2 or K1 (English & Scientific Consulting) for 60 min. Membranes are washed six times with TBS-T then treated with HRP-conjugated donkey anti-mouse Ig (Jackson Immunology), then washed six times and dots are visualized with an enhanced chemiluminescence western blot detection reagent (Amersham).

It is expected that a circular RNA creates an internal quasi-double stranded RNA segment.

Example 16: Circular RNA Includes a Quasi-Double-Stranded Structure

This example demonstrates that circular RNA includes a quasi-double-stranded structure.

Figure 10:
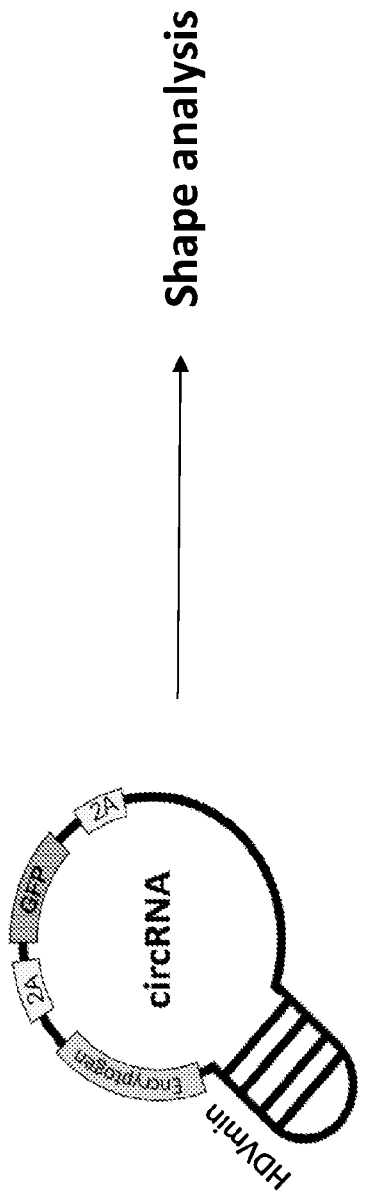
FIG. 10 shows a schematic of an exemplary circular RNA that has a qusi-helical structure (HDVmin), which can be subject to SHAPE analysis for its structural information.

In this Example, circular RNA is synthesized through one of the methods described previously, with and without addition of the expression of HDVmin (Griffin et al 2014). This RNA sequence forms a quasi-helical structure, see FIG. 10, and is used as a positive control (as shown by Griffin et al 2014).

To test if circular RNA structure includes a functional quasi-double-stranded structure we will determine the secondary structure using selective 2'OH acylation analyzed by primer extension (SHAPE). SHAPE assesses local backbone flexibility in RNA at single-nucleotide resolution. The reactivity of base positions to the SHAPE electrophile is related to secondary structure: base-paired positions are weakly reactive, while unpaired positions are more highly reactive.

SHAPE is performed on circular RNA, HDVmin, and linear RNA containing. SHAPE is performed with N-methylisatoic anhydride (NMIA) or benzoyl cyanide (BzCN) essentially as reported by Wilkinson et al 2006 and Griffin 2014 et al respectively. In brief for SHAPE with BzCN, 1 ul of 800 mM BzCN in dimethyl sulfoxide (DMSO) is added to a 20 ul reaction mixture containing 3 to 6 pmol of RNA in 160 mM Tris, pH 8.0, 1 U/1 RNAse inhibitor (e.g. SuperaseIn RNase inhibitor) and incubated for 1 min at 37° C. Control reaction mixtures include 1 ul DMSO without BzCN. After incubation with BzCN, RNAs is extracted with phenol chloroform, and purified (e.g using a RNA Clean & Concentrator-5 kit) as directed by the manufacturer, and resuspended in 6 ul 10 mM Tris, pH 8.0. A one-dye system is used to detect BzCN adducts. RNAs are annealed with a primer labeled with 6-carboxyfluorescein (6-FAM). Primer extension is performed using a reverse transcriptase (SuperScript III—Invitrogen) according to the manufacturer's recommendations with the following modifications to the incubation conditions: 5 min at 42° C., 30 min at 55° C., 25 min at 65° C., and 15 min at 75° C. Two sequencing ladders are generated using either 0.5 mM ddATP or 0.5 mM ddCTP in the primer extension reaction. Primer extension products are precipitated with ethanol, washed to remove excess salt, and resolved by capillary electrophoresis along with a commercial size standard (e.g. Liz size standard Genewiz Fragment Analysis Service).

Raw electropherograms are analyzed using a primary fragment analysis tool (e.g. PeakScanner Applied Bio-systems). The peaks at each position in the electropherogram are then integrated. For each RNA analyzed, y axis scaling to correct for loading error is performed so that the background for each primer extension reaction is normalized to that of a negative-control reaction performed on RNA that is not treated with BzCN. A signal decay correction is applied to the data for each reaction. The peaks are aligned to a ladder created from two sequencing reactions. At each position, the peak area of the negative control is subtracted from the peak area in BzCN-treated samples; these values are then converted to normalized SHAPE reactivities by dividing the subtracted peak areas by the average of the highest 2% to 10% of the subtracted peak areas.

In addition to SHAPE analysis we will perform NMR (Marchanka et al 2015); Hydroxyl radical probing (Ding et al 2012); or a combination of DMS and CMTC and Kethoxal (Tijerina et al 2007 and Ziehler et al 2001).

It is expected that a circular RNA will have a quasi-double-stranded structure.

Example 17: Circular RNA Includes a Functional Quasi-Helical Structure

This example demonstrates that circular RNA includes a functional quasi-helical structure.

Figure 11:
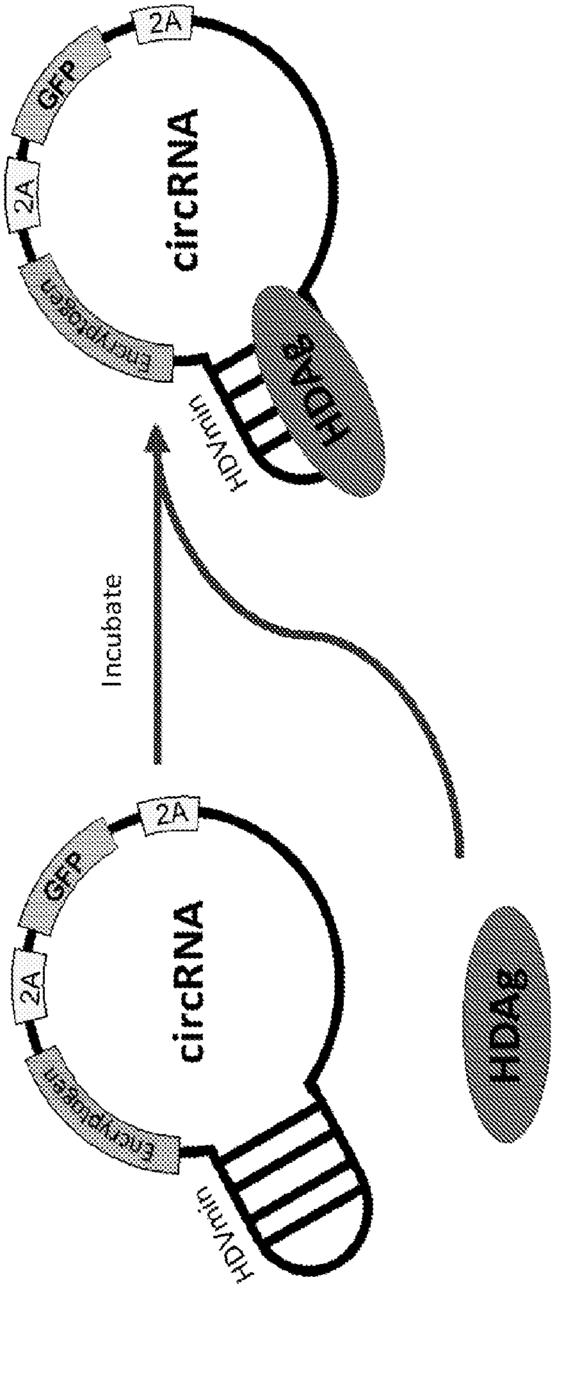
FIG. 11 shows a schematic of an exemplary circular RNA that has a functional qusi-helical structure (HDVmin), which demonstrates HDAg binding activity.

In this Example, circular RNA is synthesized through one of the methods described previously, with the addition of the expression of 395L (Defenbaugh et al 2009). This RNA sequence forms a quasi-helical structure (as shown above, by RNA secondary structure folding algorithm mfold and Defenbaugh et al 2009), FIG. 11. This structure is essential for complex formation with hepatitis D antigen (HDAg).

Therefore, to test if circular RNA structure includes a functional quasi-structure we will incubate circular RNA and linear RNA with HDAg-160 or HDAg-195 and analyze binding using EMSA assays. Binding reactions are done in 25 ul including 10 mM Tris-HCl (pH 7.0), 25 mM KCl, 10 mM NaCl, 0.1 g/l bovine serum albumin (New England Biolabs), 5% glycerol, 0.5 mM DTT, 0.2 U/1 RNase inhibitor (Applied Biosystems), and 1 mM phenylmethylsulfonyl fluoride solution. circular RNA is incubated with HDAg protein (obtained as described by Defenbaugh et al 2009) at concentrations ranging from 0-110 nM. Reaction mixtures are assembled on ice, incubated at 37° C. for 1 h, and electrophoresed on 6% native polyacrylamide gels in 0.5 Tris-borate-EDTA at 240 V for 2.5 h. Levels of free and bound RNA are determined using nucleic acid staining (e.g. gelred). Binding will be calculated as the intensity of unbound RNA relative to the intensity of the entire lane minus the background.

It is expected that a circular RNA will have a functional quasi-helical structure.

Example 18: Self-Transcription/Replication

Figure 12:
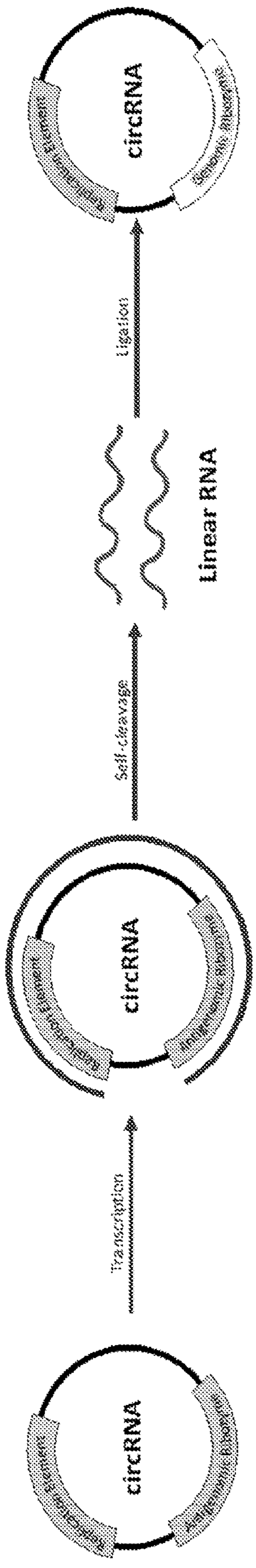
FIG. 12 is a schematic demonstrating transcription, self-cleavage, and ligation of an exemplary self-replicable circular RNA.

In this Example, circular RNA is synthesized through one of the methods described previously, with the addition of the expression of the HDV replication domain(s) (as described by Beeharry et al 2014), the antigenomic replication competent ribozyme and a nuclear localization signal. These RNA sequences allow for circular RNA to be located in the nucleus where the host RNA polymerase will bind and transcribe the RNA. Then this RNA is self-cleaved using the ribozyme. RNA is then ligated and self-replicated again, see FIG. 12.

Circular RNA (1-5 microgram) will be transfected into HeLa cells using techniques described above. HeLa cells are grown at 37° C. and 5% $CO_2$ in Dulbecco's modified Eagle's medium (DMEM) with high glucose (Life Technologies), supplemented with penicillin-streptomycin and 10% fetal bovine serum. After transfection HeLa cells are cultured for an additional 4-72 hr, then total RNA from the transfected cells is isolated using a phenol-based RNA isolation reagent (Life Technologies) as per the manufacturer's instructions between 1 hour and 20 days after transfection and total amount of circular RNA encoding the HDV domains will be determined and compared to control circular RNA using qPCR as described herein.

Example 19: Circular RNA Circularization

This Example demonstrates in vitro production of circular RNA using splint ligation.

A non-naturally occurring circular RNA can be engineered to include one or more desirable properties and may be produced using recombinant DNA technology. As shown in the following Example, splint ligation circularized linear RNA.

CircRNA1 was designed to encode triple FLAG tagged EGF without stop codon (264 nts). It has a Kozak sequence (SEQ ID NO: 11) at the start codon for translation initiation. CirRNA2 has identical sequences with circular RNA1 except it has a termination element (triple stop codons) (273 nts, SEQ ID NO: 12). Circular RNA3 was designed to encode triple FLAG tagged EGF flanked by a stagger element (2A sequence, SEQ ID NO: 13), without a termination element (stop codon) (330 nts). CircRNA4 has identical sequences with circular RNA3 except it has a termination element (triple stop codon) (339 nts).

In this example, the circular RNA was generated as follows. DNA templates for in vitro transcription were amplified from gBlocks gene fragment with corresponding sequences (IDT) with T7 promoter-harboring forward primer and 2-O-methylated nucleotide with a reverse primer. Amplified DNA templates were gel-purified with a DNA gel purification kit (Qiagen). 250-500 ng of purified DNA template was subjected to in vitro transcription. Linear, 5'-mono phosphorylated in vitro transcripts were generated using T7 RNA polymerase from each DNA template having corresponding sequences in the presence of 7.5 mM GMP, 1.5 mM GTP, 7.5 mM UTP, 7.5 mM CTP and 7.5 mM ATP. Around 40 pg of linear RNA was generated in each reaction. After incubation, each reaction was treated with DNase to remove the DNA template. The in vitro transcribed RNA was precipitated with ethanol in the presence of 2.5M ammonium acetate to remove unincorporated monomers.

Transcribed linear RNA was circularized using T4 RNA ligase 2 on a 20 nt splint DNA oligomer (SEQ ID NO: 14) as template. Splint DNA was designed to anneal 10 nt of each 5' or 3'end of linear RNA. After annealing with the splint DNA (3 μM), 1 μM linear RNA was incubated with 0.5 U/μl T4 RNA ligase 2 at 37 C or 4 hr. Mixture without T4 RNA ligase 2 was used as the negative control.

Figure 13:
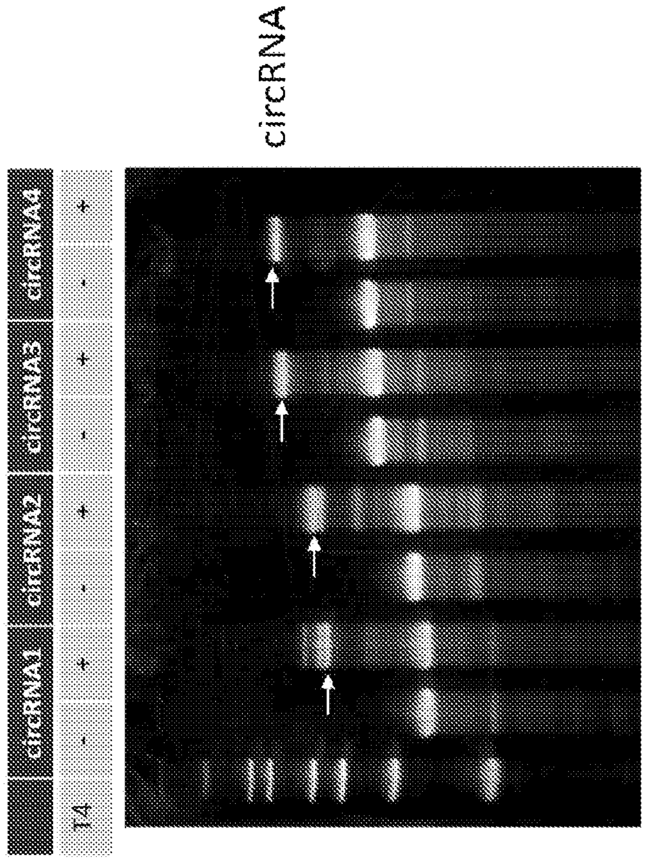
FIG. 13 is a denaturing PAGE gel image demonstrating in vitro production of different exemplary circular RNAs.

The circularization of linear RNA was monitored by separating RNA on 6% denaturing PAGE. Slower migrating RNA bands correspond with circular RNA rather than linear RNA on denaturing polyacrylamide gels because of their circular structure. As seen in FIG. 13, the addition of ligase (+lanes) to the RNA mixtures generated new bands to appear above the linear RNA bands that were present in the mixtures that lacked ligase (-lanes). Slower migrating bands appeared in all RNA mixtures indicating successful splint ligation (e.g., circularization) occurred with multiple constructs as compared to negative control.

Example 20: RNA Circularization Efficiency

This Example demonstrates circularization efficiencies of RNA splint ligation.

A non-naturally occurring circular RNA engineered to include one or more desirable properties may be produced using splint mediated circularization. As shown in the following Example, splint ligation circularized linear RNA with higher efficiency than controls.

CircRNA1, CircRNA2, CircRNA3, and CircRNA4 as described in Example 9 were also used here. CircRNA5 was designed to encode FLAG tagged EGF flanked by a 2A sequence and followed by FLAG tagged nano luciferase (873 nts, SEQ ID NO: 17). CircRNA6 has identical sequence with circular RNA5 except it included a a termination element (triple stop codon) between the EGF and nano luciferase genes, and a termination element (triple stop codon) at the end of the nano luciferase sequence (762 nts, SEQ ID NO: 18).

In this Example, to measure circularization efficiency of RNA, 6 different sizes of linear RNA (264 nts, 273 nts, 330 nts, 339 nts, 873 nts and 762 nts) were generated and circularized as described in Example 9. The circular RNAs were resolved by 6% denaturing PAGE and corresponding RNA bands on the gel for linear or circular RNA were excised for purification. Excised RNA gel bands were crushed and RNA was eluted with 800 μl of 300 mM NaCl overnight. Gel debris was removed by centrifuge filters and RNA was precipitated with ethanol in the presence of 0.3M sodium acetate.

Figure 14:
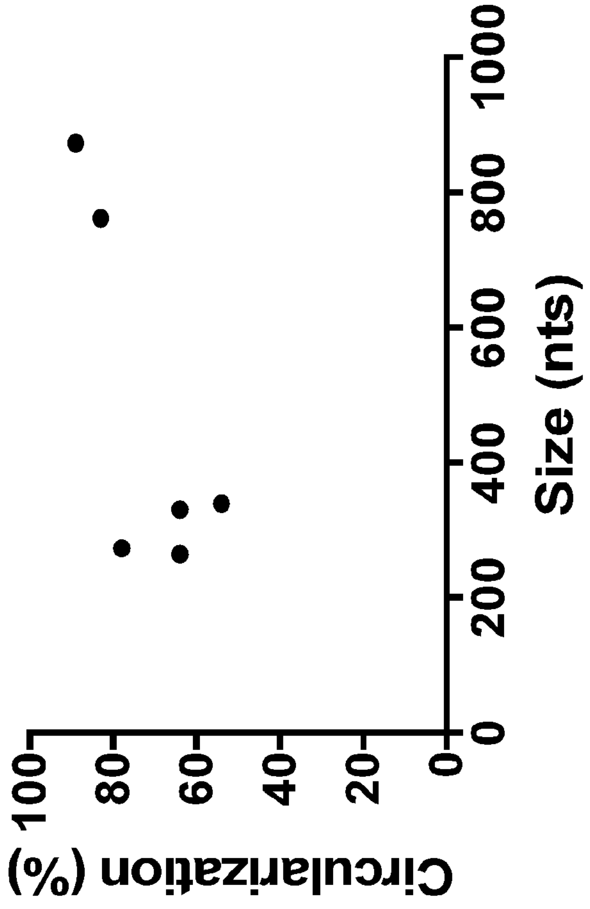
FIG. 14 is a graph summarizing circularization efficiencies of different exemplary circular RNAs.

Circularization efficiency was calculated as follows. The amount of eluted circular RNA was divided by the total eluted RNA amount (circular+linear RNA) and the result was depicted as a graph in FIG. 14.

Ligation of linear RNAs using T4 RNAse ligase 2 produced circular RNA at efficiency rates higher than control. Trending data indicated larger constructs circularized at higher rates, for instance, linear RNAs having around 800 nts were shown to have circularization efficiency around 80%, while linear RNAs having around 200-400 nts had circularization efficiency in the range of 50% to 80%.

Example 21: Circular RNA Lacking Degradation Susceptibility

This Example demonstrates circular RNA susceptibility to degradation by RNAse R compared to linear RNA.

Circular RNA is more resistant to exonuclease degradation than linear RNA due to the lack of 5' and 3' ends. As shown in the following Example, circular RNA was less susceptible to degradation than its linear RNA counterpart.

CircRNA5 was generated and circularized as described in Example 11 for use in the assay described herein.

To test circularization of CircRNA5, 20 ng/μl of linear or CircRNA5 was incubated with 2 U/μl of RNAse R, a 3' to 5' exoribonuclease that digests linear RNAs but does not digest lariat or circular RNA structures, at 37° C. for 30 min. After incubation, the reaction mixture was analyzed by 6% denaturing PAGE.

Figure 15:
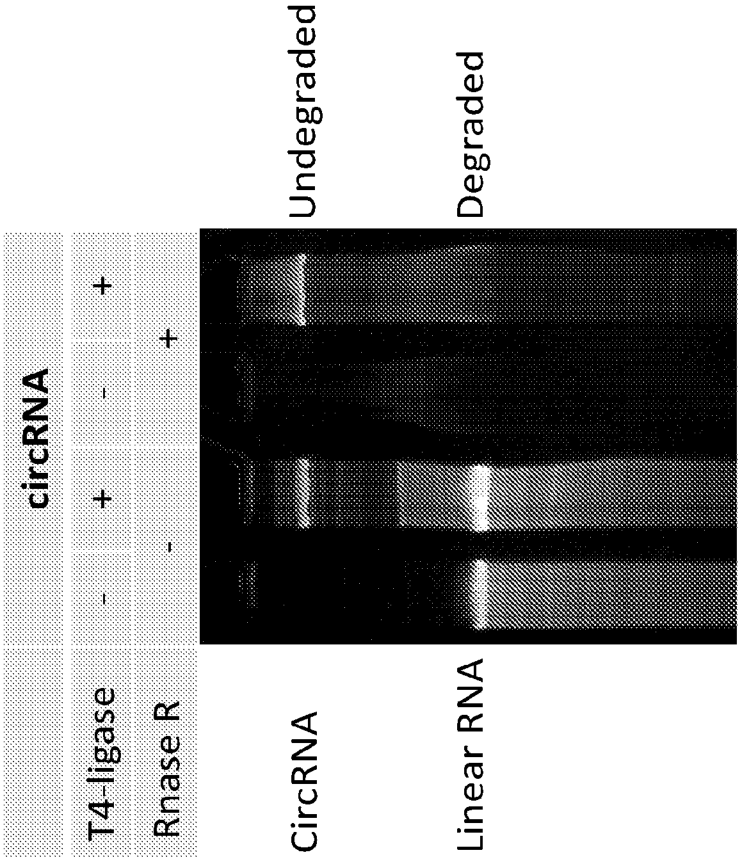
FIG. 15 is a denaturing PAGE gel image demonstrating decreased degradation susceptibility of an exemplary circular RNA as compared to its linear counterpart.

The linear RNA bands present in the lanes lacking exonuclease were absent in the CircRNA5 lane (see FIG. 15) indicating CircRNA5 showed higher resistance to exonuclease treatment as compared to linear RNA control.

Example 22: Isolation and Purification of Circular RNA

This Example demonstrates circular RNA purification.

In certain embodiments, circular RNAs, as described in the previous Examples, may be isolated and purified before expression of the encoded protein products. This Example describes isolation using UREA gel separation. As shown in the following Example, circular RNA was isolated and purified.

CircRNA1, CircRNA2, CircRNA3, CircRNA4, CircRNA5, and CircRNA6, as described in Example 11, were isolated as described herein.

Figure 16:
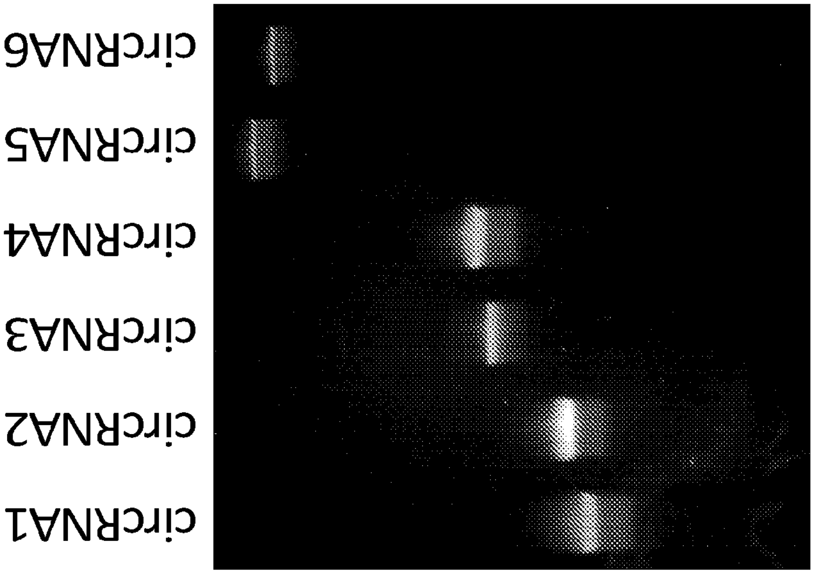
FIG. 16 is a denaturing PAGE gel image demonstrating exemplary circular RNA after an exemplary purification process.

In this Example, linear and circular RNA were generated as described. To purify the circular RNAs, ligation mixtures were resolved on 6% denaturing PAGE and RNA bands corresponding to each of the circular RNAs were excised. Excised RNA gel fragments were crushed and RNA was eluted with 800 μl of 300 mM NaCl overnight. Gel debris was removed by centrifuge filters and RNA was precipitated with ethanol in the presence of 0.3M sodium acetate. Eluted circular RNA was analyzed by 6% denaturing PAGE, see FIG. 16.

Single bands were visualized by PAGE for the circular RNAs having variable sizes.

Example 23: Detection of Protein Expression

This Example demonstrates in vitro protein expression from a circular RNA.

Protein expression is the process of generating a specific protein from mRNA. This process includes the transcription of DNA into messenger RNA (mRNA), followed by the translation of mRNA into polypeptide chains, which are ultimately folded into functional proteins and may be targeted to specific subcellular or extracellular locations.

As shown in the following Example, a protein was expressed in vitro from a circular RNA sequence.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture contained 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (3001) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

Figure 17:
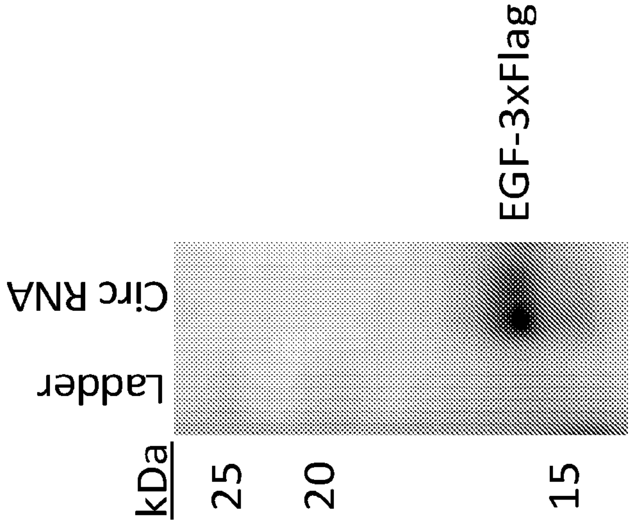
FIG. 17 is a Western blot image demonstrating expression of Flag protein (~15 kDa) by an exemplary circular RNA that lacks IRES, cap, 5' and 3' UTRs.

After being electrotransferred to a nitrocellulose membrane using dry transfer method, the blot was incubated with an anti-FLAG antibody and anti-mouse IgG peroxidase. The blot was visualized with an ECL kit (see FIG. 17) and western blot band intensity was measured by ImageJ.

Fluorescence was detected indicated expression product was present. Thus, circular RNA was shown to drive expression of a protein.

Example 24: IRES-Independent Expression

This Example demonstrates circular RNA driving expression in the absence of an IRES.

An IRES, or internal ribosome entry site, is an RNA element that allows translation initiation in a cap-independent manner. Circular RNA was shown to be drive expression of Flag protein in the absence of an IRES.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

Figure 18:
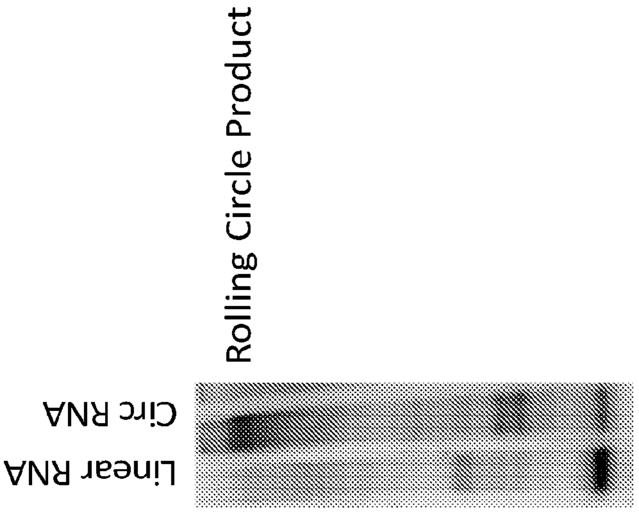
FIG. 18 is Western blot image demonstrating rolling-circle translation of an exemplary circular RNA.

After being electrotransferred to a nitrocellulose membrane using dry transfer method, the blot was incubated with an anti-FLAG antibody and anti-mouse IgG peroxidase. The blot was visualized with an enhanced chemiluminescence (ECL) kit (see FIG. 18) and western blot band intensity was measured by ImageJ.

Expression product was detected in the circular RNA reaction mixture even in the absence of an IRES.

Example 25: Cap-Independent Expression

This Example demonstrates circular RNA is able to drive expression in the absence of a cap.

A cap is a specially altered nucleotide on the 5' end of mRNA. The 5' cap is useful for stability, as well as the translation initiation, of linear mRNA. Circular RNA drove expression of product in the absence of a cap.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30 μl of 2×SDS sample buffer at 70° C. for 15 min. After centrifugation at 1400×g for 5 min, the supernatant was analyzed on 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 17) and western blot band intensity was measured by ImageJ.

Expression product was detected in the circular RNA reaction mixture even in the absence of a cap.

Example 26: Expression without a 5'-UTR

This Example demonstrates in vitro protein expression from a circular RNA lacking 5' untranslated regions.

The 5' untranslated region (5' UTR) is the region directly upstream of an initiation codon that aids in downstream protein translation of a RNA transcript.

As shown in the following Example, a 5'-untranslated region in the circular RNA sequence was not necessary for in vitro protein expression.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 17) and western blot band intensity was measured by ImageJ.

Expression product was detected in the circular RNA reaction mixture even in the absence of a 5' UTR.

Example 27: Expression without a 3'-UTR

This Example demonstrates in vitro protein expression from a circular RNA lacking a 3'-UTR.

The 3' untranslated region (3'-UTR) is the region directly downstream of a translation termination codon and includes regulatory regions that may post-transcriptionally influence gene expression. The 3'-untranslated region may also play a role in gene expression by influencing the localization, stability, export, and translation efficiency of an mRNA. In addition, the structural characteristics of the 3'-UTR as well as its use of alternative polyadenylation may play a role in gene expression.

As shown in the following Example, a 3'-UTR in the circular RNA sequence was not necessary for in vitro protein expression.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (3001) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 17) and western blot band intensity was measured by ImageJ.

Expression product was detected in the circular RNA reaction mixture even in the absence of a 3'UTR.

Example 28: Expression without a Termination Codon

This Example demonstrates generation of a polypeptide product following rolling circle translation from a circular RNA lacking a termination codon.

Proteins are based on polypeptides, which are comprised of unique sequences of amino acids. Each amino acid is encoded in mRNA by nucleotide triplets called codon. During protein translation, each codon in mRNA corresponds to the addition of an amino acid in a growing polypeptide chain. Termination element or stop codons signal the termination of this process by binding release factors, which cause the ribosomal subunits to disassociate, releasing the amino acid chain.

As shown in the following Example, a circular RNA lacking a termination codon generated a large polypeptide product comprised of repeated polypeptide sequences via rolling circle translation.

Circular RNA was designed to encode triple FLAG tagged EGF without a termination element (stop codon) (264 nts, SEQ ID NO: 20), and included a Kozak sequence at the start codon to favor translation initiation.

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 18) and western blot band intensity was measured by ImageJ.

Expression product was detected in the circular RNA reaction mixture even in the absence of a termination codon.

Example 29: Expression of Discrete Proteins without a Termination Element (Stop Codon)

This Example demonstrates generation of a discrete protein products translated from a circular RNA lacking a termination element (stop codons).

Stagger elements, such as 2A peptides, may include short amino acid sequences, ~20 aa, that allow for the production of equimolar levels of multiple genes from a single mRNA. The stagger element may function by making the ribosome skip the synthesis of a peptide bond at the C-terminus of the 2A element, leading to separation between the end of the 2A sequence and the next peptide downstream. The separation occurs between Glycine and Proline residues found on the C-terminus and the upstream cistron has a few additional residues added to the end, while the downstream cistron starts with a Proline.

Figure 19:
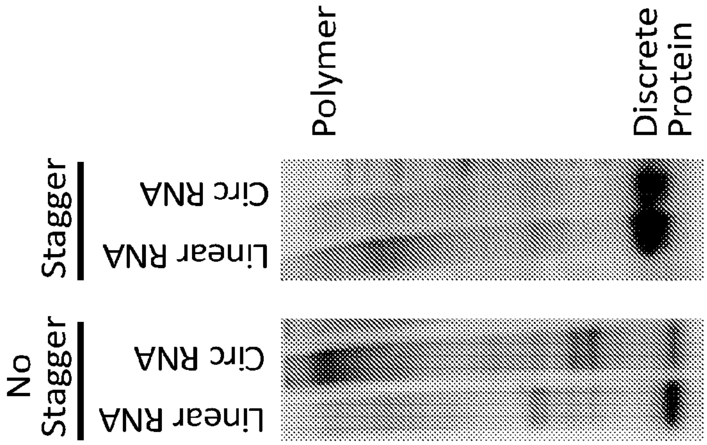
FIG. 19 shows Western blot images demonstrating production of discrete proteins or continuous long peptides from different exemplary circular RNAs with or without an exemplary stagger element.

As shown in the following Example, the circular RNA lacking a termination element (stop codon) generated a large polypeptide polymer (FIG. 19 left panel: no stagger—circular RNA lane) and inclusion of a 2A sequence at the 3' end of the coding region resulted in production of discrete protein at a size comparable to that generated by the equivalent linear RNA construct (FIG. 19 right panel: stagger—circular RNA lane).

Circular RNA was designed to encode triple FLAG tagged EGF without a termination element (stop codon) (264 nts, SEQ ID NO: 20) and without a stagger element. A second circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 19) and western blot band intensity was measured by ImageJ.

Discrete expression products were detected indicating circular RNA comprising a stagger element drove expression of the individual proteins even in the absence of a termination element (stop codons).

Example 30: Rolling Circle Translation

This Example demonstrates elevated in vitro biosynthesis of a protein from circular RNA using a stagger element.

A non-naturally occurring circular RNA was engineered to include a stagger element to compare protein expression with circular RNA lacking a stagger element. As shown in the following Example, a stagger element overexpressed protein as compared to an otherwise identical circular RNA lacking such a sequence.

Circular RNA was designed to encode triple FLAG tagged EGF with a termination element (e.g., three stop codons in tandem) (273 nts, SEQ ID NO: 21). A second circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture contained 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° 1 of 2×SDS sample buffer and incubated at 70° C. for 15 min. After centrifugation at 1400×g for 5 min, the supernatant was analyzed on a 10-20% gradient polyacrylamide/SDS gel.

Figure 20B:
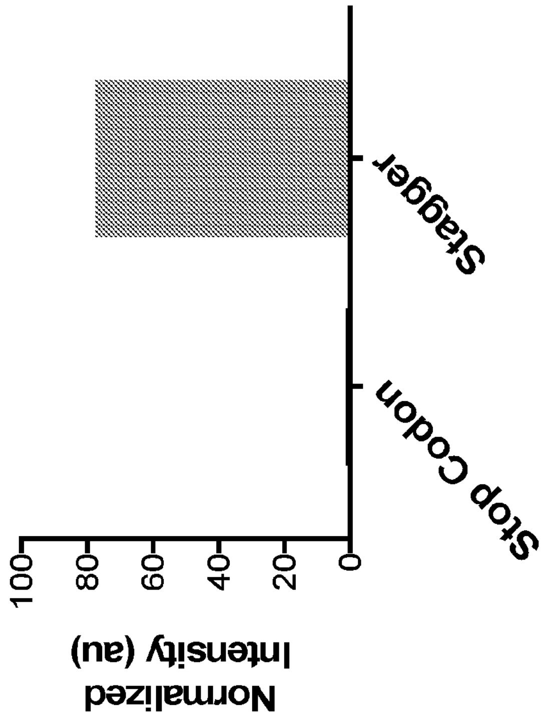
FIG. 20B is a graph summarizing the signal intensity from Western blot analysis of the protein products translated from the two exemplary circular RNAs.
Figure 20A:
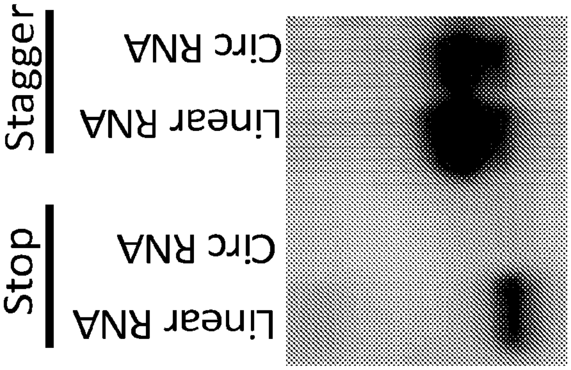
FIG. 20A is a Western blot image showing the comparison of protein expression between different exemplary circular RNAs with an exemplary stagger element or a termination element (stop codon).

After being electrotransferred to a nitrocellulose membrane using dry transfer method, the blot was incubated with an anti-FLAG antibody and anti-mouse IgG peroxidase. The blot was visualized with an ECL kit (see FIG. 20) and western blot band intensity was measured by ImageJ.

Discrete expression products were detected indicating circular RNA comprising a stagger element drove expression of the individual proteins even in the absence of a termination element (stop codons).

Example 31: Expression of a Biologically Active Protein In Vitro

This Example demonstrates in vitro biosynthesis of a biologically active protein from circular RNA.

A non-naturally occurring circular RNA was engineered to express a biologically active therapeutic protein. As shown in the following Example, a biologically active protein was expressed from the circular RNA in reticulocyte lysate.

Circular RNA was designed to encode FLAG tagged EGF flanked by a 2A sequence and followed by FLAG tagged nano-luciferase (873 nts, SEQ ID NO:17).

Linear or circular RNA was incubated for 5 hr in rabbit reticulocyte lysate at 30° C. in a volume of 25 μl. The final composition of the reaction mixture contained 70% rabbit reticulocyte lysate, 20 μM amino acids, 0.8 U/μl RNase inhibitor. Luciferase activity in the translation mixture was monitored using a luciferase assay system according to manufacturer's protocol (Promega).

Figure 21:
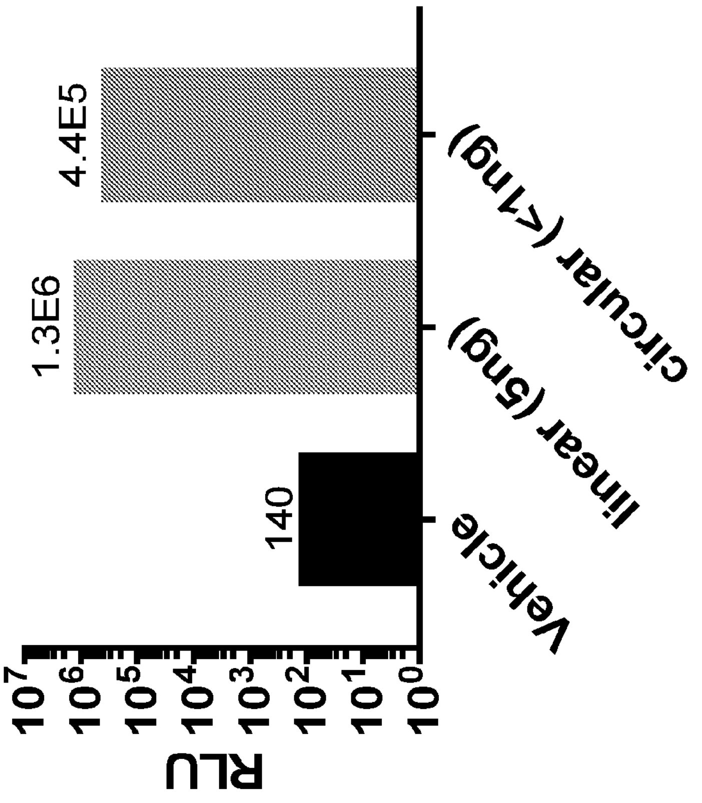
FIG. 21 is a graph summarizing the luciferase activity of translation products of an exemplary circular RNA and its linear counterpart, in comparison with a vehicle control RNA.

As shown in FIG. 21, much higher fluorescence was detected with both circular RNA and linear RNA than the control vehicle RNA, indicating expression product was present. Thus, circular RNA was shown to express a biologically active protein.

Example 32: Circular RNA with a Longer Half-Life than Linear RNA Counterpart

This Example demonstrates circular RNA engineered to have a prolonged half-life as compared to a linear RNA.

Circular RNA encoding a therapeutic protein provided recipient cells with the ability to produce greater levels of the encoded protein stemming from a prolonged biological half-life, e.g., as compared to linear RNA. As shown in the following Example, a circular RNA had a greater half-life than its linear RNA counterpart in reticulocyte lysate.

A circular RNA was designed to encode FLAG tagged EGF flanked by a 2A sequence and followed by FLAG tagged nano luciferase (873 nts, SEQ ID NO: 17).

In this Example, a time-course experiment was performed to monitor RNA stability. 100 ng of linear or circular RNA was incubated with rabbit reticulocyte lysate and samples were collected at 1 hr, 5 hr, 18 hr and 30 hr. Total RNA was isolated from lysate using a phenol-based reagent (Invitrogen) and cDNA was generated by reverse transcription. qRT-PCR analysis was performed using a dy-based quantitative PCR reaction mix (BioRad).

Figure 22:
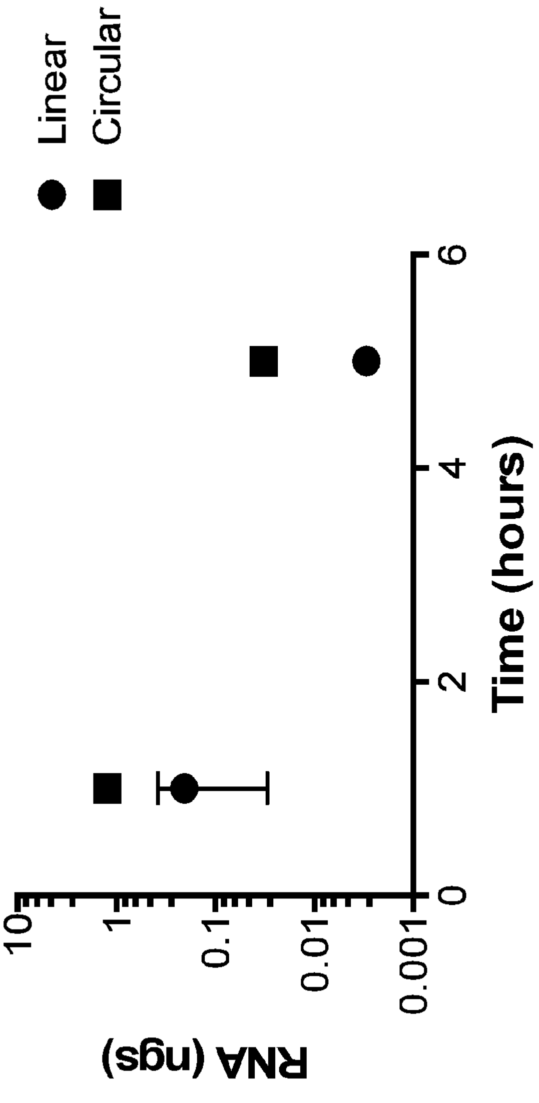
FIG. 22 is a graph summarizing RNA quantities at different collection time points in a time course experiment testing half-life of an exemplary circular RNA.

As shown in FIG. 22, greater concentrations of circular RNA were detected in the later timepoints than linear RNA. Thus, the circular RNA was more stable or had an increased half-life as compared to its linear counterpart.

Example 33: Circular RNA Demonstrated a Longer Half-Life than Linear RNA in Cells This Example demonstrates circular RNA delivered into cells and has an increased half-life in cells compared with linear RNA.

A non-naturally occurring circular RNA was engineered to express a biologically active therapeutic protein. As shown in the following Example, circular RNA was present at higher levels compared to its linear RNA counterpart, demonstrating a longer half-life for circular RNA.

In this Example, circular RNA and linear RNA were designed to encode a Kozak, EGF, flanked by a 2A, a stop or no stop sequence (SEQ ID NOs: 11, 19, 20, 21). To monitor half-life of RNA in cells, $0.1\times10^6$ cells were plated onto each well of a 12 well plate. After 1 day, 1 μg of linear or circular RNA was transfected into each well using a lipid-based transfection reagent (Invitrogen). Twenty-four hours after transfection, total RNA was isolated from cells using a phenol-based extraction reagent (Invitrogen). Total RNA (500 ng) was subjected to reverse transcription to generate cDNA. qRT-PCR analysis was performed using a dye-based quantitative PCR mix (BioRad). Primer sequences were as follow: Primers for linear or circular RNA, F: ACGACGGTGTGTGCATGTAT (SEQ ID NO: 114), R: TTCCCACCACTTCAGGTCTC (SEQ ID NO: 115); primers for circular RNA, F: TACGCCTGCAACTGTGTTGT (SEQ ID NO: 116), R: TCGATGATCTTGTCGTCGTC (SEQ ID NO: 117).

Figure 23A:
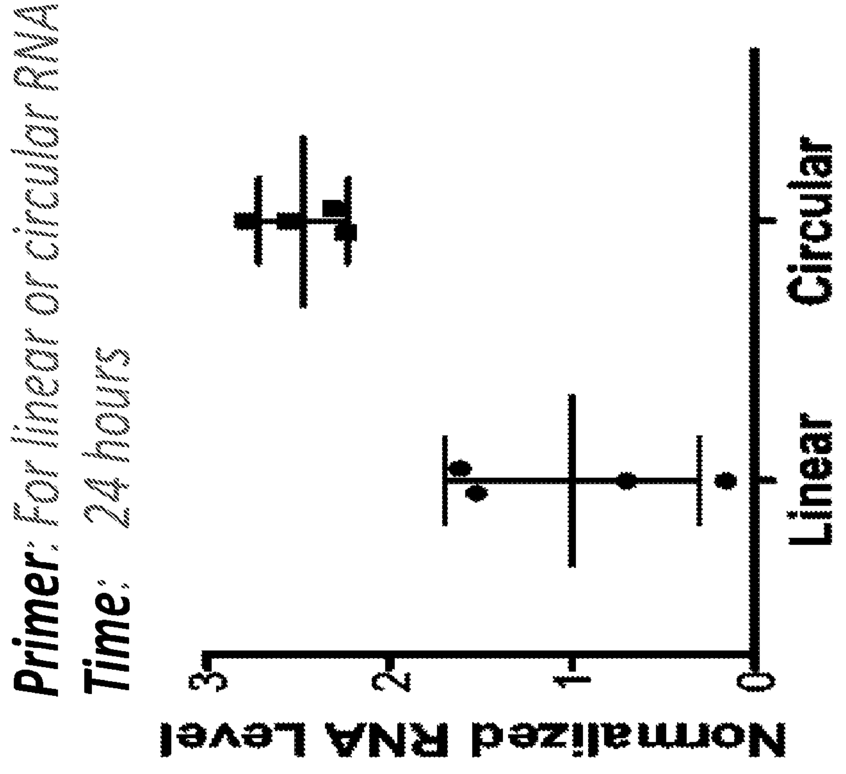
FIG. 23A is a graph showing qRT-PCR analysis of linear and circular RNA levels 24 hours after delivery to cells using primers that captured both linear and circular RNA.
Figure 23B:
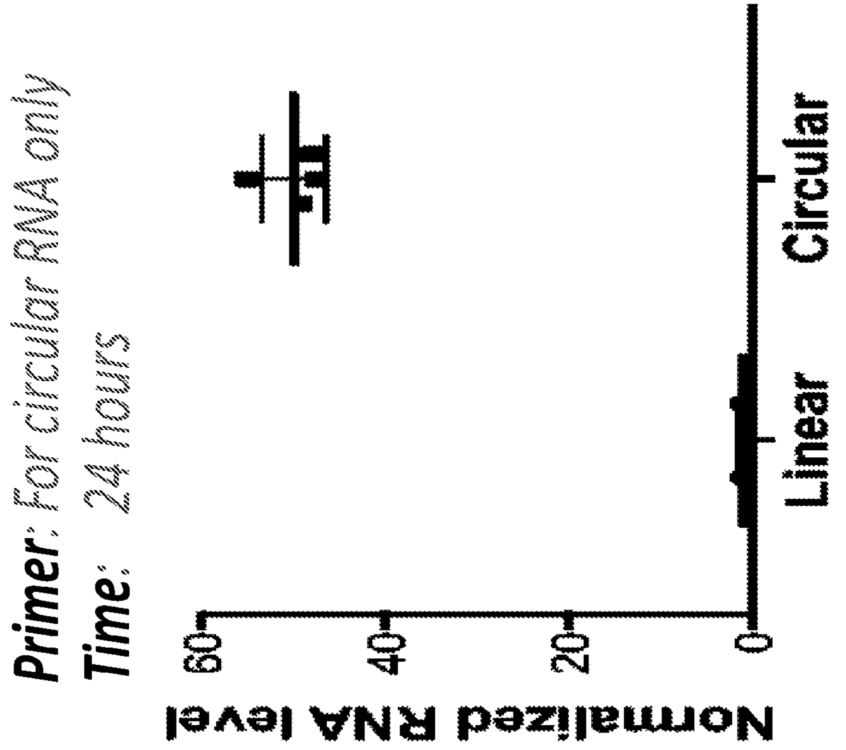
FIG. 23B is a graph showing qRT-PCR analysis of linear and circular RNA levels using a primer specific for the circular RNA.

Circular RNA was successfully transfected into 293T cells, as was its linear counterpart. After 24 hours, the circular and linear RNA that remained were measured using qPCR. As shown in FIGS. 23A and B, circular RNA was shown to have a longer half-life in cells compared to linear RNA.

Example 34: Synthetic Circular RNA were Translated in Cells, and Synthetic Circular RNA was Translated Via Rolling Circle Translation This Example demonstrates translation of synthetic circular RNA in cells.

As shown in the following Example, circular RNA and linear RNA were designed to encode a Kozak, 3×FLAG-EGF sequence with no termination element (SEQ ID NO: 11). Circular RNA was translated into polymeric EGF, while linear RNA was not, demonstrating that cells performed rolling circle translation of a synthetic circular RNA.

In this Example, $0.1\times10^6$ cells were plated onto each well of a 12 well plate to monitor translation efficiency of linear or circular RNA in cells. After 1 day, 1 μg of linear or circular RNA was transfected into each well using a lipid-based transfection reagent (Invitrogen). Twenty-four hours after transfection, cells were harvested by adding 200 μl of RIPA buffer onto each well. Next, 10 μg of cell lysate proteins were analyzed on 10-20% gradient polyacrylamide/SDS gel. After electrotransfer to a nitrocellulose membrane using dry transfer method, the blot was incubated with an anti-FLAG antibody and anti-mouse IgG peroxidase. As a loading control, anti-beta tubulin antibody was used. The blot was visualized with an enhanced chemiluminescent (ECL) kit. Western blot band intensity was measured by ImageJ.

Figure 24:
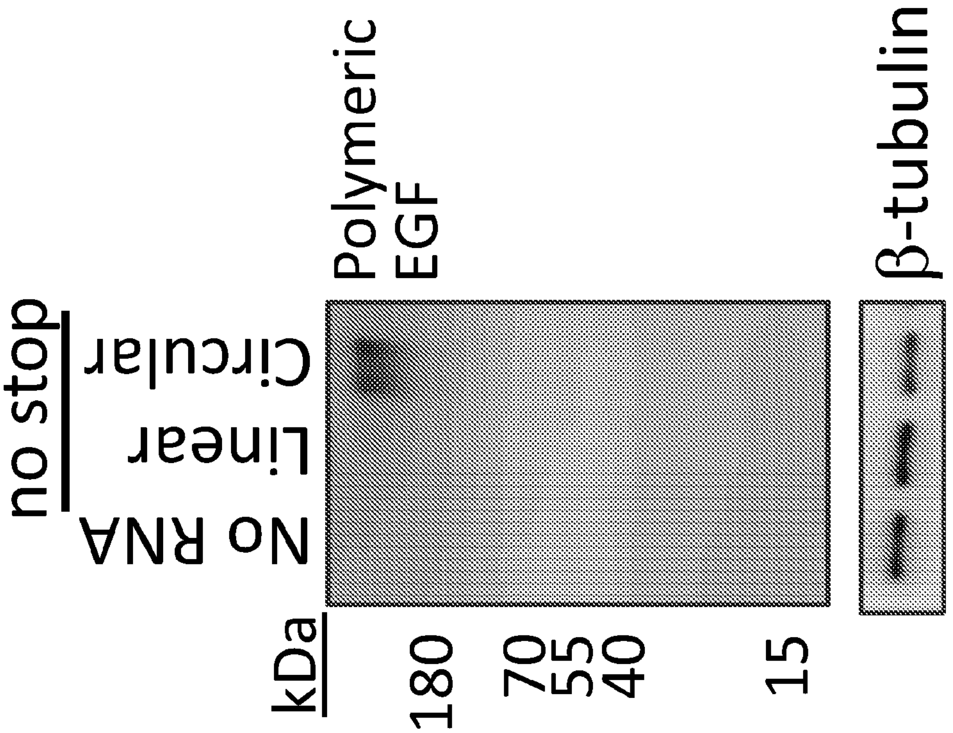
FIG. 24 is an image showing a blot of cell lysates from circular RNA and linear RNA probed for EGF protein and a beta-tubulin loading control.

Circular RNA was successfully transfected into 293T cells, as was its linear counterpart. However, FIG. 24 shows that 24 hours after transfection, EGF protein was detected in the circular RNA transfected cells, while none was detected in the linear RNA transfected cells. Thus, circular RNA was translated in cells via rolling circle translation as compared to linear RNA.

Example 35: Synthetic Circular RNA Demonstrated Reduced Immunogenic Gene Expression in Cells This Example demonstrates circular RNA engineered to have reduced immunogenicity as compared to a linear RNA.

Circular RNA that encoded a therapeutic protein provided a reduced induction of immunogenic related genes (RIG-I, MDA5, PKA and IFN-beta) in recipient cells, as compared to linear RNA. RIG-I can recognize short 5' triphosphate uncapped double stranded or single stranded RNA, while MDA5 can recognize longer dsRNAs. RIG-I and MDA5 can both be involved in activating MAVS and triggering antiviral responses. PKR can be activated by dsRNA and induced by interferons, such as IFN-beta. As shown in the following Example, circular RNA was shown to have a reduced activation of an immune related genes in 293T cells than an analogous linear RNA, as assessed by expression of RIG-I, MDA5, PKR and IFN-beta by q-PCR.

The circular RNA and linear RNA were designed to encode either (1) a Kozak, 3×FLAG-EGF sequence with no termination element (SEQ ID NO:11); (2) a Kozak, 3×FLAG-EGF, flanked by a termination element (stop codon) (SEQ ID NO:21); (3) a Kozak, 3×FLAG-EGF, flanked by a 2A sequence (SEQ ID NO:19); or (4) a Kozak, 3×FLAG-EGF sequence flanked by a 2A sequence followed by a termination element (stop codon) (SEQ ID NO:20).

In this Example, the level of innate immune response genes were monitored in cells by plating $0.1\times10^6$ cells into each well of a 12 well plate. After 1 day, 1 μg of linear or circular RNA was transfected into each well using a lipid-based transfection reagent (Invitrogen). Twenty-four hours after transfection, total RNA was isolated from cells using a phenol-based extraction reagent (Invitrogen). Total RNA (500 ng) was subjected to reverse transcription to generate cDNA. qRT-PCR analysis was performed using a dye-based quantitative PCR mix (BioRad).

Primer sequences used: Primers for GAPDH, F: AGGGCTGCTTTTAACTCTGGT (SEQ ID NO: 118), R: CCCCACTTGATTTTGGAGGGA (SEQ ID NO: 119); RIG-I, F: TGTGGGCAATGTCATCAAAA (SEQ ID NO: 40), R: GAAGCACTTGCTACCTCTTGC (SEQ ID NO: 42); MDA5, F: GGCACCATGGGAAGTGATT (SEQ ID NO: 64), R: ATTTGGTAAGGCCTGAGCTG (SEQ ID NO: 43); PKR, F: TCGCTGGTATCACTCGTCTG (SEQ ID NO: 44), R: GATTCTGAAGACCGCCAGAG (SEQ ID NO: 45); IFN-beta, F: CTCTCCTGTTGTGCTTCTCC (SEQ ID NO: 46), R: GTCAAAGTTCATCCTGTCCTTG (SEQ ID NO: 47).

Figure 25:
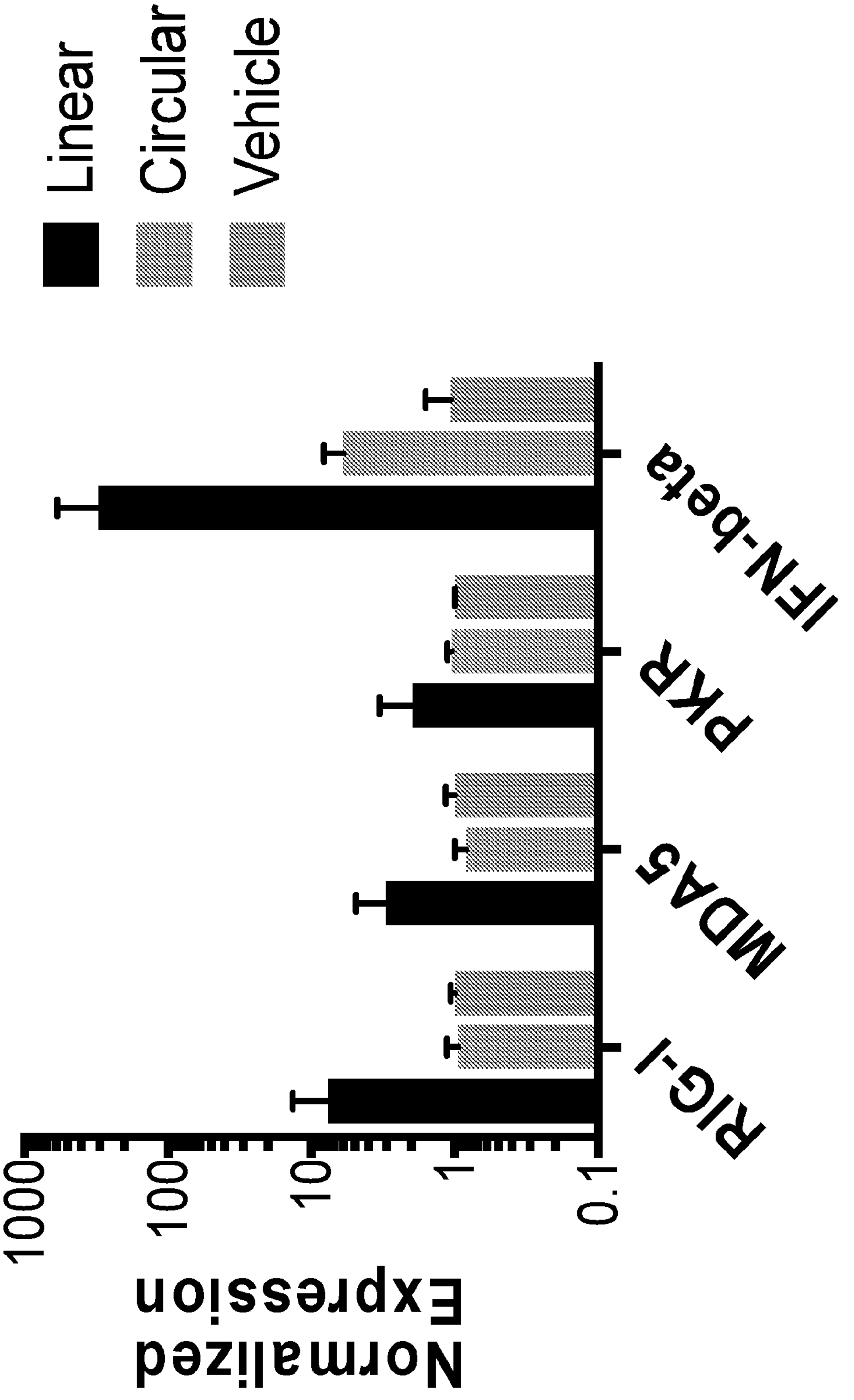
FIG. 25 is a graph showing qRT-PCR analysis of immune related genes from 293T cells transfected with circular RNA or linear RNA.

As shown in FIG. 25, qRT-PCR levels of immune related genes from 293T cells transfected with circular RNA showed reduction of RIG-I, MDA5, PKR and IFN-beta as compared to linear RNA transfected cells. Thus, induction of immunogenic related genes in recipient cells was reduced in circular RNA transfected cells, as compared to linear RNA transfected cells.

Example 36: Increased Expression from Synthetic Circular RNA Via Rolling Circle Translation in Cells This Example demonstrates increased expression from rolling circle translation of synthetic circular RNA in cells.

Circular RNAs were designed to include an IRES with a nanoluciferase gene or an EGF negative control gene without a termination element (stop codon). Cells were transfected with EGF negative control (SEQ ID NO:22); nLUC stop (SEQ ID NO:23): EMCV IRES, stagger sequence (2A sequence), 3×FLAG tagged nLUC sequences, stagger sequence (2A sequence), and a stop codon; or nLUC stagger (SEQ ID NO:24): EMCV IRES, stagger sequence (2A sequence), 3×FLAG tagged nLUC sequences, and stagger sequence (2A sequence). As shown in the FIG. 26, both circular RNAs produced translation product having functional luciferase activity.

In this Example, translation of circular RNA was monitored in cells. Specifically, $0.1\times10^6$ cells were plated onto each well of a 12 well plate. After 1 day, 300 ng of circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

Figure 26:
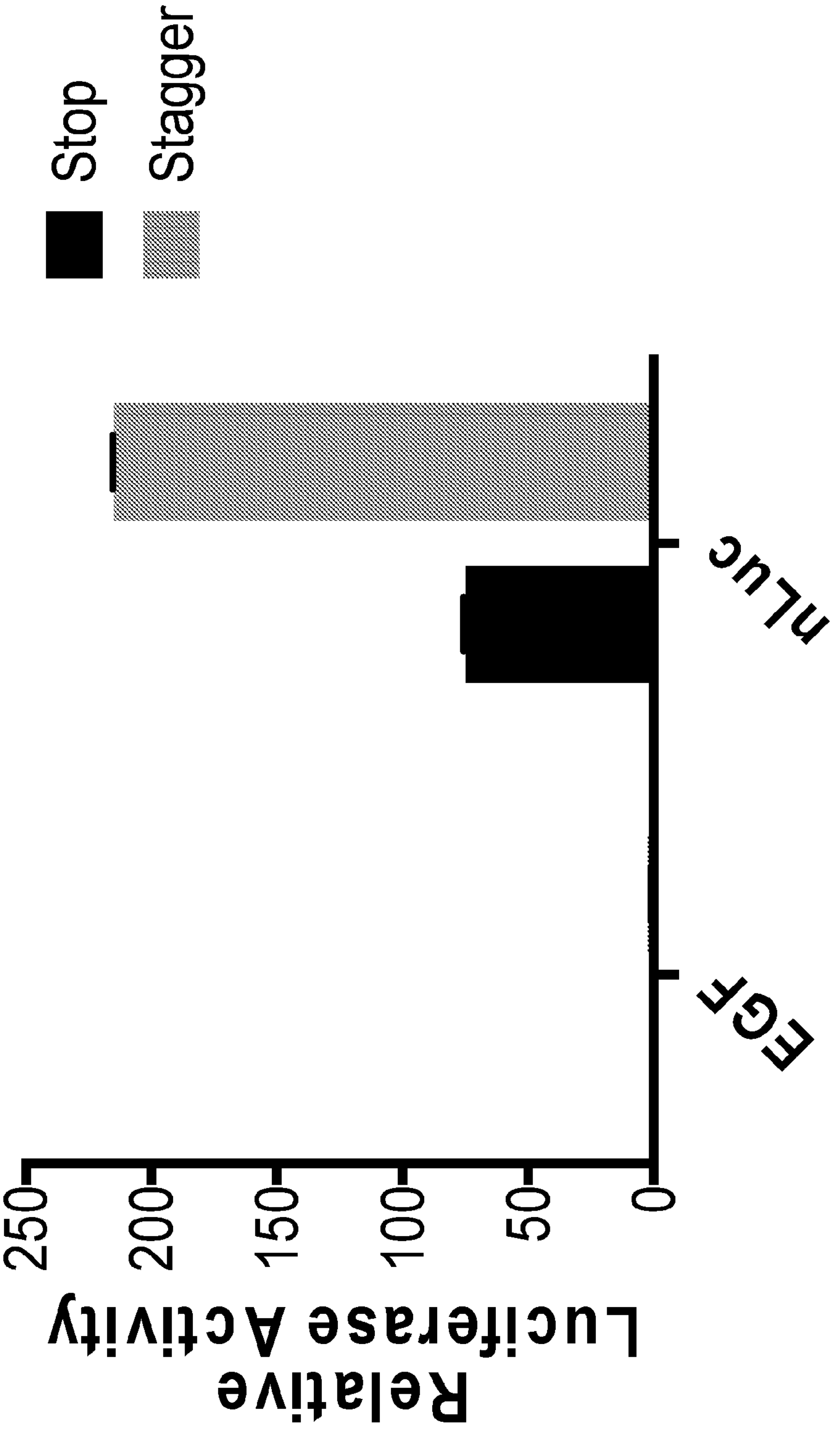
FIG. 26 is a graph showing luciferase activity of protein expressed from circular RNA via rolling circle translation.

As shown in FIG. 26, both circular RNAs expressed protein in cells. However, circular RNA with a stagger element, e.g., 2A sequence, that lacks a termination element (stop codon), produced higher levels of protein product having functional luciferase activity than circular RNA with a termination element (stop codon).

Example 37: Synthetic Circular RNA Translated in Cells

This Example demonstrates synthetic circular RNA translation in cells. Additionally, this Example shows that circular RNA produced more expression product than its linear counterpart.

Figure 27:
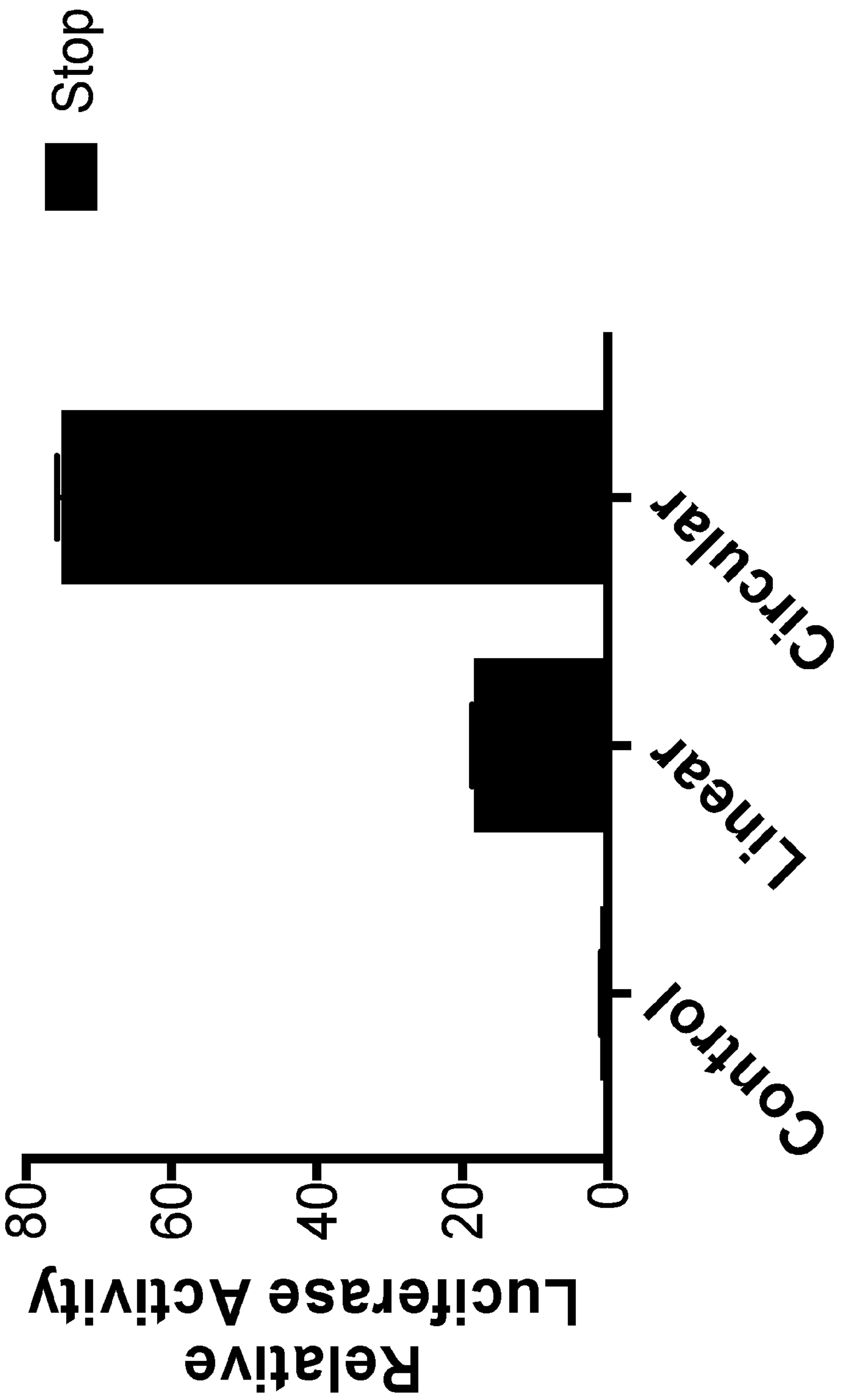
FIG. 27 is a graph showing luciferase activity of protein expressed from circular RNA or linear RNA.

Circular RNA was successfully transfected into 293T cells, as was its linear counterpart. Cells were transfected with circular RNA encoding EGF as a negative control (SEQ ID NO:22): EMCV IRES, stagger sequence (2A sequence), 3×FLAG tagged EGF sequences, stagger sequence (2A sequence); linear or circular nLUC (SEQ ID NO:23): EMCV IRES, stagger sequence (2A sequence), 3×FLAG tagged nLuc sequences, a stagger sequence (2A sequence), and stop codon. As shown in FIG. 27, circular RNA was translated into nanoluciferase in cells.

Linear or circular RNA translation was monitored in cells. Specifically, $0.1\times10^6$ cells were plated onto each well of a 12 well plate. After 1 day, 300 ng of linear or circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

As shown in FIG. 27, circular RNA translation product was detected in cells. In particular, circular RNA had higher levels of luciferase activity or increased protein produced as compared to its linear RNA counterpart.

Example 38: Rolling Circle Translation from Synthetic Circular RNA Produced Functional Protein Product in Cells This Example demonstrates rolling circle translation of functional protein product from synthetic circular RNA lacking a termination element (stop codon), e.g., having a stagger element lacking a termination element (stop codon), in cells. Additionally, this Example shows that circular RNA with a stagger element expressed more functional protein product than its linear counterpart.

Figure 28:
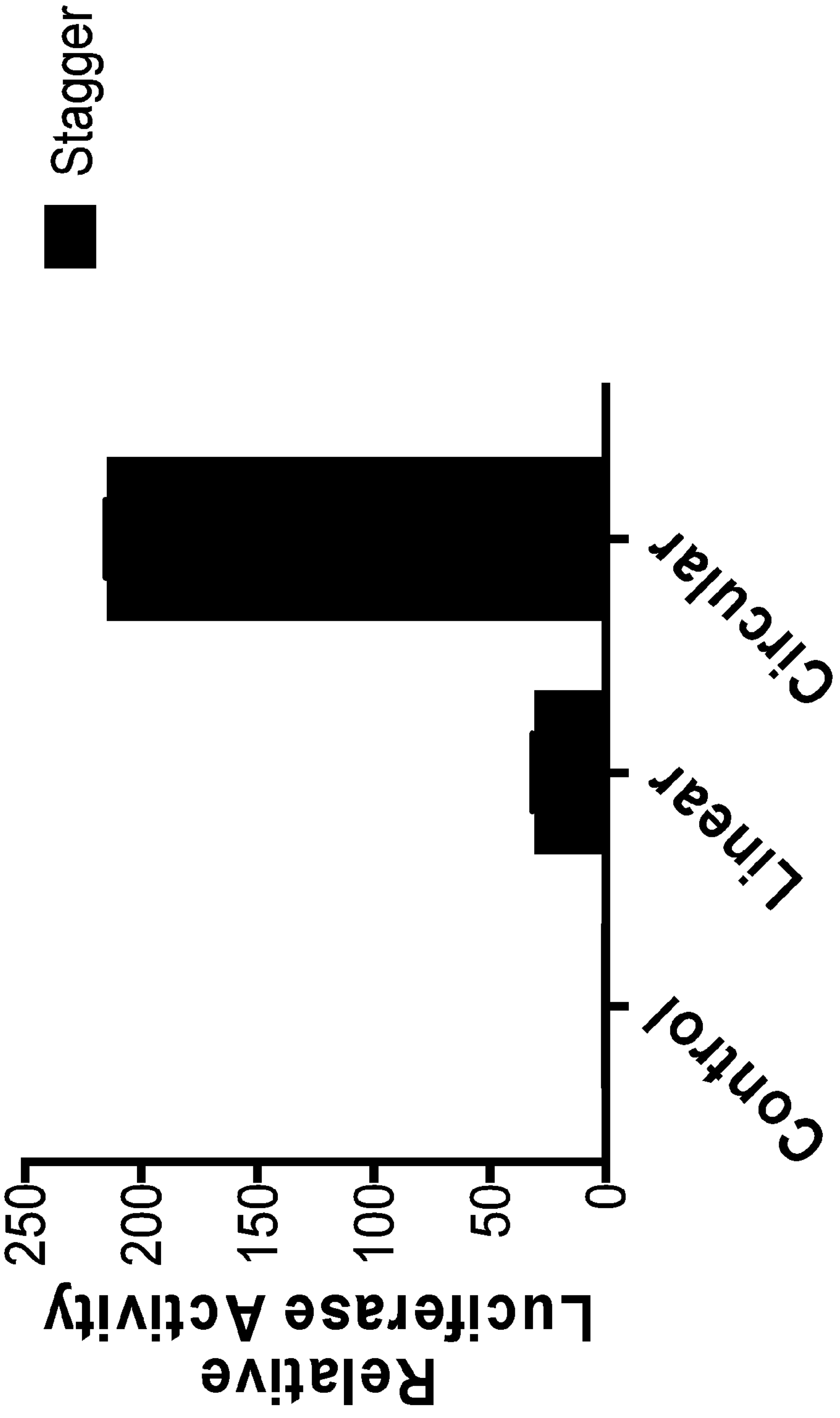
FIG. 28 is a graph showing luciferase activity of protein expressed from linear RNA or circular RNA via rolling circle translation.

Circular RNA was successfully transfected into 293T cells, as was its linear counterpart. Cells were transfected with circular RNA EGF negative control (SEQ ID NO:22); linear and circular nLUC (SEQ ID NO:24): EMCV IRES, stagger sequence (2A sequence), 3×FLAG tagged nLuc sequences, a stagger sequence (2A sequence). As shown in FIG. 28, circular RNA was translated into nanoluciferase in cells.

Linear or circular RNA translation was monitored in cells. Specifically, $0.1\times10^6$ cells were plated onto each well of a 12 well plate. After 1 day, 300 ng of linear or circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

As shown in FIG. 28, circular RNA translation product was detected in cells. In particular, circular RNA without a termination element (stop codon) produced higher levels of protein product having functional luciferase activity than its linear RNA counterpart.

Example 39: Synthetic Circular RNA Translated Via IRES Initiation in Cells

This Example demonstrates synthetic circular RNA translation initiation with an IRES in cells.

Circular RNAs were designed to include a Kozak sequence or IRES with a nanoluciferase gene or an EGF negative control gene. Cells were transfected with EGF negative control (SEQ ID NO:22), nLUC Kozak (SEQ ID NO:25): Kozak sequence, 1×FLAG tagged EGF sequence, a stagger sequence (T2A sequence), 1×FLAG tagged nLUC, stagger sequence (P2A sequence), and a stop codon; or nLUC IRES (SEQ ID NO:23): EMCV IRES, stagger sequence (2A sequence), 3×FLAG tagged nLUC sequences, stagger sequence (2A sequence) and a stop codon. As shown in the FIG. 29, the circular RNA with an IRES demonstrated higher levels of luciferase activity, corresponding to higher protein levels, as compared to circular RNA with a Kozak sequence.

In this Example, translation of circular RNA was monitored in cells. Specifically, $0.1\times10^6$ cells were plated onto each well of a 12 well plate. After 1 day, 300 ng of circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

Figure 29:
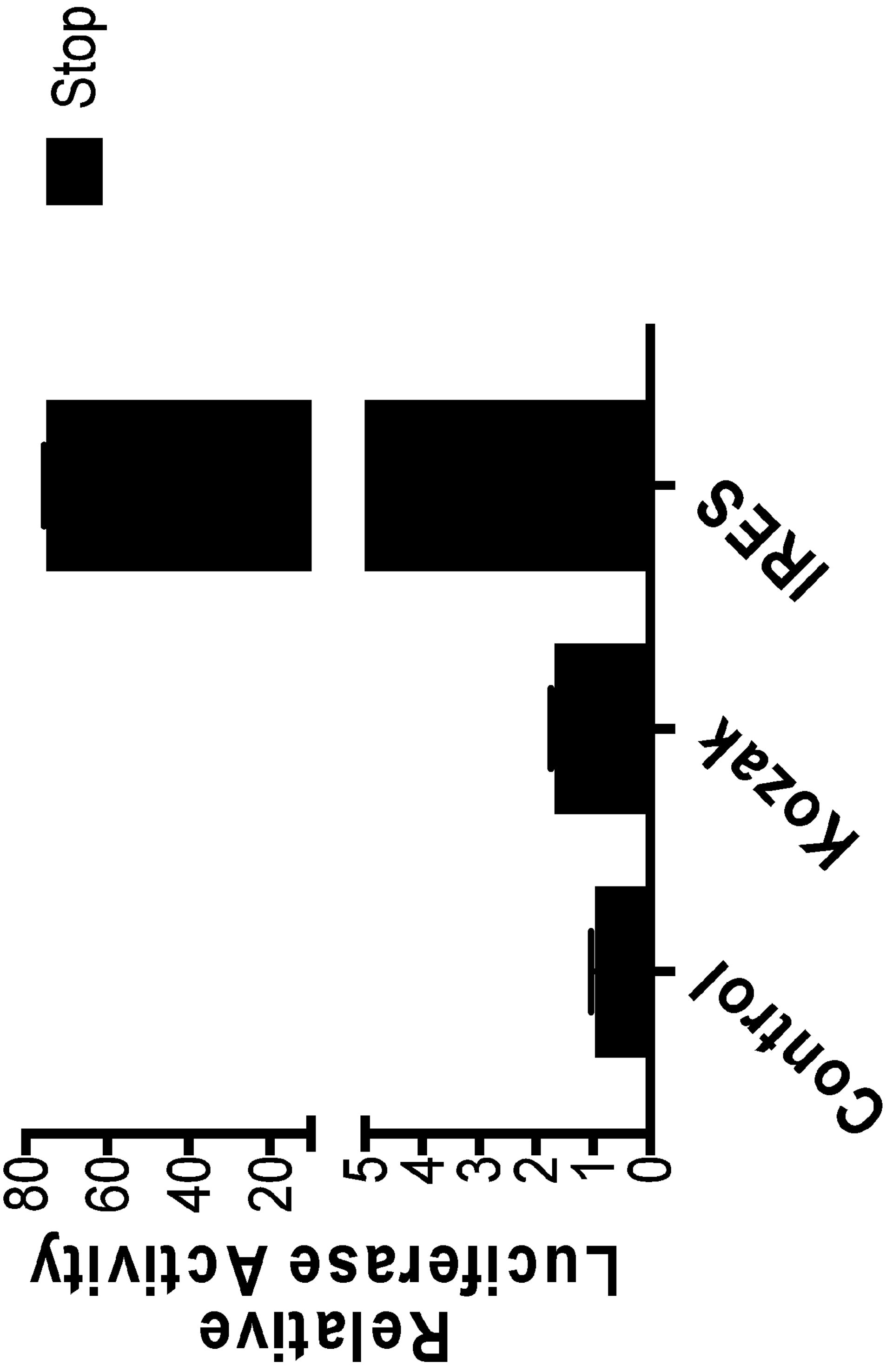
FIG. 29 is a graph showing luciferase activity of protein expressed from circular RNA via IRES translation initiation.

As shown in FIG. 29, circular RNA initiated protein expression with an IRES and produced higher levels of protein product having functional luciferase activity than circular RNA with Kozak initiated protein expression.

Example 40: Rolling Circle Translation of Synthetic Circular RNA in Cells

This Example demonstrates greater protein production via rolling circle translation of synthetic circular RNA in cells that initiated protein production with an IRES.

Circular RNAs were designed to include an a Kozak sequence or IRES with a nanoluciferase gene or an EGF negative control with or without a termination element (stop codon). Cells were transfected with EGF negative control (SEQ ID NO:22); nLUC IRES stop (SEQ ID NO:23): EMCV IRES, stagger sequence (2A sequence), 3×FLAG tagged nLUC sequences, stagger sequence (2A sequence) and a stop codon; or nLUC IRES stagger (SEQ ID NO:24): EMCV IRES, stagger sequence (2A sequence), 3×FLAG tagged nLUC sequences, and stagger sequence (2A sequence). As shown in the FIG. 30, both circular RNAs produced expression product demonstrated rolling circle translation and the circular RNA without a termination element an IRES (e.g., without a Kozak sequence) initiated and produced higher levels of protein product with functional luciferase activity than circular RNA with a termination element out an IRES (e.g., with a Kozak sequence), demonstrating rolling circle translation.

In this Example, translation of circular RNA was monitored in cells. Specifically, $0.1\times10^6$ cells were plated onto each well of a 12 well plate. After 1 day, 300 ng of circular RNA was transfected into each well using a lipid-based transfection reagent (Invitrogen). After 24 hrs, cells were harvested by adding 100 µl of RIPA buffer. Nanoluciferase activity in lysates was measured using a luciferase assay system according to its manufacturer's protocol (Promega).

Figure 30:
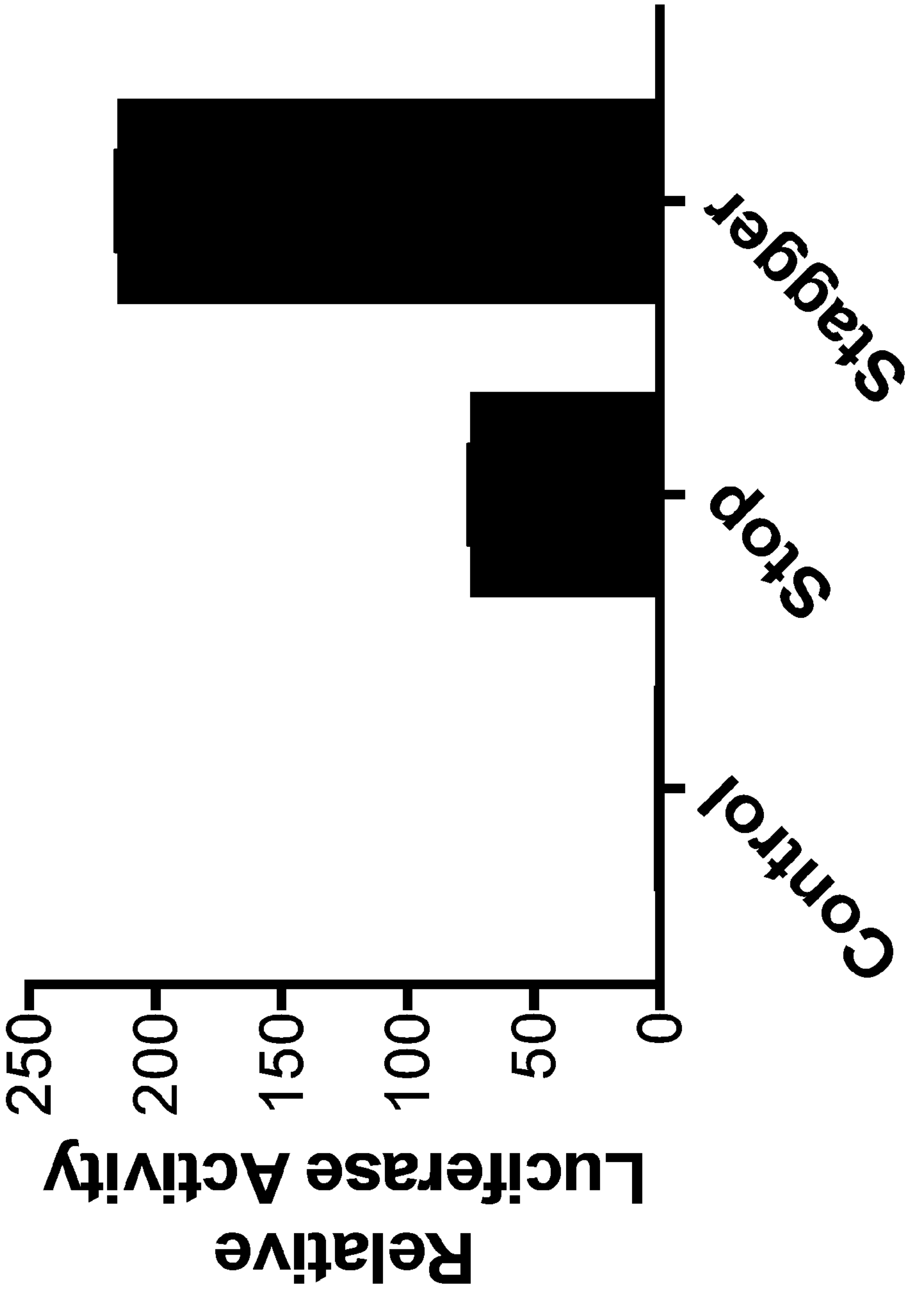
FIG. 30 is a graph showing luciferase activity of protein expressed from circular RNA via IRES initiation and rolling circle translation.

As shown in FIG. 30, circular RNA was translated into protein in cells via a rolling circle method given from both circular RNAs. However, the circular RNA that lacked a termination element (stop codon). However, the rolling circle translation of the circular RNA initiated greater protein production with an IRES and produced more protein product having functional luciferase activity as compared to a circular RNA with a termination element Kozak translation initiation.

Example 41: Increased Protein Expressed from Circular RNA

This Example demonstrates demonstrates synthetic circular RNA translation in cells. Additionally, this Example shows that circular RNA produced more expression product of the correct molecular weight than its linear counterpart.

Linear and circular RNAs were designed to include a nanoluciferase gene with a termination element (stop codon). Cells were transfected with vehicle: transfection reagent only; linear nLUC (SEQ ID NO:23): EMCV IRES, stagger element (2A sequence), 3×FLAG tagged nLuc sequences, a stagger element (2A sequence), and termination element (stop codon); or circular nLUC (SEQ ID NO:23): EMCV IRES, stagger element (2A sequence), 3×FLAG tagged nLuc sequences, a stagger element (2A sequence), and a termination element (stop codon). As shown in the FIG. 31, circular RNA produced greater levels of protein having the correct molecular weight as compared to linear RNA.

After 24 hrs, cells were harvested by adding 100 µl of RIPA buffer. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit and western blot band intensity was measured by ImageJ.

Figure 31:
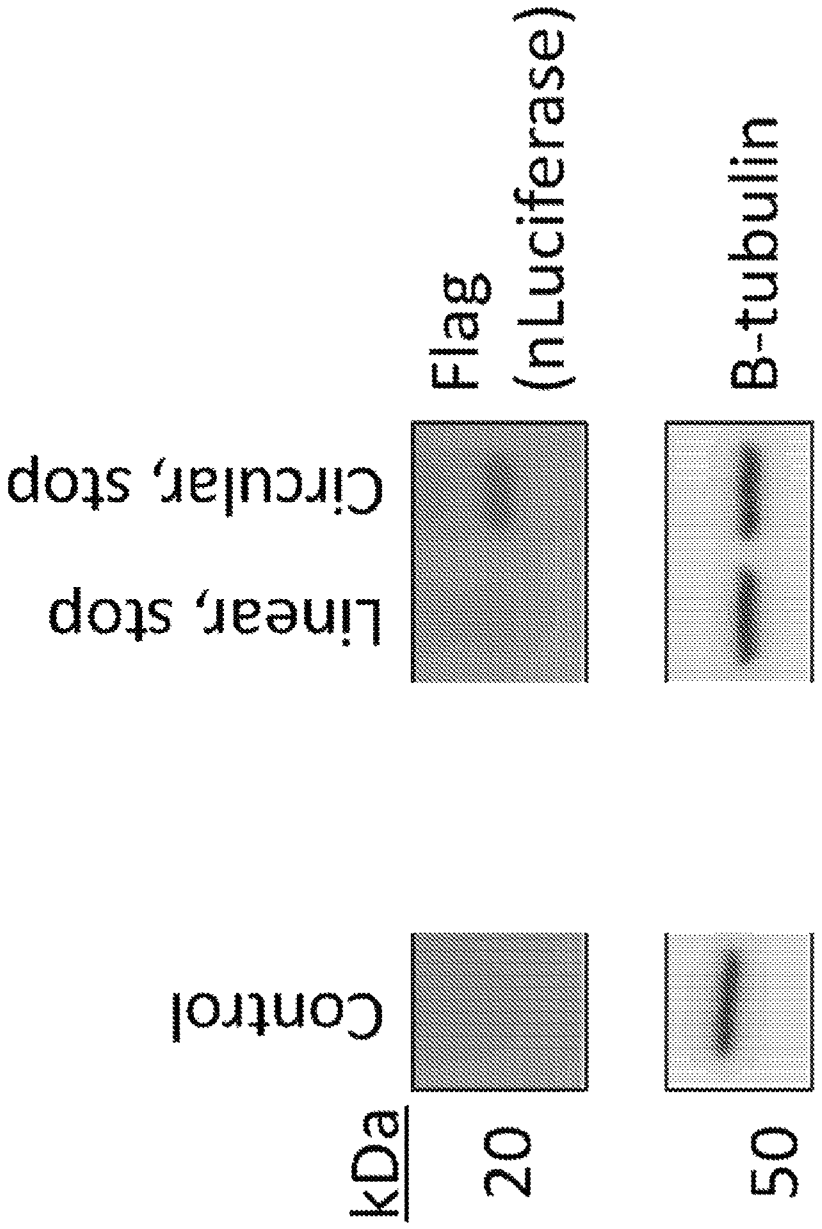
FIG. 31 is an image showing a protein blot of expression products from circular RNA or linear RNA.

As shown in FIG. 31, circular RNA was translated into protein in cells. In particular, circular RNA produced higher levels of protein having the correct molecular weight as compared to its linear RNA counterpart.

Example 42: Rolling Circle Translation of Synthetic Circular RNA Produced Discrete Protein Products in Cells This Example demonstrates discrete protein products were translated via rolling circle translation from synthetic circular RNA lacking a termination element (stop codon), e.g., having a stagger element in lieu of a termination element (stop codon), in cells. Additionally, this Example shows that circular RNA with a stagger element expressed more protein product having the correct molecular weight than its linear counterpart.

Circular RNAs were designed to include a nanoluciferase gene with a stagger element in place of a termination element (stop codon). Cells were transfected with vehicle: transfection reagent only; linear nLUC (SEQ ID NO:24): EMCV IRES, stagger element (2A sequence), 3× FLAG tagged nLuc sequences, and a stagger element (2A sequence); or circular nLUC (SEQ ID NO:24): EMCV IRES, stagger element (2A sequence), 3×FLAG tagged nLuc sequences, and a stagger element (2A sequence). As shown in the FIG. 32, circular RNA produced greater levels of protein having the correct molecular weight as compared to linear RNA.

After 24 hrs, cells were harvested by adding 100 µl of RIPA buffer. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit and western blot band intensity was measured by ImageJ.

Figure 32:
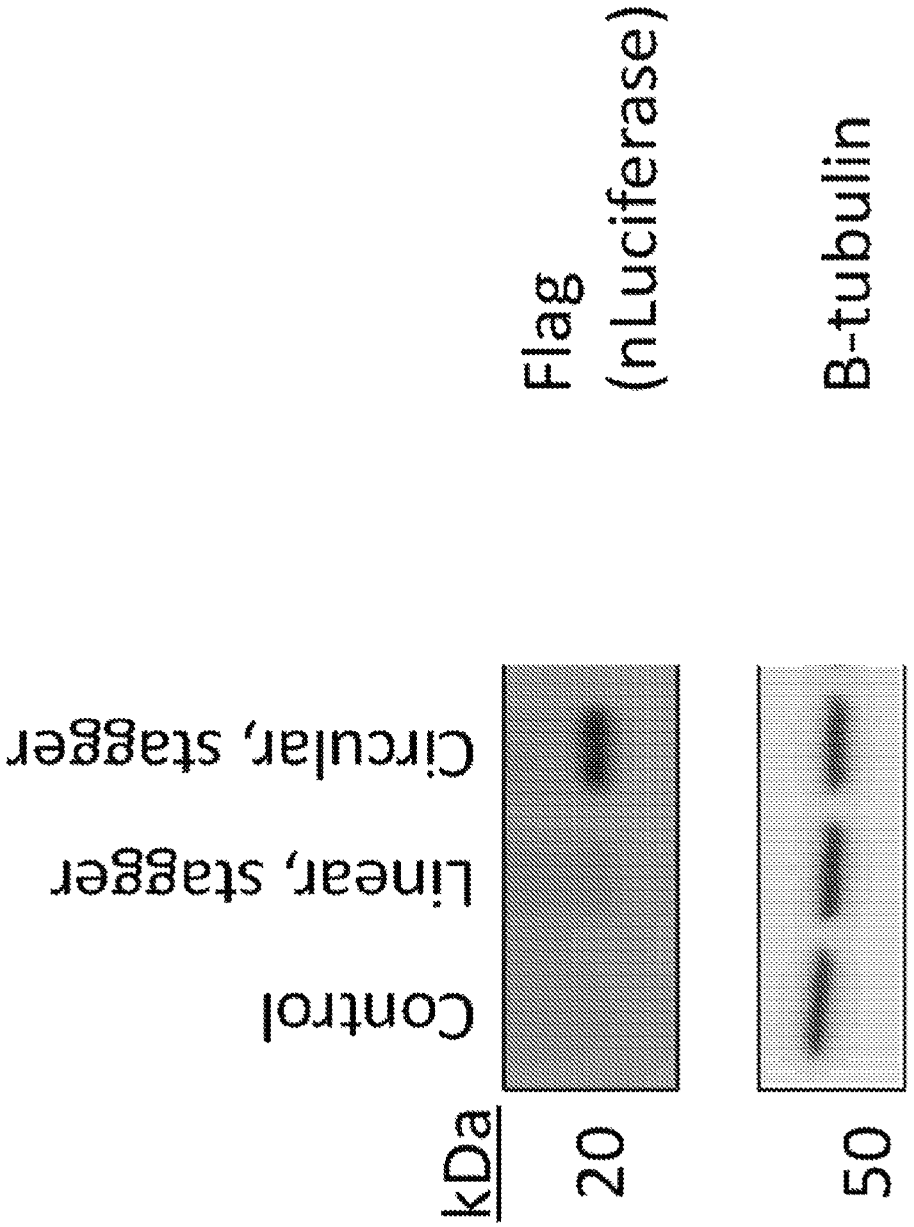
FIG. 32 is an image showing a protein blot of expression products from circular RNA or linear RNA.

As shown in FIG. 32, circular RNA translation product was detected in cells. In particular, circular RNA without a termination element (stop codon) produced higher levels of discrete protein product having the correct molecular weight than its linear RNA counterpart.

Example 43: Preparation of Circular RNA with a Quasi-Double Stranded, Helical Structure This Example demonstrates circular RNA possessed both quasi-double stranded and helical structure.

A non-naturally occurring circular RNA was engineered to adopt a quasi-double stranded, helical structure. A similar structure was shown to be involved in condensation of a naturally occurring circular RNA that possessed a uniquely long in vivo half-life (Griffin et al 2014*, J Virol.* 2014 July; 88(13):7402-11. doi: 10.1128/JVI.00443-14, Guedj et al, *Hepatology.* 2014 December; 60(6):1902-10. doi: 10.1002/hep.27357).

In this Example, circular RNA was designed to encode a EMCV IRES, Nluc tagged with 3×FLAG as ORF and stagger sequence (EMCV 2A 3×FLAG Nluc 2A no stop). To evaluate RNA secondary structure, thermodynamic RNA structure prediction tool (RNAfold) was used (Vienna RNA). Additionally, RNA tertiary structure was analyzed using an RNA modeling algorithm.

Figure 33:
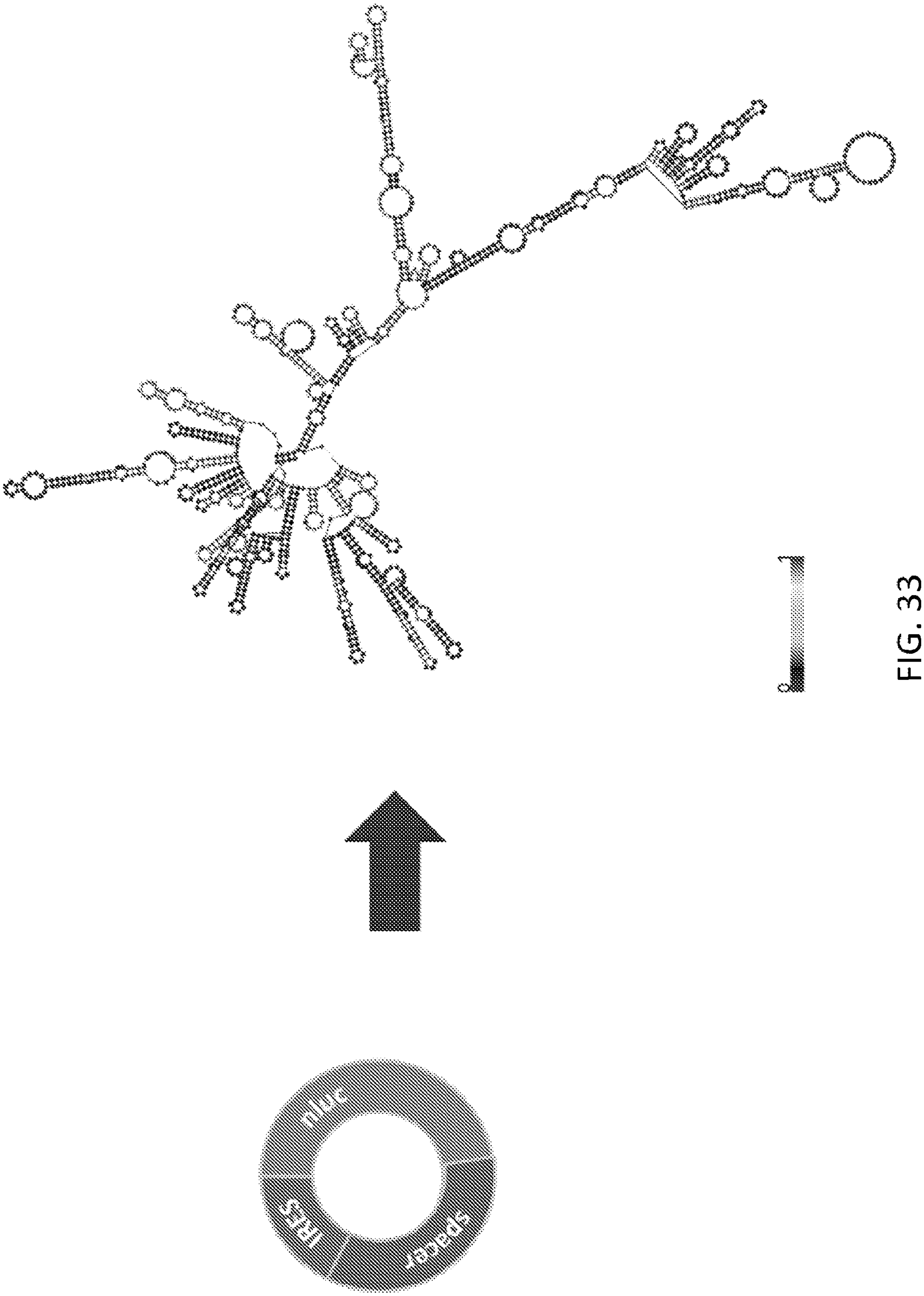
FIG. 33 shows predicted structure with a quasi-double stranded structure of an exemplary circular RNA.
Figure 34:
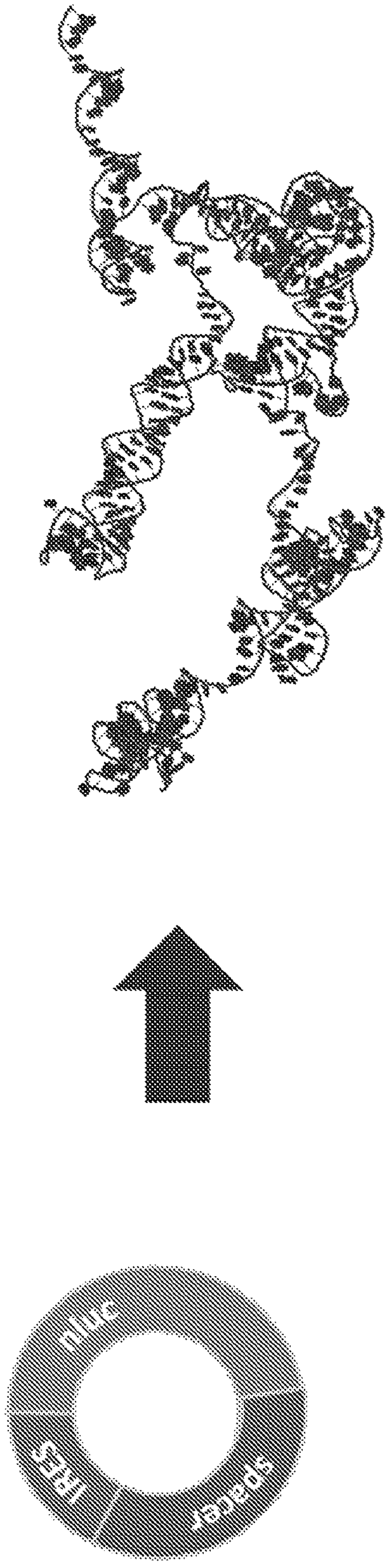
FIG. 34 shows predicted structure with a quasi-helical structure of an exemplary circular RNA.

As shown in FIGS. 33 and 34, circular RNA is modeled to have adopted a quasi-double stranded, helical structure.

Example 44: Preparation of Circular RNA with a Quasi-Helical Structure Linked with a Repetitive Sequence This Example demonstrates circular RNA can be designed to possess a quasi-helical structure linked with a repetitive sequence.

A non-naturally occurring circular RNA was engineered to adopt a quasi-helical structure linked with a repetitive sequence. A similar structure was shown to be involved in condensation of a naturally occurring circular RNA that possessed a uniquely long in vivo half-life (Griffin et al 2014, Guedj et al 2014).

In this Example, circular RNA was designed to encode a EMCV IRES, Nluc and spacer including a repetitive sequence (SEQ ID NO: 26). To evaluate RNA tertiary structure, an RNA modeling algorithm was used.

Figure 35:
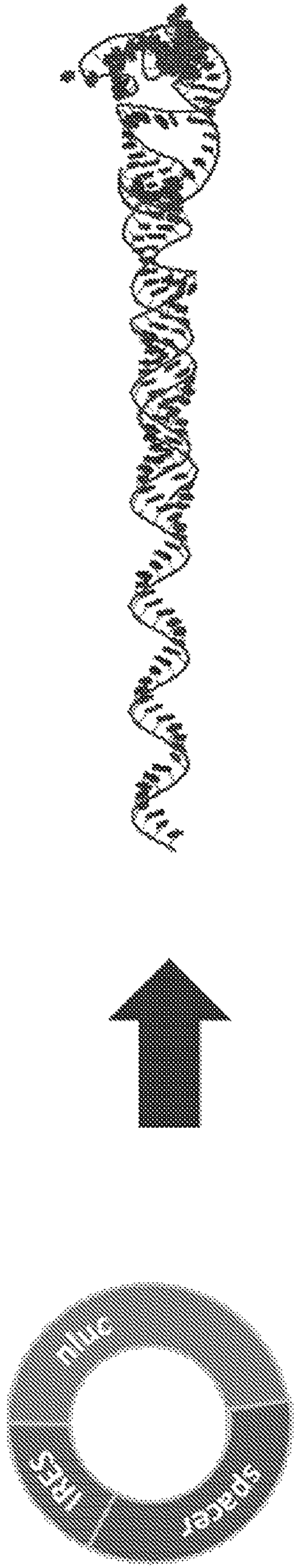
FIG. 35 shows predicted structure with a quasi-helical structure linked with a repetitive sequence of an exemplary circular RNA.

As shown in FIG. 35, circular RNA is modeled to have adopted a quasi-helical structure.

Example 45: Circularized RNA is Circular and not Concatemeric

This Example demonstrates circular RNA degradation by RNAse H produced nucleic acid degradation products consistent with a circular and not a concatemeric RNA.

RNA, when incubated with a ligase, can either not react or form an intra- or intermolecular bond, generating a circular (no free ends) or a concatemeric RNA, respectively. Treatment of each type of RNA with a complementary DNA primer and RNAse H, a nonspecific endonuclease that recognizes DNA/RNA duplexes, is expected to produce a unique number of degradation products of specific sizes depending on the starting RNA material.

As shown in the following Example, a ligated RNA was shown to be circular and not concatemeric based on the number and size of RNAs produced by RNAse H degradation.

Circular RNA and linear RNA containing EMCV T2A 3×FLAG-Nluc P2A were generated.

To test circularization status of the RNA (1299 nts), 0.05 pmole/μl of linear or circular RNA was incubated with 0.25 U/μl of RNAse H, an endoribonuclease that digests DNA/RNA duplexes, and 0.3 pmole/μl oligomer against 1037-1046 nts of RNA (CACCGCTCAGGACAATCCTT, SEQ ID NO: 55) at 37° C. for 20 min. After incubation, the reaction mixture was analyzed by 6% denaturing PAGE.

For the linear RNA used described above, it is expected that after binding of the DNA primer and subsequent cleavage by RNAse H two cleavage products are obtained of 1041 nt and 258 nt. A concatemer is expected to produce three cleavage products of 258, 1041 and 1299 nt. A circular is expected to produce a single 1299 nt cleavage product.

Figure 36:
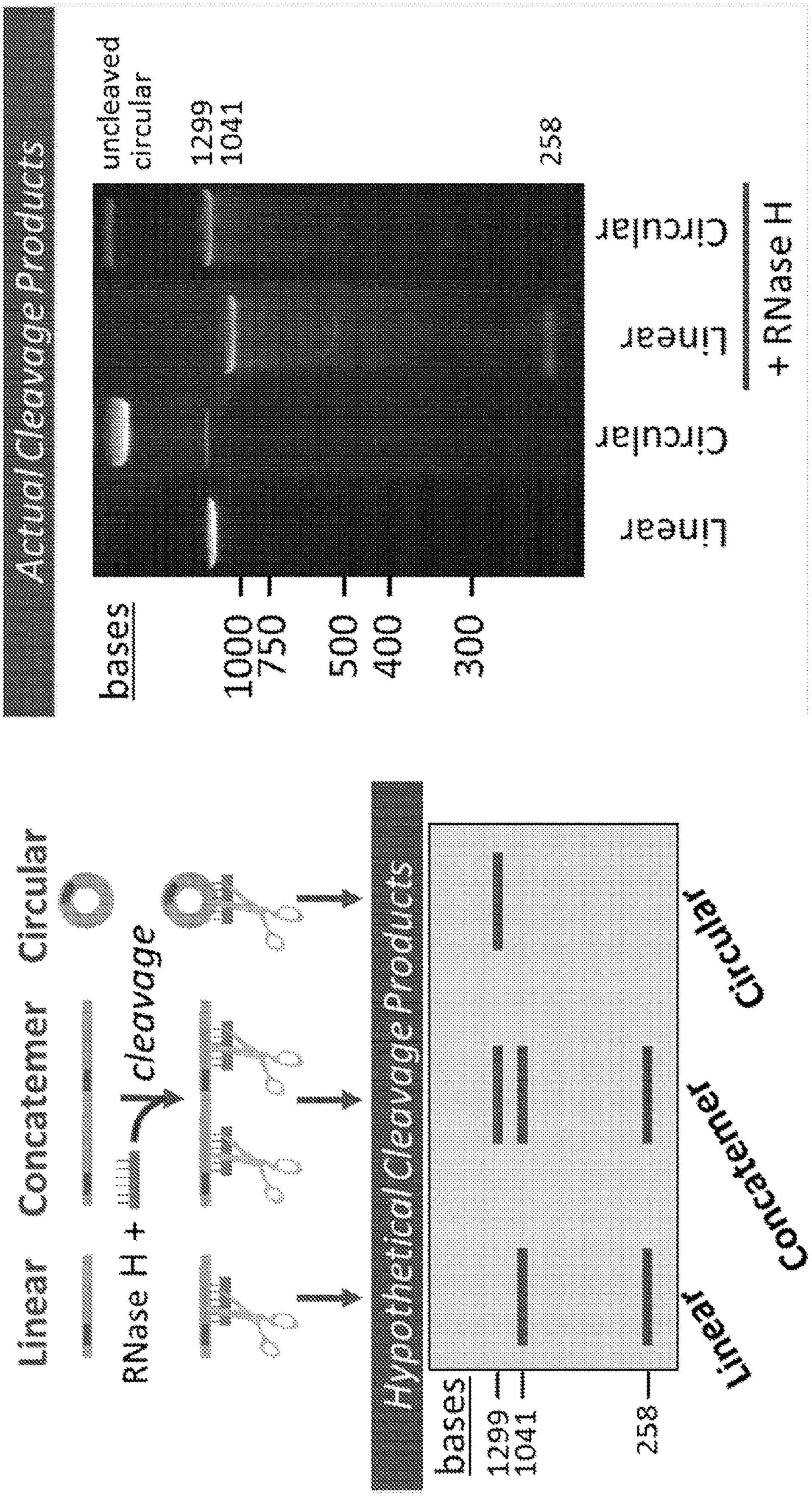
FIG. 36 demonstrates experimental data that degradation by RNAse H of an exemplary circular RNA produced nucleic acid degradation products consistent with a circular and not a concatemeric RNA.

The number of bands in the linear RNA lane incubated with RNAse endonuclease produced two bands of 1041 nt and 258 nt as expected, whereas a single band of 1299 nt was produced in the circular RNA lane (see FIG. 36), indicating that the circular RNA was in fact circular and not concatemeric.

Example 46: Preparation of Large circRNAs

This Example demonstrates the generation of circular polyribonucleotide from in the range of about 20 bases to about 6.2 Kb.

A non-naturally occurring circular RNA engineered to include one or more desirable properties was produced in a range of sizes depending on the desired function. As shown in the following Example, linear RNA of up to 6200 nt was circularized.

The plasmid pCDNA3.1/CAT (6.2 kb) was used here. Primers were designed to anneal to pCDNA3.1/CAT at regular intervals to generate DNA oligonucleotides corresponding to 500 nts, 1000 nts, 2000 nts, 4000 nts, 5000 nts and 6200 nts. In vitro transcription of the indicated DNA oligonucleotides was performed to generate linear RNA of the corresponding sizes. Circular RNAs were generated from these RNA oligonucleotides using splint DNA.

To measure circularization efficiency of RNA, 6 different sizes of linear RNA (500 nts, 1000 nts, 2000 nts, 4000 nts, 5000 nts and 6200 nts) were generated. They were circularized using a DNA splint and T4 DNA ligase 2. As a control, one reaction was performed without T4 RNA ligase. Half of the circularized sample was treated with RNAse R to remove linear RNA.

Figure 37:
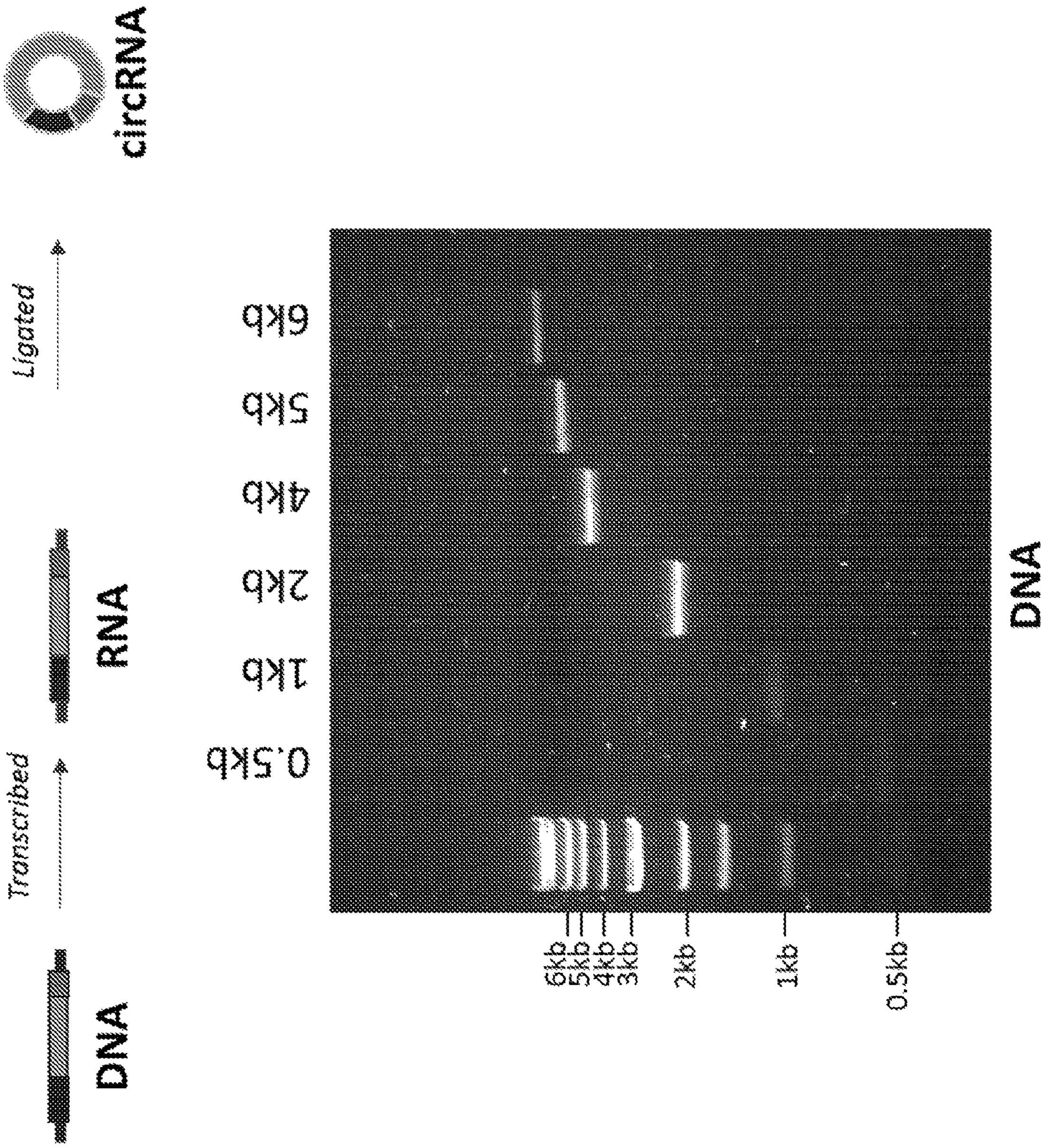
FIG. 37 shows an electrophoresis image of the different lengths of DNA that were generated for the creation of a wide variety of RNA lengths.
Figure 38:
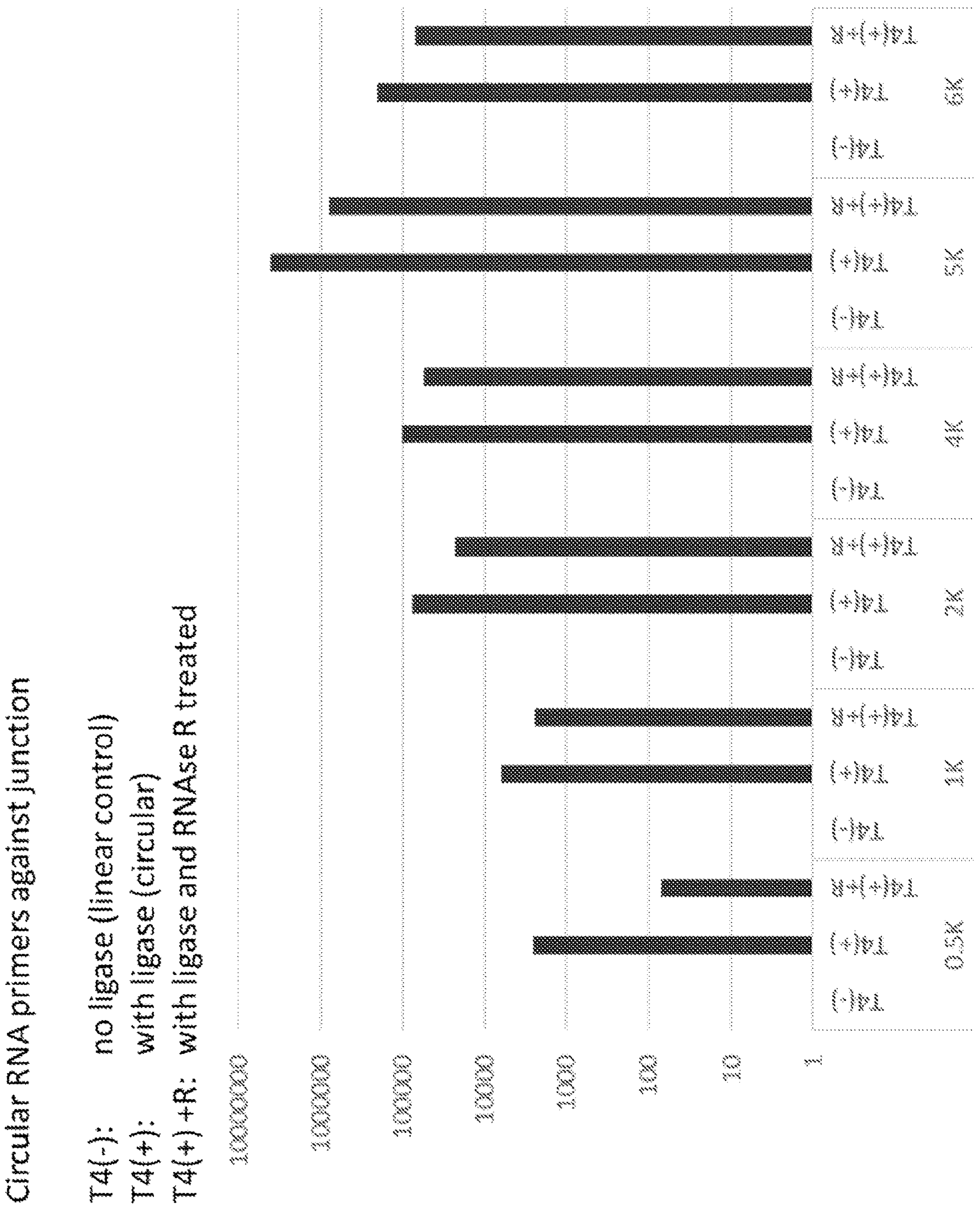
FIG. 38 shows experimental data that confirmed the circularization of RNAs using RNAse R treatment and qPCR analysis against circular junctions of a wide variety of lengths.

To monitor circularization efficiency, each sample was analyzed using qPCR. As shown in FIG. 37, circular RNA was generated from a wide variety of DNA of different lengths. As shown in FIG. 38, circularization of RNA was confirmed using RNAse R treatment and qPCR analysis against circular junctions. This Example demonstrates circular RNA production for a variety of lengths.

Example 47: Circular RNA Engineered with a Protein Binding Site

This Example demonstrates generation of a circular RNA with a protein binding site.

Figure 39:
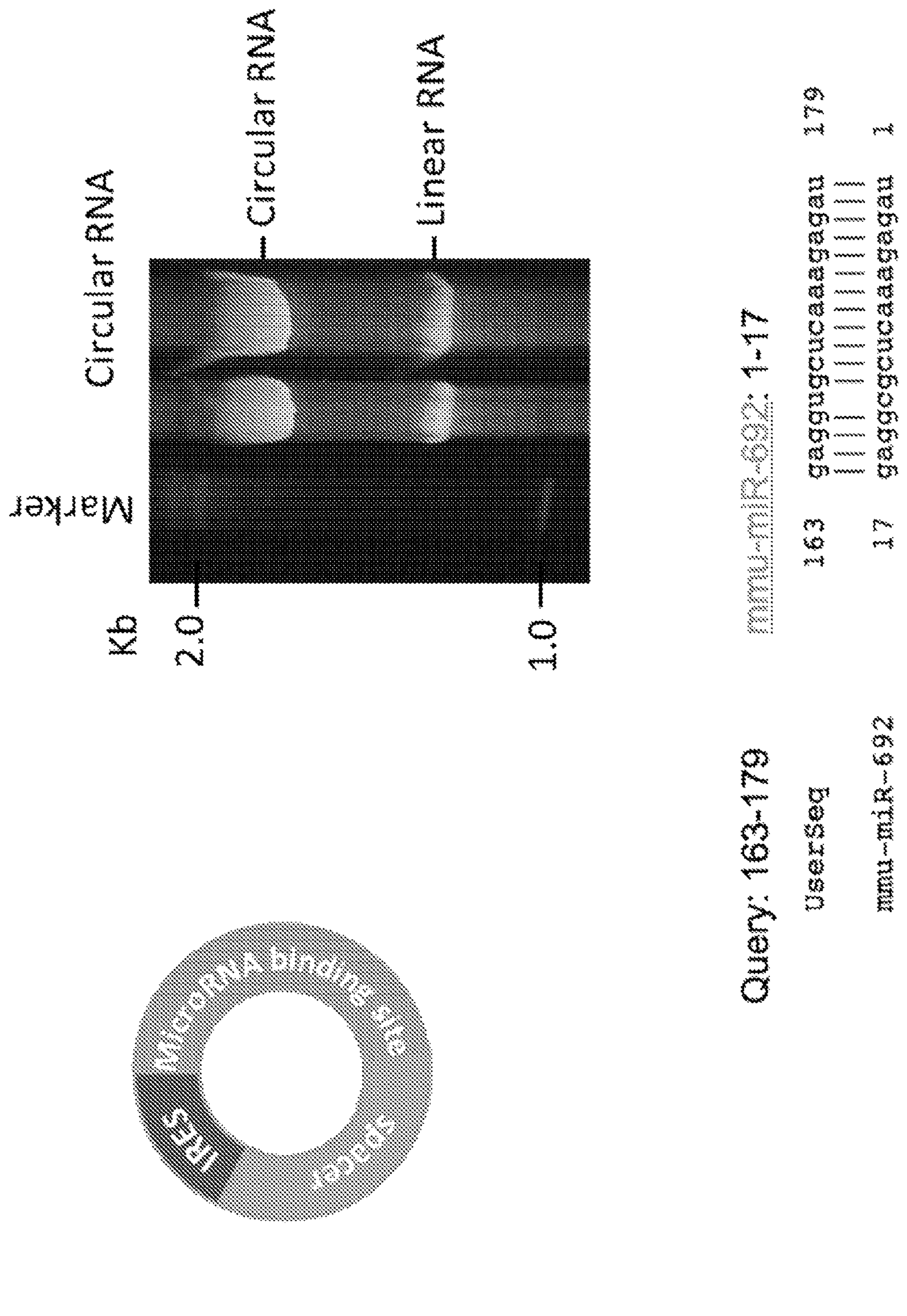
FIG. 39 shows generation of exemplary circular RNA with a protein binding site.

In this Example, one circular RNA is designed to include CVB3 IRES (SEQ ID NO:56), and an ORF encoding *Gaussia* luciferase (Gluc) (SEQ ID NO:57) followed by at least one protein binding site. For a specific example, a HuR binding sequence (SEQ ID NO:52) from Sindbis virus 3'UTR is used to test the effect of protein binding to circular RNA immunogenicity. HuR binding sequence comprises two elements, URE (U-rich element; SEQ ID NO: 50) and CSE (Conserved sequence element; SEQ ID NO: 51). Circular RNA without HuR binding sequence or with URE is used as a control. Part of the *Anabaena* autocatalytic intron and exon sequences are located prior to the CVB3 IRES (SEQ ID NO:56). The circular RNAs are generated in vitro as described. As shown in FIG. 39, circular RNA was generated to contain an HuR binding site.

To monitor the effect of RNA binding protein on circular RNA immunogenicity, cells are plated into each well of a 96 well plate. After 1 day, 500 ng of circular RNA is transfected into each well using a lipid-based transfection reagent (Invitrogen). Translation efficiency/RNA stability/immunogenicity are monitored daily, up to 72 hrs. Media is harvested to monitor Gluc activity. Cell lysate for measuring RNA level is prepared with a kit that allows measurements of relative gene expression by real-time RT-PCR (Invitrogen).

Translation efficiency is monitored by measuring Gluc activity with *Gaussia* luciferase flash assay kit according to the manufacturer's instruction (Pierce).

For qRT-PCR analysis, cDNA is generated with cell lysate preparation kit according to manufacturer's instruction (Invitrogen). qRT-PCR analysis is performed in triplicate using a PCR master mix (Brilliant II SYBR Green qRT-PCR Master Mix) and a PCR cycler (LightCycler 480). Circular RNA stability is measured by primers against Nluc. mRNA levels for well-known innate immunity regulators such as RIG-I, MDA5, OAS, OASL, and PKR are quantified and normalized to actin values.

Example 48: Preparation of Circular RNA with Regulatory Nucleic Acid Sites

This Example demonstrates in vitro production of circular RNA with a regulatory RNA binding site.

Different cell types possess unique nucleic acid regulatory machinery to target specific RNA sequences. Encoding these specific sequences in a circular RNA could confer unique properties in different cell types. As shown in the following Example, circular RNA was engineered to encode a microRNA binding site.

In this Example, circular RNA included a sequence encoding a WT EMCV IRES, a mir692 microRNA binding site (GAGGUGCUCAAAGAGAU (SEQ ID NO: 121)), and two spacer elements flanking the IRES-ORF.

The circular RNA was generated in vitro. Unmodified linear RNA was in vitro transcribed from a DNA template including all the motifs listed above, in addition to the T7 RNA polymerase promoter to drive transcription. Transcribed RNA was purified with an RNA cleanup kit (New England Biolabs, T2050), treated with RNA 5'-phosphohydrolase (RppH) (New England Biolabs, M0356) following the manufacturer's instructions, and purified again with an RNA purification column. RppH treated RNA was circularized using a splint DNA (GGCTATTCCCAATAGCCGTT (SEQ ID NO: 122)) and T4 RNA ligase 2 (New England Biolabs, M0239). Circular RNA was Urea-PAGE purified (FIG. 40), eluted in a buffer (0.5M Sodium Acetate, 0.1% SDS, 1 mM EDTA), ethanol precipitated and resuspended in RNase free water.

Figure 40:
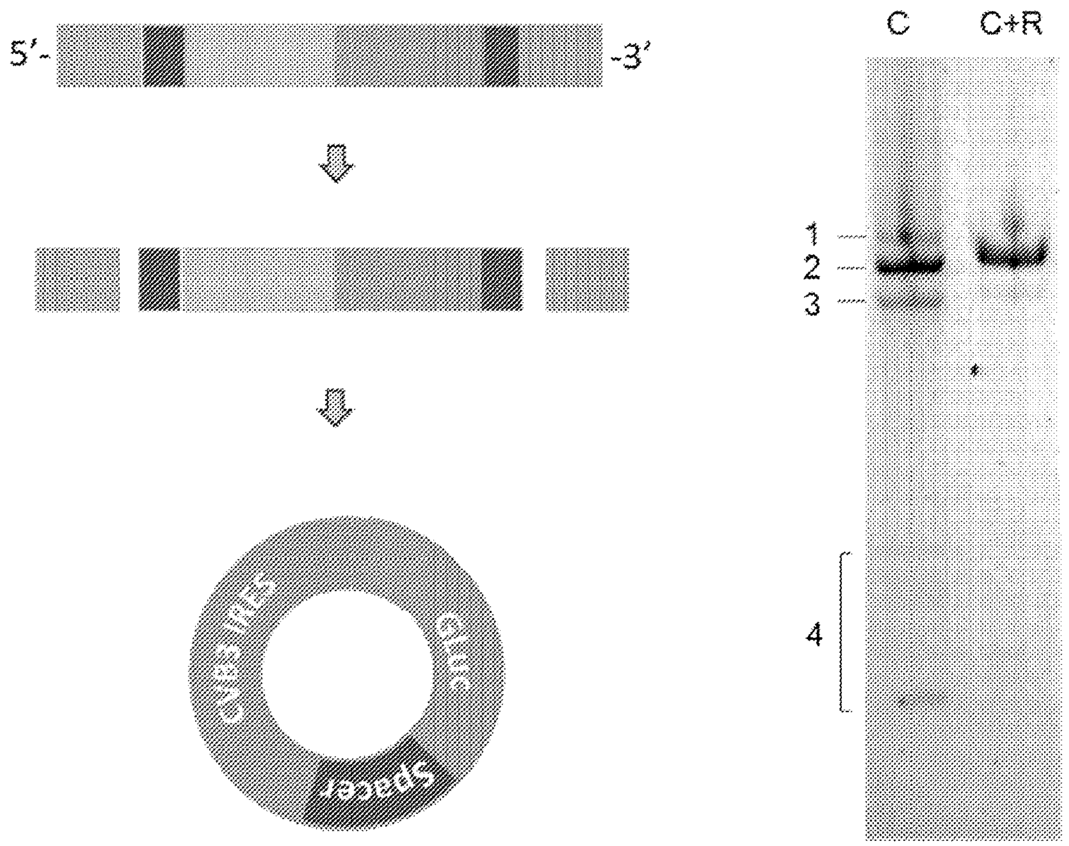
FIG. 40 shows generation of exemplary circular RNA with a miRNA binding site.

As shown in FIG. 40, circular RNA was generated with a miRNA binding site.

Example 49: Self-Splicing of Circular RNA

This example demonstrates the ability to produce a circular RNA by self-splicing.

For this Example, circular RNAs included a CVB3 IRES, an ORF encoding *Gaussia* Luciferase (GLuc), and two spacer elements flanking the IRES-ORF.

The circular RNA was generated in vitro. Unmodified linear RNA was in vitro transcribed from a DNA template including all the motifs listed above. In vitro transcription reactions included 1 μg of template DNA T7 RNA polymerase promoter, 10×T7 reaction buffer, 7.5 mM ATP, 7.5 mM CTP, 7.5 mM GTP, 7.5 mM UTP, 10 mM DTT, 40U RNase Inhibitor, and T7 enzyme. Transcription was carried out at 37° C. for 4h. Transcribed RNA was DNase treated with 1U of DNase I at 37° C. for 15 min. To favor circularization by self splicing, additional GTP was added to a final concentration of 2 mM, incubated at 55° C. for 15 min. RNA was then column purified and visualized by UREA-PAGE.

Figure 41:
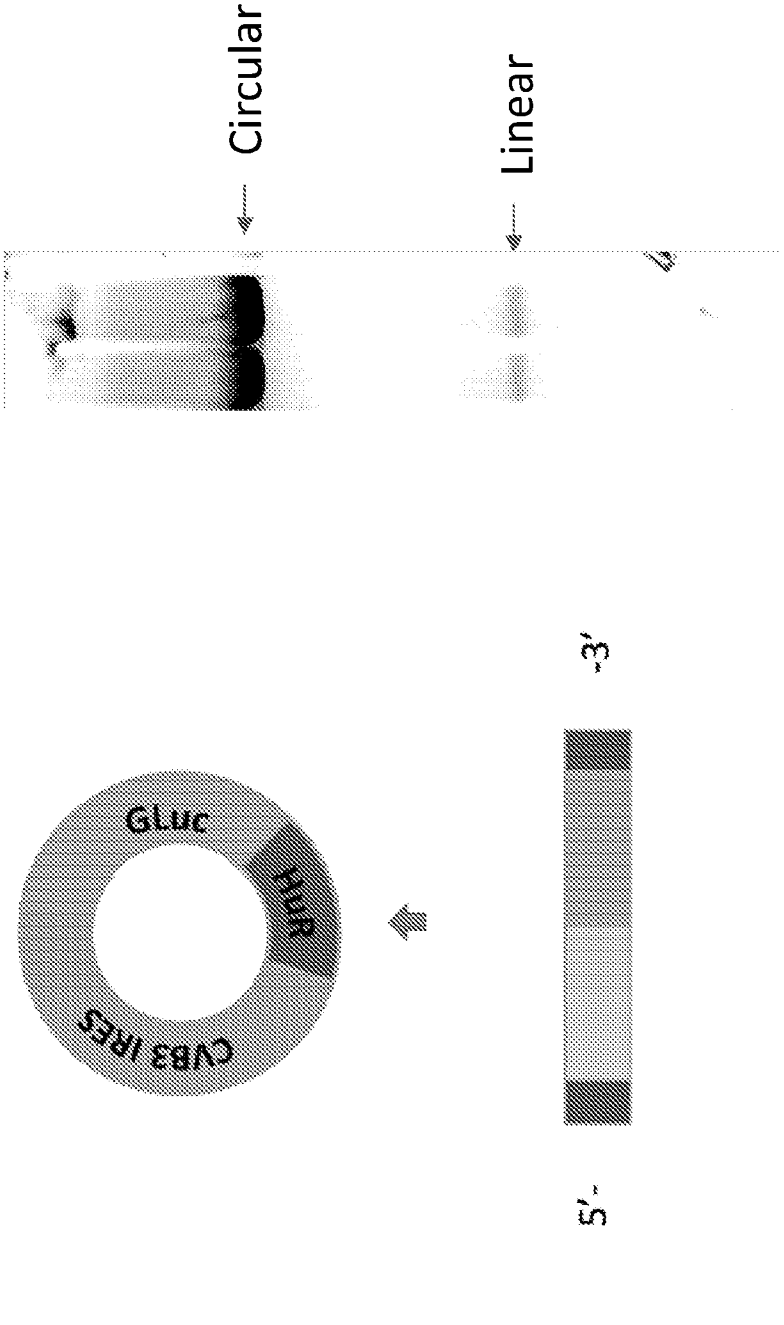
FIG. 41 shows generation of exemplary circular RNA by self-splicing.

FIG. 41 shows circular RNA generated by self-splicing.

Example 50: Circular RNA with a Splicing Element Comprising an Encryptogen

This Example demonstrates a circular RNA engineered to have reduced immunogenicity.

For this Example, a circular RNAs included a CVB3 IRES, an ORF encoding *Gaussia* Luciferase (GLuc), and two spacer elements flanking the IRES-ORF, these two spacer elements comprise a splicing element that are part of the *Anabaena* autocatalytic intron and exon sequences (SEQ ID NO:59).

The circular RNA is generated in vitro.

In this Example, the level of innate immune response genes is monitored in cells by plating cells into each well of a 12 well plate. After 1 day, 1 μg of linear or circular RNA is transfected into each well using a lipid-based transfection reagent (Invitrogen). Twenty-four hours after transfection, total RNA is isolated from cells using a phenol-based extraction reagent (Invitrogen). Total RNA (500 ng) is subjected to reverse transcription to generate cDNA. qRT-PCR analysis is performed using a dye-based quantitative PCR mix (BioRad).

qRT-PCR levels of immune related genes from BJ cells transfected with circular RNA comprising a splicing element are expected to show a reduction of RIG-I, MDA5, PKR and IFN-beta as compared to linear RNA transfected cells. Thus, induction of immunogenic related genes in recipient cells is expected to be reduced in circular RNA transfected cells, as compared to linear RNA transfected cells.

Example 51: Persistence of Circular RNA During Cell Division

This Example demonstrates the persistence of circular polyribonucleotide during cell division. A non-naturally occurring circular RNA engineered to include one or more desirable properties may persist in cells through cell division without being degraded. As shown in the following Example, circular RNA expressing *Gaussia* luciferase (GLuc) was monitored over 72h days in HeLa cells.

In this Example, a 1307 nt circular RNA included a CVB3 IRES, an ORF encoding *Gaussia* Luciferase (GLuc), and two spacer elements flanking the IRES-ORF.

Persistence of circular RNA over cell division was monitored in HeLa cells. 5000 cells/well in a 96-well plate were suspension transfected with circular RNA. Bright cell imaging was performed in a Avos imager (ThermoFisher) and cell counts were performed using luminescent cell viability assay (Promega) at 0h, 24 h, 48h, 72h, and 96h. *Gaussia* Luciferase enzyme activity was monitored daily as measure of protein expression and gLuc expression was monitored daily in supernatant removed from the wells every 24h by using the *Gaussia* Luciferase activity assay (Thermo Scientific Pierce). 50 μl of 1×Gluc substrate was added to 5 μl of plasma to carry out the Gluc luciferase activity assay. Plates were read right after mixing on a luminometer instrument (Promega).

Figure 42:
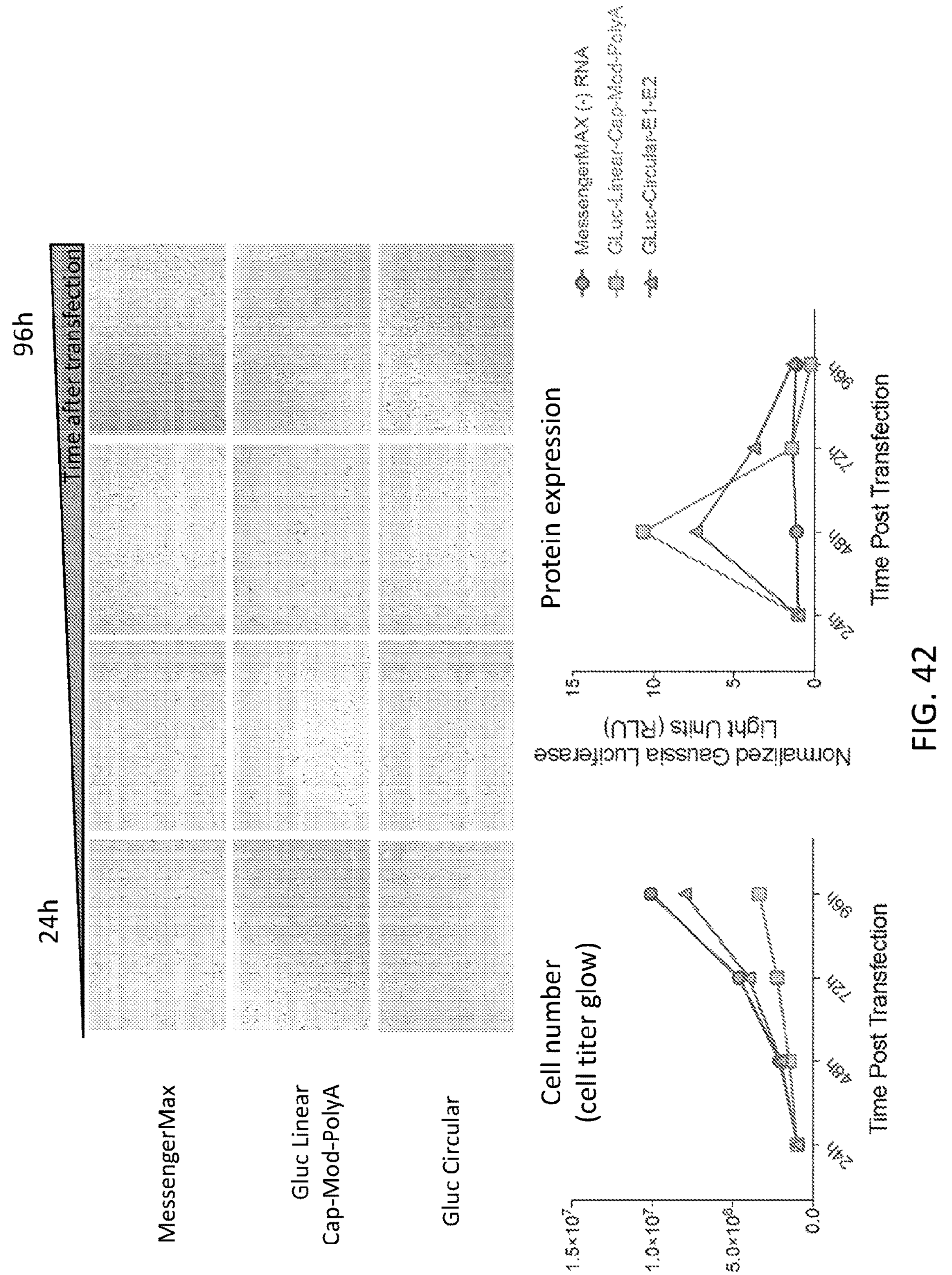
FIG. 42 shows experimental data demonstrating the higher stability of circular RNA in a dividing cell as compared to linear controls.

Expression of protein from circular RNA was detected at higher levels than linear RNA in dividing cells (FIG. 42). Cells with circular RNA had higher cell division rates as compared to linear RNA at all timepoints measured. This Example demonstrates increased detection of circular RNA during cell division than its linear RNA counterpart.

Example 52: Rolling Circle Translation Produced a Plurality of Expression Sequences This Example demonstrates the ability of circular RNA to express multiple proteins from a single construct. Additionally, this Example demonstrates rolling circle translation of circular RNA encoding multiple ORFs. This Example further demonstrates expression of two proteins from a single construct.

One circular RNA (mtEMCV T2A 3×FLAG-GFP F2A 3×FLAG-Nluc P2A IS spacer) was designed for rolling circle translation to include EMCV IRES (SEQ ID NO:58), and an ORF encoding GFP with 3×FLAG tag and an ORF encoding Nanoluciferase (Nluc) with 3×FLAG tag. Stagger elements (2A) were flanking the GFP and Nluc ORFs. Another circular RNA was designed similarly, but included a triple stop codon inbetween the Nluc ORF and the spacer. Part of the *Anabaena* autocatalytic intron and exon sequences were included prior to the EMCV IRES. The circular RNAs were generated either in vitro as described.

The expression of proteins from circular RNA was monitored either in vitro or in cells. For in vitro analysis, the circular RNAs were incubated for 3h in rabbit reticulocyte lysate (Promega, Fitchburg, WI, USA) at 30° C. The final composition of the reaction mixture included 70% rabbit reticulocyte lysate, 20 μM complete amino acids, and 0.8 U/μL RNase inhibitor (Toyobo, Osaka, Japan).

After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 2×SDS sample buffer and incubated at 70° C. for 15 min. After centrifugation at 1400×g for 5 min, the supernatant was analyzed on a 10-20% gradient polyacrylamide/SDS gel.

For analysis in cells, cells were plated into each well of a 12 well plate to monitor translation efficiency of circular RNA in cells. After 1 day, 500 ng of circular RNA was transfected into each well using a lipid-based transfection reagent (Invitrogen). 48 hours after transfection, cells were harvested by adding 200 μl of RIPA buffer onto each well. Next, 10 μg of cell lysate proteins were analyzed on 10-20% gradient polyacrylamide/SDS gel.

After electrotransfer of samples from reticulocyte lysate and cells to a nitrocellulose membrane using dry transfer method, the blot was incubated with an anti-FLAG antibody and anti-mouse IgG peroxidase. As a loading control, anti-beta tubulin antibody was used. The blot was visualized with an enhanced chemiluminescent (ECL) kit. Western blot band intensity was measured by ImageJ.

Figure 43:
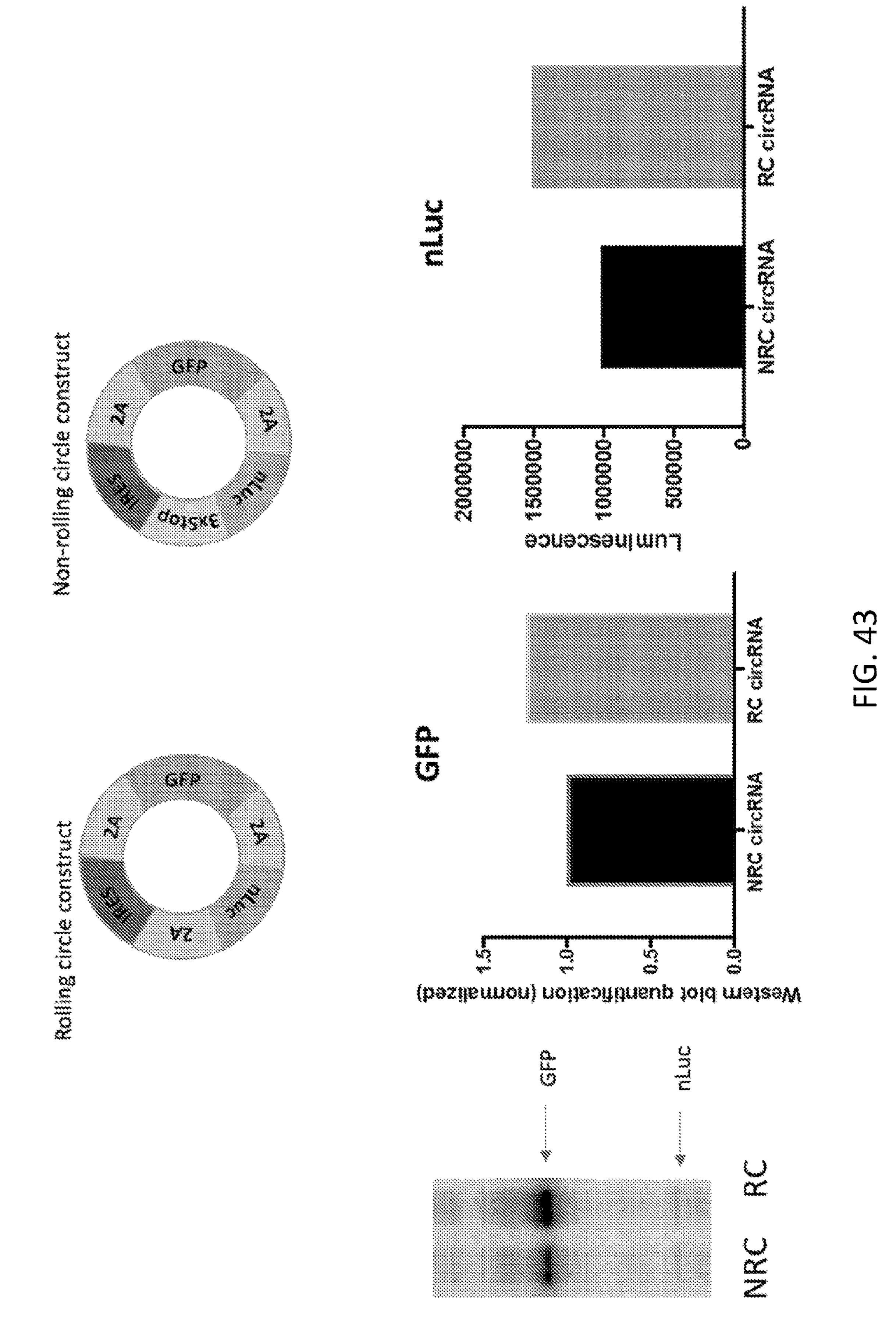
FIG. 43 shows experimental data demonstrating the protein expression from exemplary circular RNAs with a plurality of expression sequences and the rolling circle translation of exemplary circular RNAs with multiple expression sequences.

As shown in FIG. 43, the circular RNA encoding GFP and nLuc produced 2 protein products. Translation from the circular RNA without the triple stop generated more of both protein products than circular RNA with the triple stop codon. Finally, both circular RNA with and without the triple stop expressed proteins at 1/3.24 and 1/3.37 ratios, respectively.

Example 53: Circular RNA Administrated In Vivo and Displayed a Longer Half-Life/Increased Stability This Example demonstrates the ability to deliver circular RNA and the increased stability of circular RNA compared to linear RNA in vivo.

For this Example, circular RNAs were designed to include an EMCV IRES with an ORF encoding Nanoluciferase (Nluc) and stagger sequence (EMCV 2A 3×FLAG Nluc 2A no stop and EMCV 2A 3×FLAG Nluc 2A stop). The circular RNA was generated in vitro.

Balb/c mice were injected with circular RNA with Nluc ORF, or linear RNA as a control, via intravenous (IV) tail vein administration. Animals received a single dose of 5 μg of RNA formulated in a lipid-based transfection reagent (Mirus) according to manufacturer's instructions.

Mice were sacrificed, and livers were collected at 3, 4, and 7 days post-dosing (n=2 mice/time point). The livers were collected and stored in an RNA stabilization reagen (Invitrogen). The tissue was homogenized in RIPA buffer with micro tube homogenizer (Fisher scientific) and RNA was extracted using a phenol-based RNA extraction reagent for cDNA synthesis. qPCR was used to measure the presence of both linear and circular RNA in the liver.

RNA detection in tissues was performed by qPCR. To detect linear and circular RNA primers that amplify the Nluc ORF were used. (F: AGATTTCGTTGGGGACTGGC (SEQ ID NO: 123), R: CACCGCTCAGGACAATCCTT (SEQ ID NO: 55)). To detect only circular RNA, primers that amplified the 5'-3' junction allowed for detection of circular but not linear RNA constructs (F: CTGGAGACGTGGAGGAGAAC (SEQ ID NO: 124), R: CCAAAAGACGGCAATATGGT (SEQ ID NO: 125)).

Figure 44:
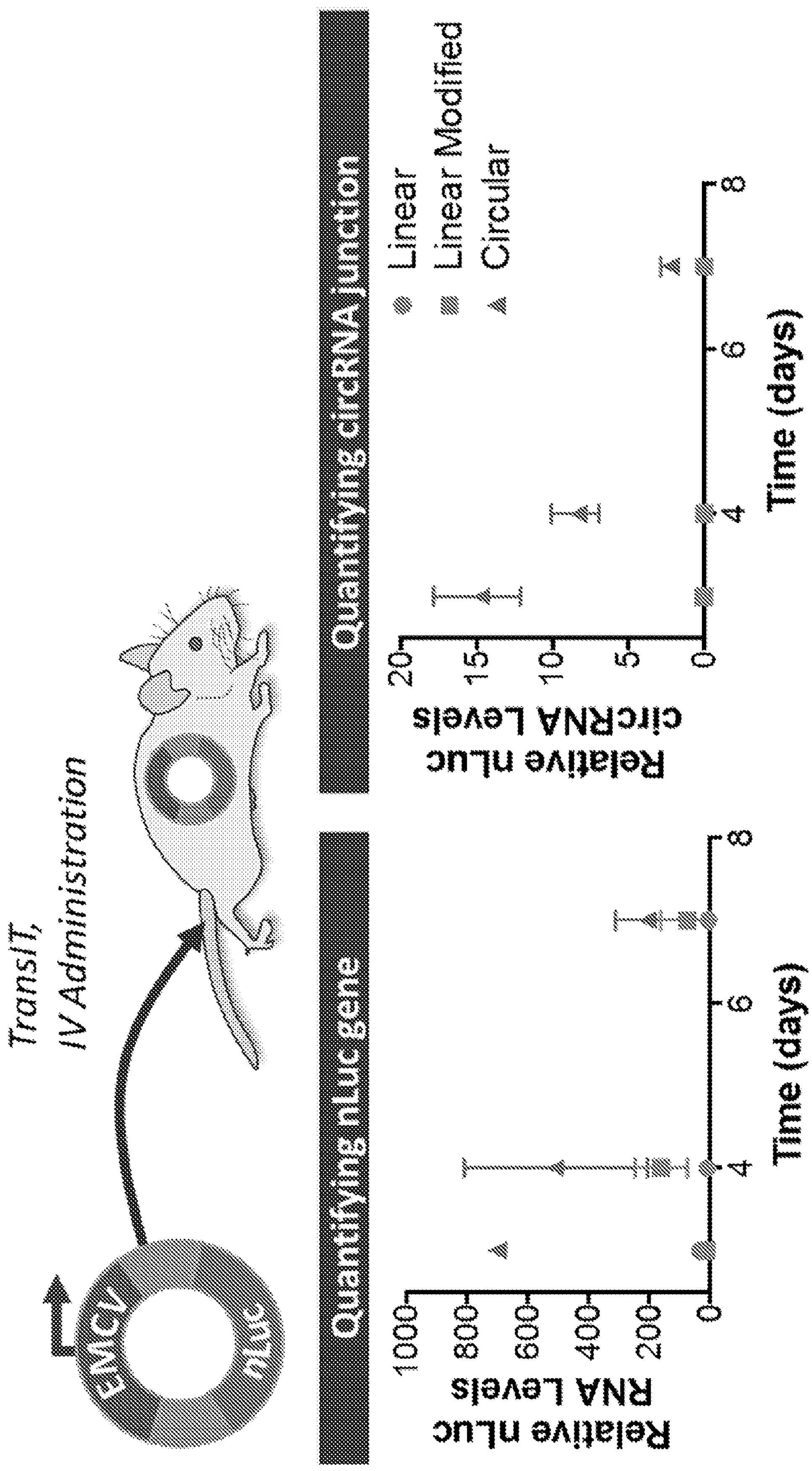
FIG. 44 shows that after injection into mice, circular RNA was detected at higher levels than linear RNA in livers of mice at 3, 4, and 7 days post-injection.

Circular RNA was detected at higher levels than linear RNA in livers of mice at 3, 4- and 7-days post-injection (FIG. 44). Therefore, circular RNA was administered and detectable in vivo for at least 7 days post administration.

Example 54: In Vivo Expression, Half-Life, and Non-Immunogenicity of Circular RNA This Example demonstrates the ability to drive expression from circular RNA in vivo. It demonstrates increased half-life of circular RNA compared to linear RNA. Finally, it demonstrates that circular RNA was engineered to be non-immunogenic in vivo For this Example, circular RNAs included a CVB3 IRES, an ORF encoding *Gaussia* Luciferase (GLuc), and two spacer elements flanking the IRES-ORF.

The circular RNA was generated in vitro. Unmodified linear RNA was in vitro transcribed from a DNA template including all the motifs listed above, as well as a T7 RNA polymerase promoter to drive transcription. Transcribed RNA was purified with an RNA cleanup kit (New England Biolabs, T2050), treated with RNA 5'-phosphohydrolase (RppH) (New England Biolabs, M0356) following the manufacturer's instructions, and purified again with an RNA purification column. RppH treated RNA was circularized using a splint DNA (GTCAACGGATTTTCCCAAGTCCGTAGCGTCTC) (SEQ ID NO: 126) and T4 RNA ligase 2 (New England Biolabs, M0239). Circular RNA was Urea-PAGE purified, eluted in a buffer (0.5M Sodium Acetate, 0.1% SDS, 1 mM EDTA), ethanol precipitated and resuspended in RNase free water.

Mice received a single tail vein injection dose of 2.5 μg of circular RNA with the *Gaussia* Luciferase ORF, or linear RNA as a control, both formulated in a lipid-based transfection reagent (Mirus) as a carrier.

Blood samples (50 μl) were collected from the tail-vein of each mouse into EDTA tubes, at 1, 2, 7, 11, 16, and 23 days post-dosing. Plasma was isolated by centrifugation for 25 min at 1300 g at 4° C. and the activity of *Gaussia* Luciferase, a secreted enzyme, was tested using a *Gaussia* Luciferase activity assay (Thermo Scientific Pierce). 50 μl of 1×Gluc substrate was added to 5 μl of plasma to carry out the Gluc luciferase activity assay. Plates were read right after mixing in a luminometer instrument (Promega).

Figure 45A:
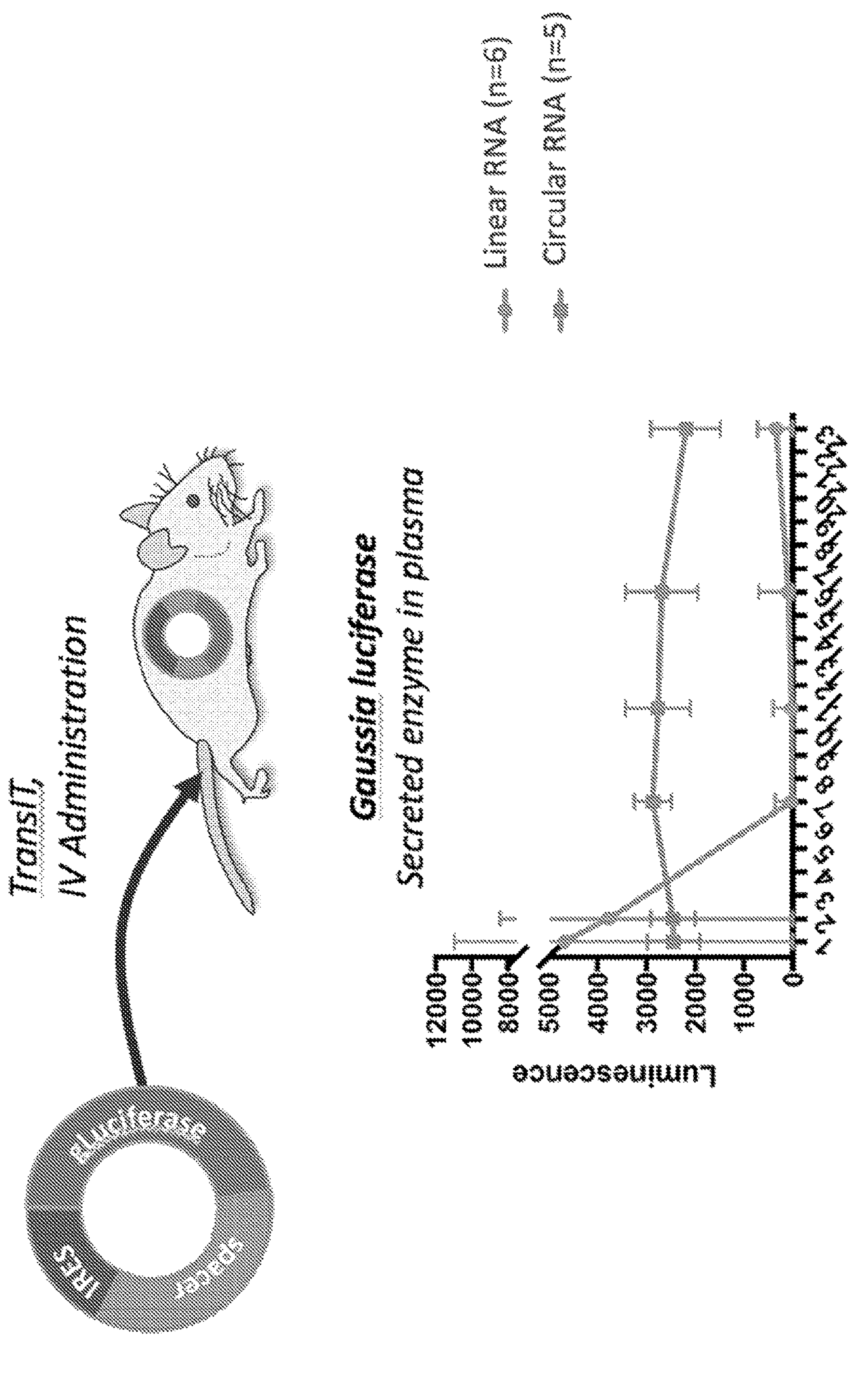
FIGS. 45A and 45B show that after injection of circular RNA or linear RNA expressing *Gaussia* Luciferase into mice, *Gaussia* Luciferase activity was detected in plasma at 1, 2, 7, 11, 16, and 23 days post-dosing of circular RNA, while its activity was only detected in plasma at 1, and 2 days post-dosing of modified linear RNA.
Figure 45B:
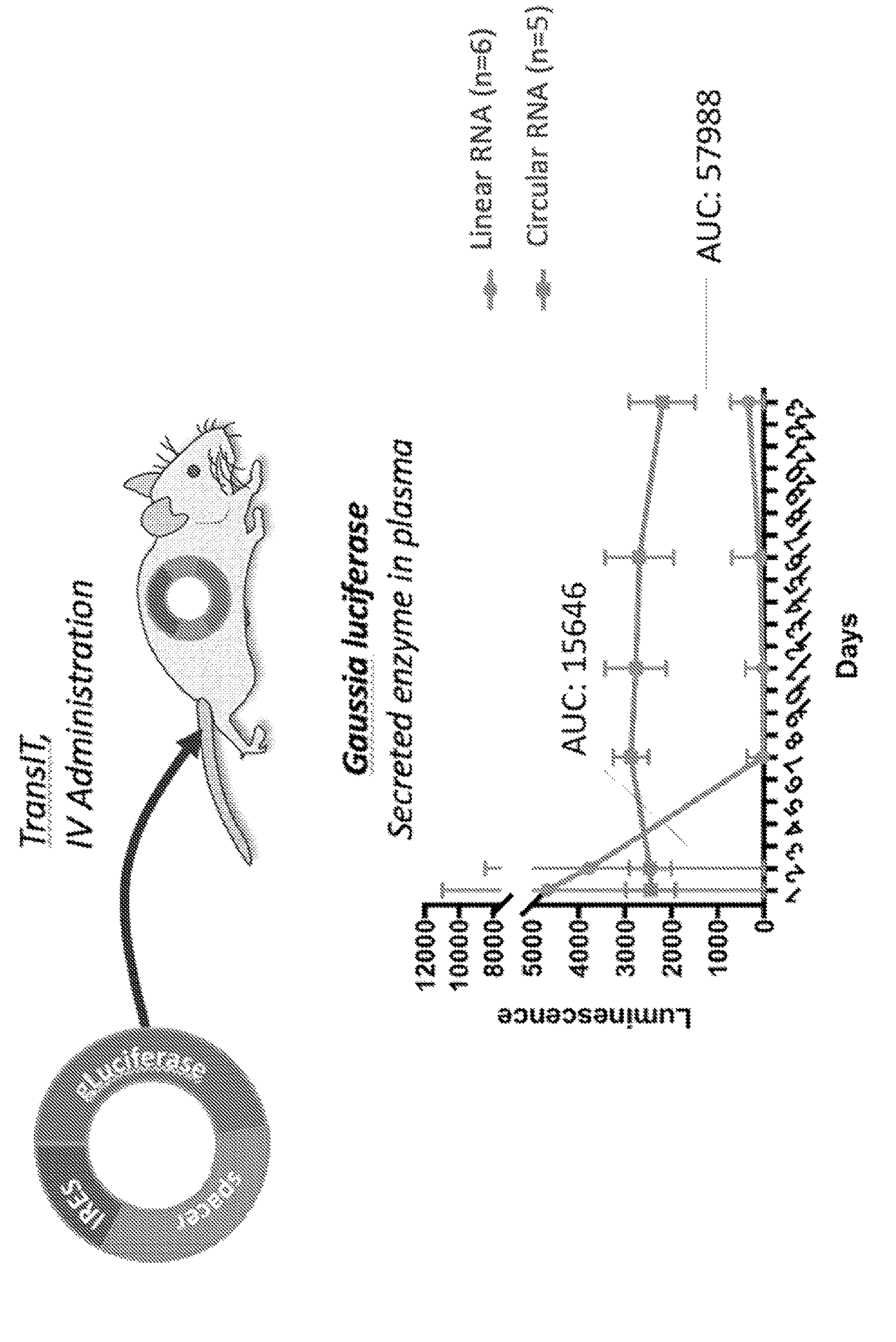

*Gaussia* Luciferase activity was detected in plasma at 1, 2, 7, 11, 16, and 23 days post-dosing of circular RNA (FIGS. 45A-B).

In contrast, *Gaussia* Luciferase activity was only detected in plasma at 1, and 2 days post-dosing of modified linear RNA. Enzyme activity from linear RNA derived protein was not detected above background levels at day 6 or beyond (FIGS. 45A-B).

At day 16, livers were dissected from three animals and total RNA was isolated from cells using a phenol-based extraction reagent (Invitrogen). Total RNA (500 ng) was subjected to reverse transcription to generate cDNA. qRT-PCR analysis was performed using a dye-based quantitative PCR mix (BioRad).

Figure 46:
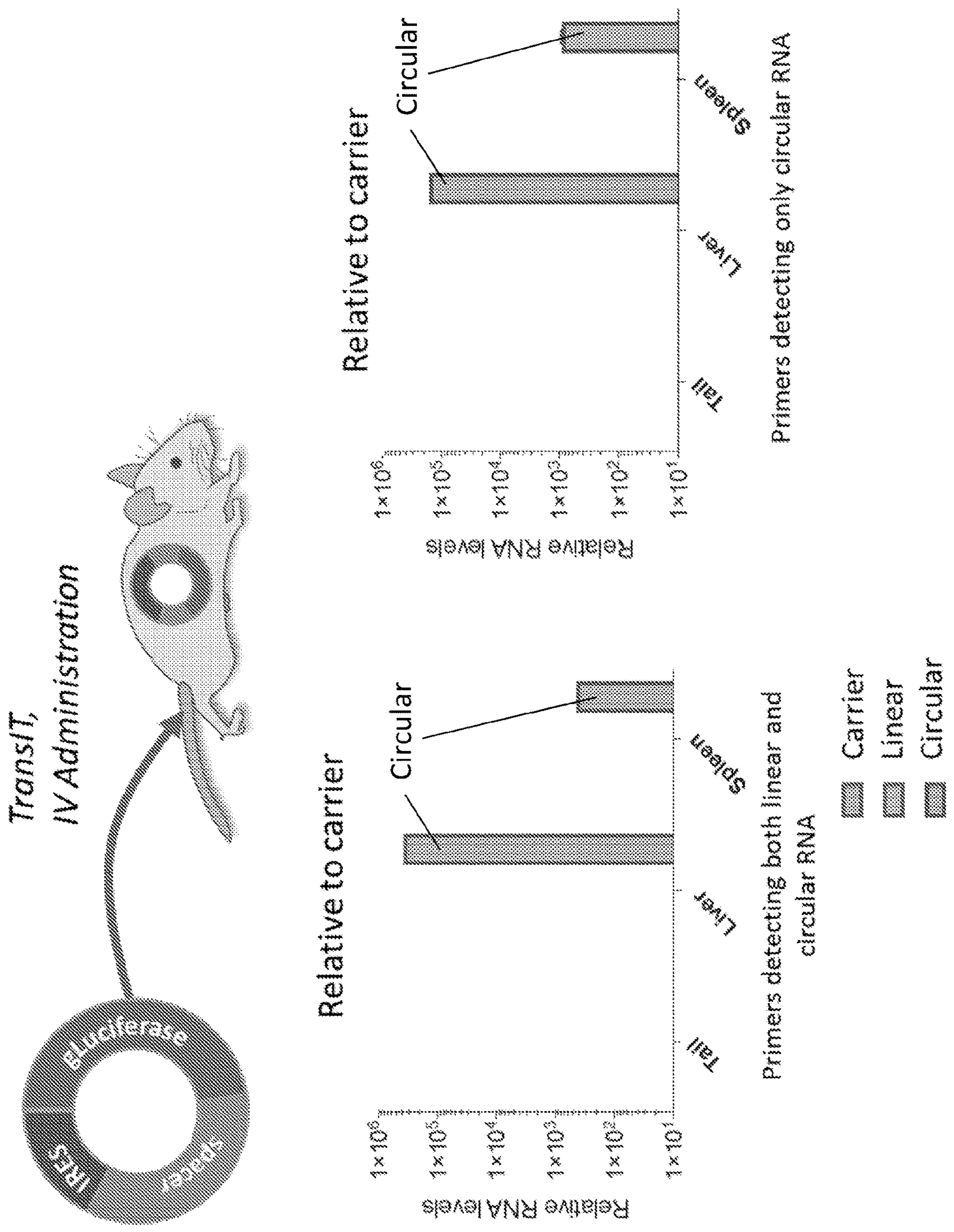
FIG. 46 show that after injection of RNA, circular RNA but not linear RNA, was detected in the liver and spleen at 16 days post-administration of RNA.
Figure 47:
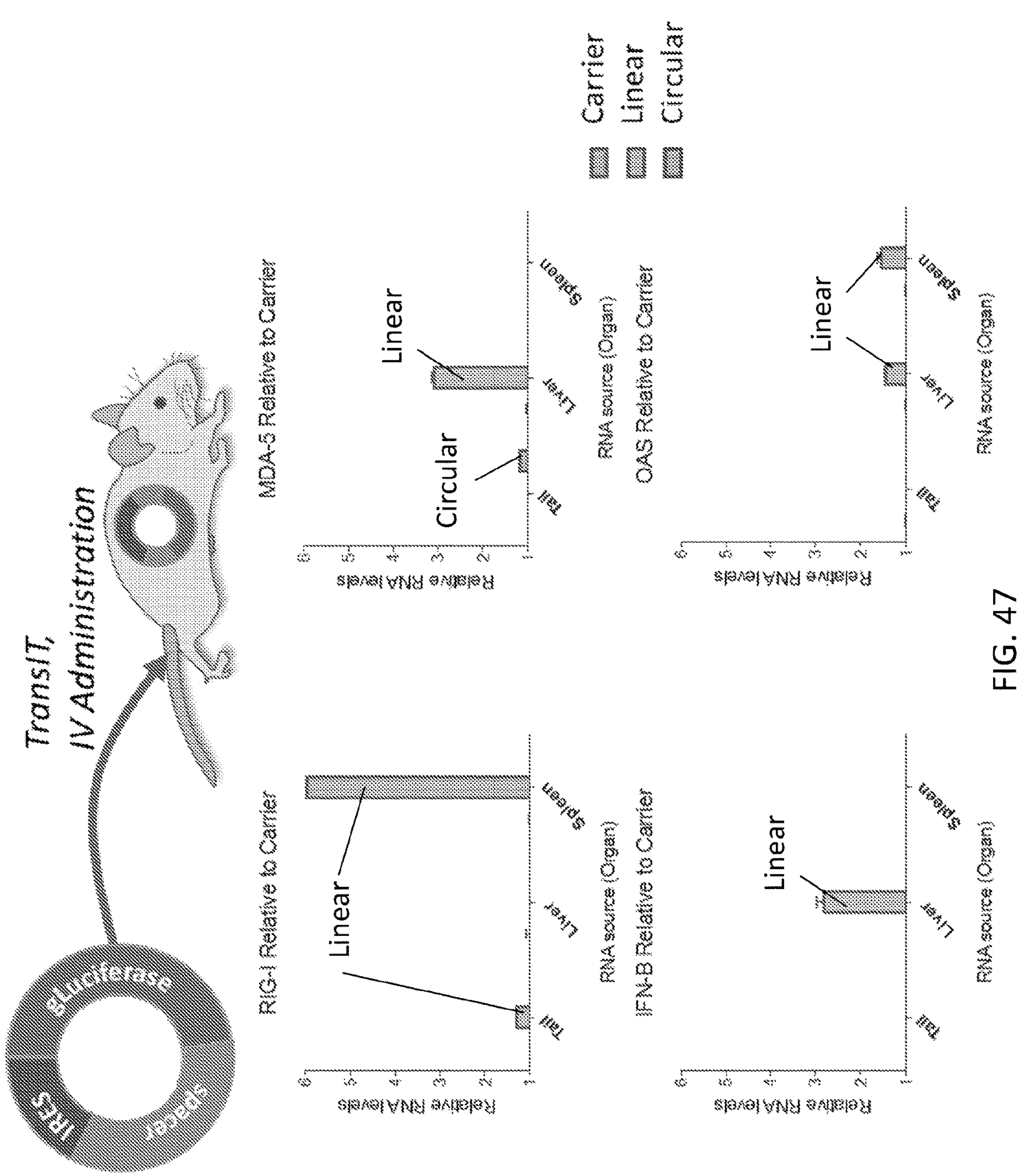
FIG. 47 show that after injection of RNA, linear RNA but not circular RNA, showed immunogenicity as assessed by RIG-I, MDA-5, IFN-B and OAS.
Figure 48:
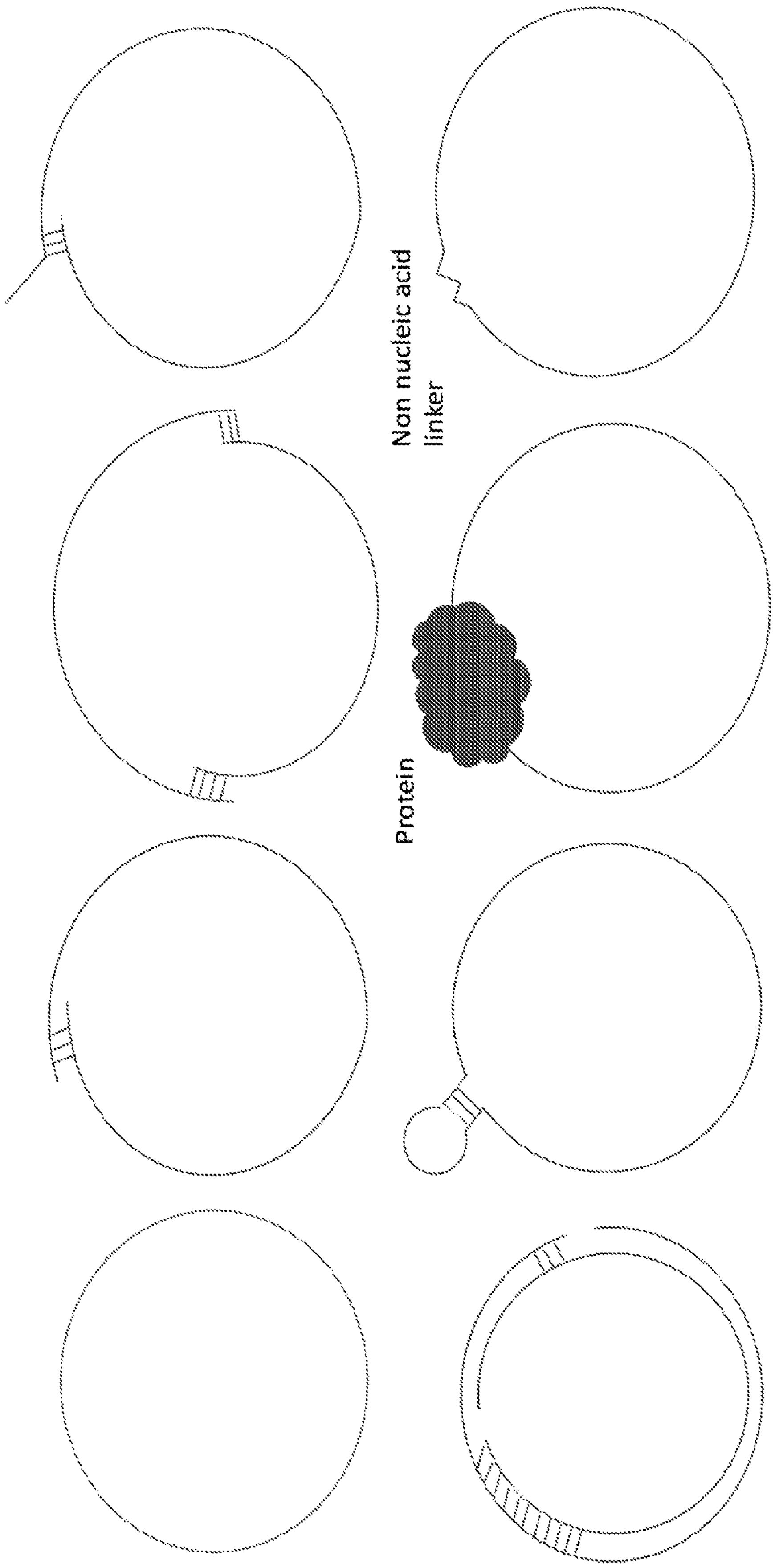
FIG. 48 shows different exemplary circularization methods.

As shown in FIG. 46, qRT-PCR levels of circular RNA but not linear RNA were detected in both liver and spleen at day 16. As shown in FIG. 47, immune related genes from livers transfected with linear RNA showed increased expression of RIG-I, MDA5, IFN-B and OAS, while livers transfected with circular RNA did not show increased expression RIG-I, MDA5, PKR and IFN-beta of these markers as compared to carrier transfected animals at day 16. Thus, induction of immunogenic related genes in recipient cells was not present in circular RNA from transfected livers.

This Example demonstrated that circular RNA expressed protein in vivo for prolonged periods of time, with levels of protein activity in the plasma at multiple days post injection. Given the half-life of Gaussian Luciferase in mouse plasma is about 20 mins (see Tannous, Nat Protoc., 2009, 4(4):582-591), the similar levels of activity indicate continual expression from circular RNA. Further, circular RNA displayed a longer expression profile than its modified linear RNA counterpart without inducing immune related genes.

SEQUENCE LISTING

```
SEQ ID NO: 1 (Start Codon)
AUG

SEQ ID NO: 2 (GFP)
EGFP:
atggtgagcaagggcgaggagctgttcaccggggtggtgcccatcctggtcgagctggacggcgacgtaaacggccacaagttcagcgt
gtccggcgagggcgagggcgatgccacctacggcaagctgaccctgaagttcatctgcaccaccggcaagctgcccgtgccctggccc
accctcgtgaccaccctgacctacggcgtgcagtgcttcagccgctaccccgaccacatgaagcagcacgacttcttcaagtccgccatgc
ccgaaggctacgtccaggagcgcaccatcttcttcaaggacgacggcaactacaagacccgcgccgaggtgaagttcgagggcgacac
cctggtgaaccgcatcgagctgaagggcatcgacttcaaggaggacggcaacatcctggggcacaagctggagtacaactacaacagcc
acaacgtctatatcatggccgacaagcagaagaacggcatcaaggtgaacttcaagatccgccacaacatcgaggacggcagcgtgcag
ctcgccgaccactaccagcagaacacccccatcggcgacggccccgtgctgctgcccgacaaccactacctgagcacccagtccgccct
gagcaaagaccccaacgagaagcgcgatcacatggtcctgctggagttcgtgaccgccgccgggatcactctcggcatggacgagctgt
acaag

SEQ ID NO: 3 (stagger element)
P2A: gctactaacttcagcctgctgaagcaggctggcgacgtggaggagaaccctggacct
T2A: gagggcaggggaagtctactaacatgcggggacgtggaggaaaatcccggccca (SEQ ID NO: 61)
E2A: cagtgtactaattatgctctcttgaaattggctggagatgttgagagcaacccaggtccc (SEQ ID NO: 62)
Others: F2A, BmCPV2A, BmIFV2A

SEQ ID NO: 4 ZKSCAN introns
GTAAAAAGAGGTGAAACCTATTATGTGTGAGCAGGGCACAGACGTTGAAACTGGAG
CCAGGAGAAGTATTGGCAGGCTTTAGGTTATTAGGTGGTTACTCTGTCTTAAAAATG
TTCTGGCTTTCTTCCTGCATCCACTGGCATACTCATGGTCTGTTTTTAAATATTTTAAT
TCCCATTTACAAAGTGATTTACCCACAAGCCCAACCTGTCTGTCTTCAG
Or

GTAAGAAGCAAGGTTTCATTTAGGGGAAGGGAAATGATTCAGGACGAGAGTCTTTG
TGCTGCTGAGTGCCTGTGATGAAGAAGCATGTTAGTcctgggcaacgtagcgagaccccatctctacaa
aaaatagaaaaattagccaggtatagtggcgcacacctgtgattccagctacgcaggaggctgaggtgggaggattgcttgagcccagga
ggttgaggctgcagtgagctgtaatcatgccactactccaacctgggcaacacagcaaggaccctgtctcaaaaGCTACTTACA
GAAAAGAATTAggctcggcacggtagctcacacctgtaatcccagcactttgggaggctgaggcgggcagatcacttgaggtc
aggagtttgagaccagcctggccaacatggtgaaaccttgtctctactaaaaatatgaaaattagccaggcatggtggcacattcctgtaatc
ccagctactcgggaggctgaggcaggagaatcacttgaacccaggaggtggaggttgcagtaagccgagatcgtaccactgtgctctagc
cttggtgacagagcgagactgtcttaaaaaaaaaaaaaaaaaaaaagaattaattaaaaatttaaaaaaaaatgaaaaaaaGCTGCA
TGCTTGTTTTTTGTTTTTAGTTATTCTACATTGTTGTCATTATTACCAAATATTGGGGA
AAATACAACTTACAGACCAATCTCAGGAGTTAAATGTTACTACGAAGGCAAATGAA
CTATGCGTAATGAACCTGGTAGGCATTA (SEQ ID NO: 63)

SEQ ID NO: 5 (IRES)
IRES (EMCV):
Acgttactggccgaagccgcttggaataaggccggtgtgcgtttgtctatatgttattttccaccatattgccgtcttttggcaatgtgagggcc
cggaaacctggccctgtcttcttgacgagcattcctaggggtctttcccctctcgccaaaggaatgcaaggtctgttgaatgtcgtgaaggaa
gcagttcctctggaagcttcttgaagacaaacaacgtctgtagcgaccctttgcaggcagcggaaccccccacctggcgacaggtgcctct
gcggccaaaagccacgtgtataagatacacctgcaaaggcggcacaaccccagtgccacgttgtgagttggatagttgtggaaagagtca
aatggctctcctcaagcgtattcaacaaggggctgaaggatgcccagaaggtaccccattgtatgggatctgatctggggcctcggtgcac
atgctttacatgtgtttagtcgaggttaaaaaacgtctaggccccccgaaccacggggacgtggttttcctttgaaaaacacgatgataata

SEQ ID NO: 6 (addgene p3.1 laccase)
pcDNA3.1(+) Laccase2 MCS Exon Vector sequence 6926 bps
GACGGATCGGGAGATCTCCCGATCCCCTATGGTGCACTCTCAGTACAATCTGCTCTG
ATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATG
AAGAATCTGCTTAGGGTTAGGCGTTTTGCGCTGCTTCGCGATGTACGGGCCAGATAT
ACGCGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATA
GTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTT
```

-continued

SEQUENCE LISTING

GGCAGTACATCAATGGGCGTGGATAGCGGTTTGACTCACGGGGATTTCCAAGTCTCC
ACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGG
GAGGTCTATATAAGCAGAGCTCTCTGGCTAACTAGAGAACCCACTGCTTACTGGCTT
ATCGAAATTAATACGACTCACTATAGGGAGACCCAAGCTGGCTAGCGTTTAAACTTA
AGCTTGGTACCGAGCTCGGATCCACTAGTCCAGTGTGGTGGAATTCCATTGAGAAAT
GACTGAGTTCCGGTGCTCTCAAGTCATTGATCTTTGTCGACTTTTATTTGGTCTCTGT
AATAACGACTTCAAAAACATTAAATTCTGTTGCGAAGCCAGTAAGCTACAAAAAGA
AAaaacaagagagaatgctatagtcgtatagtatagtttcccgactatctgatacccattacttatctaggggaatgcgaacccaaaattta
tcagttttctcggatatcgatagatattggggaataaatttaaataaataaattttgggcgggtttagggcgtggcaaaaagtttttggcaaatc
gctagaaatttacaagacttataaaattatgaaaaaatacaacaaaattttaaacacgtgggcgtgacagttttggGcggttttagggcgttag
agtaggcgaggacagggttacatcgactaggctttgatcctgatcaagaatatatatactttataccgcttccttctacatgttacctatttttcaac
gaatctagtataccttttactgtacgatttatgggtataaTAATAAGCTAAATCGAGACTAAGttttattgttatatatattttt
tttattttatGCAGAAATTAATTAAACCGGTCCTGCAGGTGATCAGGCGCGCCGGTTACCGG
CCGGCCCCGCGGAGCGTAAGTATTCAAAATTCCAAAATTTTTTACTAGAAATATTCG
ATTTTTTAATAGGCAGTTTCTATACTATTGTATACTATTGtagattcgttgaaaagtatgtaacaggaag
aataaagcatttccgaccatgtaaagtatatatattcttaataaggatcaatagccgagtcgatctcgccatgtccgtctgtcttattGttttattac
cgccgagacatcaggaactataaaagctagaaggatgagttttagcatacagattctagagacaaggacgcagagcaagtttgttgatccat
gctgccacgctttaactttctcaaattgcccaaaactgccatgcccacatttttgaactattttcgaaatttttcataattgtattactcgtgtaaat
ttccatcaatttgccaaaaaactttttgtcacgcgttaacgccctaaagccgccaatttggtcacgcccacactattgaGcaattatcaaatttttct
cattttattccccaatatctatcgatatccccgattatgaaattattaaatttcgcgttcgcattcacactagctgagtaacgagtatctgatagttgg
ggaaatcgactTATTTTTTATATACAATGAAAATGAATTTAATCATATGAATATCGATTATA
GCTTTTTATTTAATATGAATATTTATTTGGGCTTAAGGTGTAACCTcctegacataagactcacat
ggcgcaggcacattgaagacaaaaatactcaTTGTCGGGTCTCGCACCCTCCAGCAGCACCTAAAATT
ATGTCTTCAATTATTGCCAACATTGGAGACACAATTAGTCTGTGGCACCTCAGGCGG
CCGCTCGAGTCTAGAGGGCCCGTTTAAACCCGCTGATCAGCCTCGACTGTGCCTTCT
AGTTGCCAGCCATCTGTTGTTTGCCCCTCCCCCGTGCCTTCCTTGACCCTGGAAGGTG
CCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCATTAA
GCGCGGCGGGTGTGGTGGTTACGCGCAGCGTGACCGCTACACTTGCCAGCGCCCTA
GCGCCCGCTCCTTTCGCTTTCTTCCCTTCCTTTCTCGCCACGTTCGCCGGCTTTCCCCG
TCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATA
GACGGTTTTTCGCCCTTTGACGTTGGAGTCCACGTTCTTTAATAGTGGACTCTTGTTC
CAAACTGGAACAACACTCAACCCTATCTCGGTCTATTCTTTTGATTTATAAGGGATTT
TGCCGATTTCGGCCTATTGGTTAAAAAATGAGCTGATTTAACAAAAATTTAACGCGA
ATTAATTCTGTGGAATGTGTGTCAGTTAGGGTGTGGAAAGTCCCCAGGCTCCCCAGC
AGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCA
ACCATAGTCCCGCCCCTAACTCCGCCCATCCCGCCCCTAACTCCGCCCAGTTCCGCC
CATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTT
GCAAAAAGCTCCCGGGAGCTTGTATATCCATTTTCGGATCTGATCAAGAGACAGGAT
GAGGATCGTTTCGCATGATTGAACAAGATGGATTGCACGCAGGTTCTCCGGCCGCTT
GGGTGGAGAGGCTATTCGGCTATGACTGGGCACAACAGACAATCGGCTGCTCTGAT
GCCGCCGTGTTCCGGCTGTCAGCGCAGGGGCGCCCGGTTCTTTTTGTCAAGACCGAC
CTGTCCGGTGCCCTGAATGAACTGCAGGACGAGGCAGCGCGGCTATCGTGGCTGGC
CACGACGGGCGTTCCTTGCGCAGCTGTGCTCGACGTTGTCACTGAAGCGGGAAGGG
ACTGGCTGCTATTGGGCGAAGTGCCGGGGCAGGATCTCCTGTCATCTCACCTTGCTC
CTGCCGAGAAAGTATCCATCATGGCTGATGCAATGCGGCGGCTGCATACGCTTGATC
CGGCTACCTGCCCATTCGACCACCAAGCGAAACATCGCATCGAGCGAGCACGTACT
CGGATGGAAGCCGGTCTTGTCGATCAGGATGATCTGGACGAAGAGCATCAGGGGCT
CGCGCCAGCCGAACTGTTCGCCAGGCTCAAGGCGCGCATGCCCGACGGCGAGGATC
TCGTCGTGACCCATGGCGATGCCTGCTTGCCGAATATCATGGTGGAAAATGGCCGCT
TTTCTGGATTCATCGACTGTGGCCGGCTGGGTGTGGCGGACCGCTATCAGGACATAG
CGTTGGCTACCCGTGATATTGCTGAAGAGCTTGGCGGCGAATGGGCTGACCGCTTCC
TCGTGCTTTACGGTATCGCCGCTCCCGATTCGCAGCGCATCGCCTTCTATCGCCTTCT
TGACGAGTTCTTCTGAGCGGGACTCTGGGGTTCGAAATGACCGACCAAGCGACGCC
CAACCTGCCATCACGAGATTTCGATTCCACCGCCGCCTTCTATGAAAGGTTGGGCTT
CGGAATCGTTTTCCGGGACGCCGGCTGGATGATCCTCCAGCGCGGGGATCTCATGCT
GGAGTTCTTCGCCCACCCCAACTTGTTTATTGCAGCTTATAATGGTTACAAATAAAG
CAATAGCATCACAAATTTCACAAATAAAGCATTTTTTTCACTGCATTCTAGTTGTGGT
TTGTCCAAACTCATCAATGTATCTTATCATGTCTGTATACCGTCGACCTCTAGCTAGA
GCTTGGCGTAATCATGGTCATAGCTGTTTCCTGTGTGAAATTGTTATCCGCTCACAAT
TCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACC
TGTCGTGCCAGCTGCATTAATGAATCGGCCAACGCGCGGGGAGAGGCGGTTTGCGT
ATTGGGCGCTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGCACGAACC -continued

SEQUENCE LISTING

CCCCGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTAC
ACTAGAAGAACAGTATTTGGTATCTGCGCTCTGCTGAAGCCAGTTACCTTCGGAAAA
AGAGTTGGTAGCTCTTGATCCGGCAAACAAACCACCGCTGGTAGCGGTTTTTTTGTT
TGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCAT
GAGATTATCAAAAAGGATCTTCACCTAGATCCTTTTAAATTAAAAATGAAGTTTTAA
ATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCC
GTCGTGTAGATAACTACGATACGGGAGGGCTTACCATCTGGCCCCAGTGCTGCAATG
ATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGCGCAACGT
TGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTA
TCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGC
GACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCA
GCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTT
CAATATTATTGAAGCATTTATCAGGGTTATTGTCTCATGAGCGGATACATATTTGAA
TGTATTTAGAAAAATAAACAAATAGGGGTTCCGCGCACATTTCCCCGAAAAGTGCC
ACCTGACGTC

SEQ ID NO: 8 (RFP)
mCherry:
atggtgagcaagggcgaggaggataacatggccatcatcaaggagttcatgcgcttcaaggtgcacatggagggctccgtgaacggcca
cgagttcgagatcgagggcgagggcgagggccgcccctacgagggcacccagaccgccaagctgaaggtgaccaagggtggccccc
tgcccttcgcctgggacatcctgtcccctcagttcatgtacggctccaaggcctacgtgaagcaccccgccgacatccccgactacttgaag
ctgtccttccccgagggcttcaagtgggagcgcgtgatgaacttcgaggacggcggcgtggtgaccgtgacccaggactcctccctgcag
gacggcgagttcatctacaaggtgaagctgcgcggcaccaacttcccctccgacggccccgtaatgcagaagaagaccatgggctggga
ggcctcctccgagcggatgtaccccgaggacggcgccctgaagggcgagatcaagcagaggctgaagctgaaggacggcggccacta
cgacgctgaggtcaagaccacctacaaggccaagaagcccgtgcagctgcccggcgcctacaacgtcaacatcaagttggacatcacct
cccacaacgaggactacaccatcgtggaacagtacgaacgcgccgagggccgccactccaccggcggcatggacgagctgtacaag SEQ ID NO: 9 (riboswitch)
Aptazyme (Theophylline Dependent see Auslander 2010 Mol Biosys):
cugagaugcagguacauccagcugaugagucccaaauaggacgaaagccauaccagccgaaaggcccuuggcaggguuccugg
auuccacugcuauccac SEQ ID NO: 10 (luciferase)
nLuc:
ATGGTCTTCACACTCGAAGATTTCGTTGGGGACTGGCGACAGACAGCCGGCTACAA
CCTGGACCAAGTCCTTGAACAGGGAGGTGTGTCCAGTTTGTTTCAGAATCTCGGGGT
GTCCGTAACTCCGATCCAAAGGATTGTCCTGAGCGGTGAAAATGGGCTGAAGATCG
ACATCCATGTCATCATCCCGTATGAAGGTCTGAGCGGCGACCAAATGGGCCAGATC
GAAAAAATTTTTAAGGTGGTGTACCCTGTGGATGATCATCACTTTAAGGTGATCCTG
CACTATGGCACACTGGTAATCGACGGGGTTACGCCGAACATGATCGACTATTTCGGA
CGGCCGTATGAAGGCATCGCCGTGTTCGACGGCAAAAAGATCACTGTAACAGGGAC
CCTGTGGAACGGCAACAAAATTATCGACGAGCGCCTGATCAACCCCGACGGCTCCC
TGCTGTTCCGAGTAACCATCAACGGAGTGACCGGCTGGCGGCTGTGCGAACGCATTC
TGGCGTAA Sequence ID 11
Kozak 3XFLAG-EGF nostop (264 bps)
GGGAGCCACCATGGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC
GCTGTCAGTACCGAGACCTGAAGTGGTGGGAACTGCGCCT
5-13: Kozak sequence
14-262: 3XFLAG-EGF SEQ ID NO: 12
Kozak 3XFLAG-EGF stop (273 bps)
GGGAGCCACCATGGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC
GCTGTCAGTACCGAGACCTGAAGTGGTGGGAACTGCGCTGATAGTAACT
5-13: Kozak sequence
14-262: 3XFLAG-EGF
263-271: Triple stop codon -continued

SEQUENCE LISTING

SEQ ID NO: 13
Kozak 3XFLAG-EGF P2A nostop (330 bps)
GGGAGCCACCATGGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC
GCTGTCAGTACCGAGACCTGAAGTGGTGGGAACTGCGCGGAAGCGGAGCTACTAAC
TTCAGCCTGCTGAAGCAGGCTGGAGACGTGGAGGAGAACCCTGGACCTCT
5-13: Kozak sequence
14-262: 3XFLAG-EGF
263-328: P2A SEQ ID NO: 14
Splint for construct Kozak 3XFLAG-EGF nostop (264 bps)
GGTGGCTCCCAGGCGCAGTT SEQ ID NO: 15
Splint for construct Kozak 3XFLAG-EGF stop (273 bps)
GGTGGCTCCCAGTTACTATC SEQ ID NO: 16
Splint for construct Kozak 3XFLAG-EGF P2A nostop (330 bps)
GGTGGCTCCCAGAGGTCCAG SEQ ID NO: 17
Kozak 1XFLAG-EGF T2A 1XFLAG-Nluc P2A nostop (873 bps)
GGGAGCCACCATGGACTACAAGGACGACGACGACAAGATCATCAATAGTGACTCTG
AGTGTCCCCTGTCCCACGACGGGTACTGCCTCCACGACGGTGTGTGCATGTATATTG
AAGCATTGGACAAGTACGCCTGCAACTGTGTTGTTGGCTACATCGGGGAGCGCTGTC
AGTACCGAGACCTGAAGTGGTGGGAACTGCGCGGCTCCGGCGAGGGCAGGGGAAG
TCTTCTAACATGCGGGGACGTGGAGGAAAATCCCGGCCCAGACTATAAGGACGACG
ACGACAAAATCATCGTCTTCACACTCGAAGATTTCGTTGGGGACTGGCGACAGACA
GCCGGCTACAACCTGGACCAAGTCCTTGAACAGGGAGGTGTGTCCAGTTTGTTTCAG
AATCTCGGGGTGTCCGTAACTCCGATCCAAAGGATTGTCCTGAGCGGTGAAAATGG
GCTGAAGATCGACATCCATGTCATCATCCCGTATGAAGGTCTGAGCGGCGACCAAA
TGGGCCAGATCGAAAAAATTTTTAAGGTGGTGTACCCTGTGGATGATCATCACTTTA
AGGTGATCCTGCACTATGGCACACTGGTAATCGACGGGGTTACGCCGAACATGATC
GACTATTTCGGACGGCCGTATGAAGGCATCGCCGTGTTCGACGGCAAAAAGATCAC
TGTAACAGGGACCCTGTGGAACGGCAACAAAATTATCGACGAGCGCCTGATCAACC
CCGACGGCTCCCTGCTGTTCCGAGTAACCATCAACGGAGTGACCGGCTGGCGGCTGT
GCGAACGCATTCTGGCGGGAAGCGGAGCTACTAACTTCAGCCTGCTGAAGCAGGCT
GGAGACGTGGAGGAGAACCCTGGACCTCT
5-13: Kozak sequence
14-202: 1XFLAG-EGF
203-265: T2A
266-805: 1XFLAG-Nluc
806-871: P2A SEQ ID NO: 18
Kozak 1XFLAG-EGF stop 1XFLAG-Nluc stop (762 bps)
GGGAGCCACCATGGACTACAAGGACGACGACGACAAGATCATCAATAGTGACTCTG
AGTGTCCCCTGTCCCACGACGGGTACTGCCTCCACGACGGTGTGTGCATGTATATTG
AAGCATTGGACAAGTACGCCTGCAACTGTGTTGTTGGCTACATCGGGGAGCGCTGTC
AGTACCGAGACCTGAAGTGGTGGGAACTGCGCTGATAGTAAGACTATAAGGACGAC
GACGACAAAATCATCGTCTTCACACTCGAAGATTTCGTTGGGGACTGGCGACAGAC
AGCCGGCTACAACCTGGACCAAGTCCTTGAACAGGGAGGTGTGTCCAGTTTGTTTCA
GAATCTCGGGGTGTCCGTAACTCCGATCCAAAGGATTGTCCTGAGCGGTGAAAATG
GGCTGAAGATCGACATCCATGTCATCATCCCGTATGAAGGTCTGAGCGGCGACCAA
ATGGGCCAGATCGAAAAAATTTTTAAGGTGGTGTACCCTGTGGATGATCATCACTTT
AAGGTGATCCTGCACTATGGCACACTGGTAATCGACGGGGTTACGCCGAACATGAT
CGACTATTTCGGACGGCCGTATGAAGGCATCGCCGTGTTCGACGGCAAAAAGATCA
CTGTAACAGGGACCCTGTGGAACGGCAACAAAATTATCGACGAGCGCCTGATCAAC
CCCGACGGCTCCCTGCTGTTCCGAGTAACCATCAACGGAGTGACCGGCTGGCGGCTG
TGCGAACGCATTCTGGCGTGATAGTAACT
5-13: Kozak sequence
14-202: 1XFLAG-EGF
203-211: Triple stop codon
212-751: 1XFLAG-Nluc
752-760: Triple stop codon SEQ ID NO: 19
Kozak 3XFLAG-EGF P2A nostop (330 bps)
GGGAGCCACCATGGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC -continued

SEQUENCE LISTING

GCTGTCAGTACCGAGACCTGAAGTGGTGGGAACTGCGCGGAAGCGGAGCTACTAAC
TTCAGCCTGCTGAAGCAGGCTGGAGACGTGGAGGAGAACCCTGGACCTCT
5-13: Kozak sequence
14-262: 3XFLAG-EGF
263-328: P2A SEQ ID NO: 20
Kozak 3XFLAG-EGF nostop (264 bps)
GGGAGCCACCATGGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC
GCTGTCAGTACCGAGACCTGAAGTGGTGGGAACTGCGCCT
5-13: Kozak sequence
14-262: 3XFLAG-EGF SEQ ID NO: 21
Kozak 3XFLAG-EGF stop (273 bps)
GGGAGCCACCATGGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC
GCTGTCAGTACCGAGACCTGAAGTGGTGGGAACTGCGCTGATAGTAACT
5-13: Kozak sequence
14-262: 3XFLAG-EGF
263-271: Triple stop codon SEQ ID NO: 22
EMCV IRES T2A 3XFLAG-EGF P2A nostop (954 bps)
GGGACCTAACGTTACTGGCCGAAGCCGCTTGGAACAAGGCCGGTGTGCGTTTGTCTA
TATGTTATTTTCCACCATATTGCCGTCTTTTGGCAATGTGAGGGCCCGGAAACCTGG
CCCTGTCTTCTTGACGAGCATTCCTAGGGGTCTTTCCCCTCTCGCCAAAGGAATGCA
AGGTCTGTTGAATGTCGTGAAGGAAGCAGTTCCTCTGGAAGCTTCTTCAAGACAAAC
AACGTCTGTAGCGACCCTTTGCAGGCAGCGGAACCCCCCACCTGGCGACAGGTGCC
TCTGCGGCCAAAAGCCACGTGTATACGATACACCTGCAAAGGCGGCACAACCCCAG
TGCCACGTTGTGAGTTGGATAGTTGTGGAAAGAGTCAAATGGCTCTCCTCAAGCGTA
TTCAACAAGGGGCTGAAGGATGCCCAGAAGGTACCCCATTGTATGGGATCTGATCT
GGGGCCTCGGTGCACATGCTTTACATGTGTTCAGTCGAGGTTAAAAAACGTCCAGGC
CCCCCGAACCACGGGGACGTGGTTTTCCTTTGAAAAACACGATGATAATATGGCCAC
AACCATGGGCTCCGGCGAGGGCAGGGGAAGTCTTCTAACATGCGGGGACGTGGAGG
AAAATCCCGGCCCAGACTACAAGGACGACGACGACAAGATCATCGACTATAAAGAC
GACGACGATAAAGGTGGCGACTATAAGGACGACGACGACAAAGCCATTAATAGTG
ACTCTGAGTGTCCCCTGTCCCACGACGGGTACTGCCTCCACGACGGTGTGTGCATGT
ATATTGAAGCATTGGACAAGTACGCCTGCAACTGTGTTGTTGGCTACATCGGGGAGC
GCTGTCAGTACCGAGACCTGAAGTGGTGGGAACTGCGCGGAAGCGGAGCTACTAAC
TTCAGCCTGCTGAAGCAGGCTGGAGACGTGGAGGAGAACCCTGGACCTCT
5-574: EMCV IRES
575-637: T2A
638-886: 3XFALG-EGF
887-952: P2A SEQ ID NO: 23
EMCV T2A 3XFLAG Nluc P2A stop (1314 nts)
GGGACCTAACGTTACTGGCCGAAGCCGCTTGGAACAAGGCCGGTGTGCGTTTGTCTA
TATGTTATTTTCCACCATATTGCCGTCTTTTGGCAATGTGAGGGCCCGGAAACCTGG
CCCTGTCTTCTTGACGAGCATTCCTAGGGGTCTTTCCCCTCTCGCCAAAGGAATGCA
AGGTCTGTTGAATGTCGTGAAGGAAGCAGTTCCTCTGGAAGCTTCTTCAAGACAAAC
AACGTCTGTAGCGACCCTTTGCAGGCAGCGGAACCCCCCACCTGGCGACAGGTGCC
TCTGCGGCCAAAAGCCACGTGTATACGATACACCTGCAAAGGCGGCACAACCCCAG
TGCCACGTTGTGAGTTGGATAGTTGTGGAAAGAGTCAAATGGCTCTCCTCAAGCGTA
TTCAACAAGGGGCTGAAGGATGCCCAGAAGGTACCCCATTGTATGGGATCTGATCT
GGGGCCTCGGTGCACATGCTTTACATGTGTTCAGTCGAGGTTAAAAAACGTCCAGGC
CCCCCGAACCACGGGGACGTGGTTTTCCTTTGAAAAACACGATGATAATATGGCCAC
AACCATGGGCTCCGGCGAGGGCAGGGGAAGTCTTCTAACATGCGGGGACGTGGAGG
AAAATCCCGGCCCAGACTACAAGGACGACGACGACAAGATCATCGACTATAAAGAC
GACGACGATAAAGGTGGCGACTATAAGGACGACGACGACAAAGCCATTGTCTTCAC
ACTCGAAGATTTCGTTGGGGACTGGCGACAGACAGCCGGCTACAACCTGGACCAAG
TCCTTGAACAGGGAGGTGTGTCCAGTTTGTTTCAGAATCTCGGGGTGTCCGTAACTC
CGATCCAAAGGATTGTCCTGAGCGGTGAAAATGGGCTGAAGATCGACATCCATGTC
ATCATCCCGTATGAAGGTCTGAGCGGCGACCAAATGGGCCAGATCGAAAAAATTTT
TAAGGTGGTGTACCCTGTGGATGATCATCACTTTAAGGTGATCCTGCACTATGGCAC
ACTGGTAATCGACGGGGTTACGCCGAACATGATCGACTATTTCGGACGGCCGTATG
AAGGCATCGCCGTGTTCGACGGCAAAAAGATCACTGTAACAGGGACCCTGTGGAAC
GGCAACAAAATTATCGACGAGCGCCTGATCAACCCCGACGGCTCCCTGCTGTTCCGA
GTAACCATCAACGGAGTGACCGGCTGGCGGCTGTGCGAACGCATTCTGGCGGGAAG
CGGAGCTACTAACTTCAGCCTGCTGAAGCAGGCTGGAGACGTGGAGGAGAACCCTG
GACCTTGATAGTAACT

SEQUENCE LISTING 5-574: EMCV IRES
575-637: T2A
638-1237: 3XFLAG Nluc
1238-1303: P2A
1304-1312: Triple stop codon SEQ ID NO: 24
EMCV T2A 3XFLAG Nluc P2A nostop (1305 nts)
GGGACCTAACGTTACTGGCCGAAGCCGCTTGGAACAAGGCCGGTGTGCGTTTGTCTA
TATGTTATTTTCCACCATATTGCCGTCTTTTGGCAATGTGAGGGCCCGGAAACCTGG
CCCTGTCTTCTTGACGAGCATTCCTAGGGGTCTTTCCCCTCTCGCCAAAGGAATGCA
AGGTCTGTTGAATGTCGTGAAGGAAGCAGTTCCTCTGGAAGCTTCTTCAAGACAAAC
AACGTCTGTAGCGACCCTTTGCAGGCAGCGGAACCCCCCACCTGGCGACAGGTGCC
TCTGCGGCCAAAAGCCACGTGTATACGATACACCTGCAAAGGCGGCACAACCCCAG
TGCCACGTTGTGAGTTGGATAGTTGTGGAAAGAGTCAAATGGCTCTCCTCAAGCGTA
TTCAACAAGGGGCTGAAGGATGCCCAGAAGGTACCCCATTGTATGGGATCTGATCT
GGGGCCTCGGTGCACATGCTTTACATGTGTTCAGTCGAGGTTAAAAAACGTCCAGGC
CCCCCGAACCACGGGGACGTGGTTTTCCTTTGAAAAACACGATGATAATATGGCCAC
AACCATGGGCTCCGGCGAGGGCAGGGGAAGTCTTCTAACATGCGGGGACGTGGAGG
AAAATCCCGGCCCAGACTACAAGGACGACGACGACAAGATCATCGACTATAAAGAC
GACGACGATAAAGGTGGCGACTATAAGGACGACGACGACAAAGCCATTGTCTTCAC
ACTCGAAGATTTCGTTGGGGACTGGCGACAGACAGCCGGCTACAACCTGGACCAAG
TCCTTGAACAGGGAGGTGTGTCCAGTTTGTTTCAGAATCTCGGGGTGTCCGTAACTC
CGATCCAAAGGATTGTCCTGAGCGGTGAAAATGGGCTGAAGATCGACATCCATGTC
ATCATCCCGTATGAAGGTCTGAGCGGCGACCAAATGGGCCAGATCGAAAAAATTTT
TAAGGTGGTGTACCCTGTGGATGATCATCACTTTAAGGTGATCCTGCACTATGGCAC
ACTGGTAATCGACGGGGTTACGCCGAACATGATCGACTATTTCGGACGGCCGTATG
AAGGCATCGCCGTGTTCGACGGCAAAAAGATCACTGTAACAGGGACCCTGTGGAAC
GGCAACAAAATTATCGACGAGCGCCTGATCAACCCCGACGGCTCCCTGCTGTTCCGA
GTAACCATCAACGGAGTGACCGGCTGGCGGCTGTGCGAACGCATTCTGGCGGGAAG
CGGAGCTACTAACTTCAGCCTGCTGAAGCAGGCTGGAGACGTGGAGGAGAACCCTG
GACCTCT
5-574: EMCV IRES
575-637: T2A
638-1237: 3XFLAG Nluc
1238-1303: P2A SEQ ID NO: 25
Kozak 1XFLAG-EGF T2A 1XFLAG-NLuc P2A stop (882 bps)
GGGAGCCACCATGGACTACAAGGACGACGACGACAAGATCATCAATAGTGACTCTG
AGTGTCCCCTGTCCCACGACGGGTACTGCCTCCACGACGGTGTGTGCATGTATATTG
AAGCATTGGACAAGTACGCCTGCAACTGTGTTGTTGGCTACATCGGGGAGCGCTGTC
AGTACCGAGACCTGAAGTGGTGGGAACTGCGCGGCTCCGGCGAGGGCAGGGGAAG
TCTTCTAACATGCGGGGACGTGGAGGAAAATCCCGGCCCAGACTATAAGGACGACG
ACGACAAAATCATCGTCTTCACACTCGAAGATTTCGTTGGGGACTGGCGACAGACA
GCCGGCTACAACCTGGACCAAGTCCTTGAACAGGGAGGTGTGTCCAGTTTGTTTCAG
AATCTCGGGGTGTCCGTAACTCCGATCCAAAGGATTGTCCTGAGCGGTGAAAATGG
GCTGAAGATCGACATCCATGTCATCATCCCGTATGAAGGTCTGAGCGGCGACCAAA
TGGGCCAGATCGAAAAAATTTTTAAGGTGGTGTACCCTGTGGATGATCATCACTTTA
AGGTGATCCTGCACTATGGCACACTGGTAATCGACGGGGTTACGCCGAACATGATC
GACTATTTCGGACGGCCGTATGAAGGCATCGCCGTGTTCGACGGCAAAAAGATCAC
TGTAACAGGGACCCTGTGGAACGGCAACAAAATTATCGACGAGCGCCTGATCAACC
CCGACGGCTCCCTGCTGTTCCGAGTAACCATCAACGGAGTGACCGGCTGGCGGCTGT
GCGAACGCATTCTGGCGGGAAGCGGAGCTACTAACTTCAGCCTGCTGAAGCAGGCT
GGAGACGTGGAGGAGAACCCTGGACCTTGATAGTAACT
5-13: Kozak sequence
14-202: 1XFLAG-EGF
266-805: 1XFLAG-NLuc
806-871: P2A
872-880: Triple stop codon SEQ ID NO: 26
Exemplary Repetitive Spacer Sequence
AAAAAACAAAAAACAAAACGGCTATTATGCGTTACCGGCGAGACGCTACGG
ACTTGGGAAAATCCGTTGACCTTAAACGGTCGTGTGGGTTCAAGTCCCTCCACCCCC
ACGCCGGAAACGCAATAGCCGAAAAACAAAAAACAAAAAAAACAAAAAAAAAACC
AAAAAAACAAAACACA SEQ ID NO: 27
Forward primer used in Example 43 to amplify template from pCDNA3.1/CAT
CGCGGATCCTAATACGACTCACTATAGGGAGACCCAAGCTGGC SEQ ID NO: 28
Reverse primer used in Example 43 to amplify 0.5 kb template from pCDNA3.1/CAT
AATAGCCGTTTTGTTTTTTGGATTACCAGTGTGCCATAGTGCAGGATCACATCGTCGT
GGTATTCACTCCAGAGCGATG -continued

SEQUENCE LISTING

SEQ ID NO: 29
Reverse primer used in Example 43 to amplify 1 kb template from pCDNA3.1/CAT
AATAGCCGTTTTGTTTTTTGGATTACCAGTGTGCCATAGTGCAGGATCACACGGGGG
AGGGGCAAACAACAGATGG SEQ ID NO: 30
Reverse primer used in Example 43 to amplify 2 kb template from pCDNA3.1/CAT
AATAGCCGTTTTGTTTTTTGGATTACCAGTGTGCCATAGTGCAGGATCACGCTTTTTG
CAAAAGCCTAGGCCTCCAAAAAAGCC SEQ ID NO: 31
Reverse primer used in Example 43 to amplify 4 kb template from pCDNA3.1/CAT
AATAGCCGTTTTGTTTTTTGGATTACCAGTGTGCCATAGTGCAGGATCACTAGCACC
GCCTACATACCTCGCTCTGC SEQ ID NO: 32
Reverse primer used in Example 43 to amplify 5 kb template from pCDNA3.1/CAT
AATAGCCGTTTTGTTTTTTGGATTACCAGTGTGCCATAGTGCAGGATCACCTATGTG
GCGCGGTATTATCCCGTATTGAC SEQ ID NO: 33
Reverse primer used in Example 43 to amplify 6.2 kb template from pCDNA3.1/CAT
AATAGCCGTTTTGTTTTTTGGATTACCAGTGTGCCATAGTGCAGGATCACATTTCGAT
AAGCCAGTAAGCAGTGGGTTCTCTAG SEQ ID NO: 34
Forward qPCR primer used in Example 43 to detect linear transcript from
pCDNA3.1/CAT
ATTCTTGCCCGCCTGATGAA SEQ ID NO: 35
Reverse qPCR primer used in Example 43 to detect linear transcript from pCDNA3.1/CAT
TTGCTCATGGAAAACGGTGT SEQ ID NO: 36
Forward qPCR primer used in Example 43 to detect circular transcript from
pCDNA3.1/CAT
TGATCCTGCACTATGGCACA SEQ ID NO: 37
Reverse qPCR primer used in Example 43 to detect circular transcript from
pCDNA3.1/CAT
CTGGACTAGTGGATCCGAGC SEQ ID NO: 38
Forward primer sequence used in Example 44 to detect ACTIN
GACGAGGCCCAGAGCAAGAGAGG SEQ ID NO: 39
Reverse primer sequence used in Example 44 to detect ACTIN
GGTGTTGAAGGTCTCAAACATG SEQ ID NO: 40
Forward primer sequence used in Example 44 to detect RIG-1
TGTGGGCAATGTCATCAAAA SEQ ID NO: 42
Reverse primer sequence used in Example 44 to detect RIG-1
GAAGCACTTGCTACCTCTTGC SEQ ID NO: 42
Forward primer sequence used in Example 44 to detect MDA5
GGCACCATGGGAAGTGATT (SEQ ID NO: 64)

SEQ ID NO: 43
Reverse primer sequence used in Example 44 to detect MDA5
ATTTGGTAAGGCCTGAGCTG SEQ ID NO: 44
Forward primer sequence used in Example 44 to detect PKR
TCGCTGGTATCACTCGTCTG SEQ ID NO: 45
Reverse primer sequence used in Example 44 to detect PKR
GATTCTGAAGACCGCCAGAG -continued

SEQUENCE LISTING

SEQ ID NO: 46
Forward primer sequence used in Example 44 to detect IFN-beta
CTCTCCTGTTGTGCTTCTCC SEQ ID NO: 47
Reverse primer sequence used in Example 44 to detect IFN-beta
GTCAAAGTTCATCCTGTCCTTG.

SEQ ID NO: 48
EMCV T2A 3XFLAG-GFP F2A 3XFALG-Nluc P2A IS
GGGAATAGCCGAAAAACAAAAAACAAAAAAAACAAAAAAAAAACCAAAAAAACA
AAACACAACGTTACTGGCCGAAGCCGCTTGGAACAAGGCCGGTGTGCGTTTGTCTAT
ATGTTATTTTCCACCATATTGCCGTCTTTTGGCAATGTGAGGGCCCGGAAACCTGGC
CCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGTAGACAAACA
ACGTCTGTAGCGACCCTTTGCAGGCAGCGGAACCCCCCACCTGGCGACAGGTGCCTC
TGCGGCCAAAAGCCACGTGTATACGATACACCTGCAAAGGCGGCACAACCCCAGTG
CCACGTTGTGAGTTGGATAGTTGTGGAAAGAGTCAAATGGCTCTCCTCAAGCGTATT
CAACAAGGGGCTGAAGGATGCCCAGAAGGTACCCCATTGTATGGGATCTGATCTGG
GGCCTCGGTGCACATGCTTTACATGTGTTCAGTCGAGGTTAAAAAACGTCCAGGCCC
CCCGAACCACGGGGACGTGGTTTTCCTTTGAAAAACACGATGATAATATGGCCACA
ACCATGGGCTCCGGCGAGGGCAGGGGAAGTCTTCTAACATGCGGGGACGTGGAGGA
AAATCCCGGCCCAGACTACAAGGACGACGACGACAAGATCATCGACTATAAAGACG
ACGACGATAAAGGTGGCGACTATAAGGACGACGACGACAAAGCCATTGTGAGCAA
GGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCCACC
CTCGTGACCACCCTGACCTACGGCGTGCAGTGCTTCAGCCGCTACCCCGACCACATG
AAGCAGCACGACTTCTTCAAGTCCGCCATGCCCGAAGGCTACGTCCAGGAGCGCAC
CATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGC
AACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCG
AGGACGGCAGCGTGCAGCTCGCCGACCACTACCAGCAGAACACCCCCATCGGCGAC
GGCCCCGTGCTGCTGCCCGACAACCACTACCTGAGCACCCAGTCCGCCCTGAGCAA
AGACCCCAACGAGAAGCGCGATCACATGGTCCTGCTGGAGTTCGTGACCGCCGCCG
GGATCACTCTCGGCATGGACGAGCTGTACAAGGGAAGCGGAGTGAAACAGACTTTG
AATTTTGACCTTCTCAAGTTGGCGGGAGACGTGGAGTCCAACCCTGGACCTGACTAC
AAGGACGACGACGACAAGATCATCGACTATAAAGACGACGACGATAAAGGTGGCG
ACTATAAGGACGACGACGACAAAGCCATTATCATCGTCTTCACACTCGAAGATTTCG
TTGGGGACTGGCGACAGACAGCCGGCTACAACCTGGACCAAGTCCTTGAACAGGGA
GGTGTGTCCAGTTTGTTTCAGAATCTCGGGGTGTCCGTAACTCCGATCCAAAGGATT
GTCCTGAGCGGTGAAAATGGGCTGAAGATCGACATCCATGTCATCATCCCGTATGA
AGGTCTGAGCGGCGACCAAATGGGCCAGATCGAAAAAATTTTTAAGGTGGTGTACC
CTGTGGATGATCATCACTTTAAGGTGATCCTGCACTATGGCACACTGGTAATCGACG
GGGTTACGCCGAACATGATCGACTATTTCGGACGGCCGTATGAAGGCATCGCCGTGT
TCGACGGCAAAAAGATCACTGTAACAGGGACCCTGTGGAACGGCAACAAAATTATC
GACGAGCGCCTGATCAACCCCGACGGCTCCCTGCTGTTCCGAGTAACCATCAACGG
AGTGACCGGCTGGCGGCTGTGCGAACGCATTCTGGCGGGAAGCGGAGCTACTAACT
TCAGCCTGCTGAAGCAGGCTGGAGACGTGGAGGAGAACCCTGGACCTTAAAAAAAA
CAAAAAACAAAACGGCTATT SEQ ID NO: 49
EMCV T2A 3XFLAG-GFP F2A 3XFALG-Nluc P2A IS
GGGAATAGCCGAAAAACAAAAAACAAAAAAAACAAAAAAAAAACCAAAAAAACA
AAACACAACGTTACTGGCCGAAGCCGCTTGGAACAAGGCCGGTGTGCGTTTGTCTAT
ATGTTATTTTCCACCATATTGCCGTCTTTTGGCAATGTGAGGGCCCGGAAACCTGGC
CCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGTAGACAAACA
ACGTCTGTAGCGACCCTTTGCAGGCAGCGGAACCCCCCACCTGGCGACAGGTGCCTC
TGCGGCCAAAAGCCACGTGTATACGATACACCTGCAAAGGCGGCACAACCCCAGTG
CCACGTTGTGAGTTGGATAGTTGTGGAAAGAGTCAAATGGCTCTCCTCAAGCGTATT
CAACAAGGGGCTGAAGGATGCCCAGAAGGTACCCCATTGTATGGGATCTGATCTGG
GGCCTCGGTGCACATGCTTTACATGTGTTCAGTCGAGGTTAAAAAACGTCCAGGCCC
CCCGAACCACGGGGACGTGGTTTTCCTTTGAAAAACACGATGATAATATGGCCACA
ACCATGGGCTCCGGCGAGGGCAGGGGAAGTCTTCTAACATGCGGGGACGTGGAGGA
AAATCCCGGCCCAGACTACAAGGACGACGACGACAAGATCATCGACTATAAAGACG
ACGACGATAAAGGTGGCGACTATAAGGACGACGACGACAAAGCCATTGTGAGCAA
GGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCCACC
CTCGTGACCACCCTGACCTACGGCGTGCAGTGCTTCAGCCGCTACCCCGACCACATG
AAGCAGCACGACTTCTTCAAGTCCGCCATGCCCGAAGGCTACGTCCAGGAGCGCAC
CATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGC
AACATCCTGGGGCACAAGCTGGAGTACAACTACAACAGCCACAACGTCTATATCAT -continued

SEQUENCE LISTING

GGCCGACAAGCAGAAGAACGGCATCAAGGTGAACTTCAAGATCCGCCACAACATCG
AGGACGGCAGCGTGCAGCTCGCCGACCACTACCAGCAGAACACCCCCATCGGCGAC
GGCCCCGTGCTGCTGCCCGACAACCACTACCTGAGCACCCAGTCCGCCCTGAGCAA
AGACCCCAACGAGAAGCGCGATCACATGGTCCTGCTGGAGTTCGTGACCGCCGCCG
GGATCACTCTCGGCATGGACGAGCTGTACAAGGGAAGCGGAGTGAAACAGACTTTG
AATTTTGACCTTCTCAAGTTGGCGGGAGACGTGGAGTCCAACCCTGGACCTTGATAG
TAAGACTACAAGGACGACGACGACAAGATCATCGACTATAAAGACGACGACGATA
AAGGTGGCGACTATAAGGACGACGACGACAAAGCCATTATCATCGTCTTCACACTC
GAAGATTTCGTTGGGGACTGGCGACAGACAGCCGGCTACAACCTGGACCAAGTCCT
TGAACAGGGAGGTGTGTCCAGTTTGTTTCAGAATCTCGGGGTGTCCGTAACTCCGAT
CCAAAGGATTGTCCTGAGCGGTGAAAATGGGCTGAAGATCGACATCCATGTCATCA
TCCCGTATGAAGGTCTGAGCGGCGACCAAATGGGCCAGATCGAAAAAATTTTTAAG
GTGGTGTACCCTGTGGATGATCATCACTTTAAGGTGATCCTGCACTATGGCACACTG
GTAATCGACGGGGTTACGCCGAACATGATCGACTATTTCGGACGGCCGTATGAAGG
CATCGCCGTGTTCGACGGCAAAAAGATCACTGTAACAGGGACCCTGTGGAACGGCA
ACAAAATTATCGACGAGCGCCTGATCAACCCCGACGGCTCCCTGCTGTTCCGAGTAA
CCATCAACGGAGTGACCGGCTGGCGGCTGTGCGAACGCATTCTGGCGGGAAGCGGA
GCTACTAACTTCAGCCTGCTGAAGCAGGCTGGAGACGTGGAGGAGAACCCTGGACC
TTAAAAAAAACAAAAAACAAAACGGCTATT

SEQ ID NO: 50
URE
UCAUAAUCAAUUUAUUAUUUUCUUUUAUUUUAUUCACAUAAUUUUGUUUUU

SEQ ID NO: 51
CSE
AUUUUGUUUUUAACAUUUC

SEQ ID NO: 52
URE/CSE
UCAUAAUCAAUUUAUUAUUUUCUUUUAUUUUAUUCACAUAAUUUUGUUUUUAUU
UUGUUUUUAACAUUUC

SEQ ID NO: 53
CVB3-GLuc-STOP-URE
AAAAUCCGUUGACCUUAAACGGUCGUGUGGGUUCAAGUCCCUCCACCCCCACGCC
GGAAACGCAAUAGCCGAAAAACAAAAAACAAAAAAAACAAAAAAAAAACCAAAA
AAACAAAACACAUUAAAACAGCCUGUGGGUUGAUCCCACCCACAGGCCCAUUGGG
CGCUAGCACUCUGGUAUCACGGUACCUUUGUGCGCCUGUUUUAUACCCCCUCCCC
CAACUGUAACUUAGAAGUAACACACACCGAUCAACAGUCAGCGUGGCACACCAGC
CACGUUUUGAUCAAGCACUUCUGUUACCCCGGACUGAGUAUCAAUAGACUGCUCA
CGCGGUUGAAGGAGAAAGCGUUCGUUAUCCGGCCAACUACUUCGAAAAACCUAG
UAACACCGUGGAAGUUGCAGAGUGUUUCGCUCAGCACUACCCCAGUGUAGAUCAG
GUCGAUGAGUCACCGCAUUCCCCACGGGCGACCGUGGCGGUGGCUGCGUUGGCGG
CCUGCCCAUGGGGAAACCCAUGGGACGCUCUAAUACAGACAUGGUGCGAAGAGUC
UAUUGAGCUAGUUGGUAGUCCUCCGGCCCCUGAAUGCGGCUAAUCCUAACUGCGG
AGCACACACCCUCAAGCCAGAGGGCAGUGUGUCGUAACGGGCAACUCUGCAGCGG
AACCGACUACUUUGGGUGUCCGUGUUUCAUUUUAUUCCUAUACUGGCUGCUUAU
GGUGACAAUUGAGAGAUCGUUACCAUAUAGCUAUUGGAUUGGCCAUCCGGUGAC
UAAUAGAGCUAUUAUAUAUCCCUUUGUUGGGUUUAUACCACUUAGCUUGAAAGA
GGUUAAAACAUUACAAUUCAUUGUUAAGUUGAAUACAGCAAAAUGGGAGUCAAA
GUUCUGUUUGCCCUGAUCUGCAUCGCUGUGGCCGAGGCCAAGCCCACCGAGAACA
ACGAAGACUUCAACAUCGUGGCCGUGGCCAGCAACUUCGCGACCACGGAUCUCGA
UGCUGACCGCGGGAAGUUGCCCGGCAAGAAGCUGCCGCUGGAGGUGCUCAAAGAG
AUGGAAGCCAAUGCCCGGAAAGCUGGCUGCACCAGGGGCUGUCUGAUCUGCCUGU
CCCACAUCAAGUGCACGCCCAAGAUGAAGAAGUUCAUCCCAGGACGCUGCCACAC
CUACGAAGGCGACAAAGAGUCCGCACAGGGCGGCAUAGGCGAGGCGAUCGUCGAC
AUUCCUGAGAUUCCUGGGUUCAAGGACUUGGAGCCCAUGGAGCAGUUCAUCGCAC
AGGUCGAUCUGUGUGUGGACUGCACAACUGGCUGCCUCAAAGGGCUUGCCAACGU
GCAGUGUUCUGACCUGCUCAAGAAGUGGCUGCCGCAACGCUGUGCGACCUUUGCC
AGCAAGAUCCAGGGCCAGGUGGACAAGAUCAAGGGGGCCGGUGGUGACUAAUCA
UAAUCAAUUUAUUAUUUUCUUUUAUUUUAUUCACAUAAUUUUGUUUUUAUUUUG
UUUUUAACAUUUCAAAAAACAAAAAACAAAACGGCUAUUAUGCGUUACCGGCGA
GACGCUACGGACUU

SEQ ID NO: 54
CVB3-GLuc-STOP-URE/CSE
AAAAUCCGUUGACCUUAAACGGUCGUGUGGGUUCAAGUCCCUCCACCCCCACGCC
GGAAACGCAAUAGCCGAAAAACAAAAAACAAAAAAAACAAAAAAAAAACCAAAA
AAACAAAACACAUUAAAACAGCCUGUGGGUUGAUCCCACCCACAGGCCCAUUGGG
CGCUAGCACUCUGGUAUCACGGUACCUUUGUGCGCCUGUUUUAUACCCCCUCCCC
CAACUGUAACUUAGAAGUAACACACACCGAUCAACAGUCAGCGUGGCACACCAGC
CACGUUUUGAUCAAGCACUUCUGUUACCCCGGACUGAGUAUCAAUAGACUGCUCA
CGCGGUUGAAGGAGAAAGCGUUCGUUAUCCGGCCAACUACUUCGAAAAACCUAG
UAACACCGUGGAAGUUGCAGAGUGUUUCGCUCAGCACUACCCCAGUGUAGAUCAG
GUCGAUGAGUCACCGCAUUCCCCACGGGCGACCGUGGCGGUGGCUGCGUUGGCGG
CCUGCCCAUGGGGAAACCCAUGGGACGCUCUAAUACAGACAUGGUGCGAAGAGUC

-continued

SEQUENCE LISTING

UAUUGAGCUAGUUGGUAGUCCUCCGGCCCCUGAAUGCGGCUAAUCCUAACUGCGG
AGCACACACCCUCAAGCCAGAGGGCAGUGUGUCGUAACGGGCAACUCUGCAGCGG
AACCGACUACUUUGGGUGUCCGUGUUUCAUUUUAUUCCUAUACUGGCUGCUUAU
GGUGACAAUUGAGAGAUCGUUACCAUAUAGCUAUUGGAUUGGCCAUCCGGUGAC
UAAUAGAGCUAUUAUAUAUCCCUUUGUUGGGUUUAUACCACUUAGCUUGAAAGA
GGUUAAAACAUUACAAUUCAUUGUUAAGUUGAAUACAGCAAAAUGGGAGUCAAA
GUUCUGUUUGCCCUGAUCUGCAUCGCUGUGGCCGAGGCCAAGCCCACCGAGAACA
ACGAAGACUUCAACAUCGUGGCCGUGGCCAGCAACUUCGCGACCACGGAUCUCGA
UGCUGACCGCGGGAAGUUGCCCGGCAAGAAGCUGCCGCUGGAGGUGCUCAAAGAG
AUGGAAGCCAAUGCCCGGAAAGCUGGCUGCACCAGGGGCUGUCUGAUCUGCCUGU
CCCACAUCAAGUGCACGCCCAAGAUGAAGAAGUUCAUCCCAGGACGCUGCCACAC
CUACGAAGGCGACAAAGAGUCCGCACAGGGCGGCAUAGGCGAGGCGAUCGUCGAC
AUUCCUGAGAUUCCUGGGUUCAAGGACUUGGAGCCCAUGGAGCAGUUCAUCGCAC
AGGUCGAUCUGUGUGUGGACUGCACAACUGGCUGCCUCAAAGGGCUUGCCAACGU
GCAGUGUUCUGACCUGCUCAAGAAGUGGCUGCCGCAACGCUGUGCGACCUUUGCC
AGCAAGAUCCAGGGCCAGGUGGACAAGAUCAAGGGGGCCGGUGGUGACUAAUCA
UAAUCAAUUUAUUAUUUUCUUUUAUUUUAUUCACAUAAUUUUGUUUUUAUUUUG
UUUUUAACAUUUCAAAAAACAAAAAACAAAACGGCUAUUAUGCGUUACCGGCGA
GACGCUACGGACUU

SEQ ID NO: 55
Complementary primer used for example 42
CACCGCTCAGGACAATCCTT

SEQ ID NO: 56
CVB3 IRES
TTAAAACAGCCTGTGGGTTGATCCCACCCACAGGCCCATTGGGCGCTAGCACTCTGG
TATCACGGTACCTTTGTGCGCCTGTTTTATACCCCCTCCCCCAACTGTAACTTAGAAG
TAACACACACCGATCAACAGTCAGCGTGGCACACCAGCCACGTTTTGATCAAGCAC
TTCTGTTACCCCGGACTGAGTATCAATAGACTGCTCACGCGGTTGAAGGAGAAAGC
GTTCGTTATCCGGCCAACTACTTCGAAAAACCTAGTAACACCGTGGAAGTTGCAGAG
TGTTTCGCTCAGCACTACCCCAGTGTAGATCAGGTCGATGAGTCACCGCATTCCCCA
CGGGCGACCGTGGCGGTGGCTGCGTTGGCGGCCTGCCCATGGGGAAACCCATGGGA
CGCTCTAATACAGACATGGTGCGAAGAGTCTATTGAGCTAGTTGGTAGTCCTCCGGC
CCCTGAATGCGGCTAATCCTAACTGCGGAGCACACACCCTCAAGCCAGAGGGCAGT
GTGTCGTAACGGGCAACTCTGCAGCGGAACCGACTACTTTGGGTGTCCGTGTTTCAT
TTTATTCCTATACTGGCTGCTTATGGTGACAATTGAGAGATCGTTACCATATAGCTAT
TGGATTGGCCATCCGGTGACTAATAGAGCTATTATATATCCCTTTGTTGGGTTTATAC
CACTTAGCTTGAAAGAGGTTAAAACATTACAATTCATTGTTAAGTTGAATACAGCAA
A

SEQ ID NO: 57
Gluc
ATGGGAGTCAAAGTTCTGTTTGCCCTGATCTGCATCGCTGTGGCCGAGGCCAAGCCC
ACCGAGAACAACGAAGACTTCAACATCGTGGCCGTGGCCAGCAACTTCGCGACCAC
GGATCTCGATGCTGACCGCGGGAAGTTGCCCGGCAAGAAGCTGCCGCTGGAGGTGC
TCAAAGAGATGGAAGCCAATGCCCGGAAAGCTGGCTGCACCAGGGGCTGTCTGATC
TGCCTGTCCCACATCAAGTGCACGCCCAAGATGAAGAAGTTCATCCCAGGACGCTG
CCACACCTACGAAGGCGACAAAGAGTCCGCACAGGGCGGCATAGGCGAGGCGATC
GTCGACATTCCTGAGATTCCTGGGTTCAAGGACTTGGAGCCCATGGAGCAGTTCATC
GCACAGGTCGATCTGTGTGTGGACTGCACAACTGGCTGCCTCAAAGGGCTTGCCAAC
GTGCAGTGTTCTGACCTGCTCAAGAAGTGGCTGCCGCAACGCTGTGCGACCTTTGCC
AGCAAGATCCAGGGCCAGGTGGACAAGATCAAGGGGGCCGGTGGTGACTAA SEQ ID NO: 58
EMCV IRES with stop mutations
ACGTTACTGGCCGAAGCCGCTTGGAACAAGGCCGGTGTGCGTTTGTCTATATGTTAT
TTTCCACCATATTGCCGTCTTTTGGCAATGTGAGGGCCCGGAAACCTGGCCCTGTCTT
CTTGACGAGCATTCCTAGGGGTCTTTCCCCTCTCGCCAAAGGAATGCAAGGTCTGTT
GAATGTCGTGAAGGAAGCAGTTCCTCTGGAAGCTTCTTCAAGACAAACAACGTCTGT
AGCGACCCTTTGCAGGCAGCGGAACCCCCCACCTGGCGACAGGTGCCTCTGCGGCC
AAAAGCCACGTGTATACGATACACCTGCAAAGGCGGCACAACCCCAGTGCCACGTT
GTGAGTTGGATAGTTGTGGAAAGAGTCAAATGGCTCTCCTCAAGCGTATTCAACAA
GGGGCTGAAGGATGCCCAGAAGGTACCCCATTGTATGGGATCTGATCTGGGGCCTC
GGTGCACATGCTTTACATGTGTTCAGTCGAGGTTAAAAAACGTCCAGGCCCCCCGAA
CCACGGGGACGTGGTTTTCCTTTGAAAAACACGATGATAATATGGCCACAACCATG SEQ ID NO: 59
SPACER 1
AAAAUCCGUUGACCUUAAACGGUCGUGUGGGUUCAAGUCCCUCCACCCCCACGCC
GGAAACGCAAUAGCCGAAAAACAAAAAACAAAAAAAACAAAAAAAAAACCAAAA
AAACAAAACACA SPACER 2
AAAAAACAAAAAACAAAACGGCUAUUAUGCGUUACCGGCGAGACGCUACGGACU
U (SEQ ID NO: 65)

-continued

SEQUENCE LISTING

SEQ ID: 60
ATACCAGCCGAAAGGCCCTTGGCAGAGAGGTCTGAAAAGACCTCTGCTGACTATGT
GATCTTATTAAAATTAGGTTAAATTTCGAGGTTAAAAATAGTTTTAATATTGCTATA
GTCTTAGAGGTCTTGTATATTTATACTTACCACACAAGATGGACCGGAGCAGCCCTC
CAATATCTAGTGTACCCTCGTGCTCGCTCAAACATTAAGTGGTGTTGTGCGAAAAGA
ATCTCACTTCAAGAAAAAGAAACTAGT

WT EMCV Gluc IS
GGGAATAGCCGAAAAACAAAAAACAAAAAAAACAAAAAAAAAACCAAAAAAACA
AAACACAACGTTACTGGCCGAAGCCGCTTGGAATAAGGCCGGTGTGCGTTTGTCTAT
ATGTTATTTTCCACCATATTGCCGTCTTTTGGCAATGTGAGGGCCCGGAAACCTGGC
CCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGAAGACAAACA
ACGTCTGTAGCGACCCTTTGCAGGCAGCGGAACCCCCCACCTGGCGACAGGTGCCTC
TGCGGCCAAAAGCCACGTGTATAAGATACACCTGCAAAGGCGGCACAACCCCAGTG
CCACGTTGTGAGTTGGATAGTTGTGGAAAGAGTCAAATGGCTCTCCTCAAGCGTATT
CAACAAGGGGCTGAAGGATGCCCAGAAGGTACCCCATTGTATGGGATCTGATCTGG
GGCCTCGGTGCACATGCTTTACATGTGTTTAGTCGAGGTTAAAAAACGTCTAGGCCC
CCCGAACCACGGGGACGTGGTTTTCCTTTGAAAAACACGATGATAATAGCCACCAT
GGGAGTCAAAGTTCTGTTTGCCCTGATCTGCATCGCTGTGGCCGAGGCCAAGCCCAC
CGAGAACAACGAAGACTTCAACATCGTGGCCGTGGCCAGCAACTTCGCGACCACGG
ATCTCGATGCTGACCGCGGGAAGTTGCCCGGCAAGAAGCTGCCGCTGGAGGTGCTC
AAAGAGATGGAAGCCAATGCCCGGAAAGCTGGCTGCACCAGGGGCTGTCTGATCTG
CCTGTCCCACATCAAGTGCACGCCCAAGATGAAGAAGTTCATCCCAGGACGCTGCC
ACACCTACGAAGGCGACAAAGAGTCCGCACAGGGCGGCATAGGCGAGGCGATCGT
CGACATTCCTGAGATTCCTGGGTTCAAGGACTTGGAGCCCATGGAGCAGTTCATCGC
ACAGGTCGATCTGTGTGTGGACTGCACAACTGGCTGCCTCAAAGGGCTTGCCAACGT
GCAGTGTTCTGACCTGCTCAAGAAGTGGCTGCCGCAACGCTGTGCGACCTTTGCCAG
CAAGATCCAGGGCCAGGTGGACAAGATCAAGGGGGCCGGTGGTGACTAAAAAAAA
CAAAAAACAAAACGGCTATT (SEQ ID NO: 127)

5' spacer
AATAGCCGAAAAACAAAAAACAAAAAAAAACAAAAAAAAAACCAAAAAAACAAAA
CACA (SEQ ID NO: 128)

3' spacer
AAAAAACAAAAAACAAAACGGCTATT (SEQ ID NO: 129)

Sequence #1 (First section: 5'spacer + WT EMCV IRES + 38 nts ORF)
GGGAATAGCCGAAAAACAAAAAACAAAAAAAAACAAAAAAAAAACCAAAAAAACA
AAACACAACGTTACTGGCCGAAGCCGCTTGGAATAAGGCCGGTGTGCGTTTGTCTAT
ATGTTATTTTCCACCATATTGCCGTCTTTTGGCAATGTGAGGGCCCGGAAACCTGGC
CCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGAAGACAAACA
ACGTCTGTAGCGACCCTTTGCAGGCAGCGGAACCCCCCACCTGGCGACAGGTGCCTC
TGCGGCCAAAAGCCACGTGTATAAGATACACCTGCAAAGGCGGCACAACCCCAGTG
CCACGTTGTGAGTTGGATAGTTGTGGAAAGAGTCAAATGGCTCTCCTCAAGCGTATT
CAACAAGGGGCTGAAGGATGCCCAGAAGGTACCCCATTGTATGGGATCTGATCTGG
GGCCTCGGTGCACATGCTTTACATGTGTTTAGTCGAGGTTAAAAAACGTCTAGGCCC
CCCGAACCACGGGGACGTGGTTTTCCTTTGAAAAACACGATGATAATAGCCACCAT
GGGAGTCAAAGTTCTGTTTGCCCTGATCTGCATCGCTGT (SEQ ID NO: 130)

Sequence #2 (Second section: ORF + 3' spacer)
GGCCGAGGCCAAGCCCACCGAGAACAACGAAGACTTCAACATCGTGGCCGTGGCCA
GCAACTTCGCGACCACGGATCTCGATGCTGACCGCGGGAAGTTGCCCGGCAAGAAG
CTGCCGCTGGAGGTGCTCAAAGAGATGGAAGCCAATGCCCGGAAAGCTGGCTGCAC
CAGGGGCTGTCTGATCTGCCTGTCCCACATCAAGTGCACGCCCAAGATGAAGAAGTT
CATCCCAGGACGCTGCCACACCTACGAAGGCGACAAAGAGTCCGCACAGGGCGGCA
TAGGCGAGGCGATCGTCGACATTCCTGAGATTCCTGGGTTCAAGGACTTGGAGCCCA
TGGAGCAGTTCATCGCACAGGTCGATCTGTGTGTGGACTGCACAACTGGCTGCCTCA
AAGGGCTTGCCAACGTGCAGTGTTCTGACCTGCTCAAGAAGTGGCTGCCGCAACGCT
GTGCGACCTTTGCCAGCAAGATCCAGGGCCAGGTGGACAAGATCAAGGGGGCCGGT
GGTGACTAAAAAAAACAAAAAACAAAACGGCTATT (SEQ ID NO: 131)

Forward primer to amplify first section
CGCGGATCCTAATACGACTCACTATAGGGAATAGCCGAAAAACAAAAAACAAAAA
AAACAAAAAAAAAACCAAAAAAACAAAACACAACGTTACTGGCCGAAGCCGC (SEQ ID NO: 132)

Reverse primer to amplify first section
mAmCAGCGATGCAGATCAGGGC (SEQ ID NO: 133)

Forward primer to amplify second section
CGCGGATCCTAATACGACTCACTATAGGCCGAGGCCAAGCCCACCG (SEQ ID NO: 134)

Reverse primer to amplify second section
mAmATAGCCGTTTTGTTTTTTGTTTTTTTAGTCACCACCGGCCCCCT (SEQ ID NO: 135)

-continued

| SEQUENCE LISTING |
| --- |

Globin GLuc
GGGACTCTTCTGGTCCCCACAGACTCAGAGAGAACCCACCATGGGAGTCAAAGTTC
TGTTTGCCCTGATCTGCATCGCTGTGGCCGAGGCCAAGCCCACCGAGAACAACGAA
GACTTCAACATCGTGGCCGTGGCCAGCAACTTCGCGACCACGGATCTCGATGCTGAC
CGCGGGAAGTTGCCCGGCAAGAAGCTGCCGCTGGAGGTGCTCAAAGAGATGGAAGC
CAATGCCCGGAAAGCTGGCTGCACCAGGGGCTGTCTGATCTGCCTGTCCCACATCAA
GTGCACGCCCAAGATGAAGAAGTTCATCCCAGGACGCTGCCACACCTACGAAGGCG
ACAAAGAGTCCGCACAGGGCGGCATAGGCGAGGCGATCGTCGACATTCCTGAGATT
CCTGGGTTCAAGGACTTGGAGCCCATGGAGCAGTTCATCGCACAGGTCGATCTGTGT
GTGGACTGCACAACTGGCTGCCTCAAAGGGCTTGCCAACGTGCAGTGTTCTGACCTG
CTCAAGAAGTGGCTGCCGCAACGCTGTGCGACCTTTGCCAGCAAGATCCAGGGCCA
GGTGGACAAGATCAAGGGGGCCGGTGGTGACTAAGCTGGAGCCTCGGTAGCCGTTC
CTCCTGCCCGCTGGGCCTCCCAACGGGCCCTCCTCCCCTCCTTGCACCGGCCCTTCCT
GGTCTTTGAATAAAGTCTGAGTGGGCAGCA (SEQ ID NO: 136)

Human Globin 5'UTR
ACTCTTCTGGTCCCCACAGACTCAGAGAGAACCCACC (SEQ ID NO: 137)

Human Globin 3'UTR
GCTGGAGCCTCGGTAGCCGTTCCTCCTGCCCGCTGGGCCTCCCAACGGGCCCTCCTC
CCCTCCTTGCACCGGCCCTTCCTGGTCTTTGAATAAAGTCTGAGTGGGCAGCA (SEQ ID NO: 138)

Globin GLuc Forward primer
CGCGGATCCTAATACGACTCACTATAGGGACTCTTCTGGTCCCCACAGACTCAG (SEQ ID NO: 139)

Globin GLuc Reverse primer
TGCTGCCCACTCAGACTTTATTC (SEQ ID NO: 120)

What is claimed is:

1. A pharmaceutical composition comprising a pharmaceutically acceptable carrier or excipient and a hybrid modified circular polyribonucleotide, wherein the hybrid modified circular polyribonucleotide comprises a first portion of contiguous nucleotides comprising an internal ribosome entry site (IRES) consisting of unmodified nucleotides and a second portion of contiguous nucleotides consisting of cytidines, adenine, guanine, and modified uridines.

2. The pharmaceutical composition of claim 1, wherein the circular polyribonucleotide is translationally competent.

3. The pharmaceutical composition of claim 1, wherein the hybrid modified circular polyribonucleotide has a higher half-life than a corresponding unmodified circular polyribonucleotide.

4. The pharmaceutical composition of claim 1, wherein the modified uridines comprise 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, or 4-methoxy-2-thio-pseudouridine.

5. The pharmaceutical composition of claim 1, wherein the hybrid modified circular polyribonucleotide comprises a binding site consisting of unmodified nucleotides configured to bind to a protein, peptide, biomolecule, DNA, RNA, or a cell target.

6. The pharmaceutical composition of claim 1, wherein the hybrid modified circular polyribonucleotide comprises one or more expression sequences.

7. The pharmaceutical composition of claim 1, wherein the hybrid modified circular polyribonucleotide has a lower immunogenicity than a corresponding unmodified circular polyribonucleotide.

8. The pharmaceutical composition of claim 1, wherein the modified uridines are pseudouridine.

9. The pharmaceutical composition of claim 8, wherein the modified uridines are N1-methyl-pseudouridine.

10. A method of decreasing immunogenicity of a circular polyribonucleotide in a subject comprising:

administering the pharmaceutical composition of claim 1 to the subject; and obtaining decreased immunogenicity for the hybrid modified circular polyribonucleotide compared to a corresponding unmodified circular polyribonucleotide in a cell or tissue of the subject.

11. A method of expressing one or more expression sequences in a subject comprising:

administering the pharmaceutical composition of claim 1 to the subject; and obtaining increased expression of the one or more expression sequences compared to expression of a corresponding one or more expression sequences in a fully modified circular polyribonucleotide counterpart in a cell or tissue of the subject.

12. A method of increasing stability of a circular polyribonucleotide in a subject comprising:

administering the pharmaceutical composition of claim 1 to the subject; and obtaining increased stability for the hybrid modified circular polyribonucleotide compared to a corresponding unmodified circular polyribonucleotide in a cell or tissue of the subject.

* * * * *

SEQUENCE LISTING

<160> NUMBER OF SEQ ID NOS: 139

<210> SEQ ID NO 1
<211> LENGTH: 3
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1 aug 3

<210> SEQ ID NO 2
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 2
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480

-continued

```
ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaag       717
```

<210> SEQ ID NO 3
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3

```
gctactaact tcagcctgct gaagcaggct ggcgacgtgg aggagaaccc tggacct        57
```

<210> SEQ ID NO 4
<211> LENGTH: 221
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
gtaaaaagag gtgaaaccta ttatgtgtga gcagggcaca gacgttgaaa ctggagccag     60

gagaagtatt ggcaggcttt aggttattag gtggttactc tgtcttaaaa atgttctggc    120

tttcttcctg catccactgg catactcatg gtctgttttt aaatatttta attcccattt    180

acaaagtgat ttacccacaa gcccaacctg tctgtcttca g                        221
```

<210> SEQ ID NO 5
<211> LENGTH: 552
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

```
acgttactgg ccgaagccgc ttggaataag gccggtgtgc gtttgtctat atgttatttt     60

ccaccatatt gccgtctttt ggcaatgtga gggcccggaa acctggccct gtcttcttga    120

cgagcattcc taggggtctt tcccctctcg ccaaaggaat gcaaggtctg ttgaatgtcg    180

tgaaggaagc agttcctctg gaagcttctt gaagacaaac aacgtctgta gcgacccttt    240

gcaggcagcg gaacccccca cctggcgaca ggtgcctctg cggccaaaag ccacgtgtat    300

aagatacacc tgcaaaggcg gcacaacccc agtgccacgt tgtgagttgg atagttgtgg    360

aaagagtcaa atggctctcc tcaagcgtat tcaacaaggg gctgaaggat gcccagaagg    420

taccccattg tatgggatct gatctggggc ctcggtgcac atgctttaca tgtgtttagt    480

cgaggttaaa aaacgtctag gccccccgaa ccacggggac gtggttttcc tttgaaaaac    540

acgatgataa ta                                                        552
```

<210> SEQ ID NO 6
<211> LENGTH: 6926
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattccat    960
tgagaaatga ctgagttccg gtgctctcaa gtcattgatc tttgtcgact tttatttggt   1020
ctctgtaata acgacttcaa aaacattaaa ttctgttgcg aagccagtaa gctacaaaaa   1080
gaaaaaacaa gagagaatgc tatagtcgta tagtatagtt tcccgactat ctgataccca   1140
ttacttatct agggggaatg cgaacccaaa attttatcag ttttctcgga tatcgataga   1200
tattggggaa taaatttaaa taaataaatt ttgggcgggt ttagggcgtg gcaaaaagtt   1260
ttttggcaaa tcgctagaaa tttacaagac ttataaaatt atgaaaaaat acaacaaaat   1320
tttaaacacg tgggcgtgac agttttgggc ggttttaggg cgttagagta ggcgaggaca   1380
gggttacatc gactaggctt tgatcctgat caagaatata tatactttat accgcttcct   1440
tctacatgtt acctattttt caacgaatct agtatacctt tttactgtac gatttatggg   1500
tataataata agctaaatcg agactaagtt ttattgttat atatattttt tttattttat   1560
gcagaaatta attaaaccgg tcctgcaggt gatcaggcgc gccggttacc ggccggcccc   1620
gcggagcgta agtattcaaa attccaaaat tttttactag aaatattcga ttttttaata   1680
ggcagtttct atactattgt atactattgt agattcgttg aaaagtatgt aacaggaaga   1740
ataaagcatt tccgaccatg taaagtatat atattcttaa taaggatcaa tagccgagtc   1800
gatctcgcca tgtccgtctg tcttattgtt ttattaccgc cgagacatca ggaactataa   1860
aagctagaag gatgagtttt agcatacaga ttctagagac aaggacgcag agcaagtttg   1920
ttgatccatg ctgccacgct ttaactttct caaattgccc aaaactgcca tgcccacatt   1980
tttgaactat tttcgaaatt ttttcataat tgtattactc gtgtaaattt ccatcaattt   2040
gccaaaaaac tttttgtcac gcgttaacgc cctaaagccg ccaatttggt cacgcccaca   2100
ctattgagca attatcaaat tttttctcat tttattcccc aatatctatc gatatccccg   2160
```

-continued

```
attatgaaat tattaaattt cgcgttcgca ttcacactag ctgagtaacg agtatctgat   2220
agttggggaa atcgacttat tttttatata caatgaaaat gaatttaatc atatgaatat   2280
cgattatagc tttttattta atatgaatat ttatttgggc ttaaggtgta acctcctcga   2340
cataagactc acatggcgca ggcacattga agacaaaaat actcattgtc gggtctcgca   2400
ccctccagca gcacctaaaa ttatgtcttc aattattgcc aacattggag acacaattag   2460
tctgtggcac ctcaggcggc cgctcgagtc tagagggccc gtttaaaccc gctgatcagc   2520
ctcgactgtg ccttctagtt gccagccatc tgttgtttgc ccctcccccg tgccttcctt   2580
gaccctggaa ggtgccactc ccactgtcct ttcctaataa aatgaggaaa ttgcatcgca   2640
ttgtctgagt aggtgtcatt ctattctggg gggtggggtg gggcaggaca gcaaggggga   2700
ggattgggaa gacaatagca ggcatgctgg ggatgcggtg ggctctatgg cttctgaggc   2760
ggaaagaacc agctggggct ctagggggta tccccacgcg ccctgtagcg gcgcattaag   2820
cgcggcgggt gtggtggtta cgcgcagcgt gaccgctaca cttgccagcg ccctagcgcc   2880
cgctcctttc gctttcttcc cttcctttct cgccacgttc gccggctttc cccgtcaagc   2940
tctaaatcgg gggctccctt tagggttccg atttagtgct ttacggcacc tcgaccccaa   3000
aaaacttgat tagggtgatg gttcacgtag tgggccatcg ccctgataga cggtttttcg   3060
ccctttgacg ttggagtcca cgttctttaa tagtggactc ttgttccaaa ctggaacaac   3120
actcaaccct atctcggtct attcttttga tttataaggg attttgccga tttcggccta   3180
ttggttaaaa aatgagctga tttaacaaaa atttaacgcg aattaattct gtggaatgtg   3240
tgtcagttag ggtgtggaaa gtccccaggc tccccagcag gcagaagtat gcaaagcatg   3300
catctcaatt agtcagcaac caggtgtgga aagtccccag gctccccagc aggcagaagt   3360
atgcaaagca tgcatctcaa ttagtcagca accatagtcc cgcccctaac tccgcccatc   3420
ccgcccctaa ctccgcccag ttccgcccat tctccgcccc atggctgact aatttttttt   3480
atttatgcag aggccgaggc cgcctctgcc tctgagctat tccagaagta gtgaggaggc   3540
ttttttggag gcctaggctt ttgcaaaaag ctcccgggag cttgtatatc cattttcgga   3600
tctgatcaag agacaggatg aggatcgttt cgcatgattg aacaagatgg attgcacgca   3660
ggttctccgg ccgcttgggt ggagaggcta ttcggctatg actgggcaca acagacaatc   3720
ggctgctctg atgccgccgt gttccggctg tcagcgcagg ggcgcccggt tctttttgtc   3780
aagaccgacc tgtccggtgc cctgaatgaa ctgcaggacg aggcagcgcg gctatcgtgg   3840
ctggccacga cgggcgttcc ttgcgcagct gtgctcgacg ttgtcactga agcgggaagg   3900
gactggctgc tattgggcga agtgccgggg caggatctcc tgtcatctca ccttgctcct   3960
gccgagaaag tatccatcat ggctgatgca atgcggcggc tgcatacgct tgatccggct   4020
acctgcccat tcgaccacca agcgaaacat cgcatcgagc gagcacgtac tcggatggaa   4080
gccggtcttg tcgatcagga tgatctggac gaagagcatc aggggctcgc gccagccgaa   4140
ctgttcgcca ggctcaaggc gcgcatgccc gacggcgagg atctcgtcgt gacccatggc   4200
gatgcctgct tgccgaatat catggtggaa aatggccgct tttctggatt catcgactgt   4260
ggccggctgg gtgtggcgga ccgctatcag gacatagcgt tggctacccg tgatattgct   4320
gaagagcttg gcggcgaatg ggctgaccgc ttcctcgtgc tttacggtat cgccgctccc   4380
gattcgcagc gcatcgcctt ctatcgcctt cttgacgagt tcttctgagc gggactctgg   4440
ggttcgaaat gaccgaccaa gcgacgccca acctgccatc acgagatttc gattccaccg   4500
ccgccttcta tgaaaggttg ggcttcggaa tcgttttccg ggacgccggc tggatgatcc   4560
```

-continued tccagcgcgg ggatctcatg ctggagttct tcgcccaccc caacttgttt attgcagctt 4620
ataatggtta caaataaagc aatagcatca caaatttcac aaataaagca tttttttcac 4680
tgcattctag ttgtggtttg tccaaactca tcaatgtatc ttatcatgtc tgtataccgt 4740
cgacctctag ctagagcttg gcgtaatcat ggtcatagct gtttcctgtg tgaaattgtt 4800
atccgctcac aattccacac aacatacgag ccggaagcat aaagtgtaaa gcctggggtg 4860
cctaatgagt gagctaactc acattaattg cgttgcgctc actgcccgct ttccagtcgg 4920
gaaacctgtc gtgccagctg cattaatgaa tcggccaacg cgcggggaga ggcggtttgc 4980
gtattgggcg ctcttccgct tcctcgctca ctgactcgct gcgctcggtc gttcggctgc 5040
ggcgagcggt atcagctcac tcaaaggcgg taatacggtt atccacagaa tcaggggata 5100
acgcaggaaa gaacatgtga gcaaaaggcc agcaaaaggc caggaaccgt aaaaaggccg 5160
cgttgctggc gtttttccat aggctccgcc cccctgacga gcatcacaaa aatcgacgct 5220
caagtcagag gtggcgaaac ccgacaggac tataaagata ccaggcgttt ccccctggaa 5280
gctccctcgt gcgctctcct gttccgaccc tgccgcttac cggatacctg tccgcctttc 5340
tcccttcggg aagcgtggcg ctttctcata gctcacgctg taggtatctc agttcggtgt 5400
aggtcgttcg ctccaagctg ggctgtgtgc acgaaccccc cgttcagccc gaccgctgcg 5460
ccttatccgg taactatcgt cttgagtcca acccggtaag acacgactta tcgccactgg 5520
cagcagccac tggtaacagg attagcagag cgaggtatgt aggcggtgct acagagttct 5580
tgaagtggtg gcctaactac ggctacacta gaagaacagt atttggtatc tgcgctctgc 5640
tgaagccagt taccttcgga aaaagagttg gtagctcttg atccggcaaa caaaccaccg 5700
ctggtagcgg tttttttgtt tgcaagcagc agattacgcg cagaaaaaaa ggatctcaag 5760
aagatccttt gatcttttct acggggtctg acgctcagtg gaacgaaaac tcacgttaag 5820
ggattttggt catgagatta tcaaaaagga tcttcaccta gatcctttta aattaaaaat 5880
gaagttttaa atcaatctaa agtatatatg agtaaacttg gtctgacagt taccaatgct 5940
taatcagtga ggcacctatc tcagcgatct gtctatttcg ttcatccata gttgcctgac 6000
tccccgtcgt gtagataact acgatacggg agggcttacc atctggcccc agtgctgcaa 6060
tgataccgcg agacccacgc tcaccggctc cagatttatc agcaataaac cagccagccg 6120
gaagggccga gcgcagaagt ggtcctgcaa ctttatccgc ctccatccag tctattaatt 6180
gttgccggga agctagagta agtagttcgc cagttaatag tttgcgcaac gttgttgcca 6240
ttgctacagg catcgtggtg tcacgctcgt cgtttggtat ggcttcattc agctccggtt 6300
cccaacgatc aaggcgagtt acatgatccc ccatgttgtg caaaaaagcg gttagctcct 6360
tcggtcctcc gatcgttgtc agaagtaagt tggccgcagt gttatcactc atggttatgg 6420
cagcactgca taattctctt actgtcatgc catccgtaag atgcttttct gtgactggtg 6480
agtactcaac caagtcattc tgagaatagt gtatgcggcg accgagttgc tcttgcccgg 6540
cgtcaatacg ggataatacc gcgccacata gcagaacttt aaaagtgctc atcattggaa 6600
aacgttcttc ggggcgaaaa ctctcaagga tcttaccgct gttgagatcc agttcgatgt 6660
aacccactcg tgcacccaac tgatcttcag catcttttac tttcaccagc gtttctgggt 6720
gagcaaaaac aggaaggcaa aatgccgcaa aaaagggaat aagggcgaca cggaaatgtt 6780
gaatactcat actcttcctt tttcaatatt attgaagcat ttatcagggt tattgtctca 6840
tgagcggata catatttgaa tgtatttaga aaaataaaca aataggggtt ccgcgcacat 6900
ttccccgaaa agtgccacct gacgtc 6926

<210> SEQ ID NO 7

<400> SEQUENCE: 7

000

<210> SEQ ID NO 8
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8
atggtgagca agggcgagga ggataacatg gccatcatca aggagttcat gcgcttcaag 60
gtgcacatgg agggctccgt gaacggccac gagttcgaga tcgagggcga gggcgagggc 120
cgcccctacg agggcaccca gaccgccaag ctgaaggtga ccaagggtgg cccccctgccc 180 ttcgcctggg acatcctgtc ccctcagttc atgtacggct ccaaggccta cgtgaagcac 240
cccgccgaca tccccgacta cttgaagctg tccttccccg agggcttcaa gtgggagcgc 300
gtgatgaact tcgaggacgg cggcgtggtg accgtgaccc aggactcctc cctgcaggac 360
ggcgagttca tctacaaggt gaagctgcgc ggcaccaact tcccctccga cggccccgta 420
atgcagaaga agaccatggg ctgggaggcc tcctccgagc ggatgtaccc cgaggacggc 480
gccctgaagg gcgagatcaa gcagaggctg aagctgaagg acggcggcca ctacgacgct 540
gaggtcaaga ccacctacaa ggccaagaag cccgtgcagc tgcccggcgc ctacaacgtc 600
aacatcaagt tggacatcac ctcccacaac gaggactaca ccatcgtgga acagtacgaa 660
cgcgccgagg gccgccactc caccggcggc atggacgagc tgtacaag 708

<210> SEQ ID NO 9
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9
cugagaugca gguacaucca gcugaugagu cccaaauagg acgaaagcca uaccagccga 60
aaggcccuug gcaggguucc uggauuccac ugcuauccac 100

<210> SEQ ID NO 10
<211> LENGTH: 516
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10
atggtcttca cactcgaaga tttcgttggg gactggcgac agacagccgg ctacaacctg 60
gaccaagtcc ttgaacaggg aggtgtgtcc agtttgtttc agaatctcgg ggtgtccgta 120
actccgatcc aaaggattgt cctgagcggt gaaaatgggc tgaagatcga catccatgtc 180
atcatcccgt atgaaggtct gagcggcgac caaatgggcc agatcgaaaa aatttttaag 240
gtggtgtacc ctgtggatga tcatcacttt aaggtgatcc tgcactatgg cacactggta 300
atcgacgggg ttacgccgaa catgatcgac tatttcggac ggccgtatga aggcatcgcc 360
gtgttcgacg gcaaaaagat cactgtaaca gggaccctgt ggaacggcaa caaaattatc 420
gacgagcgcc tgatcaaccc cgacggctcc ctgctgttcc gagtaaccat caacggagtg 480
accggctggc ggctgtgcga acgcattctg gcgtaa 516

<210> SEQ ID NO 11
<211> LENGTH: 264
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
gggagccacc atggactaca aggacgacga cgacaagatc atcgactata aagacgacga 60
cgataaaggt ggcgactata aggacgacga cgacaaagcc attaatagtg actctgagtg 120
tcccctgtcc cacgacgggt actgcctcca cgacggtgtg tgcatgtata ttgaagcatt 180
ggacaagtac gcctgcaact gtgttgttgg ctacatcggg gagcgctgtc agtaccgaga 240
cctgaagtgg tgggaactgc gcct 264

<210> SEQ ID NO 12
<211> LENGTH: 273
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12
gggagccacc atggactaca aggacgacga cgacaagatc atcgactata aagacgacga 60
cgataaaggt ggcgactata aggacgacga cgacaaagcc attaatagtg actctgagtg 120
tcccctgtcc cacgacgggt actgcctcca cgacggtgtg tgcatgtata ttgaagcatt 180
ggacaagtac gcctgcaact gtgttgttgg ctacatcggg gagcgctgtc agtaccgaga 240
cctgaagtgg tgggaactgc gctgatagta act 273

<210> SEQ ID NO 13
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13
gggagccacc atggactaca aggacgacga cgacaagatc atcgactata aagacgacga 60
cgataaaggt ggcgactata aggacgacga cgacaaagcc attaatagtg actctgagtg 120
tcccctgtcc cacgacgggt actgcctcca cgacggtgtg tgcatgtata ttgaagcatt 180
ggacaagtac gcctgcaact gtgttgttgg ctacatcggg gagcgctgtc agtaccgaga 240
cctgaagtgg tgggaactgc gcggaagcgg agctactaac ttcagcctgc tgaagcaggc 300
tggagacgtg gaggagaacc ctggacctct 330

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 14
ggtggctccc aggcgcagtt 20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 15
ggtggctccc agttactatc 20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
ggtggctccc agaggtccag 20

<210> SEQ ID NO 17
<211> LENGTH: 873
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17
gggagccacc atggactaca aggacgacga cgacaagatc atcaatagtg actctgagtg 60
tcccctgtcc cacgacgggt actgcctcca cgacggtgtg tgcatgtata ttgaagcatt 120
ggacaagtac gcctgcaact gtgttgttgg ctacatcggg gagcgctgtc agtaccgaga 180
cctgaagtgg tgggaactgc gcggctccgg cgagggcagg ggaagtcttc taacatgcgg 240
ggacgtggag gaaaatcccg gcccagacta taaggacgac gacgacaaaa tcatcgtctt 300
cacactcgaa gatttcgttg gggactggcg acagacagcc ggctacaacc tggaccaagt 360
ccttgaacag ggaggtgtgt ccagtttgtt tcagaatctc ggggtgtccg taactccgat 420
ccaaaggatt gtcctgagcg gtgaaaatgg gctgaagatc gacatccatg tcatcatccc 480
gtatgaaggt ctgagcggcg accaaatggg ccagatcgaa aaaattttta aggtggtgta 540
ccctgtggat gatcatcact ttaaggtgat cctgcactat ggcacactgg taatcgacgg 600
ggttacgccg aacatgatcg actatttcgg acggccgtat gaaggcatcg ccgtgttcga 660
cggcaaaaag atcactgtaa cagggaccct gtggaacggc aacaaaatta tcgacgagcg 720

```
cctgatcaac cccgacggct ccctgctgtt ccgagtaacc atcaacggag tgaccggctg    780

gcggctgtgc gaacgcattc tggcgggaag cggagctact aacttcagcc tgctgaagca    840

ggctggagac gtggaggaga accctggacc tct                                 873


<210> SEQ ID NO 18
<211> LENGTH: 762
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18

gggagccacc atggactaca aggacgacga cgacaagatc atcaatagtg actctgagtg     60

tcccctgtcc cacgacgggt actgcctcca cgacggtgtg tgcatgtata ttgaagcatt    120

ggacaagtac gcctgcaact gtgttgttgg ctacatcggg gagcgctgtc agtaccgaga    180

cctgaagtgg tgggaactgc gctgatagta agactataag gacgacgacg acaaaatcat    240

cgtcttcaca ctcgaagatt tcgttgggga ctggcgacag acagccggct acaacctgga    300

ccaagtcctt gaacagggag gtgtgtccag tttgtttcag aatctcgggg tgtccgtaac    360

tccgatccaa aggattgtcc tgagcggtga aaatgggctg aagatcgaca tccatgtcat    420

catcccgtat gaaggtctga gcggcgacca aatgggccag atcgaaaaaa tttttaaggt    480

ggtgtaccct gtggatgatc atcactttaa ggtgatcctg cactatggca cactggtaat    540

cgacggggtt acgccgaaca tgatcgacta tttcggacgg ccgtatgaag gcatcgccgt    600

gttcgacggc aaaaagatca ctgtaacagg gaccctgtgg aacggcaaca aaattatcga    660

cgagcgcctg atcaaccccg acggctccct gctgttccga gtaaccatca acggagtgac    720

cggctggcgg ctgtgcgaac gcattctggc gtgatagtaa ct                       762


<210> SEQ ID NO 19
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

gggagccacc atggactaca aggacgacga cgacaagatc atcgactata aagacgacga     60

cgataaaggt ggcgactata aggacgacga cgacaaagcc attaatagtg actctgagtg    120

tcccctgtcc cacgacgggt actgcctcca cgacggtgtg tgcatgtata ttgaagcatt    180

ggacaagtac gcctgcaact gtgttgttgg ctacatcggg gagcgctgtc agtaccgaga    240

cctgaagtgg tgggaactgc gcggaagcgg agctactaac ttcagcctgc tgaagcaggc    300

tggagacgtg gaggagaacc ctggacctct                                     330


<210> SEQ ID NO 20
<211> LENGTH: 264
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
```

```
gggagccacc atggactaca aggacgacga cgacaagatc atcgactata aagacgacga     60

cgataaaggt ggcgactata aggacgacga cgacaaagcc attaatagtg actctgagtg    120

tcccctgtcc cacgacgggt actgcctcca cgacggtgtg tgcatgtata ttgaagcatt    180

ggacaagtac gcctgcaact gtgttgttgg ctacatcggg gagcgctgtc agtaccgaga    240

cctgaagtgg tgggaactgc gcct                                          264


<210> SEQ ID NO 21
<211> LENGTH: 273
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

gggagccacc atggactaca aggacgacga cgacaagatc atcgactata aagacgacga     60

cgataaaggt ggcgactata aggacgacga cgacaaagcc attaatagtg actctgagtg    120

tcccctgtcc cacgacgggt actgcctcca cgacggtgtg tgcatgtata ttgaagcatt    180

ggacaagtac gcctgcaact gtgttgttgg ctacatcggg gagcgctgtc agtaccgaga    240

cctgaagtgg tgggaactgc gctgatagta act                                 273


<210> SEQ ID NO 22
<211> LENGTH: 954
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

gggacctaac gttactggcc gaagccgctt ggaacaaggc cggtgtgcgt ttgtctatat     60

gttattttcc accatattgc cgtcttttgg caatgtgagg gcccggaaac ctggccctgt    120

cttcttgacg agcattccta ggggtctttc ccctctcgcc aaaggaatgc aaggtctgtt    180

gaatgtcgtg aaggaagcag ttcctctgga agcttcttca agacaaacaa cgtctgtagc    240

gaccctttgc aggcagcgga accccccacc tggcgacagg tgcctctgcg gccaaaagcc    300

acgtgtatac gatacacctg caaaggcggc acaaccccag tgccacgttg tgagttggat    360

agttgtggaa agagtcaaat ggctctcctc aagcgtattc aacaaggggc tgaaggatgc    420

ccagaaggta ccccattgta tgggatctga tctggggcct cggtgcacat gctttacatg    480

tgttcagtcg aggttaaaaa acgtccaggc cccccgaacc acggggacgt ggttttcctt    540

tgaaaaacac gatgataata tggccacaac catgggctcc ggcgagggca ggggaagtct    600

tctaacatgc ggggacgtgg aggaaaatcc cggcccagac tacaaggacg acgacgacaa    660

gatcatcgac tataaagacg acgacgataa aggtggcgac tataaggacg acgacgacaa    720

agccattaat agtgactctg agtgtcccct gtcccacgac gggtactgcc tccacgacgg    780

tgtgtgcatg tatattgaag cattggacaa gtacgcctgc aactgtgttg ttggctacat    840

cggggagcgc tgtcagtacc gagacctgaa gtggtgggaa ctgcgcggaa gcggagctac    900

taacttcagc ctgctgaagc aggctggaga cgtggaggag aaccctggac ctct          954


<210> SEQ ID NO 23
```

```
<211> LENGTH: 1314
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

gggacctaac gttactggcc gaagccgctt ggaacaaggc cggtgtgcgt ttgtctatat     60

gttattttcc accatattgc cgtcttttgg caatgtgagg gcccggaaac ctggccctgt    120

cttcttgacg agcattccta ggggtctttc ccctctcgcc aaaggaatgc aaggtctgtt    180

gaatgtcgtg aaggaagcag ttcctctgga agcttcttca agacaaacaa cgtctgtagc    240

gaccctttgc aggcagcgga acccccccacc tggcgacagg tgcctctgcg gccaaaagcc    300

acgtgtatac gatacacctg caaaggcggc acaaccccag tgccacgttg tgagttggat    360

agttgtggaa agagtcaaat ggctctcctc aagcgtattc aacaaggggc tgaaggatgc    420

ccagaaggta ccccattgta tgggatctga tctggggcct cggtgcacat gctttacatg    480

tgttcagtcg aggttaaaaa acgtccaggc cccccgaacc acggggacgt ggttttcctt    540

tgaaaaacac gatgataata tggccacaac catgggctcc ggcgagggca ggggaagtct    600

tctaacatgc ggggacgtgg aggaaaatcc cggcccagac tacaaggacg acgacgacaa    660

gatcatcgac tataaagacg acgacgataa aggtggcgac tataaggacg acgacgacaa    720

agccattgtc ttcacactcg aagatttcgt tggggactgg cgacagacag ccggctacaa    780

cctggaccaa gtccttgaac agggaggtgt gtccagtttg tttcagaatc tcggggtgtc    840

cgtaactccg atccaaagga ttgtcctgag cggtgaaaat gggctgaaga tcgacatcca    900

tgtcatcatc ccgtatgaag gtctgagcgg cgaccaaatg ggccagatcg aaaaaatttt    960

taaggtggtg taccctgtgg atgatcatca ctttaaggtg atcctgcact atggcacact   1020

ggtaatcgac ggggttacgc cgaacatgat cgactatttc ggacggccgt atgaaggcat   1080

cgccgtgttc gacggcaaaa agatcactgt aacagggacc ctgtggaacg gcaacaaaat   1140

tatcgacgag cgcctgatca accccgacgg ctccctgctg ttccgagtaa ccatcaacgg   1200

agtgaccggc tggcggctgt gcgaacgcat tctggcggga agcggagcta ctaacttcag   1260

cctgctgaag caggctggag acgtggagga gaaccctgga ccttgatagt aact         1314


<210> SEQ ID NO 24
<211> LENGTH: 1305
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24

gggacctaac gttactggcc gaagccgctt ggaacaaggc cggtgtgcgt ttgtctatat     60

gttattttcc accatattgc cgtcttttgg caatgtgagg gcccggaaac ctggccctgt    120

cttcttgacg agcattccta ggggtctttc ccctctcgcc aaaggaatgc aaggtctgtt    180

gaatgtcgtg aaggaagcag ttcctctgga agcttcttca agacaaacaa cgtctgtagc    240

gaccctttgc aggcagcgga acccccccacc tggcgacagg tgcctctgcg gccaaaagcc    300

acgtgtatac gatacacctg caaaggcggc acaaccccag tgccacgttg tgagttggat    360

agttgtggaa agagtcaaat ggctctcctc aagcgtattc aacaaggggc tgaaggatgc    420
```

```
ccagaaggta ccccattgta tgggatctga tctggggcct cggtgcacat gctttacatg    480

tgttcagtcg aggttaaaaa acgtccaggc cccccgaacc acggggacgt ggttttcctt    540

tgaaaaacac gatgataata tggccacaac catgggctcc ggcgagggca ggggaagtct    600

tctaacatgc ggggacgtgg aggaaaatcc cggcccagac tacaaggacg acgacgacaa    660

gatcatcgac tataaagacg acgacgataa aggtggcgac tataaggacg acgacgacaa    720

agccattgtc ttcacactcg aagatttcgt tggggactgg cgacagacag ccggctacaa    780

cctggaccaa gtccttgaac agggaggtgt gtccagtttg tttcagaatc tcggggtgtc    840

cgtaactccg atccaaagga ttgtcctgag cggtgaaaat gggctgaaga tcgacatcca    900

tgtcatcatc ccgtatgaag gtctgagcgg cgaccaaatg ggccagatcg aaaaaatttt    960

taaggtggtg taccctgtgg atgatcatca ctttaaggtg atcctgcact atggcacact   1020

ggtaatcgac ggggttacgc cgaacatgat cgactatttc ggacggccgt atgaaggcat   1080

cgccgtgttc gacggcaaaa agatcactgt aacagggacc ctgtggaacg gcaacaaaat   1140

tatcgacgag cgcctgatca accccgacgg ctccctgctg ttccgagtaa ccatcaacgg   1200

agtgaccggc tggcggctgt gcgaacgcat tctggcggga agcggagcta ctaacttcag   1260

cctgctgaag caggctggag acgtggagga gaaccctgga cctct                   1305
```

<210> SEQ ID NO 25
<211> LENGTH: 882
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
gggagccacc atggactaca aggacgacga cgacaagatc atcaatagtg actctgagtg     60

tcccctgtcc cacgacgggt actgcctcca cgacggtgtg tgcatgtata ttgaagcatt    120

ggacaagtac gcctgcaact gtgttgttgg ctacatcggg gagcgctgtc agtaccgaga    180

cctgaagtgg tgggaactgc gcggctccgg cgagggcagg ggaagtcttc taacatgcgg    240

ggacgtggag gaaaatcccg gcccagacta taaggacgac gacgacaaaa tcatcgtctt    300

cacactcgaa gatttcgttg gggactggcg acagacagcc ggctacaacc tggaccaagt    360

ccttgaacag ggaggtgtgt ccagtttgtt tcagaatctc ggggtgtccg taactccgat    420

ccaaaggatt gtcctgagcg gtgaaaatgg gctgaagatc gacatccatg tcatcatccc    480

gtatgaaggt ctgagcggcg accaaatggg ccagatcgaa aaaattttta aggtggtgta    540

ccctgtggat gatcatcact ttaaggtgat cctgcactat ggcacactgg taatcgacgg    600

ggttacgccg aacatgatcg actatttcgg acggccgtat gaaggcatcg ccgtgttcga    660

cggcaaaaag atcactgtaa cagggaccct gtggaacggc aacaaaatta tcgacgagcg    720

cctgatcaac cccgacggct ccctgctgtt ccgagtaacc atcaacggag tgaccggctg    780

gcggctgtgc gaacgcattc tggcgggaag cggagctact aacttcagcc tgctgaagca    840

ggctggagac gtggaggaga accctggacc ttgatagtaa ct                       882
```

<210> SEQ ID NO 26
<211> LENGTH: 179
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic polynucleotide"

<400> SEQUENCE: 26
aaaaaacaaa aaacaaaacg gctattatgc gttaccggcg agacgctacg gacttgggaa 60
aatccgttga ccttaaacgg tcgtgtgggt tcaagtccct ccaccccccac gccggaaacg 120 caatagccga aaaacaaaaa acaaaaaaaa caaaaaaaaa accaaaaaaa caaaacaca 179

<210> SEQ ID NO 27
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 27
cgcggatcct aatacgactc actataggga gacccaagct ggc 43

<210> SEQ ID NO 28
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 28
aatagccgtt ttgtttttg gattaccagt gtgccatagt gcaggatcac atcgtcgtgg 60
tattcactcc agagcgatg 79

<210> SEQ ID NO 29
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 29
aatagccgtt ttgtttttg gattaccagt gtgccatagt gcaggatcac acgggggagg 60
ggcaaacaac agatgg 76

<210> SEQ ID NO 30
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 30
aatagccgtt ttgtttttg gattaccagt gtgccatagt gcaggatcac gctttttgca 60
aaagcctagg cctccaaaaa agcc 84

<210> SEQ ID NO 31
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 31
aatagccgtt ttgtttttg gattaccagt gtgccatagt gcaggatcac tagcaccgcc 60
tacatacctc gctctgc 77

<210> SEQ ID NO 32
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 32
aatagccgtt ttgtttttg gattaccagt gtgccatagt gcaggatcac ctatgtggcg 60
cggtattatc ccgtattgac 80

<210> SEQ ID NO 33
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 33
aatagccgtt ttgtttttg gattaccagt gtgccatagt gcaggatcac atttcgataa 60
gccagtaagc agtgggttct ctag 84

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 34
attcttgccc gcctgatgaa 20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 35
ttgctcatgg aaaacggtgt 20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 36
tgatcctgca ctatggcaca 20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 37
ctggactagt ggatccgagc 20

<210> SEQ ID NO 38
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 38
gacgaggccc agagcaagag agg 23

<210> SEQ ID NO 39
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 39
ggtgttgaag gtctcaaaca tg 22

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 40
tgtgggcaat gtcatcaaaa 20

<210> SEQ ID NO 41

<400> SEQUENCE: 41

000

<210> SEQ ID NO 42
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 42
gaagcacttg ctacctcttg c 21

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 43
atttggtaag gcctgagctg 20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 44
tcgctggtat cactcgtctg 20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 45
gattctgaag accgccagag 20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 46
ctctcctgtt gtgcttctcc 20

<210> SEQ ID NO 47
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 47
gtcaaagttc atcctgtcct tg 22

<210> SEQ ID NO 48
<211> LENGTH: 2270
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 48
gggaatagcc gaaaaacaaa aaacaaaaaa aacaaaaaaa aaaccaaaaa aacaaaacac 60
aacgttactg gccgaagccg cttggaacaa ggccggtgtg cgtttgtcta tatgttattt 120
tccaccatat tgccgtcttt tggcaatgtg agggcccgga aacctggccc tgtcttcttg 180
acgagcattc ctaggggtct ttcccctctc gccaaaggaa tgcaaggtct gttgaatgtc 240
gtgaaggaag cagttcctct ggaagcttct tgtagacaaa caacgtctgt agcgaccctt 300
tgcaggcagc ggaacccccc acctggcgac aggtgcctct gcggccaaaa gccacgtgta 360
tacgatacac ctgcaaaggc ggcacaaccc cagtgccacg ttgtgagttg gatagttgtg 420
gaaagagtca aatggctctc ctcaagcgta ttcaacaagg ggctgaagga tgcccagaag 480
gtaccccatt gtatgggatc tgatctgggg cctcggtgca catgctttac atgtgttcag 540
tcgaggttaa aaaacgtcca ggccccccga accacgggga cgtggttttc ctttgaaaaa 600
cacgatgata atatggccac aaccatgggc tccggcgagg gcaggggaag tcttctaaca 660
tgcggggacg tggaggaaaa tcccggccca gactacaagg acgacgacga caagatcatc 720
gactataaag acgacgacga taaaggtggc gactataagg acgacgacga caaagccatt 780
gtgagcaagg gcgaggagct gttcaccggg gtggtgccca tcctggtcga gctggacggc 840
gacgtaaacg gccacaagtt cagcgtgtcc ggcgagggcg agggcgatgc cacctacggc 900
aagctgaccc tgaagttcat ctgcaccacc ggcaagctgc ccgtgccctg gcccaccctc 960
gtgaccaccc tgacctacgg cgtgcagtgc ttcagccgct accccgacca catgaagcag 1020
cacgacttct tcaagtccgc catgcccgaa ggctacgtcc aggagcgcac catcttcttc 1080
aaggacgacg gcaactacaa gacccgcgcc gaggtgaagt tcgagggcga caccctggtg 1140
aaccgcatcg agctgaaggg catcgacttc aaggaggacg gcaacatcct ggggcacaag 1200
ctggagtaca actacaacag ccacaacgtc tatatcatgg ccgacaagca gaagaacggc 1260
atcaaggtga acttcaagat ccgccacaac atcgaggacg gcagcgtgca gctcgccgac 1320
cactaccagc agaacacccc catcggcgac ggccccgtgc tgctgcccga caaccactac 1380
ctgagcaccc agtccgccct gagcaaagac cccaacgaga agcgcgatca catggtcctg 1440
ctggagttcg tgaccgccgc cgggatcact ctcggcatgg acgagctgta caagggaagc 1500
ggagtgaaac agactttgaa ttttgacctt ctcaagttgg cgggagacgt ggagtccaac 1560
cctggacctg actacaagga cgacgacgac aagatcatcg actataaaga cgacgacgat 1620
aaaggtggcg actataagga cgacgacgac aaagccatta tcatcgtctt cacactcgaa 1680
gatttcgttg gggactggcg acagacagcc ggctacaacc tggaccaagt ccttgaacag 1740
ggaggtgtgt ccagtttgtt tcagaatctc ggggtgtccg taactccgat ccaaaggatt 1800
gtcctgagcg gtgaaaatgg gctgaagatc gacatccatg tcatcatccc gtatgaaggt 1860
ctgagcggcg accaaatggg ccagatcgaa aaaattttta aggtggtgta ccctgtggat 1920
gatcatcact ttaaggtgat cctgcactat ggcacactgg taatcgacgg ggttacgccg 1980
aacatgatcg actatttcgg acggccgtat gaaggcatcg ccgtgttcga cggcaaaaag 2040
atcactgtaa cagggaccct gtggaacggc aacaaaatta tcgacgagcg cctgatcaac 2100
cccgacggct ccctgctgtt ccgagtaacc atcaacggag tgaccggctg gcggctgtgc 2160

-continued

```
gaacgcattc tggcgggaag cggagctact aacttcagcc tgctgaagca ggctggagac   2220

gtggaggaga accctggacc ttaaaaaaaa caaaaaacaa aacggctatt              2270


<210> SEQ ID NO 49
<211> LENGTH: 2279
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

gggaatagcc gaaaaacaaa aaacaaaaaa aacaaaaaaa aaaccaaaaa aacaaaacac     60

aacgttactg gccgaagccg cttggaacaa ggccggtgtg cgtttgtcta tatgttattt    120

tccaccatat tgccgtcttt tggcaatgtg agggcccgga aacctggccc tgtcttcttg    180

acgagcattc ctaggggtct ttcccctctc gccaaaggaa tgcaaggtct gttgaatgtc    240

gtgaaggaag cagttcctct ggaagcttct tgtagacaaa caacgtctgt agcgaccctt    300

tgcaggcagc ggaacccccc acctggcgac aggtgcctct gcggccaaaa gccacgtgta    360

tacgatacac ctgcaaaggc ggcacaaccc cagtgccacg ttgtgagttg gatagttgtg    420

gaaagagtca aatggctctc ctcaagcgta ttcaacaagg ggctgaagga tgcccagaag    480

gtaccccatt gtatgggatc tgatctgggg cctcggtgca catgctttac atgtgttcag    540

tcgaggttaa aaaacgtcca ggccccccga accacgggga cgtggttttc ctttgaaaaa    600

cacgatgata atatggccac aaccatgggc tccggcgagg gcaggggaag tcttctaaca    660

tgcggggacg tggaggaaaa tcccggccca gactacaagg acgacgacga caagatcatc    720

gactataaag acgacgacga taaaggtggc gactataagg acgacgacga caaagccatt    780

gtgagcaagg gcgaggagct gttcaccggg gtggtgccca tcctggtcga gctggacggc    840

gacgtaaacg gccacaagtt cagcgtgtcc ggcgagggcg agggcgatgc cacctacggc    900

aagctgaccc tgaagttcat ctgcaccacc ggcaagctgc ccgtgccctg gcccaccctc    960

gtgaccaccc tgacctacgg cgtgcagtgc ttcagccgct accccgacca catgaagcag   1020

cacgacttct tcaagtccgc catgcccgaa ggctacgtcc aggagcgcac catcttcttc   1080

aaggacgacg gcaactacaa gacccgcgcc gaggtgaagt tcgagggcga caccctggtg   1140

aaccgcatcg agctgaaggg catcgacttc aaggaggacg gcaacatcct ggggcacaag   1200

ctggagtaca actacaacag ccacaacgtc tatatcatgg ccgacaagca gaagaacggc   1260

atcaaggtga acttcaagat ccgccacaac atcgaggacg gcagcgtgca gctcgccgac   1320

cactaccagc agaacacccc catcggcgac ggccccgtgc tgctgcccga caaccactac   1380

ctgagcaccc agtccgccct gagcaaagac cccaacgaga agcgcgatca catggtcctg   1440

ctggagttcg tgaccgccgc cgggatcact ctcggcatgg acgagctgta caagggaagc   1500

ggagtgaaac agactttgaa ttttgacctt ctcaagttgg cgggagacgt ggagtccaac   1560

cctggacctt gatagtaaga ctacaaggac gacgacgaca agatcatcga ctataaagac   1620

gacgacgata aaggtggcga ctataaggac gacgacgaca aagccattat catcgtcttc   1680

acactcgaag atttcgttgg ggactggcga cagacagccg gctacaacct ggaccaagtc   1740

cttgaacagg gaggtgtgtc cagtttgttt cagaatctcg gggtgtccgt aactccgatc   1800

caaaggattg tcctgagcgg tgaaaatggg ctgaagatcg acatccatgt catcatcccg   1860

tatgaaggtc tgagcggcga ccaaatgggc cagatcgaaa aaatttttaa ggtggtgtac   1920
```

cctgtggatg atcatcactt taaggtgatc ctgcactatg gcacactggt aatcgacggg 1980
gttacgccga acatgatcga ctatttcgga cggccgtatg aaggcatcgc cgtgttcgac 2040
ggcaaaaaga tcactgtaac agggaccctg tggaacggca acaaaattat cgacgagcgc 2100
ctgatcaacc ccgacggctc cctgctgttc cgagtaacca tcaacggagt gaccggctgg 2160
cggctgtgcg aacgcattct ggcgggaagc ggagctacta acttcagcct gctgaagcag 2220
gctggagacg tggaggagaa ccctggacct taaaaaaaac aaaaaacaaa acggctatt 2279

<210> SEQ ID NO 50
<211> LENGTH: 51
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
ucauaaucaa uuuauuauuu ucuuuuauuu uauucacaua auuuuguuuu u 51

<210> SEQ ID NO 51
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51
auuuuguuuu uaacauuuc 19

<210> SEQ ID NO 52
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
ucauaaucaa uuuauuauuu ucuuuuauuu uauucacaua auuuuguuuu uauuuuguuu 60
uuaacauuuc 70

<210> SEQ ID NO 53
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53
aaaauccguu gaccuuaaac ggucgugugg guucaagucc cuccaccccc acgccggaaa 60
cgcaauagcc gaaaaacaaa aaacaaaaaa aacaaaaaaa aaaccaaaaa aacaaaacac 120
auuaaaacag ccugugggu u gaucccaccc acaggcccau ugggcgcuag cacucuggua 180
ucacgguacc uuugugcgcc uguuuuauac cccucccccc aacuguaacu uagaaguaac 240
acacaccgau caacagucag cguggcacac cagccacguu uugaucaagc acuucuguua 300

```
ccccggacug aguaucaaua gacugcucac gcgguugaag gagaaagcgu ucguuauccg    360

gccaacuacu ucgaaaaacc uaguaacacc guggaaguug cagaguguuu cgcucagcac    420

uaccccagug uagaucaggu cgaugaguca ccgcauuccc cacgggcgac cguggcggug    480

gcugcguugg cggccugccc augggggaaac ccaugggacg cucuaauaca gacauggugc    540

gaagagucua uugagcuagu ugguaguccu ccggccccug aaugcggcua auccuaacug    600

cggagcacac acccucaagc cagagggcag ugugucguaa cgggcaacuc ugcagcggaa    660

ccgacuacuu ugggguguccg uguuucauuu uauuccuaua cuggcugcuu auggugacaa    720

uugagagauc guuaccauau agcuauugga uuggccaucc ggugacuaau agagcuauua    780

uauaucccuu uguuggguuu auaccacuua gcuugaaaga gguuaaaaca uuacaauuca    840

uuguuaaguu gaauacagca aaaugggagu caaaguucug uuugcccuga ucugcaucgc    900

uguggccgag gccaagccca ccgagaacaa cgaagacuuc aacaucgugg ccguggccag    960

caacuucgcg accacggauc ucgaugcuga ccgcgggaag uugcccggca agaagcugcc   1020

gcuggaggug cucaaagaga uggaagccaa ugcccggaaa gcuggcugca ccaggggcug   1080

ucugaucugc cugucccaca ucaagugcac gcccaagaug aagaaguuca ucccaggacg   1140

cugccacacc uacgaaggcg acaaagaguc cgcacagggc ggcauaggcg aggcgaucgu   1200

cgacauuccu gagauuccug gguucaagga cuuggagccc auggagcagu ucaucgcaca   1260

ggucgaucug uguguggacu gcacaacugg cugccucaaa gggcuugcca acgugcagug   1320

uucugaccug cucaagaagu ggcugccgca acgcugugcg accuuugcca gcaagaucca   1380

gggccaggug gacaagauca agggggccgg uggugacuaa ucauaaucaa uuuauuauuu   1440

ucuuuuauuu uauucacaua auuuuguuuu uauuuuguuu uuaacauuuc aaaaaacaaa   1500

aaacaaaacg gcuauuaugc guuaccggcg agacgcuacg gacuu                     1545
```

<210> SEQ ID NO 54
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

```
aaaauccguu gaccuuaaac ggucgugugg guucaagucc cuccaccccc acgccggaaa     60

cgcaauagcc gaaaaacaaa aaacaaaaaa aacaaaaaaa aaaccaaaaa aacaaaacac    120

auuaaaacag ccugugggu u gaucccaccc acaggcccau ugggcgcuag cacucuggua    180

ucacgguacc uuugugcgcc uguuuuauac ccccuccccc aacuguaacu uagaaguaac    240

acacaccgau caacagucag cguggcacac cagccacguu uugaucaagc acuucuguua    300

ccccggacug aguaucaaua gacugcucac gcgguugaag gagaaagcgu ucguuauccg    360

gccaacuacu ucgaaaaacc uaguaacacc guggaaguug cagaguguuu cgcucagcac    420

uaccccagug uagaucaggu cgaugaguca ccgcauuccc cacgggcgac cguggcggug    480

gcugcguugg cggccugccc augggggaaac ccaugggacg cucuaauaca gacauggugc    540

gaagagucua uugagcuagu ugguaguccu ccggccccug aaugcggcua auccuaacug    600

cggagcacac acccucaagc cagagggcag ugugucguaa cgggcaacuc ugcagcggaa    660

ccgacuacuu ugggguguccg uguuucauuu uauuccuaua cuggcugcuu auggugacaa    720

uugagagauc guuaccauau agcuauugga uuggccaucc ggugacuaau agagcuauua    780
```

uauaucccuu uguuggguuu auaccacuua gcuugaaaga gguuaaaaca uuacaauuca 840
uuguuaaguu gaauacagca aaaugggagu caaaguucug uuugcccuga ucugcaucgc 900
uguggccgag gccaagccca ccgagaacaa cgaagacuuc aacaucgugg ccguggccag 960
caacuucgcg accacggauc ucgaugcuga ccgcgggaag uugcccggca agaagcugcc 1020
gcuggaggug cucaaagaga uggaagccaa ugcccggaaa gcuggcugca ccaggggcug 1080
ucugaucugc cugucccaca ucaagugcac gcccaagaug aagaaguuca ucccaggacg 1140
cugccacacc uacgaaggcg acaaagaguc cgcacagggc ggcauaggcg aggcgaucgu 1200
cgacauuccu gagauuccug gguucaagga cuuggagccc auggagcagu ucaucgcaca 1260
ggucgaucug ugugugacu gcacaacugg cugccucaaa gggcuugcca acgugcagug 1320
uucugaccug cucaagaagu ggcugccgca acgcugugcg accuuugcca gcaagaucca 1380
gggccaggug gacaagauca agggggccgg uggugacuaa ucauaaucaa uuuauuauuu 1440
ucuuuuauuu uauucacaua auuuuguuuu uauuuuguuu uuaacauuuc aaaaaacaaa 1500
aaacaaaacg gcuauuaugc guuaccggcg agacgcuacg gacuu 1545

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 55
caccgctcag gacaatcctt 20

<210> SEQ ID NO 56
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56
ttaaaacagc ctgtgggttg atcccaccca caggcccatt gggcgctagc actctggtat 60
cacggtacct ttgtgcgcct gttttatacc ccctccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tggggaaacc catgggacgc tctaatacag acatggtgcg 420
aagagtctat tgagctagtt ggtagtcctc cggcccctga atgcggctaa tcctaactgc 480
ggagcacaca ccctcaagcc agagggcagt gtgtcgtaac gggcaactct gcagcggaac 540
cgactacttt gggtgtccgt gtttcatttt attcctatac tggctgctta tggtgacaat 600
tgagagatcg ttaccatata gctattggat tggccatccg gtgactaata gagctattat 660
atatcccttt gttgggttta taccacttag cttgaaagag gttaaaacat tacaattcat 720
tgttaagttg aatacagcaa a 741

<210> SEQ ID NO 57
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

```
atgggagtca aagttctgtt tgccctgatc tgcatcgctg tggccgaggc caagcccacc      60

gagaacaacg aagacttcaa catcgtggcc gtggccagca acttcgcgac cacggatctc     120

gatgctgacc gcgggaagtt gcccggcaag aagctgccgc tggaggtgct caaagagatg     180

gaagccaatg cccggaaagc tggctgcacc aggggctgtc tgatctgcct gtcccacatc     240

aagtgcacgc ccaagatgaa gaagttcatc ccaggacgct gccacaccta cgaaggcgac     300

aaagagtccg cacagggcgg cataggcgag gcgatcgtcg acattcctga gattcctggg     360

ttcaaggact tggagcccat ggagcagttc atcgcacagg tcgatctgtg tgtggactgc     420

acaactggct gcctcaaagg gcttgccaac gtgcagtgtt ctgacctgct caagaagtgg     480

ctgccgcaac gctgtgcgac ctttgccagc aagatccagg gccaggtgga caagatcaag     540

ggggccggtg gtgactaa                                                  558
```

<210> SEQ ID NO 58
<211> LENGTH: 566
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

```
acgttactgg ccgaagccgc ttggaacaag gccggtgtgc gtttgtctat atgttatttt      60

ccaccatatt gccgtctttt ggcaatgtga gggcccggaa acctggccct gtcttcttga     120

cgagcattcc taggggtctt tcccctctcg ccaaaggaat gcaaggtctg ttgaatgtcg     180

tgaaggaagc agttcctctg gaagcttctt caagacaaac aacgtctgta gcgacccttt     240

gcaggcagcg gaacccccca cctggcgaca ggtgcctctg cggccaaaag ccacgtgtat     300

acgatacacc tgcaaaggcg gcacaacccc agtgccacgt tgtgagttgg atagttgtgg     360

aaagagtcaa atggctctcc tcaagcgtat tcaacaaggg gctgaaggat gcccagaagg     420

taccccattg tatgggatct gatctggggc ctcggtgcac atgctttaca tgtgttcagt     480

cgaggttaaa aaacgtccag gccccccgaa ccacggggac gtggttttcc tttgaaaaac     540

acgatgataa tatggccaca accatg                                          566
```

<210> SEQ ID NO 59
<211> LENGTH: 121
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
aaaauccguu gaccuuaaac ggucgugugg guucaagucc cuccaccccc acgccggaaa      60

cgcaauagcc gaaaaacaaa aaacaaaaaa aacaaaaaaa aaaccaaaaa aacaaaacac     120
```

a 121

<210> SEQ ID NO 60
<211> LENGTH: 254
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 60
ataccagccg aaaggccctt ggcagagagg tctgaaaaga cctctgctga ctatgtgatc 60
ttattaaaat taggttaaat ttcgaggtta aaaatagttt taatattgct atagtcttag 120
aggtcttgta tatttatact taccacacaa gatggaccgg agcagccctc caatatctag 180
tgtaccctcg tgctcgctca aacattaagt ggtgttgtgc gaaaagaatc tcacttcaag 240
aaaaagaaac tagt 254

<210> SEQ ID NO 61
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
gagggcaggg gaagtctact aacatgcggg gacgtggagg aaaatcccgg ccca 54

<210> SEQ ID NO 62
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
cagtgtacta attatgctct cttgaaattg gctggagatg ttgagagcaa cccaggtccc 60

<210> SEQ ID NO 63
<211> LENGTH: 796
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 63
gtaagaagca aggtttcatt taggggaagg gaaatgattc aggacgagag tctttgtgct 60
gctgagtgcc tgtgatgaag aagcatgtta gtcctgggca acgtagcgag accccatctc 120
tacaaaaaat agaaaaatta gccaggtata gtggcgcaca cctgtgattc cagctacgca 180
ggaggctgag gtgggaggat tgcttgagcc caggaggttg aggctgcagt gagctgtaat 240
catgccacta ctccaacctg ggcaacacag caaggaccct gtctcaaaag ctacttacag 300
aaaagaatta ggctcggcac ggtagctcac acctgtaatc ccagcacttt gggaggctga 360
ggcgggcaga tcacttgagg tcaggagttt gagaccagcc tggccaacat ggtgaaacct 420
tgtctctact aaaaatatga aaattagcca ggcatggtgg cacattcctg taatcccagc 480
tactcgggag gctgaggcag gagaatcact tgaacccagg aggtggaggt tgcagtaagc 540
cgagatcgta ccactgtgct ctagccttgg tgacagagcg agactgtctt aaaaaaaaaa 600
aaaaaaaaaa aagaattaat taaaaattta aaaaaaaatg aaaaaaagct gcatgcttgt 660
tttttgtttt tagttattct acattgttgt cattattacc aaatattggg gaaaatacaa 720
cttacagacc aatctcagga gttaaatgtt actacgaagg caaatgaact atgcgtaatg 780
aacctggtag gcatta 796

<210> SEQ ID NO 64
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 64
ggcaccatgg gaagtgatt 19

<210> SEQ ID NO 65
<211> LENGTH: 55
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65
aaaaaacaaa aaacaaaacg gcuauuaugc guuaccggcg agacgcuacg gacuu 55

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: MOD_RES
<222> LOCATION: (4)..(4)
<223> OTHER INFORMATION: Any amino acid
<220> FEATURE:
<221> NAME/KEY: SITE
<222> LOCATION: (1)..(8)
<223> OTHER INFORMATION: /note="Variant residues given in the sequence have no preference with respect to those in the annotations for variant positions"

<400> SEQUENCE: 66

Asp Val Glu Xaa Asn Pro Gly Pro
1               5

<210> SEQ ID NO 67
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 67

Gly Asp Val Glu Ser Asn Pro Gly Pro
1 5

<210> SEQ ID NO 68
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 68

Gly Asp Ile Glu Glu Asn Pro Gly Pro
1 5

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 69

Val Glu Pro Asn Pro Gly Pro
1 5

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 70

Ile Glu Thr Asn Pro Gly Pro
1 5

<210> SEQ ID NO 71
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 71

Gly Asp Ile Glu Ser Asn Pro Gly Pro
1 5

<210> SEQ ID NO 72
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 72

-continued

Gly Asp Val Glu Leu Asn Pro Gly Pro
1 5

<210> SEQ ID NO 73
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 73

Gly Asp Ile Glu Thr Asn Pro Gly Pro
1 5

<210> SEQ ID NO 74
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 74

Gly Asp Val Glu Asn Pro Gly Pro
1 5

<210> SEQ ID NO 75
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 75

Gly Asp Val Glu Glu Asn Pro Gly Pro
1 5

<210> SEQ ID NO 76
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 76

Gly Asp Val Glu Gln Asn Pro Gly Pro
1 5

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 77

Ile Glu Ser Asn Pro Gly Pro
1 5

-continued

<210> SEQ ID NO 78
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

Gly Asp Ile Glu Leu Asn Pro Gly Pro
1 5

<210> SEQ ID NO 79
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

His Asp Ile Glu Thr Asn Pro Gly Pro
1 5

<210> SEQ ID NO 80
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

His Asp Val Glu Thr Asn Pro Gly Pro
1 5

<210> SEQ ID NO 81
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

His Asp Val Glu Met Asn Pro Gly Pro
1 5

<210> SEQ ID NO 82
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Gly Asp Met Glu Ser Asn Pro Gly Pro
1 5

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 83

Gly Asp Val Glu Thr Asn Pro Gly Pro
1 5

<210> SEQ ID NO 84
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 84

Gly Asp Ile Glu Gln Asn Pro Gly Pro
1 5

<210> SEQ ID NO 85
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 85

Asp Ser Glu Phe Asn Pro Gly Pro
1 5

<210> SEQ ID NO 86
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 86

Gly Leu Asn Asp Ile Phe Glu Ala Gln Lys Ile Glu Trp His Glu
1 5 10 15

<210> SEQ ID NO 87
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 87

Lys Arg Arg Trp Lys Lys Asn Phe Ile Ala Val Ser Ala Ala Asn Arg
1 5 10 15

Phe Lys Lys Ile Ser Ser Ser Gly Ala Leu
20 25

<210> SEQ ID NO 88
<211> LENGTH: 6
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 88

Glu Glu Glu Glu Glu Glu
1               5


<210> SEQ ID NO 89
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Ala Pro Val Pro Tyr Pro Asp Pro Leu Glu Pro Arg
1               5                   10


<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Asp Tyr Lys Asp Asp Asp Asp Lys
1               5


<210> SEQ ID NO 91
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Tyr Pro Tyr Asp Val Pro Asp Tyr Ala
1               5


<210> SEQ ID NO 92
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 92

His His His His His His
1               5


<210> SEQ ID NO 93
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 93

Glu Gln Lys Leu Ile Ser Glu Glu Asp Leu
1 5 10

<210> SEQ ID NO 94
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 94

Thr Lys Glu Asn Pro Arg Ser Asn Gln Glu Glu Ser Tyr Asp Asp Asn
1 5 10 15

Glu Ser

<210> SEQ ID NO 95
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 95

Lys Glu Thr Ala Ala Ala Lys Phe Glu Arg Gln His Met Asp Ser
1 5 10 15

<210> SEQ ID NO 96
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 96

Met Asp Glu Lys Thr Thr Gly Trp Arg Gly Gly His Val Val Glu Gly
1 5 10 15

Leu Ala Gly Glu Leu Glu Gln Leu Arg Ala Arg Leu Glu His His Pro
20 25 30

Gln Gly Gln Arg Glu Pro
35

<210> SEQ ID NO 97
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 97

Ser Leu Ala Glu Leu Leu Asn Ala Gly Leu Gly Gly Ser
1 5 10

<210> SEQ ID NO 98
<211> LENGTH: 8
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 98

Thr Gln Asp Pro Ser Arg Val Gly
1 5

<210> SEQ ID NO 99
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

Pro Asp Arg Val Arg Ala Val Ser His Trp Ser Ser
1 5 10

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 100

Trp Ser His Pro Gln Phe Glu Lys
1 5

<210> SEQ ID NO 101
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 101

Cys Cys Pro Gly Cys Cys
1 5

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 102

Glu Val His Thr Asn Gln Asp Pro Leu Asp
1 5 10

<210> SEQ ID NO 103
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 103

Gly Lys Pro Ile Pro Asn Pro Leu Leu Gly Leu Asp Ser Thr
1 5 10

<210> SEQ ID NO 104
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 104

Tyr Thr Asp Ile Glu Met Asn Arg Leu Gly Lys
1 5 10

<210> SEQ ID NO 105
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 105

Asp Leu Tyr Asp Asp Asp Asp Lys
1 5

<210> SEQ ID NO 106
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
gaaagaaaga aagaaagaaa gaaagaaaga aagaaagaaa gaaagaaaga aagaaagaaa 60
gaaa 64

<210> SEQ ID NO 107
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 107
uagagaaacu cgcggag 17

<210> SEQ ID NO 108
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace=" " or "His"
<220> FEATURE:

<221> NAME/KEY: VARIANT
<222> LOCATION: (2)..(2)
<223> OTHER INFORMATION: /replace=" " or "Gly"
<220> FEATURE:
<221> NAME/KEY: VARIANT
<222> LOCATION: (3)..(3)
<223> OTHER INFORMATION: /replace="Val" or "Ile" or "Ser" or "Met"
<220> FEATURE:
<221> NAME/KEY: MOD_RES
<222> LOCATION: (5)..(5)
<223> OTHER INFORMATION: Any amino acid
<220> FEATURE:
<221> NAME/KEY: SITE
<222> LOCATION: (1)..(9)
<223> OTHER INFORMATION: /note="Variant residues given in the sequence have no preference with respect to those in the annotations for variant positions"

<400> SEQUENCE: 108

Gly Asp Asp Glu Xaa Asn Pro Gly Pro
1               5

<210> SEQ ID NO 109
<211> LENGTH: 96
<212> TYPE: RNA
<213> ORGANISM: Hepatitis delta virus

<400> SEQUENCE: 109
ggcucaucuc gacaagaggc ggcaguccuc aguacucuua cucuuuucug uaaagaggag 60
acugcuggac ucgccgccca aguucgagca ugagcc 96

<210> SEQ ID NO 110
<211> LENGTH: 74
<212> TYPE: RNA
<213> ORGANISM: Hepatitis delta virus

<400> SEQUENCE: 110
ggcuagaggc ggcaguccuc aguacucuua cucuuuucug uaaagaggag acugcuggac 60
ucgccgcccg agcc 74

<210> SEQ ID NO 111
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 111
ggcttggcct cggccacagc gatgcagatc 30

<210> SEQ ID NO 112
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 112
gtttttcggc tattcccaat agccgttttg 30

<210> SEQ ID NO 113
<211> LENGTH: 30
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 113
gaccagaaga gtccctgctg cccactcaga 30

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 114
acgacggtgt gtgcatgtat 20

<210> SEQ ID NO 115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 115
ttcccaccac ttcaggtctc 20

<210> SEQ ID NO 116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 116
tacgcctgca actgtgttgt 20

<210> SEQ ID NO 117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 117
tcgatgatct tgtcgtcgtc 20

<210> SEQ ID NO 118
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 118
agggctgctt ttaactctgg t 21

```
<210> SEQ ID NO 119
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119

ccccacttga ttttggaggg a                                              21


<210> SEQ ID NO 120
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120

tgctgcccac tcagacttta ttc                                            23


<210> SEQ ID NO 121
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121

gaggugcuca aagagau                                                   17


<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122

ggctattccc aatagccgtt                                                20


<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123

agatttcgtt ggggactggc                                                20


<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 124
ctggagacgt ggaggagaac 20

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 125
ccaaaagacg gcaatatggt 20

<210> SEQ ID NO 126
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 126
gtcaacggat tttcccaagt ccgtagcgtc tc 32

<210> SEQ ID NO 127
<211> LENGTH: 1203
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127
gggaatagcc gaaaaacaaa aaacaaaaaa aacaaaaaaa aaaccaaaaa aacaaaacac 60
aacgttactg gccgaagccg cttggaataa ggccggtgtg cgtttgtcta tatgttattt 120
tccaccatat tgccgtcttt tggcaatgtg agggcccgga aacctggccc tgtcttcttg 180
acgagcattc ctaggggtct ttcccctctc gccaaaggaa tgcaaggtct gttgaatgtc 240
gtgaaggaag cagttcctct ggaagcttct tgaagacaaa caacgtctgt agcgaccctt 300
tgcaggcagc ggaacccccc acctggcgac aggtgcctct gcggccaaaa gccacgtgta 360
taagatacac ctgcaaaggc ggcacaaccc cagtgccacg ttgtgagttg gatagttgtg 420
gaaagagtca aatggctctc ctcaagcgta ttcaacaagg ggctgaagga tgcccagaag 480
gtaccccatt gtatgggatc tgatctgggg cctcggtgca catgctttac atgtgtttag 540
tcgaggttaa aaaacgtcta ggccccccga accacgggga cgtggttttc ctttgaaaaa 600
cacgatgata atagccacca tgggagtcaa agttctgttt gccctgatct gcatcgctgt 660
ggccgaggcc aagcccaccg agaacaacga agacttcaac atcgtggccg tggccagcaa 720
cttcgcgacc acggatctcg atgctgaccg cgggaagttg cccggcaaga agctgccgct 780
ggaggtgctc aaagagatgg aagccaatgc ccggaaagct ggctgcacca ggggctgtct 840
gatctgcctg tcccacatca agtgcacgcc caagatgaag aagttcatcc caggacgctg 900
ccacacctac gaaggcgaca aagagtccgc acagggcggc ataggcgagg cgatcgtcga 960
cattcctgag attcctgggt tcaaggactt ggagcccatg gagcagttca tcgcacaggt 1020
cgatctgtgt gtggactgca caactggctg cctcaaaggg cttgccaacg tgcagtgttc 1080
tgacctgctc aagaagtggc tgccgcaacg ctgtgcgacc tttgccagca agatccaggg 1140
ccaggtggac aagatcaagg gggccggtgg tgactaaaaa aaacaaaaaa caaaacggct 1200
att 1203

<210> SEQ ID NO 128
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 128
aatagccgaa aaacaaaaaa caaaaaaaac aaaaaaaaaa ccaaaaaaac aaaacaca 58

<210> SEQ ID NO 129
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 129
aaaaaacaaa aaacaaaacg gctatt 26

<210> SEQ ID NO 130
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130
gggaatagcc gaaaaacaaa aaacaaaaaa aacaaaaaaa aaaccaaaaa aacaaaacac 60
aacgttactg gccgaagccg cttggaataa ggccggtgtg cgtttgtcta tatgttattt 120
tccaccatat tgccgtcttt tggcaatgtg agggcccgga aacctggccc tgtcttcttg 180
acgagcattc ctaggggtct ttcccctctc gccaaaggaa tgcaaggtct gttgaatgtc 240
gtgaaggaag cagttcctct ggaagcttct tgaagacaaa caacgtctgt agcgaccctt 300
tgcaggcagc ggaacccccc acctggcgac aggtgcctct gcggccaaaa gccacgtgta 360
taagatacac ctgcaaaggc ggcacaaccc cagtgccacg ttgtgagttg gatagttgtg 420
gaaagagtca aatggctctc ctcaagcgta ttcaacaagg ggctgaagga tgcccagaag 480
gtaccccatt gtatgggatc tgatctgggg cctcggtgca catgctttac atgtgtttag 540
tcgaggttaa aaaacgtcta ggccccccga accacgggga cgtggttttc ctttgaaaaa 600
cacgatgata atagccacca tgggagtcaa agttctgttt gccctgatct gcatcgctgt 660

<210> SEQ ID NO 131
<211> LENGTH: 543
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic polynucleotide"

<400> SEQUENCE: 131
ggccgaggcc aagcccaccg agaacaacga agacttcaac atcgtggccg tggccagcaa 60
cttcgcgacc acggatctcg atgctgaccg cgggaagttg cccggcaaga agctgccgct 120
ggaggtgctc aaagagatgg aagccaatgc ccggaaagct ggctgcacca ggggctgtct 180
gatctgcctg tcccacatca agtgcacgcc caagatgaag aagttcatcc caggacgctg 240
ccacacctac gaaggcgaca aagagtccgc acagggcggc ataggcgagg cgatcgtcga 300
cattcctgag attcctgggt tcaaggactt ggagcccatg gagcagttca tcgcacaggt 360
cgatctgtgt gtggactgca caactggctg cctcaaaggg cttgccaacg tgcagtgttc 420
tgacctgctc aagaagtggc tgccgcaacg ctgtgcgacc tttgccagca agatccaggg 480
ccaggtggac aagatcaagg gggccggtgg tgactaaaaa aaacaaaaaa caaaacggct 540
att 543

<210> SEQ ID NO 132
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 132
cgcggatcct aatacgactc actataggga atagccgaaa aacaaaaaac aaaaaaaaca 60
aaaaaaaaac caaaaaaaca aaacacaaac gttactggcc gaagccgc 108

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 133
acagcgatgc agatcagggc 20

<210> SEQ ID NO 134
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 134
cgcggatcct aatacgactc actataggcc gaggccaagc ccaccg 46

<210> SEQ ID NO 135
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 135

-continued aatagccgtt ttgtttttg tttttttag tcaccaccgg cccct 46

<210> SEQ ID NO 136
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 136
gggactcttc tggtccccac agactcagag agaacccacc atgggagtca aagttctgtt 60
tgccctgatc tgcatcgctg tggccgaggc caagcccacc gagaacaacg aagacttcaa 120
catcgtggcc gtggccagca acttcgcgac cacggatctc gatgctgacc gcgggaagtt 180
gcccggcaag aagctgccgc tggaggtgct caaagagatg gaagccaatg cccggaaagc 240
tggctgcacc aggggctgtc tgatctgcct gtcccacatc aagtgcacgc ccaagatgaa 300
gaagttcatc ccaggacgct gccacaccta cgaaggcgac aaagagtccg cacagggcgg 360
cataggcgag gcgatcgtcg acattcctga gattcctggg ttcaaggact tggagcccat 420
ggagcagttc atcgcacagg tcgatctgtg tgtggactgc acaactggct gcctcaaagg 480
gcttgccaac gtgcagtgtt ctgacctgct caagaagtgg ctgccgcaac gctgtgcgac 540
ctttgccagc aagatccagg gccaggtgga caagatcaag gggccggtg gtgactaagc 600 tggagcctcg gtagccgttc ctcctgcccg ctgggcctcc caacgggccc tcctccccctc 660 cttgcaccgg cccttcctgg tctttgaata aagtctgagt gggcagca 708

<210> SEQ ID NO 137
<211> LENGTH: 37
<212> TYPE: DNA
<213> ORGANISM: Homo sapiens

<400> SEQUENCE: 137
actcttctgg tccccacaga ctcagagaga acccacc 37

<210> SEQ ID NO 138
<211> LENGTH: 110
<212> TYPE: DNA
<213> ORGANISM: Homo sapiens

<400> SEQUENCE: 138
gctggagcct cggtagccgt tcctcctgcc cgctgggcct cccaacgggc cctcctcccc 60
tccttgcacc ggcccttcct ggtctttgaa taaagtctga gtgggcagca 110

<210> SEQ ID NO 139
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 139
cgcggatcct aatacgactc actataggga ctcttctggt ccccacagac tcag 54